US008673291B2

(12) United States Patent
Scholl et al.

(10) Patent No.: US 8,673,291 B2
(45) Date of Patent: Mar. 18, 2014

(54) DIFFOCIN AND METHODS OF USE THEREOF

(75) Inventors: Dean M. Scholl, Burlingame, CA (US); Dana M. Gebhart, San Francisco, CA (US); Steven R. Williams, San Francisco, CA (US); Gregory R. Govoni, San Carlos, CA (US); David W. Martin, Jr., Mill Valley, CA (US)

(73) Assignee: AvidBiotics Corp., South San Francisco, CA (US)

( * ) Notice: Subject to any disclaimer, the term of this patent is extended or adjusted under 35 U.S.C. 154(b) by 0 days.

(21) Appl. No.: 13/117,467

(22) Filed: May 27, 2011

(65) Prior Publication Data

US 2011/0293566 A1 Dec. 1, 2011

Related U.S. Application Data

(60) Provisional application No. 61/349,145, filed on May 27, 2010.

(51) Int. Cl.

| | |
|---|---|
| ***C12N 1/20*** | (2006.01) |
| ***C12N 7/00*** | (2006.01) |
| ***C07H 21/00*** | (2006.01) |
| ***C07K 14/00*** | (2006.01) |

(52) U.S. Cl.

USPC .................... 424/93.21; 435/235.1; 435/243; 435/252.7; 536/23.7; 530/350

(58) Field of Classification Search

None

See application file for complete search history.

(56) References Cited

U.S. PATENT DOCUMENTS

| | | | | |
|---|---|---|---|---|
| 7,585,957 | B2 | 9/2009 | Miller et al. | |
| 7,700,729 | B2 | 4/2010 | Scholl et al. | |
| 7,732,586 | B2 | 6/2010 | Martin, Jr. et al. | |
| 8,206,971 | B2 | 6/2012 | Scholl et al. | |
| 2008/0171376 | A1 * | 7/2008 | Scholl et al. | 435/235.1 |

FOREIGN PATENT DOCUMENTS

| | | | | |
|---|---|---|---|---|
| WO | WO01/01786 | * 1/2001 | | A23C 19/11 |
| WO | WO02/077183 | * 10/2002 | | |
| WO | 2011/150342 A1 | 12/2011 | | |

OTHER PUBLICATIONS

Steven R. Williams et al., Retargeting R-Type Pyocins to Generate Novel Bactericidal Protein Complexes. Applied and Environmental Microbiology, Jun. 2008, p. 3868-3876.*

Dana Gebhart,et al., Novel high molecular weight, R-type bacteriocins of *Clostridium difficile*. J. Bacteriol. doi:10.1128/JB. 01272-12. Published online ahead of print on Sep. 14, 2012. pp. 1-40.*

Mohammed Sebaihia et al.The multidrug-resistant human pathogen *Clostridium difficile* has a highly mobile, mosaic genome. Nature Genetics vol. 38 [No. 7 [Jul. 2006 779-786.*

Lidia Westers et al., *Bacillus subtilis* as cell factory for pharmaceutical proteins: a biotechnological approach to optimize the host organism. Biochimica et Biophysica Acta 1694 (2004) 299-310.*

Pulvirenti et al., Difference in the Incidence of *Clostridium difficile* Among Patients Infected With Human Immunodeficiency Virus Admitted to a Public Hospital and a Private Hospital. Infection Control and Hospital Epidemiology, vol. 23, No. 11 (Nov. 2002), pp. 641-647.*

Database EMBL [Online] Oct. 1, 2009, "*Clostridium difficile* R20291 complete genome," XP00000268912, retrieved from EBI Accession No. EM_PRO: FN545816 p. 638-p. 641; sequence.

Database UniProt [Online] Nov. 24, 2009, "Subname: Full=Putative phage tail fiber protein;", XP000002658913, retrieved from EBI Accession No. UNIPORT: C9XPN8 the whole document.

Database UniProt [Online] Nov. 24, 2009 "Subname: Full=Putative phage protein;" XP000002658914, retrieved from EBI Accession No. UNIPROT: C9YKW6 Database accession No. C9YKW6 sequence A13.

Anastasio, KL, JA Soucheck and H Sugiyama, 1971. "Boticinogeny and Actions of the Bacteriocin," J. of Bacteriology, 107 143-149.

Blackwell, C.C. and J.A. Law, 1981. Typing of Non-Serogroupable *Neisseria meningitidis* by Means of Sensitivity to R-Type Pyocins of *Pseudomonas aeruginosa*. J. Infect. 3(4): 370-378.

Blackwell, C.C., F.P. Wistanley, and W.A. Telfer-Brunton, 1982. "Sensitivity of Thermophilic Campylobacters to R-Type Pyocins of *Pseudomonas aeruginosa*," J. Med. Microbiol. 15:247-251.

Bradley, DE, "Ultrastructure of Bacteriphage and Bacteriocins," Bacteriol. Rev. 21:230-314, 1967.

Campagnari, A.A.R. Karalus, M. Apicella, W. Melaugh, A.J. Lesse, and B.W. Gibson, 1994. Use of Pyocin to Select a *Haemophilus ducreyi* Variant Defective in Lipooligosaccharide Biosynthesis, Infect. Immun. 62:2379-2386.

Coetzee, H.L., H.C. De Klerk, J.N. Coetzee, and J.A. Smit. 1968. "Bacteriophage-tail-like Particles Associated With. Intra-species Killing of *Proteus vulgaris*," J. Gen. Virol. 2:29-36.

Daw, MA, and FR Falkiner, 1996. "Bacteriocins: Nature, Function, and Structure," Review Article. Micron. 27:467-479.

Ellison, JS and JA Kautter, 1970. "Purification and Some Properties of Two Boticins," J. of Bacteriology, 104: 19-26.

(Continued)

*Primary Examiner* — Kevin Hill
*Assistant Examiner* — Arthur S Leonard
(74) *Attorney, Agent, or Firm* — Sughrue Mion, PLLC

(57) ABSTRACT

This disclosure relates to the discovery and isolation of the entire cluster of genes encoding R-type high molecular weight bacteriocins that specifically kill *Clostridium difficile* bacteria, dangerous human pathogens. Also disclosed are methods of producing the R-type bacteriocins in innocuous producer cells that, unlike *C. difficile*, do not die in the presence of oxygen. Disclosed also is the specific gene of the isolated gene cluster that determines the killing spectrum of the R-type bacteriocin and the demonstration that the killing spectra of diffocins can be altered by engineering orf1374 of the diffocin genetic locus. This invention offers a potent bactericidal agent and a means to make it in order to kill selectively *C. difficile* bacteria in the environment of the gastrointestinal tract where they can cause great harm and even death of the infected patient or farm animal.

38 Claims, 43 Drawing Sheets

(56) References Cited

OTHER PUBLICATIONS

Filiatrault, M.J., R.S. Munson, Jr., and A.A. Campagnari, 2001. "Genetic Analysis of A Pyocin-Resistant Lipooligosaccharide (LOS) mutant of *Haemophilus ducreyi*: Restoration of Full-Length LOS Restores Pyocin Sensitivity," J. Inhibition. Bacteriol. 183: 5756-5761.

Fortier, LC and S Moineau, 2007. "Morphological and Genetic Diversity of Temperate Phages In *Clostridium difficile*," Appl. Environ. Microbiol. 73:7358-7366.

Goh, S., PF Ong, KP Song, TV Riley and BJ Chang, 2007. "The Complete Genome Sequence of *Clostridium difficile* Phage and PhiC2 and Comparisons to phiCD119 and Inducible Prophages of CD630," Microbiology, 153:676-685.

Govind, R, JA Fralick, and RD Rolfe, 2006. "Genomic Organization and Molecular Characterization of *Clostridium difficile* Bacteriophage phiCD119," J. Bacteriol. 188:2568-2577.

Jabrane, A., A. Sabri, P. Comp re, P. Jacques, I. Vandenberghe, J. Van Beeumen, and P. Thenart. 2002. "Characterization of Serracin P, a Phagetail-like Bacteriocin, and its Activity Against Erwinia amylovora, the Fire Blight Pathogen," Appl. Environ. Microbiol. 68:5704-5710.

Kageyama, et al, Life Sciences 9:471-476, 1962.

Kageyama, M. 1975. "Bacteriocins and Bacteriophages in *Pseudomonas aeruginosa*," 291-305. In T. Mitsuhashi and H. Hashimoto (ed.), Microbial Drug Resistance. University of Tokyo Press, Tokyo, Japan.

Kageyama, M. K. Ikeda, and F. Egami, 1964. "Studies of a Pyocin. III. Biological Properties of the Pyocin," J. Biochem. 55:59-64.

Sell, et al. 1983. "Bacteriophage and Bacteriocin Typing Scheme for *Clostridium difficile*," J. Clin. Microb. 17(6): 1148-1152.

Kageyama, M. Ikeda, and F. Egami. 1964. "Studies of a Pyocin I. Physical and Chemical Properties," J. Biochem. 55:49-53.

Kingsbury, D., 1966. "Bacteriocin Production by Strains of *Neisseria meningitidis*," J. Bacteriol. 91:1696-1699.

Krogh, S., M. O'Reilly, N. Nolan, and KM Devine, 1996. "The Phage-like Element PBSX and Part of the Skin Element, Which are Resident at Different Locations on the *Bacillus subtilis* Chromosome, are Highly Homologous, " Microbiology. 142:2031-2040.

Liu, S., Endo K., Ara K, Ozaki K, Ogasawara N. 2008. "Introduction of Marker-Free Deletions in *Bacillus subtilis* Using the AraR Repressor and the ara Promoter." Microbiology, 154:2562-2570.

Long, J. et al, 2008. "Differential Requirements of Two recA Mutants for Constitutive SOS Expression in *Escherichia coli* K-12," PLos ONE 3(12): e-4100. DOi: 10. 1371/journal.pone. 0004100.

Loo VG, Poirier L., Miller MA, Oughton M., Libman MD, Michaud S., et al. "A Predominantly Clonal Multi-Institutional Outbreak of *Clostridium difficile*-Associated Diarrhea With High Morbidity and Mortality, " N. Engl. J. Med. 2005; 353:2442-2449.

Morse, S.A., B.V. Jones, and P.G. Lysko. 1980. "Pyocin of *Neisseria Gonorrhoeae*: Mechanism of Action," Antimicrob. Agents Chemother. 18:416-423.

Nieves, BM, F. Gil and FJ Castillo, 1981. "Growth Inhibition Activity and Bacteriophage and Bacteriocinlike Particles Associated With Different Species of *Clostridium*," Can. J. Microbiol. 27:216-225.

Scholl, D., and DW Martin, Jr. 2008. "Antibacterial Efficacy of R-Type Pyocins Towards *Pseudomonas aeruginosa* in a Murine Peritonitis Model," Antimicrob. Agents Chemother. 52:1647-1652.

Scholl, D., M. Cooley, SR Williams, D. Gebhart, D. Martin, A. Bates, and R. Mandrell, 2009. "An Engineered R-Type Pyocin is a Highly Specific and Sensitive Bactericidal Agent for the Food-Borne Pathogen *Escherichia coli* O157:H7," Antimicrob. Agents Chemother. 53:3074-3080.

Strauch, E., H. Kaspar, C. Schaudinn, P. Dersch, K. Madela, C. Gewinner, S. Hertwig, J. Wecke, and B. Appel. 2001. "Characterization of Enterocoliticin, a Phage Tail-Like Bacteriocin and Its Effect on Pathogenic *Yersinia enterocolitica* Strains," Appl. Environ. Microbiol. 67:5634-5642.

Williams, S., D.Gebhart, D.W. Martin, D. Scholl. 2008. "Re-Targeting R-Type Pyocins to Generate Novel Bactericidal Protein Complexes," Appl. Envrion. Microbiol. 74:3868-3876.

Thompson, N. et al., "Genetic Transformation in *Staphylococcus aureus*: Demonstration of a Competence-Conferring Factor of Bacteriophage Origin in Bacteriphage 80a Lysates," J. Bacteriology, 148:294-300, 1981.

Wood, HE, MT Dawson, KM Devine, D.J. McConell, 1990. "Characterization of PBSX, A Defective Prophage of *Bacillus subtilis*," J. Bacteriology 172:2667-2674.

Zink, R., M.J. Loessner, and S. Schere. 1995. "Characterization of Cryptic Prophages (monocins) In *Listeria* and Sequence Analysis of a Holin/Endolysin Gene," Microbiology 141:2577-2584.

* cited by examiner

SEQ ID NO:1-61

SEQ ID NO:1 >Dif16 locus
GGCCGCAATACCCACTACACCTTCgTCATCTTTAAATTTAAGAGTTTTTACTATTGAATAATAA
AGGTATATTCCAGTAAAAATAATCTTTAAATACAAGAAAAATAAACTCTTTGGGTATATTAAAA
AGCTAAAAAGTGTAAATATAAAAGCAAGTAGAGTACTTATCCTGTAAAAGAAATCTATTTGTGT
AATGTCTTTATATTTTATCATAAACACCGAATATAAAATGATGAAAATAATTGCGACGATTGCA
TATATGGTAAATAACATATTTTCAAGAGTACCATTTGAAATTACTATCCACTTATACCACATAA
TTGGCCAAAATAATAGTGCTAAGAACTTAAAATAATTATCAAACAACTTTTCTTTATACATTCA
TCAAACAACCTTTCTTAACAAAAGCATATATTTGTTTTTAGAATTTTAAATAATATGATATCAT
TATTATATATTAATATTGAATTTATAGAAACCAAAATTTGTTAAAATAAATATATAGATTTTAC
TGTTAAGCCAGTTAAAATTACTACTATTTTTATTATGAAATTGGATCAAATATGTAGAAATACG
GCAAATTAGTTAATATTAAATATTTATTATTTCCAAGTTGTAAAGACTGTTTTTTTAATGATAA
AAATTCTAATCTTTTTTGAAAGAAAGTAATATCCACATTAAGTATGTCTGCCATTTCATAAACG
CAAGTGATGCCAGAATTAATTATGTTTATTATATCTTCTTCAGTAATTAAGAACTCACAAGCCC
ATTTTAAGGCTTTATTTTCGCACTTATCTATAATAATTTTTGTATAATAATCGTTATAAGAGGA
TACATAGTATCCAAGGCTAGTGAAATGATGTCCAAGTTCTTCAGCTAAGATGGATGTCAATTTT
TTTGAGTTTTGTTTTAAATTACTGAGTAATGATATAATTTTAATACCATGTTTGTTTATATATA
GCCCTTCTAAATCACCTGCAATATAAGTGGTATAATGAATTATTATCTCTTCTTGAGAAGCTAA
TTCAAAAAGCTTATCCAAATTATTCATAAAAATCCCCCTAAAATAGAATGTATGTTTGCCTTTA
AATTATATTAAAAGAGCAGAAAAATAGACTGCTCATCATATGGTTTATTTTTTTTTATATTTAT
TTAGTAAAAATTCTATATAATCATTAAGTTGTTCTTGTGCTTCTTCAGGTAACTCTTCATGTGG
ATTTTTTCTATGTGCAGCTACTGTATCAATATTTTCCTTAACTAAGGTTCTTCCAAGAAGGTAA
TCAACTGATACATTAAATACATCAGCCAATTTGTTTAAAATGTGTTCATCAGGAAATCTGTTTT
CTGTTTCATAGTACCCTAAGACTCTTTGGGAAACGCCTACTTTTTCTCCAAGTTCTCTTTGAGT
CAATCCAAATTCCTTTCTAAGTTCTCTTAATCTTTTGGCAAACATTATAACACCACCTTATGTA
TAGATTATAACAAATTGTTCTAAAAAATAAAACTAATAAAATATAAAAGAATATTTTTTCTAAA
ATCTATTGATAAAGAACAAATGATTCTATATAATCTAAGTGTGGAAGAACAAAATATTCTTAAT
GGTAATGGAGGTATAAAACAATGTTTAAAAATAACTTGAAATATTATAGAAAATGCAAAGGTAT
GACACAAATTCAACTTGCCAGAAAGGCTGGAATTACAAATGACTATATATCTCAAATAGAAAGA
GGTATAAAAAATCCTGGTCTTCTTATGGCTAAGAAGATTTCTAGTATTTTAGAACAAAATATAG
AAGAAGTTTTTTTATACAGTTATAGAACAATATGTTCTTGAAAGTTGTGAGATTAGTAAAAAA
CTGTGCACTAAAGAGATTATTGTAAATTTGAAGCTAATAATAAGTATATAAAAAAGGAGAAGTA
CTATGGAAAACAAAAAAGATATATTATTTAAAGAAACAGATGAAAGATTACATAATTATAAGTA
TTTGGATATAAAGATAAAGAATATTAATTTGGACATAAAAAGATGTGAGAATGAATACTCTGGA
TGTGGAGCAATGGTATATACAGAAAAGACTAGTAACACATATAACATAAGTTCTTCTGTGGAAA
ATGAGGTGTTAAAAAGAGAGGAAAGATTAAGAAAATTAAAAATGGAAAAAGAAGATATAGAAAT
AGAAAAAGAGAAGATAGAAAATGCTCTAACATGTCTAAATGATATAGAAATGGAATTTTTTAAT
CTTTTTTATAATAGTAAGACAAAAAACAATATGACATATATTTCTATGAAACTACACTTAGATA
GAACATCTTGCTACAATTTAAAGAAAAAAATGATATTTAAATTGAGTGAGATATTATAAAAAAT
ATGACAACTTTACAACACTTTATATACACTATTGCAACACTAGGCAATAAAATATGTGAGATAA
TGTTATTGTGAAAGAAATCCATATTGAAGGAGGTGATAAATTGAAAAGAATAATATTACCTAAA
AATATAGAAGATATTTGACAGGAATAAATGAGATGTATATTTAAAAATGACTTATATCATTTAT
AGTAAGATTATCAGATTAAGCAAGAATATTTAGTGATAGTGTGGTGATTATTTGCTTAAATACA
AGGAAATATTAGAAACAATTATTGAGATTCTCAAAAAAAACTTTACTGAAAGTATTTTTATTGA
TGATGAAAGTGTGCAAGGCTCTGAAGGGTCTTGTTTTTTTGTAAGTATACTATCAGTTATTTGT
ACACCTATAATGTTAAATACGAATAATAAAGATATTGTTATCTCTATAAAATACTTACCAAAAC

Figure 1A

CACAGTCAAAGAGTATTAGAATGTATGAAATTTCAGATGAATTAAATAAGTTATTCAACAGAAA
TATAAAGGTAACAGACAGAAAATTAAATATAACAAAGCTAGAACAAAGTATTAAAAAAGAAGAG
TCAATTTATGTATTGAACTTTACAATTACACTAAATTATCTGGATAGTGTATATGAAGAAGATG
TAGTATATGAAAATATGGAAGAAATCAATTTAAATTTAGGAGAGTGATAGTATGGCTATAGGAT
TACCAAGTATCAACATATCATTTAAGGAGCTAGCTACAACTGTTAAAGAACGTTCAGCTAGAGG
AATAATTGCAATGGTGCTTAAAGATGCTAAGGCACTAGGTCTTAATGAAATACATGAAAAAGAG
GATATACCAGTTGATTTATCTGCTGAAAATAAAGAGTATATAAATTTAGCTTTGATGGGAAATG
TTAACACTCCAAATAAATTATTAGTTTATGTAATAGAAGGAGAAGCAGATATTCAAACTGCATT
AGATTTTTTAGAGACTAAGGAATTTAATTATCTATGTATGCCAAAAGCAGTAGAAGCTGATAAG
ACTGCTATAAAAAATTGGATAATTAAACTTAGAGATATAGATAAGGTTAAGGTTAAAGCTGTAT
TAGGAAAAGTTGTAGGAAATCATGAAGGGATAATTAATTTTACTACAGAAGATGTGTTAGTTGG
AGAAAAGAAATACAGTGTTGATGAGTTTACAAGTAGGGTGGCTGGACTTATAGCAGGAACACCT
TTAAGTCAATCAGTAACTTATACTAAGCTTAGTGATGTAGTTGATATACCTAAGATGACGAAAG
TTGATGCAGAATCAAGGGTTAATAAAGGAGAGCTTATACTTATTAAGGAAGCAGGGGCTATAAG
AATTGCAAGAGGAGTAAATTCTTTAACTGAGTTAACAGAAGAAAAAGGAGAAATGTTCCAGAAA
ATAAAAATAGTTGACACTTTAGATATTATACATAGTGACATAAGAAAGGTGATAATAGATGACT
ATATAGGAAAGGTTACTAACAGTTATGACAACAAATGTTTATTGATAGTAGCTATAAAAAGTTA
TTTAGAAGAATTAGAAAAGTCAGCACTTATAGAATCTGATTCTACTGTTGAAATAGATTTTGAA
GCACAAAAATCGTATTTAAAATCAAAAGGAGTAGATTTATCTTATATGACATTACAAGAAATAA
AAGAAGCTAACACAGGTTCTAAAGTATTTTTAAAAGCAAAAATAAAAGTACTTGATGCTATGGA
AGATATAGATTTATCAATAGAAATATAGGAGGATTATTAATATGGCAAATATGGAAGCTAGAAA
TGTAATGAGTGGTACTTGGGGAGAACTTTGGCTTGATGGAAACAAAGTAGCAGAAGTAAAGAAG
TTTCAAGCAAAGATGGAATTTACAAAAGAGGATATTATAATAGCAGGTCAAATGGGTACTGATA
CAAAGTATATGGGATATAAAGGAAAAGGTTCAATAACTCTATACCATGTTAGTTCAAGAATGCA
CAAGTTAATTGGAGAAAAGATAAAGAGAGGTTCTGAACCTAGATTTGTTGCTATATCTAAATTA
AATGACCCAGATTCTTATGGAGCAGAAAGAATAGCAGTAAAAAATATAGCATTTGATGATTTAA
CTTTAGCTGATTGGGAGGTTGGAGTAAAAGGAGAGATAGAAGCACCTTTCACATTTACTGAGTA
TGATTTTCTTGATATAATTTAGTTTTATATTTGGTTTTATACTGATATTTAGTAGATATATACT
TAATAAATTTAGGTAGTTAATAAGTAAAAAAGTTAGTTGATTGAATTTGATTGATAAAGGAGCA
AATAATAATGAATGAAAATGGATTATCAAAAAATATAAACATAGTAGATTTACTTTTAAATGCA
GATACAGAAAACTTAGAAAGACCAAGTACTATAGTTGAACTTAAGAGATTATCAACTATATTTG
GGCAGGAATTTAAAGTAATGTGTAGAGCTTTAACAATAAGTAAAGATGAAGAGATACAAAATAC
TTGTCTTAAAATTGATGAAAATATGAAAACGGATATAGACTTACCGGAGATGCAGATGCTTACA
ATTATAGAAGGTGTTTGTGATTTGGATGGAAAGCTTTTATTTAAAAATAAGGAACTAATGGATA
AATTTAAGGCTCCAACACCAAAAGAATTGGCAAGAAAACTATTATTACCAGGTGAAATTACCAA
CCTATATAGAATACTTCAAGATGTTATGGGTTATGGTAAAAATGCAGTGATAGAAGAGGTAAAA
AACTAATAGGGACGGATACCAAGACTACAATAATGTACTATTATTGGAAGAAAAAGGTATAAG
ACCGTCCCTTTTTTATGCAATGGATAAAGGCGAATTAAAGCTTATTGAAGCTTTTTTCGCCTTA
GAAATTGAGGAAGAAGTTGAAAAAATGAAACATGGATATGGAGTGTGTCCTTTGACAGGAGGTG
GTATGTAATGGGAAATGTGAGAGAAGAAGGTATAAATATGTATCTTACAGATAATTACACACCA
AAAATGAACCAAATTATATCAGTAACTGATAATTTTAGGAGAGCAACTGTGGCTGTTTCACTTT
CCACTAATGTAATGGCTAGTAGCATAAAAAATTCTATTGGAAGTGCAAGTAGTAGAGTAAACAG
TTTAAATTCCTCGTTAAGAAAAGTTCAAACTACTGCTAGTAGTGTAAGTTCAACTATGGCAAAA
TTAAGTTCTAGCATAAATGCTGTTTCAGGAGTTATTGGAAGTTTAAATGGAAGTATTATGAGAC
TAGCAATAACTATAGCTATGATTATTGATTATTTTAATAAGTTGATTCAAAAGAAAAATGAGTT
TAATTCAAATATTATGATTATATTAATATTTAAAGCTAAAAGTGATGAAGTAGAAAAAACTAAA
AATAAATTACTTGGAAATTTAAAAAAGATTGGTGGCAAGATTTGGAATATCGTAATAAAAGCAA

Figure 1B

AAGATATGACTAAGAGAGTGATAAGTAGTATCTTGGGAAAATTAAAACGAGTAGAGAAACGTCC
TTATCAAGGAAGTATTAATCTTAAAGATATGGTAAGTAGTGCTATGGCTAGAATTTTGCCTAAG
TTAATGTTGTTTAAAAATACTTTTTGGAGTGGTGTAATAGCTATAAAAGATATGGCAAGTAGCA
TTATAAGTAAAGTATTTCCCAAATTGAGATTGTTTGCAGGTAAGGTATGGAGTGGTGCAATAGC
TGTAAAGGATATGGCAAGTGGAATACTTGGTTCGATAAAAGGGAAGATATCTGATTTGACAAAT
GGTGCTACTATAGGTGTCGCTGTGAAAAAGGGTGTTGACTTACTTGGTCAGGAACAAAATCAGA
AAGTTGTTCTAGAAAGTGTAATGAAAAGAAATACTGGAAAAACTAGCCAAAAAGATGTTGATAA
GTATTATGACAGTTTAGTAAATATGGCAAATGATACGCCTTTTGACCCTGAAGATGTTGTTGCA
ATGGGAACTAAAGCTAAAATGATTAGTAATATTACTGGTGGCAAAAAAGAAAAAGATATAACTC
AAGCTATGGTAGATGTTAGAGCTTTAAATATGAATACAAGTAGTGAACAAGATGTATCAGCAGC
TTTCTTAAGTGCAGCAAAAGGAAATATGGAATCTCTTAATACTCTGGTAGGAGAAAATTATAAA
ACTTTTGATGAAGCATTGGAAGGCATAAGTGTAAAGCAGATGGGGTTAGCTAAAGAAATGAGTA
ATACAATACCAGGTATAATATCAGGAGCTCAAACAAGCATTAACAATGGTTTGAAGAGTATTGT
TAAACCTTTTGATGATATTTTAGGTCAAGGACTAAAGAAAATAAAAACTTTTATAGAAAGTGGA
TTAGGGAATTTAGCTGGCTTATCTGAAAAAATGGCTGGTAAAATAGGCAATGTAATGAATGGTA
AGATAATTATTGGCAACAAATATGACCAGATGCAATCTAGAAGTGTAAAAAATGGAAAAGAGTT
TTCTGATTCTACTCAATATCGAATTTCTAATGAGGCTGAAAAGCGTAAAATGATGGTTGAAAAT
AAGCAAGAACGTTTTGAAAATCATGCAGCAACAATGATAGGGAATGCACCAAAAGCAATTGTTA
ACGCAGGAAGTACACTATTACAAAATATTGATTTTACAGCATTAATAGATTCACTACTTCCAGT
AGTAAACTTAGTAAATAATTTACTAGATAGTATAAACAATAAATCACCAATTGCACAAGGATTA
ATAAGTATATTTGGTACAATAGTAACTACAGCATTCCAACTAATCGGACCTGTAGTTGAAGCTG
TTAGTCCTATTATCACAAGAATTTTTACTTTTTTAGGTGAATATGCACCTCAAATAAACAATTT
TATAGAGACACTGGGTGTTATTTGGAAAACTGTATGGGAGACCTTAGGACCTCTGTTGGAAACT
GGATGGAAAATTATAGAGCCAATATTGGGAGCTTTTTTTAACATATTAGATAAAGTATGTAAAA
TAGTTAAAGATATATGCAAATGGTGGCAAACTATGATTAATAAGATAAAAAATGGAAGCATCAC
AGGAACAGTTTTAAATCTAGTGGAAAAGAGTAAAAAAAATTACAAAGATAATCCATATGCTGGA
ACAAAGGCTGGTGATTCTGGTAAAGCTTATTCAAGTAAGAAAGGTAATAATGCATTTGGATTGA
ACTATGTTCCTTATAATGACTATCAAACCAGACTCCATGAAGGTGAAATGGTTTTAACTAAACA
AGAAGCAAATCAATATAGAAGCAGAAAAAATGGTGGAAATATAAACATAGCTAAGTTAGCTGAT
ACAATAGTGATTAGAGAAGAAGCTGATATAGAAAAGATAACATCAAAATTAGTTGCAAGTATCC
AATTGGCACAGTTAGGGGGTGTCTTATAATGGAAATGTGGCTTAGACAAGCAGAAGATAGATTT
AGATTTCCAGTATTTCCATCTTCCTTTAGTATTAATGGAAAAGCTGCTGTAAACTCTTCTAGTA
TACTCAAAATAGGTGAAGTAGCAACTTTTGGTGGTGTAGCTCTTAAAAGCATTTCAATATCAAG
TTTTTTTCCAAATAAAGACTACACTTTCTGTGACTATACAGGTTTTCCATCACCATATGATTGT
GTAAATAAGATAGAAAAATGGATGAAGGAAGGTTTTATATTAAGATTTACAATTACGGAAACAA
ATATAAATATGGAAGTCATAATTGAAGGGTTTAGTTATGAAGAAAGAGATGGGAC
TCGAGATGTATATTTTACATTAGATTTAAAAGAGTATAAAAGAATAAAGATACCAAAAGTAACT
CCAAAACAATAACTATTATAGATAATAAGTTGTAAGTAACTGCTGATAGAATTAAATGAAAAGG
CAGGTGATTTTTTATTATTAAGATTTGGGTACACATAAAAAACGGAAGTATATATGACATAACT
GACATAGTAGACAAGGTATCATGGTCAGGTGATTATAAATCTCCATCAAGGACACTAGAGTTTT
CAATAATACAATCATCATTTGATGTAAATTTCCAACAAATCGATATACCAATAGCTAGTACAGT
CTGTTTCTATGTAGATGAGAAAGAACTCTTTAGAGGAATGATAATTAATAGGTCTAAAGATTCA
AGCAGTAATGAAATTAGTTTTGTATCTAAAGATATGGGATTTTTACTTACACAAAGTGAAGTGT
CATACAATTTTAAAGATAAGTTAGTTGAAGACATAGCAAAGCAAGTATTTGCTGAAAATAGGCT
TTCAGTTGGAACAATAGCAAAGACCAATGTCAAGTATACAAAGATGTTTATAGGAGTAAATGGT
TATGACACAATAATGAGTGCATATACAGAGGCAAGTAAAAAGACAAAGAAAAAGTATATGATAG
AGGCTAATTTAGATAAGTTTAATGTTATTGAAAAAGGAACTGTTACATTAAGTGTTATGTTTGA

Figure 1C

AGAGGGATTTAATATTATAAATACCACCTTTTCGGAGAGCATGGAAAATGTAAAAAATAAAGTA
ATAGTGGTAGACCAGTATGGAAGCAAGATTAGCGAAAAAATAGATAATGAAATTTTTAAGGAAG
TAAATGTAATAATGCAAAAAGTAATTCAGCAACAAGAAAATCAAGATGTAGATATTGATAGCGA
GTTTAATGGGATAGAAAAAAGCTGTTCTCTTAAaGGTTATGGAGATGTAAGTTGTATAACTGGT
AGAGGAGTAAAAGTTAAAGATTCTTATACAAAGCTTGTAGGACTATTTTATATAGATACAGACA
AACATACTTGGCAAAATGGAGAATATCAAATTGAGCTTGAACTTAATTTTCAAAATCTTATGGA
TGAAAAGTCAGCAGGACAGGATGAACCTAAGGAAGAAAGTAATTTAGGGGGAGAAGATTATGCA
GGAGGAAAAGAGTTTACAGCAGAATTTACAGCTTACTGTCCTAGAAAAGAAGAAGGTGGAGATA
CAGATTGTAGAAAGAAAAAACTTGACCCATCTAAAAAACTTGCGCTGCTCCTATGGTTGGTAAA
TATGAGCAAACTTATTATACAAAAGAGTTTTTAAATAAACATCCTTTATTGAACTATGGAGATG
AAATACAGGTAATTACAGGAGTTTCTGGTCGTGATGGAGTCTATAAAGTAAATGACGTAGGACC
TGCAATAACTATAGAAAAAAATGGAACATACCATATAGATATTTTATTTGGAAATGTTGAAGAA
GCTAGTAAATTTGGAAGAAGAAAAGGAAAAATTATTATTGGTGGTTATTCTGGTAATGTATCTG
ATAAAGCTAAAATAGTAATATCAGAGGCAAAAAAACATCTAGGTAAACCTTATAAATGGGGTGG
AAATGGACCAAGTAGTTTTGACTGTTCTGGTTTAATGGTCTACTGTTTTAAAAAAGTTAATGTT
AGTTTGCCAAGAACGTCAAATCAACAATCTAAAAAAGGCAAGAAAGTAGAACAAAAAAATCTTC
AAGCAGGAGATTTAGTATTTTTTCATAATCCAGTCAGCCATGTTGGATTATATATAGGTAATGG
AGAATTTTTACATGCTCCACAAAAAGGTGATGTAGTTAAAATAAGTAAGTTAAGTAGTAGAAGA
GATTTTAATACAGCTAGGAGAGTATTATAAAAGGATGGTGATATAATGGCTAATCCAATAAATG
AATTTATAGGAATAATAAGAGAAGAAGGAAAGTATCATAATCAACCTTCTTTTTTATTGGAAAA
TTAAAAGTAAATTACCAGATTTAAAAATAGAGACAAATAACATCATATTAGAAAAAGAAGATAT
TTTGATAGATAGTTGGATGATTGATAGACAGCTAGAAACATTTGACACAGAAACAAATCAAGAA
CACCAGCATGAAGTAAAAAATCCTTTTATAGATAACTTTGAATCTGGGGATATGGTAATAATGT
TTAGAATAGGCGAAAAATTTGCTGTTGTAAGTAAGTTGGTGAGCTTATAATGAGTACAATATTT
CCTTTTATAGGTGTCCCAGAGGATTATATCTTACCTAAAACAGAAGAATTGCCAATCTTTCGTG
AAGTGGCATGGGATTTTGAAAAAGATGAACCTATTTTAGAAAAAGGTGACTTTAAAATAATTGA
AAAAAAAAGAAGCCTTAAAAGTTTGGATATACAAGTGTATAAAGACAAATAGATATGAACATGA
GATATACTCTTTAGAATATGGGACAGAGCTTTCAGAACTAATAGGACAAAAATATACAAAAGGT
CTTACAGAAAGTGAAGCTAGTAGATTCATAAAAGAGGCCCTTCTAATAAATCCATATATATTAG
AAGTAAACGTAAAAAGTGCTAACTTTAACAGAGACGTATTGAGTGCAAATGTAAAAGTATCCAC
TATCTATGGGGAGGTGGAAATAAATGTATAGTGACCAGACATATGAAGTAATAAAAAATAGAAC
TCTTGAAAATATTAATCTTGATATTTATAAAGGAGAAGGTTCTTTTCTAAACAACATGGTATCT
GGAAATAATCTAGAACTTTCGAAGATATATCTAGAACTTTCAAAGATACATAAAATGGCTTTTA
TACAAGACACATATAACCAGTTTCTTGATAAAAGAGTCAATGAATTTGGTGTATATAGAAAGTT
AGGTACAGAGTCAAATGGAGAAGTTGAATTTATTGGAGAGAAAGGAACTGTAATAAATAATGGC
ACAATAATATCATATAGAGATTTACTATTTGTAGTAATAAAAGATGTAACTATTGGTAGTGAAG
AAGGTGACAATAGCCCAGTTCAAGCTCTGGAAGTTGGTAAGAAATATAATTTACCTACAAATTG
TGAATTTAAACTAGTTGATAATATATCTGGAGTAACAAAGATTACTAACACAAGAAGTTTTGAA
GGTGGTACAGATATAGAGACAGATGAAGAACTAAAAGAAAGATTTTATAAAATCCAAAGAAATC
AAGCTACAAGTGGAAATAAAGCTCACTATGAAGAATGGGCTTTGGAAGTAGATGGAGTCTATAA
TGTTAAGGTTTATCCAAGATGGGATGGTCCAGGAACAGTTAAGGTCTTGATATTTGGGGAAAAT
AATCAAGCTGTTGATACAGAAACGATTGAAAGGTGTCAGCAACATATAGATGAAGAGAAGCCTA
TTGGACCAACTATAACAGTTGTGACACCATTACCAATAGAAATAAGTATAAGTGCAGTAATGAA
ACTAGAAGATGGATATACATTAGACAATGTAAAAGAATCTTTCCTAGAAAGTATAAATACATAC
TTTAGAGATATTAGAGGAGAGATAATCTATACAAAAGTCATGGGAATACTTATAAATACTACTG
GTGTACACGATTTAAGTAATCTACTTATAAATGGAAGTACAGATAATATAACTATTAATGAAGA
TAAAATACCTAGTGTAACAACTGTTAATTTTAGTGAGGTGGAAAATCAATGAAGCTAATTGATA

Figure 1D

AACTACCATCATTTGATAGAAATTACATTGTAGAGGAGATACAAGGTGCATACGATACAGAATT
AAATATTCTTAAAGAAGATATTGATGATACCTTTAACCAATTATTTGTTGATACAGCGACATGG
GGATTAGATATGTGGGAAGACATACTCTGCATTGaAAAAAAAGAACTTGATTTTGACACAAGAC
GTAGCAATATAAAAGCTAAAATGAGAAGCAGAGGTACTAGTACTATTGAAGTTATAAAAAGTAT
ATGTGAGGCATATACAAAATCAGAAACAGATATAAAAGTTTATAGTGATGAATTTACATTCGTA
TTGAGTTTTATAGCAAATAACTGTGACTATAAAACTCTTTTAGATTGTAGCGAGATGATTGAAA
GAGTAAAACCTGCTCACTTATTACACTATTTAGAACCAATAATACTAGATAAAAGTATGGTCTA
TTGTGGTGGAGGTATGGTATGTAGTGAAGAGGTAAAAGTTCATCCATACTTTGAACCAATTATA
AAATGTAGTGCTGTTGTAAACTGTGGAGCTGGAATGTTAAGTAGAGAAGAAATAAAGGTTTATC
CTTTAAGCATTAAATGCATTGAAAATAATTGTAAGATTAATATAGCTATTGCAAATGATACAGG
CGTAGAAAATGTAGTAGTTTATCCTAAATCGGAGGTGGTATAATTGGAAGAAAAATTTTATATA
ATATTAACCAAAATTGGTAGAGAAAAAATAGCAAATGCAACTGCACTAGGAGAGCTTGTTGGAT
TAACCAAGTTTCAAGTTGGAGATAGTAATGGAGAATATTATGAGCCAACAGAGGAACAAACTGC
TTTAAAGAATGTAGTTTGGGAAGGAAATATAAATTCTCTAAGAATTGATGAAAAAAATCCTAAT
TGGATAGTTATAGAGACTATTTTACCAGGAACAGTTGGTGGATTTATGATAAGAGAAGCTGCTG
TTCTGGATAATGAGAATAATATAATAGCTATWGGTAAGTATCCAGAGACGTATAAGCCACGTGC
TGAAGATGGCAGTATTAAAGATTTGGTTGTAAAAATGATTTTACAATTGTCCAATACTTCAAAT
GTTACATTAGAAGTAGACCCGACGTTGGTTTTTGTAACTCAAAAGGATATTCAAGATTTAGATG
ATAAGTTTGATAAAAATATAAAAGAAATAAAAGTAAAAATTGGAGATACAGATATATTAACTAC
AGATTCTAAAGATTTATCAGGAGCTATAAATGAGGTAGTTAAAAAAATAGAAAATATATCTTTT
GATGATGTTATAAGTGGTCAAATACAAACTGATATATCAGTATTAAAAAATAGCTATAACAAAT
TATCTGAAAAAGTGCTAGATATATTAATATACCTAGAATTAGAGTCAGAAGTAACTGTAGATGA
GGCTGGTTATTGGTATGATACATTAGCAAATGGAAATAACATAGTAGCTATAGAAGGGCTTAAG
TTAGATTTAAATAGAAAATGTATAACAGGTGAAATTGGTAATGTGATTTTTAGAGATGTAGTAT
TACCATTTAGTGCAAATAGAGTTAGATATATACATGATATGGATAATAACTTTGTTGAGACAAA
ATCTAGTAACACTTATTTAAAAGAACAAAAAGATATAACTCTAAGTAAATATTCATATGAAATA
AGATAAATAAAGGAGGTAGTACTAATAATGAAGCAAAATAAACTTTTACAGCGTGGTGCTTATT
TTAATGATAAGAACATATTGATTGATGATTTTGATAAAAGATATAATGATTATGATTTTGTAGA
ATTTTTTACTGGTATAAGTAATAGTACCTTTGGTTTAAAATCAGATGGTAATTTATATGCTTGT
GGCGATAATACAGGTTTTCAACTAGGACTTGGAAAAGATTCGTCAGAGAGAAGGATGTTTAGTA
AAGTAAAAATTGATAATGTAAAATATGTATCTTGTGGTTCAAAACACAGTGTAGCAGTAACTAA
AGATGGATTTGCATATGGAGCAGGAACAAGTAATGTAGGTCAATTAGGTGTAATTGAGTCTACA
GTATATTATGAATTTACTAAGCTACCAATAGATGATGTAAAAACTGTTGCATGTGGTTATGACT
TTACATTTGTGCTTAAAAATGATGGAACATTATATTCAGCAGGTTTAAACTCAAGTGGTCAACT
TGGACTAGGTGATACTAACAATAGAGCTACTTTTACTAAAGTAAATATAGATAGTGTGAAAGAT
GTAGTGACTTATAATCAATCTGTATTTATCATAAAAATGGATGGGACAGCACATGCATGTGGAT
TAAATTCAAATGGGCAGTTGGGAATTAATAGTACTTTAAATAAAAGTGTATTTAATAAAATAGA
AGGTATGGATAATGTAAAACAGATAGCGTGTGGTAGTAGTCATACAATTCTTATTAAGAATGAT
GGAACTATGTATACTACAGGCTATAATGGAGTTGGTCAGCTTGGTACAGGAAATAATAATAATT
CAATTGTATTTACTCTTTCTAGTATAAATAATGTTAAGTATGCTTCTTGTGGAAATAATCATAC
TATGATATTAAAATACGATAATACACTGTTTAGTACAGGACAAAACAATTATGGTCAACTAGCC
AATGCCAATAAAGATGTAGCATCAAGAAATACTTTTGCTAAGGTTAATGTAGAAAATATAAAAG
ATATTAAATGTGGTTCTCAATTTAATTTTTtAATAAATGGTTCAAAAGAGATATTTGTATCTGG
CTGTAATTTAGCAGGTCAACTTGGTTCATTTTTTCATACAACTTTTCTGTATGAGTTTTCAAAT
GTGCAATCTTCAAATTTAGATAATTATTCAGGTTTATTGGTTAATGATGATTATTTATATGTTA
CAAAGGACAATAGTGAATTTTTAAATGTAAAGTTAAGTGATAATTTTCAAGATTATAAGAAGAT
AGAGTTAACAGATAGCAATATGTTTATTGTTATGAATGATGGTACATTGTATGCTTGTGGTTTA

Figure 1E

AATAATTATGGACAGTTAGGATTGGGAGATACTGTTAACAGGTCAGTTATGACTAAGGTGGATA
TAGATAATGTTTTGGATATAAAAGGAAACGGAAACTCAACTTTTGTGCTTAAGAATAATGGAAC
ATTATATTCATGTGGTTTAAATAGTAATGGACAATTGGGTTTAAGAGATGAAGTTAATAGAAAT
ATATTTACAAAAATAGAAATAGAGAATGTAAAGGATTTTTGTGTAGGAAGCAATTATGTCATAG
CTTTAAATCACTCAAAAGAAGTATATGGATGGGGAAATAATCCTTATAATAATATAGAAAAAAC
TTCTAATTATCCATATAAGCAGGGAATAAGTAATATTGAAAAGATAGCAGCATATGATTATTCT
GTATATATGATAAACAGTGAAGGGAAACTATATGTTTCTGGATACAATTATAATTATCAATTAG
GTAAAGGAAATAATAGTAACCAAAGCAAAGCATTAGTATCTCAATGTAGAACAAATTCAACATC
TTCTACATCAAATGGACTTAGAACGTTACCTAAAATAACTAATGTTTTtCCTTTTTATGATGGT
TGTGCAATAATTGACGAAGGAGGTTATGTTTATTTAACAGGATATCATGGATATTTAAGAACAT
TAAATAGCAGTCCAAGTATATCTGATTATTCAAGATATGGAACTTTTATTGAGGCTACAAATTC
AAATCATAATACTTATTTTATACAAGAGACTGATTTTAGTGGAATTGAAAAAGTAATAGGGATG
TCAAATAATATATTATTTTTTAAGAAAGGAAGTTCATATATTACTGGATATCCAAAAACATTTG
GCTCAACCATTACTGGACATAGAAGTTATACTAGTATTAATTCTGAGAGTTCTAATTTAGGAAG
TAATTTTATAATATATCATAGTAATTCCAAGTTATATGGAAAAGGGATTGCTAATAGTGGGCAA
TTTGGGAATTCAACAAATATAGATGGCACAAGTAACTATGATACAGGATTAAAAGACATAAAAG
ATATAATTGTAAAAGGAAATACTGTAGTAGTAGTAGATAAAAATAACAATATATATGTAACAGG
AATGAATCAGAATAACAAACTTGGGATAGGGGAATATAACAACGAACCAGTAAAAAAATTCACA
AATATAACTGAACAATCAAACTCATTTATATTTATGGATGATATAAAAGAAATTACAACATCAA
GAAATACAATGTTTATAGTAAAAAATGATGGAACAGCCTATGCCACAGGAAATAATAGTTCTGG
ACAATTAGGATTAGGTGACACAATAAATAGAAATAAGTTCACTCAGATAAACCTTGATAATATA
AAGAAAATATCAACAAGTATAGATGGTAACACAACATTTGCAATTAGAAATGATGGAACACTAT
ACTCCACAGGATTAAATACCAAAGGACAACTGGGATTAGGTGATATAGTAAATAGAAATACATT
TACCAAAGTAAACATCCAAAATGTAAGAGATGTTGTTTTAGGGACTACTCACTCGCATGCAATC
AAAGATGATAACACATTATATTCATGTGGAGaAAACACTCATGGGCAACTGGGCTTAGGAAGCG
AAAGCAACCATCCAGACGTATTGACATTTACTGTAAACAATATAACTAATGTAAGAGATGTGTA
CTGCTCAGATACAACAACATTTATTGTAAAGGACACAAACATTGCATATTGTTGTGGATACAAT
AATAATTCACAACTAGGTATGGGAAATACTACTGACCAGTATAGTTTTATAAAGTGTATGGAAA
ATGTAAAAGAAGTTATACCAAATGAAATAAATACCTATATAATAACAATCTATAATACTGCATA
TAGTACAGGTTTAAATACTGATTATTGCTTAGGTCTAAATAGTAATAGCAATCAAAGTTCATTT
TCTGAAATTCCAATTTCAAATGTAGTAAAAGTAGCTCCAAACAGAAATAATGCAGTACTTTTAC
TTACAAGTGAAGGGGATGTATATACTGCAGGCAAATGTAGTAATGGTTCAGGTACAGGAAGTGA
GACTCCAGAGAAGATTAAAAAAATAGCATCAAAGGCAAAGGATATTGGAATGAATTATAGATGT
GGACATTATGTAAGTGATAATGGAGACCTATATGGTACAGGTTTTAATAATAATGGACAATTAG
GTGTTGGTGATGTAACAAAAAGAGATACATTTATAAAAACCAATACAAGAGTAAAGAAAATACT
TCCTTTAGAATATGCAAATATAGCAATAAAAGATACTAATGATATATATATTTGTGGATTAAAT
AACTATGGACAATTAGGTGTTGGAAATAGATACGATAGTAGAAATAATGATAATAGAATATTTA
ATTATAAGCATATGAATTTTGTAATGGGTGATTTGACATCTATTAAAAACAGACATAACTTTAT
ACTTCTAAACAATAAGATAGTGATACCTACCACAAAAGACATAGATTATGGTTTAGTATTAGGA
AATTTATACAAAGGAGACCTTTATACTGAGCTTCCATATGAAGATATAAAAGAAGTATCTATTT
CTAAGACTCATATTATTATATTACTTAATGATGGAACAATGTATGGATGTGGTACAAACTACCA
TGGAGAATTATTGCAAGACTTGTCTATAAATCAAGTGGATGAATTTGTGCAGATTAATGTATCA
GATGTAAAGCATGTTTCATGTGGAGATAACTTTACTTATTTTATAAAATCTGATGATAGTCTTT
GGTCTATTGGTAAAAATTCCGAATATCAATTAGGTATAGGTCACAATAATCCAGTTACTGAATT
ACAAAGAATTACAACTATATCTAGCTGTAAAGAAGTACATTGTGGTAAAAACTATACATTAGTA
GTAACTACAGGTAATGAATTATTTGTACAAGGATATAATGATAAGGGAGCTTTAGGATTAGGAA
GCGATAGTGAAAATACTATAATTAAGTTCTTTACAAAAGCACTAACAGACATAAGAGAAATAAA

Figure 1F

ATCTTATGGAAGTGACCATATATTAGTACTTAAAAATGATAATTCAGTATGGGTTACTGGAAAA
AATAGGGATGTATATAAAATTGAACAACCAGTAGAATTTTTAAAAGAATTTACTATAGTACCTA
TTTCTGAAGATGTAAATACAGTAAAGGATGTACTTGCAACAGACAATACATTATATATTATATC
AGAAGTAGGAACGACAAATGCTGCTATAGAAATTACTGAAAAATCAATTTCATCAATTAAGATA
AAAATACAAGACCCTAATAAAGATATAAGTAGAATAGAAATGCTTATAAATGGTGAAAGTGTAA
AATCTGTAAGTGATTTAACTACTGAAAAAATATCCTTTGAAGTACCACCAGATAAAATTAAAAT
AGGAGAGAATAAGATACTATTTAGAGCTTATTGTAAAGGTGATGATTTATATGCATCTTTATTT
ATTTTTAAAGAGAGTACTGGAAATTCTATAATTAAAGATTCTTATGTTATGATAGGTAATAGAA
TGTACAAGGTAGTTAATACAACATCTAATGAACAAGATATTACAATTACACTAGATAGAGGACT
TGAAGAAGATTTAAATCTTGGAGACCCTATATATCAATTAATAAATAAAACTAAAGTTCAAGTA
AAAATAAATAAATCTGACTTATTCAAAGACATGAAACTAGTTGAAATCAAAAAATCAGACTCAA
GTTATCAAGAAATCTATGAATTAGAAGAAGCCAACATAAAAAGTGCTCAGCCTAAAATCATAGT
AGAAAAAGGAGATAAATGGACAGCTATAAAACGTCCATCTATGATTTTTAGATATGATGCTGAA
AACAACGAGCCACAAGCTTAAAATGGAGGTGTAAAAATTGTTTAAATTCGATAAAAATAAAATA
GAACAAATCAAACAAGGTAGAAAAGTAGAAATGCAGTATAAAGACATTTCAGACATAAGTATAG
GTCAAGCAAAGCAAGATGATGATATAACAAATAATTTTATAGCAAATGCAGAAATATATGAGAT
GTTGTTAAGTCAAAGTTCTGTCAATGAAGCAAGTAATATAAGCACTTTTAGTGTAAGAAAATCT
GGAGGTGAGAGTGGAATGGTAGAAGTATATGTAGCTTTAATTTTAAGAGGCAGAAAAACAATAG
AAGAAGTACCAGCAGTAATTAGAGAGCAAGTTAGAATTAGATGTAAAGAATTAGAAATACCAGT
TGAATAGTAAATTTAGAATAACTATGTATTAGTTAtTTTTTTTATGTAAAGTACAAGGTCTTAA
CTTTAATAAGTAAGCCTTGTACTTATTTTTTGTTATATTAGAAATTGTATATATATTTATTATT
TATTCAATCTATAAATTAAACCTACAATTTAAAGTACAGAAGATTAAATTGATAATCCTGAAAA
TATAATATTGCATGATGTAAGAATATAACAAAAATTAAAGCTATAAGTATAAAAAATTTAGACA
ATAGGAGGCTATAATGGATAAATTAATAACCGAATTGAGTAGTCTGGGGGCAATAGGTATACTA
TGTGCTCTATTATTTAAAAATACTATGCAGGAGAAAAAAGAAGATAGAGACATGTATAAAAAAA
CTGTAGAAAATTTTATAGAATTATCTACACAACAACAAGAAATAAACAAAAATATACTTGTTCA
AATGGGAATAATGAAAACAGATGTAGAGGAAATTAAGGAAGATGTTACTGATATAAAAGGTATG
TTACAAAACGGTGTATAACATGAAAGTAGCAGTAGCACCAGATTATATATTATTAGGAAAAGAT
AAAGTAGTATTGTAGATAGTGCCCTATTTTATTGAGAAGGATTTTATATTTTAAAATATTAATT
AAAAAAAGTAATAAAAATAATATATAAAAATAACATATAAAAATTCAAAAAGGAGTTAAGCTTA
AATTTGATTAGAAAAAATCAATTTTAAGACAACTCCTTTTTTTtATTAAATTATTGTCTATTAA
CCAAAATAGCTATTTTAGCATCTGGATTATAACTTATCTGAACCATTTGATTTTTCTTAACATG
TTCAAGGTCTTCACCACCATAAGCTATTTGTAACTTAACTGGTAACTTACCTTGTTTTATAATA
GCAACGTACTCTTTTTTACCTTTTTCTCTAAACTAATCAAATTGCCAACATAAGGTTTAAAGTT
CTGATACTTTTTACTAGAATTTCTTATGTAGAAGAAAGCACCAACAGCAATAACTAAATTTATG
CCAAGTGTAACCCAAGAATTGATTTTAAGCATAGCTCCAGCGATTATTATCACGAACATTAAAA
CGATAGGTAATATAGCTTTCTTAAGAAGCAATTTACCCATTATTTCATTAGCCTTTTTCTCAGG
GCCACTCATAGTTTTTGATCTAGCAAATGATTGCGCGAATTTGTCTCTTAAGCCCATTTTATCC
TCCTAATTTTAATAAATATTTAGTTATAATAACGAGATATTACTTGAAACTAAAAATTTACTAC
ATTTATATTATGTTTGACTTTTGTATAAATAATTACATTCAAGTAAAGCAAAATATACTAATTA
TTTTATCATAAAATTATAAAAAAGAAAATAAATGAAATAAAAATATTAGAACAAAGAAATGATG
TAAAATCGTATCAAAAGCAACATAAAAATTATTTATCTATTTTCTCATCTTTATTTTTGTTATA
CTCAATTTTTCCTAAATCCTTCTCTTTTTCATATTCATGAAGTTTTAATTCAATCATACCTTCT
ATTTTGGCTTTATCATAATCATTTAACTTTCTAAAGTTGTTTAAAAGCTTTATTTCATTAGAGT
TTATGCTATTAAGTGGATAGTTTGAGGAGGAATCGCAAATTAAATCTGATTTATGTGATAGATT
ATCTCCATTTAATAGCCAGTCTACTGAAACATTAAATATCTCAGCTATAGATTTTAATATTTCA
TAATTTGGTTTTCTAATGTTTCTCTCAAATTTACTTAAGTTGTCACAGCCTAACATTTCTTCTA

Figure 1G

GTTCATATTGTTTAAGGTTTTTTGCTTTTCTCAAATAAACAATTCTTTCTCCTAAAGTATCCAT
AAACACTCTCCATTCAATTAATGTCAAAAAGACTTTTTAAGATGTAAATAGTTTCAAATTAAAG
GTCAAAATGACATAAAAACCATTGACTTAAGGTCAAAATGACTTTATAATTAACTTAATGATAC
GAATTTACATCCTAATTTTAGCACAAAGTAATCAAAAAATCTTATTTAGTATTAAATAAATTTA
TATACTTAATATGTGTACATATTAAAAATATATACTAAATAGAGGGGGTGCGTAAGCTAAAGTA
ATATAAAAGTAAATATAAATCACTTAGAAAGGAAGTTGATAAATGGATGCTCGAAAAAAATGGA
TACCTTTTTTGGGAGTGCAAGTCAAGCAAAGACTTATTGAATTAAATATGACTCAAAGGGAATT
AGCGAAGAAAATAGGTGTTAATGAAAACTATTTGTCAGCTATTTTAAATGGAAGAAGAACAGGT
AAAAAATATAAATCATCAATTTATCAATTACTTAATATAGAATATTCAGAAGATGATTAATAAA
TAGTATATAAAGTAGGTGAATATTCTTGTGTGCAAATTGGATTCAGATGGGGTTATAGAGTGTT
GTAGAGCAATTGATGATTTTATTACAGCACTTAGTAATATAAAAAGCTTAAATATGGAAAGATT
AAATACTTTAACTAAATATTCTAGTACATGTTCAATCCTTCTTAAAGAGGGGAATTATGAAGGA
TGTACAATTGTGTATAGAAAGATGTTGGAAGAATTAAAAACATGAGTAATGCATTTCTTAGGAA
TATAAATTATACATAGAAATGTATTATATTTTTCAAAGTACTTAAACTAAAATATGGATAAGAT
AATCTAAATATTATAAATGTGCTTGAAATTAGACTATACTTGTTTTTAAATAATCCAATATCCA
TATTTTAGTAATATACTACAAAAAAAGAAGGTTAATAGATGATGTAAAATCGTATCAAATTATG
TATGTTTAAACCATTTTATCTTCATTATTATTAGAGGAATGCTTTTTTAAGTCTTTATATTCAG
ATATCTTAAGTTCAAGTATTCCTTCTATTTTTATTTTATCACGTTCGTTTAGTTGTCTGTATAG
ATTTAATATCATCATTTCATCATTAGTAACATGTAAGTAATCTTCTTTATCTTCTTTTACACTA
CTATTGACATTTACCTTCTCTTTACCATAGAGAAGCCAGTCAGTCGTAACATTAAAATAATCAG
CTATTGACATTAGTATATCACAATTAGGTTTTCTATCTCCTGTTTCATACTTGCCTAAGTTTTC
AAATTTTAAAATATCCATAAGTTTGCGCTGAGTAAGTTTTTTGGAGTTTCTCAAATAAGCAATT
CTTTTTCCTAAAGTATCCACAAAATACACTCCTTTCTTTTTATGAGTAATGTCTAAATGACATT
TGAAATTAAAAATATATAAATTTATAATATAAAACTACTAAATTAAAGTCTAAATGACATTTTG
CTTAAATTAATATGCTCATAATATGATTTTAACATATTATAGTTGAAAATATATGGTTTATTTT
GATTTGTATATATAACAATAGATTTAATTGTTATAAAAATGTAAAGGGGTGTATGAATAGATTG
TATAAATTTATTTCGATAAACTAAGATTGCTTTTTGATTGTCTGTAAAAGAGAAAAAGATTAAG
ATAAAAATAGTATTATATTGTAATTTATATTAATCAATTACAAAGATTTTATGAATTTATTCTT
TAGGGTAAAATATTTAAGAATAAGATAAATTTACAATATAATACTATAACACTCTTTTATCTAG
TTTTATTTTCTTTATAGAACAATAATATTATAAATGCTAGTAGATTTACACAGAATACTGTTAT
ATACATCTGTTTGAATCCTGAGTTTAGAGTAGATTGTAGTGtGGATCCGG

SEQ ID NO:2 > orf 1360A (100% 630)
MFKNNLKYYRKCKGMTQIQLARKAGITNDYISQIERGIKNPGLLMAKKISSILEQNIEEVFFIQ
L SEQ ID NO:3 > orf 1361 (100% 630)
MENKKDILFKETDERLHNYKYLDIKIKNINLDIKRCENEYSGCGAMVYTEKTSNTYNISSSVEN
EVLKREERLRKLKMEKEDIEIEKEKIENALTCLNDIEMEFFNLFYNSKTKNNMTYISMKLHLDR
TSCYNLKKKMIFKLSEIL SEQ ID NO:4 > orf 1362
NFTESIFIDDESVQGSEGSCFFVSILSVICTPIMLNTNNKDIVISIKYLPKPQSKSIRMYEISD
ELNKLFNRNIKVTDRKLNITKLEQSIKKEESIYVLNFTITLNYLDSVYEEDVVYENMEEINLNL
GE

Figure 1H

SEQ ID NO:5 > orf 1363 (99+% 630)
MAIGLPSINISFKELATTVKERSARGIIAMVLKDAKALGLNEIHEKEDIPVDLSAENKEYINLA
LMGNVNTPNKLLVYVIEGEADIQTALDFLETKEFNYLCMPKAVEADKTAIKNWIIKLRDIDKVK
VKAVLGKVVGNHEGIINFTTEDVLVGEKKYSVDEFTSRVAGLIAGTPLSQSVTYTKLSDVVDIP
KMTKVDAESRVNKGELILIKEAGAIRIARGVNSLTELTEEKGEMFQKIKIVDTLDIIHSDIRKV
IIDDYIGKVTNSYDNKCLLIVAIKSYLEELEKSALIESDSTVEIDFEAQKSYLKSKGVDLSYMT
LQEIKEANTGSKVFLKAKIKVLDAMEDIDLSIEI SEQ ID NO:6 > orf 1364 (100% 630)
MANMEARNVMSGTWGELWLDGNKVAEVKKFQAKMEFTKEDIIIAGQMGTDTKYMGYKGKGSITL
YHVSSRMHKLIGEKIKRGSEPRFVAISKLNDPDSYGAERIAVKNIAFDDLTLADWEVGVKGEIE
APFTFTEYDFLDII SEQ ID NO:7 > orf 1365 (98+% 630)
MNENGLSKNINIVDLLLNADTENLERPSTIVELKRLSTIFGQEFKVMCRALTISKDEEIQNTCL
KIDENMKTDIDLPEMQMLTIIEGVCDLDGKLLFKNKELMDKFKAPTPKELARKLLLPGEITNLY
RILQDVMGYGKNAVIEEVKN SEQ ID NO:8 > orf 1365A (100% 630)
MYYYWKKKGIRPSLFYAMDKGELKLIEAFFALEIEEEVEKMKHGYGVCPLTGGGM SEQ ID NO:9 > orf 1366 (98% 630) Tape Measure
MGNVREEGINMYLTDNYTPKMNQIISVTDNFRRATVAVSLSTNVMASSIKNSIGSASSRVNSLN
SSLRKVQTTASSVSSTMAKLSSSINAVSGVIGSLNGSIMRLAITIAMIIDYFNKLIQKKNEFNS
NIMIILIFKAKSDEVEKTKNKLLGNLKKIGGKIWNIVIKAKDMTKRVISSILGKLKRVEKRPYQ
GSINLKDMVSSAMARILPKLMLFKNTFWSGVIAIKDMASSIISKVFPKLRLFAGKVWSGAIAVK
DMASGILGSIKGKISDLTNGATIGVAVKKGVDLLGQEQNQKVVLESVMKRNTGKTSQKDVDKYY
DSLVNMANDTPFDPEDVVAMGTKAKMISNITGGKKEKDITQAMVDVRALNMNTSSEQDVSAAFL
SAAKGNMESLNTLVGENYKTFDEALEGISVKQMGLAKEMSNTIPGIISGAQTSINNGLKSIVKP
FDDILGQGLKKIKTFIESGLGNLAGLSEKMAGKIGNVMNGKIIIGNKYDQMQSRSVKNGKEFSD
STQYRISNEAEKRKMMVENKQERFENHAATMIGNAPKAIVNAGSTLLQNIDFTALIDSLLPVVN
LVNNLLDSINNKSPIAQGLISIFGTIVTTAFQLIGPVVEAVSPIITRIFTFLGEYAPQINNFIE
TLGVIWKTVWETLGPLLETGWKIIEPILGAFFNILDKVCKIVKDICKWWQTMINKIKNGSITGT
VLNLVEKSKKNYKDNP
YAGTKAGDSGKAYSSKKGNNAFGLNYVPYNDYQTRLHEGEMVLTKQEANQYRSRKNGGNINIAK
LADTIVIREEADIEKITSKLVASIQLAQLGGVL SEQ ID NO:10 > orf 1367 (100% 630) Baseplate
MEMWLRQAEDRFRFPVFPSSFSINGKAAVNSSSILKIGEVATFGGVALKSISISSFFPNKDYTF
CDYTGFPSPYDCVNKIEKWMKEGFILRFTITETNINMEVIIEGFSYEERDGTRDVYFTLDLKEY
KRIKIPKVTPKQ

Figure 1I

SEQ ID NO:11 > orf 1368 (100% 630) Baseplate
MIINRSKDSSSNEISFVSKDMGFLLTQSEVSYNFKDKLVEDIAKQVFAENRLSVGTIAKTNVKY
TKMFIGVNGYDTIMSAYTEASKKTKKKYMIEANLDKFNVIEKGTVTLSVMFEEGFNIINTTFSE
SMENVKNKVIVVDQYGSKISEKIDNEIFKEVNVIMQKVIQQQENQDVDIDSEFNGIEKSCSLKG
YGDVSCITGRGVKVKDSYTKLVGLFYIDTDKHTWQNGEYQIELELNFQNLMDEKSAGQDEPKEE
SNLGGEDYAGGKEFTAEFTAYCPRKEEGGDTDCRKKKLDPSKKTCAAPMVGKYEQTYYTKEFLN
KHPLLNYGDEIQVITGVSGRDGVYKVNDVGPAITIEKNGTYHIDILFGNVEEASKFGRRKGKII
IGGYSGNVSDKAKIVISEAKKHLGKPYKWGGNGPSSFDCSGLMVYCFKKVNVSLPRTSNQQSKK
GKKVEQKNLQAGDLVFFHNPVSHVGLYIGNGEFLHAPQKGDVVKISKLSSRRDFNTARRVL SEQ ID NO:12 > orf 1369 (100% 630)
MANPINEFIGIIREEGKYHNQPSFFIGKIKSKLPDLKIETNNIILEKEDILIDSWMIDRQLETF
DTETNQEHQHEVKNPFIDNFESGDMVIMFRIGEKFAVVSKLVSL SEQ ID NO:13 > orf 1370 (99+% 630)
MSTIFPFIGVPEDYILPKTEELPIFREVAWDFEKDEPILEKGDFKIIEKKEALKVWIYKCIKTN
RYEHEIYSLEYGTELSELIGQKYTKGLTESEASRFIKEALLINPYILEVNVKSANFNRDVLSAN
VKVSTIYGEVEINV SEQ ID NO:14 > orf 1371 (100% 630) Tail
MYSDQTYEVIKNRTLENINLDIYKGEGSFLNNMVSGNNLELSKIYLELSKIHKMAFIQDTYNQF
LDKRVNEFGVYRKLGTESNGEVEFIGEKGTVINNGTIISYRDLLFVVIKDVTIGSEEGDNSPVQ
ALEVGKKYNLPTNCEFKLVDNISGVTKITNTRSFEGGTDIETDEELKERFYKIQRNQATSGNKA
HYEEWALEVDGVYNVKVYPRWDGPGTVKVLIFGENNQAVDTETIERCQQHIDEEKPIGPTITVV
TPLPIEISISAVMKLEDGYTLDNVKESFLESINTYFRDIRGEIIYTKVMGILINTTGVHDLSNL
LINGSTDNITINEDKIPSVTTVNFSEVENQ SEQ ID NO:15 > orf 1372 (100% 630)
MKLIDKLPSFDRNYIVEEIQGAYDTELNILKEDIDDTFNQLFVDTATWGLDMWEDILCIEKKEL
DFDTRRSNIKAKMRSRGTSTIEVIKSICEAYTKSETDIKVYSDEFTFVLSFIANNCDYKTLLDC
SEMIERVKPAHLLHYLEPIILDKSMVYCGGGMVCSEEVKVHPYFEPIIKCSAVVNCGAGMLSRE
EIKVYPLSIKCIENNCKINIAIANDTGVENVVVYPKSEVV SEQ ID NO:16 > orf 1373 (99% 630) Tail fiber
MEEKFYIILTKIGREKIANATALGELVGLTKFQVGDSNGEYYEPTEEQTALKNVVWEGNINSLR
IDEKNPNWIVIETILPGTVGGFMIREAAVLDNENNIIAIGKYPETYKPRAEDGSIKDLVVKMIL
QLSNTSNVTLEVDPTLVFVTQKDIQDLDDKFDKNIKEIKVKIGDTDILTTDSKDLSGAINEVVK
KIENISFDDVISGQIQTDISVLKNSYNKLSEKVLDILIYLELESEVTVDEAGYWYDTLANGNNI
VAIEGLKLDLNRKCITGEIGNVIFRDVVLPFSANRVRYIHDMDNNFVETKSSNTYLKEQKDITL
SKYSYEIR SEQ ID NO:17 > orf 1374 of #16 receptor binding-variable
MKQNKLLQRGAYFNDKNILIDDFDKRYNDYDFVEFFTGISNSTFGLKSDGNLYACGDNTGFQLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN
GVGQLGTGNNNNSIVFTLSSINNVKYASCGNNHTMILKYDNTLFSTGQNNYGQLANANKDVASR

Figure 1J

NTFAKVNVENIKDIKCGSQFNFLINGSKEIFVSGCNLAGQLGSFFHTTFLYEFSNVQSSNLDNY
SGLLVNDDYLYVTKDNSEFLNVKLSDNFQDYKKIELTDSNMFIVMNDGTLYACGLNNYGQLGLG
DTVNRSVMTKVDIDNVLDIKGNGNSTFVLKNNGTLYSCGLNSNGQLGLRDEVNRNIFTKIEIEN
VKDFCVGSNYVIALNHSKEVYGWGNNPYNNIEKTSNYPYKQGISNIEKIAAYDYSVYMINSEGK
LYVSGYNYNYQLGKGNNSNQSKALVSQCRTNSTSSTSNGLRTLPKITNVFPFYDGCAIIDEGGY
VYLTGYHGYLRTLNSSPSISDYSRYGTFIEATNSNHNTYFIQETDFSGIEKVIGMSNNILFFKK
GSSYITGYPKTFGSTITGHRSYTSINSESSNLGSNFIIYHSNSKLYGKGIANSGQFGNSTNIDG
TSNYDTGLKDIKDIIVKGNTVVVVDKNNNIYVTGMNQNNKLGIGEYNNEPVKKFTNITEQSNSF
IFMDDIKEITTSRNTMFIVKNDGTAYATGNNSSGQLGLGDTINRNKFTQINLDNIKKISTSIDG
NTTFAIRNDGTLYSTGLNTKGQLGLGDIVNRNTFTKVNIQNVRDVVLGTTHSHAIKDDNTLYSC
GENTHGQLGLGSESNHPDVLTFTVNNITNVRDVYCSDTTTFIVKDTNIAYCCGYNNNSQLGMGN
TTDQYSFIKCMENVKEVIPNEINTYIITIYNTAYSTGLNTDYCLGLNSNSNQSSFSEIPISNVV
KVAPNRNNAVLLLTSEGDVYTAGKCSNGSGTGSETPEKIKKIASKAKDIGMNYRCGHYVSDNGD
LYGTGFNNNGQLGVGDVTKRDTFIKTNTRVKKILPLEYANIAIKDTNDIYICGLNNYGQLGVGN
RYDSRNNDNRIFNYKHMNFVMGDLTSIKNRHNFILLNNKIVIPTTKDIDYGLVLGNLYKGDLYT
ELPYEDIKEVSISKTHIIILLNDGTMYGCGTNYHGELLQDLSINQVDEFVQINVSDVKHVSCGD
NFTYFIKSDDSLWSIGKNSEYQLGIGHNNPVTELQRITTISSCKEVHCGKNYTLVVTTGNELFV
QGYNDKGALGLGSDSENTIIKFFTKALTDIREIKSYGSDHILVLKNDNSVWVTGKNRDVYKIEQ
PVEFLKEFTIVPISEDVNTVKDVLATDNTLYIISEVGTTNAAIEITEKSISSIKIKIQDPNKDI
SRIEMLINGESVKSVSDLTTEKISFEVPPDKIKIGENKILFRAYCKGDDLYASLFIFKESTGNS
IIKDSYVMIGNRMYKVVNTTSNEQDITITLDRGLEEDLNLGDPIYQLINKTKVQVKINKSDLFK
DMKLVEIKKSDSSYQEIYELEEANIKSAQPKIIVEKGDKWTAIKRPSMIFRYDAENNEPQA

SEQ ID NO:18 >orf1375
MQYKDISDISIGQAKQDDDITNNFIANAEIYEMLLSQSSVNEASNISTFSVRKSGGESGMVEVY
VALILRGRKTIEEVPAVIREQVRIRCKELEIPVE SEQ ID NO:19 >orf 1376 (100% 630)
MDKLITELSSLGAIGILCALLFKNTMQEKKEDRDMYKKTVENFIELSTQQQEINKNILVQMGIM
KTDVEEIKEDVTDIKGMLQNGV SEQ ID NO:20 >1377 (100% 630)
MGLRDKFAQSFARSKTMSGPEKKANEIMGKLLLKKAILPIVLMFVIIIAGAMLKINSWVTLGIN
LVIAVGAFFYIRNSSKKYQNFKPYVGNLISLEKKGKKEYVAIIKQGKLPVKLQIAYGGEDLEHV
KKNQMVQISYNPDAKIAILVNRQ SEQ ID NO:21 >AV1378 (100% 630)
MDTLGERIVYLRKAKNLKQYELEEMLGCDNLSKFERNIRKPNYEILKSIAEIFNVSVDWLLNGD
NLSHKSDLICDSSSNYPLNSINSNEIKLLNNFRKLNDYDKAKIEGMIELKLHEYEKEKDLGKIE
YNKNKDEKIDK SEQ ID NO:22 >1378A (100% 630) regulatory
MDARKKWIPFLGVQVKQRLIELNMTQRELAKKIGVNENYLSAILNGRRTGKKYKSSIYQLLNIE
YSEDD

Figure 1K

SEQ ID NO:23 >AV1379
VDTLGKRIAYLRNSKKLTQRKLMDILKFENLGKYETGDRKPNCDILMSIADYFNVTTDWLLYGK
EKVNVNSSVKEDKEDYLHVTNDEMMILNLYRQLNERDKIKIEGILELKISEYKDLKKHSSNNNE
DKMV

SEQ ID NO:24 >AV1419
tttcttGAAGACcAtcgaAgcaccaccaccaccaccactg

SEQ ID NO:25 >AV1420
ttttttGAAGACAAtcgaAgggcttcgccctgtcgctcgac

SEQ ID NO:26 >AV1416
ttccttGAAGACCTaattTggggcaatcccgcaaggag

SEQ ID NO:27 >AV1245
ccccttGAAGACCCaattTcgtatggcaatgaaagacgg

SEQ ID NO:28 >AV1372
aattGCGGCCGCagctcGCTAGCggtacCTCGAGgatatcttcgaaGAAGACACATCCg SEQ ID NO:29 >AV1373
aattccgggatGCATGCctctaGGATCCGGCGCGCC SEQ ID NO:30 >AV1374
agctGGCGCGCCGGATCCtagagGCATGCatcccggaattcGGATGTGTCTTCtt SEQ ID NO:31 >AV1375
cgaagatatcCTCGAGgtaccGCTAGCgagctGCGGCCGC SEQ ID NO:32 5′ fragment
GGCCGCAATACCCACTACACCTTCgTCATCTTTAAATTTAAGAGTTTTTACTATTGAATAATAA
AGGTATATTCCAGTAAAAATAATCTTTAAATACAAGAAAAATAAACTCTTTGGGTATATTAAAA
AGCTAAAAAGTGTAAATATAAAAGCAAGTAGAGTACTTATCCTGTAAAAGAAATCTATTTGTGT
AATGTCTTTATATTTTATCATAAACACCGAATATAAAATGATGAAAATAATTGCGACGATTGCA
TATATGGTAAATAACATATTTTCAAGAGTACCATTTGAAATTACTATCCACTTATACCACATAA
TTGGCCAAAATAATAGTGCTAAGAACTTAAAATAATTATCAAACAACTTTTCTTTATACATTCA
TCAAACAACCTTTCTTAACAAAAGCATATATTTGTTTTTAGAATTTTAAATAATATGATATCAT
TATTATATATTAATATTGAATTTATAGAAACCAAAATTTGTTAAAATAAATATATAGATTTTAC
TGTTAAGCCAGTTAAAATTACTACTATTTTTATTATGAAATTGGATCAAATATGTAGAAATACG
GCAAATTAGTTAATATTAAATATTTATTATTTCCAAGTTGTAAAGACTGTTTTTTTAATGATAA
AAATTCTAATCTTTTTTGAAAGAAAGTAATATCCACATTAAGTATGTCTGCCATTTCATAAACG
CAAGTGATGCCAGAATTAATTATGTTTATTATATCTTCTTCAGTAATTAAGAACTCACAAGCCC
ATTTTAAGGCTTTATTTTCGCACTTATCTATAATAATTTTTGTATAATAATCGTTATAAGAGGA
TACATAGTATCCAAGGCTAGTGAAATGATGTCCAAGTTCTTCAGCTAAGATGGATGTCAATTTT
TTTGAGTTTTGTTTTAAATTACTGAGTAATGATATAATTTTAATACCATGTTTGTTTATATATA
GCCCTTCTAAATCACCTGCAATATAAGTGGTATAATGAATTATTATCTCTTCTTGAGAAGCTAA
TTCAAAAAGCTTATCCAAATTATTCATAAAAATCCCCCTAAAATAGAATGTATGTTTGCCTTTA

Figure 1L

AATTATATTAAAAGAGCAGAAAAATAGACTGCTCATCATATGGTTTATTTTTTTTTATATTTAT
TTAGTAAAAATTCTATATAATCATTAAGTTGTTCTTGTGCTTCTTCAGGTAACTCTTCATGTGG
ATTTTTTCTATGTGCAGCTACTGTATCAATATTTTCCTTAACTAAGGTTCTTCCAAGAAGGTAA
TCAACTGATACATTAAATACATCAGCCAATTTGTTTAAAATGTGTTCATCAGGAAATCTGTTTT
CTGTTTCATAGTACCCTAAGACTCTTTGGGAAACGCCTACTTTTTCTCCAAGTTCTCTTTGAGT
CAATCCAAATTCCTTTCTAAGTTCTCTTAATCTTTTGGCAAACATTATAACACCACCTTATGTA
TAGATTATAACAAATTGTTCTAAAAAATAAAACTAATAAAATATAAAAGAATATTTTTTCTAAA
ATCTATTGATAAAGAACAAATGATTCTATATAATCTAAGTGTGGAAGAACAAAATATTCTTAAT
GGTAATGGAGGTATAAAACAATGTTTAAAAATAACTTGAAATATTATAGAAAATGCAAAGGTAT
GACACAAATTCAACTTGCCAGAAAGGCTGGAATTACAAATGACTATATATCTCAAATAGAAAGA
GGTATAAAAAATCCTGGTCTTCTTATGGCTAAGAAGATTTCTAGTATTTTAGAACAAAATATAG
AAGAAGTTTTTTTATACAGTTATAGAACAATATGTTCTTGAAAGTTGTGAGATTAGTAAAAAA
CTGTGCACTAAAGAGATTATTGTAAATTTGAAGCTAATAATAAGTATATAAAAAAGGAGAAGTA
CTATGGAAAACAAAAAAGATATATTATTTAAAGAAACAGATGAAAGATTACATAATTATAAGTA
TTTGGATATAAAGATAAAGAATATTAATTTGGACATAAAAAGATGTGAGAATGAATACTCTGGA
TGTGGAGCAATGGTATATACAGAAAAGACTAGTAACACATATAACATAAGTTCTTCTGTGGAAA
ATGAGGTGTTAAAAAGAGAGGAAAGATTAAGAAAATTAAAAATGGAAAAAGAAGATATAGAAAT
AGAAAAAGAGAAGATAGAAAATGCTCTAACATGTCTAAATGATATAGAAATGGAATTTTTTAAT
CTTTTTTATAATAGTAAGACAAAAAACAATATGACATATATTTCTATGAAACTACACTTAGATA
GAACATCTTGCTACAATTTAAAGAAAAAAATGATATTTAAATTGAGTGAGATATTATAAAAAAT
ATGACAACTTTACAACACTTTATATACACTATTGCAACACTAGGCAATAAAATATGTGAGATAA
TGTTATTGTGAAAGAAATCCATATTGAAGGAGGTGATAAATTGAAAAGAATAATATTACCTAAA
AATATAGAAGATATTTGACAGGAATAAATGAGATGTATATTTAAAAATGACTTATATCATTTAT
AGTAAGATTATCAGATTAAGCAAGAATATTTAGTGATAGTGTGGTGATTATTTGCTTAAATACA
AGGAAATATTAGAAACAATTATTGAGATTCTCAAAAAAAACTTTACTGAAAGTATTTTTATTGA
TGATGAAAGTGTGCAAGGCTCTGAAGGGTCTTGTTTTTTTGTAAGTATACTATCAGTTATTTGT
ACACCTATAATGTTAAATACGAATAATAAAGATATTGTTATCTCTATAAAATACTTACCAAAAC
CACAGTCAAAGAGTATTAGAATGTATGAAATTTCAGATGAATTAAATAAGTTATTCAACAGAAA
TATAAAGGTAACAGACAGAAAATTAAATATAACAAAGCTAGAACAAAGTATTAAAAAAGAAGAG
TCAATTTATGTATTGAACTTTACAATTACACTAAATTATCTGGATAGTGTATATGAAGAAGATG
TAGTATATGAAAATATGGAAGAAATCAATTTAAATTTAGGAGAGTGATAGTATGGCTATAGGAT
TACCAAGTATCAACATATCATTTAAGGAGCTAGCTACAACTGTTAAAGAACGTTCAGCTAGAGG
AATAATTGCAATGGTGCTTAAAGATGCTAAGGCACTAGGTCTTAATGAAATACATGAAAAAGAG
GATATACCAGTTGATTTATCTGCTGAAAATAAAGAGTATATAAATTTAGCTTTGATGGGAAATG
TTAACACTCCAAATAAATTATTAGTTTATGTAATAGAAGGAGAAGCAGATATTCAAACTGCATT
AGATTTTTTAGAGACTAAGGAATTTAATTATCTATGTATGCCAAAAGCAGTAGAAGCTGATAAG
ACTGCTATAAAAAATTGGATAATTAAACTTAGAGATATAGATAAGGTTAAGGTTAAAGCTGTAT
TAGGAAAAGTTGTAGGAAATCATGAAGGGATAATTAATTTTACTACAGAAGATGTGTTAGTTGG
AGAAAAGAAATACAGTGTTGATGAGTTTACAAGTAGGGTGGCTGGACTTATAGCAGGAACACCT
TTAAGTCAATCAGTAACTTATACTAAGCTTAGTGATGTAGTTGATATACCTAAGATGACGAAAG
TTGATGCAGAATCAAGGGTTAATAAAGGAGAGCTTATACTTATTAAGGAAGCAGGGGCTATAAG
AATTGCAAGAGGAGTAAATTCTTTAACTGAGTTAACAGAAGAAAAAGGAGAAATGTTCCAGAAA
ATAAAAATAGTTGACACTTTAGATATTATACATAGTGACATAAGAAAGGTGATAATAGATGACT
ATATAGGAAAGGTTACTAACAGTTATGACAACAAATGTTTATTGATAGTAGCTATAAAAAGTTA
TTTAGAAGAATTAGAAAAGTCAGCACTTATAGAATCTGATTCTACTGTTGAAATAGATTTTGAA
GCACAAAAATCGTATTTAAAATCAAAAGGAGTAGATTTATCTTATATGACATTACAAGAAATAA
AAGAAGCTAACACAGGTTCTAAAGTATTTTTAAAAGCAAAAATAAAAGTACTTGATGCTATGGA

Figure 1M

AGATATAGATTTATCAATAGAAATATAGGAGGATTATTAATATGGCAAATATGGAAGCTAGAAA
TGTAATGAGTGGTACTTGGGGAGAACTTTGGCTTGATGGAAACAAAGTAGCAGAAGTAAAGAAG
TTTCAAGCAAAGATGGAATTTACAAAAGAGGATATTATAATAGCAGGTCAAATGGGTACTGATA
CAAAGTATATGGGATATAAAGGAAAAGGTTCAATAACTCTATACCATGTTAGTTCAAGAATGCA
CAAGTTAATTGGAGAAAAGATAAAGAGAGGTTCTGAACCTAGATTTGTTGCTATATCTAAATTA
AATGACCCAGATTCTTATGGAGCAGAAAGAATAGCAGTAAAAAATATAGCATTTGATGATTTAA
CTTTAGCTGATTGGGAGGTTGGAGTAAAAGGAGAGATAGAAGCACCTTTCACATTTACTGAGTA
TGATTTTCTTGATATAATTTAGTTTTATATTTGGTTTTATACTGATATTTAGTAGATATATACT
TAATAAATTTAGGTAGTTAATAAGTAAAAAAGTTAGTTGATTGAATTTGATTGATAAAGGAGCA
AATAATAATGAATGAAAATGGATTATCAAAAAATATAAACATAGTAGATTTACTTTTAAATGCA
GATACAGAAAACTTAGAAAGACCAAGTACTATAGTTGAACTTAAGAGATTATCAACTATATTTG
GGCAGGAATTTAAAGTAATGTGTAGAGCTTTAACAATAAGTAAAGATGAAGAGATACAAAATAC
TTGTCTTAAAATTGATGAAAATATGAAAACGGATATAGACTTACCGGAGATGCAGATGCTTACA
ATTATAGAAGGTGTTTGTGATTTGGATGGAAAGCTTTTATTTAAAAATAAGGAACTAATGGATA
AATTTAAGGCTCCAACACCAAAAGAATTGGCAAGAAAACTATTATTACCAGGTGAAATTACCAA
CCTATATAGAATACTTCAAGATGTTATGGGTTATGGTAAAAATGCAGTGATAGAAGAGGTAAAA
AACTAATAGGGACGGATACCAAGACTACAATAATGTACTATTATTGGAAGAAAAAAGGTATAAG
ACCGTCCCTTTTTTATGCAATGGATAAAGGCGAATTAAAGCTTATTGAAGCTTTTTTCGCCTTA
GAAATTGAGGAAGAAGTTGAAAAAATGAAACATGGATATGGAGTGTGTCCTTTGACAGGAGGTG
GTATGTAATGGGAAATGTGAGAGAAGAAGGTATAAATATGTATCTTACAGATAATTACACACCA
AAAATGAACCAAATTATATCAGTAACTGATAATTTTAGGAGAGCAACTGTGGCTGTTTCACTTT
CCACTAATGTAATGGCTAGTAGCATAAAAAATTCTATTGGAAGTGCAAGTAGTAGAGTAAACAG
TTTAAATTCCTCGTTAAGAAAAGTTCAAACTACTGCTAGTAGTGTAAGTTCAACTATGGCAAAA
TTAAGTTCTAGCATAAATGCTGTTTCAGGAGTTATTGGAAGTTTAAATGGAAGTATTATGAGAC
TAGCAATAACTATAGCTATGATTATTGATTATTTTAATAAGTTGATTCAAAAGAAAAATGAGTT
TAATTCAAATATTATGATTATATTAATATTTAAAGCTAAAAGTGATGAAGTAGAAAAAACTAAA
AATAAATTACTTGGAAATTTAAAAAAGATTGGTGGCAAGATTTGGAATATCGTAATAAAAGCAA
AAGATATGACTAAGAGAGTGATAAGTAGTATCTTGGGAAAATTAAAACGAGTAGAGAAACGTCC
TTATCAAGGAAGTATTAATCTTAAAGATATGGTAAGTAGTGCTATGGCTAGAATTTTGCCTAAG
TTAATGTTGTTTAAAAATACTTTTTGGAGTGGTGTAATAGCTATAAAAGATATGGCAAGTAGCA
TTATAAGTAAAGTATTTCCCAAATTGAGATTGTTTGCAGGTAAGGTATGGAGTGGTGCAATAGC
TGTAAAGGATATGGCAAGTGGAATACTTGGTTCGATAAAAGGGAAGATATCTGATTTGACAAAT
GGTGCTACTATAGGTGTCGCTGTGAAAAAGGGTGTTGACTTACTTGGTCAGGAACAAAATCAGA
AAGTTGTTCTAGAAAGTGTAATGAAAAGAAATACTGGAAAAACTAGCCAAAAAGATGTTGATAA
GTATTATGACAGTTTAGTAAATATGGCAAATGATACGCCTTTTGACCCTGAAGATGTTGTTGCA
ATGGGAACTAAAGCTAAAATGATTAGTAATATTACTGGTGGCAAAAAAGAAAAAGATATAACTC
AAGCTATGGTAGATGTTAGAGCTTTAAATATGAATACAAGTAGTGAACAAGATGTATCAGCAGC
TTTCTTAAGTGCAGCAAAAGGAAATATGGAATCTCTTAATACTCTGGTAGGAGAAAATTATAAA
ACTTTTGATGAAGCATTGGAAGGCATAAGTGTAAAGCAGATGGGGTTAGCTAAAGAAATGAGTA
ATACAATACCAGGTATAATATCAGGAGCTCAAACAAGCATTAACAATGGTTTGAAGAGTATTGT
TAAACCTTTTGATGATATTTTAGGTCAAGGACTAAAGAAAATAAAAACTTTTATAGAAAGTGGA
TTAGGGAATTTAGCTGGCTTATCTGAAAAAATGGCTGGTAAAATAGGCAATGTAATGAATGGTA
AGATAATTATTGGCAACAAATATGACCAGATGCAATCTAGAAGTGTAAAAAAATGGAAAAGAGTT
TTCTGATTCTACTCAATATCGAATTTCTAATGAGGCTGAAAAGCGTAAAATGATGGTTGAAAAT
AAGCAAGAACGTTTTGAAAATCATGCAGCAACAATGATAGGGAATGCACCAAAAGCAATTGTTA
ACGCAGGAAGTACACTATTACAAAATATTGATTTTACAGCATTAATAGATTCACTACTTCCAGT
AGTAAACTTAGTAAATAATTTACTAGATAGTATAAACAATAAATCACCAATTGCACAAGGATTA

Figure 1N

ATAAGTATATTTGGTACAATAGTAACTACAGCATTCCAACTAATCGGACCTGTAGTTGAAGCTG
TTAGTCCTATTATCACAAGAATTTTTACTTTTTTAGGTGAATATGCACCTCAAATAAACAATTT
TATAGAGACACTGGGTGTTATTTGGAAAACTGTATGGGAGACCTTAGGACCTCTGTTGGAAACT
GGATGGAAAATTATAGAGCCAATATTGGGAGCTTTTTTTAACATATTAGATAAAGTATGTAAAA
TAGTTAAAGATATATGCAAATGGTGGCAAACTATGATTAATAAGATAAAAAATGGAAGCATCAC
AGGAACAGTTTTAAATCTAGTGGAAAAGAGTAAAAAAAATTACAAAGATAATCCATATGCTGGA
ACAAAGGCTGGTGATTCTGGTAAAGCTTATTCAAGTAAGAAAGGTAATAATGCATTTGGATTGA
ACTATGTTCCTTATAATGACTATCAAACCAGACTCCATGAAGGTGAAATGGTTTTAACTAAACA
AGAAGCAAATCAATATAGAAGCAGAAAAAATGGTGGAAATATAAACATAGCTAAGTTAGCTGAT
ACAATAGTGATTAGAGAAGAAGCTGATATAGAAAAGATAACATCAAAATTAGTTGCAAGTATCC
AATTGGCACAGTTAGGGGGTGTCTTATAATGGAAATGTGGCTTAGACAAGCAGAAGATAGATTT
AGATTTCCAGTATTTCCATCTTCCTTTAGTATTAATGGAAAAGCTGCTGTAAACTCTTCTAGTA
TACTCAAAATAGGTGAAGTAGCAACTTTTGGTGGTGTAGCTCTTAAAAGCATTTCAATATCAAG
TTTTTTTCCAAATAAAGACTACACTTTCTGTGACTATACAGGTTTTCCATCACCATATGATTGT
GTAAATAAGATAGAAAAATGGATGAAGGAAGGTTTTATATTAAGATTTACAATTACGGAAACAA
ATATAAATATGGAAGTCATAATTGAAGGGTTTAGTTATGAAGAAAGAGATGGGAC

SEQ ID NO:33 Middle fragment
TCGAGATGTATATTTTACATTAGATTTAAAAGAGTATAAAAGAATAAAGATACCAAAAGTAACT
CCAAAACAATAACTATTATAGATAATAAGTTGTAAGTAACTGCTGATAGAATTAAATGAAAAGG
CAGGTGATTTTTTATTATTAAGATTTGGGTACACATAAAAAACGGAAGTATATATGACATAACT
GACATAGTAGACAAGGTATCATGGTCAGGTGATTATAAATCTCCATCAAGGACACTAGAGTTTT
CAATAATACAATCATCATTTGATGTAAATTTCCAACAAATCGATATACCAATAGCTAGTACAGT
CTGTTTCTATGTAGATGAGAAAGAACTCTTTAGAGGAATGATAATTAATAGGTCTAAAGATTCA
AGCAGTAATGAAATTAGTTTTGTATCTAAAGATATGGGATTTTTACTTACACAAAGTGAAGTGT
CATACAATTTTAAAGATAAGTTAGTTGAAGACATAGCAAAGCAAGTATTTGCTGAAAATAGGCT
TTCAGTTGGAACAATAGCAAAGACCAATGTCAAGTATACAAAGATGTTTATAGGAGTAAATGGT
TATGACACAATAATGAGTGCATATACAGAGGCAAGTAAAAAGACAAAGAAAAAGTATATGATAG
AGGCTAATTTAGATAAGTTTAATGTTATTGAAAAAGGAACTGTTACATTAAGTGTTATGTTTGA
AGAGGGATTTAATATTATAAATACCACCTTTTCGGAGAGCATGGAAAATGTAAAAAATAAAGTA
ATAGTGGTAGACCAGTATGGAAGCAAGATTAGCGAAAAAATAGATAATGAAATTTTTAAGGAAG
TAAATGTAATAATGCAAAAAGTAATTCAGCAACAAGAAAATCAAGATGTAGATATTGATAGCGA
GTTTAATGGGATAGAAAAAAGCTGTTCTCTTAAaGGTTATGGAGATGTAAGTTGTATAACTGGT
AGAGGAGTAAAAGTTAAAGATTCTTATACAAAGCTTGTAGGACTATTTTATATAGATACAGACA
AACATACTTGGCAAAATGGAGAATATCAAATTGAGCTTGAACTTAATTTTCAAAATCTTATGGA
TGAAAAGTCAGCAGGACAGGATGAACCTAAGGAAGAAAGTAATTTAGGGGGAGAAGATTATGCA
GGAGGAAAAGAGTTTACAGCAGAATTTACAGCTTACTGTCCTAGAAAAGAAGAAGGTGGAGATA
CAGATTGTAGAAAGAAAAAACTTGACCCATCTAAAAAACTTGCGCTGCTCCTATGGTTGGTAAA
TATGAGCAAACTTATTATACAAAAGAGTTTTTAAATAAACATCCTTTATTGAACTATGGAGATG
AAATACAGGTAATTACAGGAGTTTCTGGTCGTGATGGAGTCTATAAAGTAAATGACGTAGGACC
TGCAATAACTATAGAAAAAAATGGAACATACCATATAGATATTTTATTTGGAAATGTTGAAGAA
GCTAGTAAATTTGGAAGAAGAAAAGGAAAAATTATTATTGGTGGTTATTCTGGTAATGTATCTG
ATAAAGCTAAAATAGTAATATCAGAGGCAAAAAAACATCTAGGTAAACCTTATAAATGGGGTGG
AAATGGACCAAGTAGTTTTGACTGTTCTGGTTTAATGGTCTACTGTTTTAAAAAAGTTAATGTT
AGTTTGCCAAGAACGTCAAATCAACAATCTAAAAAAGGCAAGAAAGTAGAACAAAAAAATCTTC
AAGCAGGAGATTTAGTATTTTTTCATAATCCAGTCAGCCATGTTGGATTATATATAGGTAATGG
AGAATTTTTACATGCTCCACAAAAAGGTGATGTAGTTAAAATAAGTAAGTTAAGTAGTAGAAGA

Figure 1O

GATTTTAATACAGCTAGGAGAGTATTATAAAAGGATGGTGATATAATGGCTAATCCAATAAATG
AATTTATAGGAATAATAAGAGAAGAAGGAAAGTATCATAATCAACCTTCTTTTTTATTGGAAAA
TTAAAAGTAAATTACCAGATTTAAAAATAGAGACAAATAACATCATATTAGAAAAAGAAGATAT
TTTGATAGATAGTTGGATGATTGATAGACAGCTAGAAACATTTGACACAGAAACAAATCAAGAA
CACCAGCATGAAGTAAAAAATCCTTTTATAGATAACTTTGAATCTGGGGATATGGTAATAATGT
TTAGAATAGGCGAAAAATTTGCTGTTGTAAGTAAGTTGGTGAGCTTATAATGAGTACAATATTT
CCTTTTATAGGTGTCCCAGAGGATTATATCTTACCTAAAACAGAAGAATTGCCAATCTTTCGTG
AAGTGGCATGGGATTTTGAAAAAGATGAACCTATTTTAGAAAAAGGTGACTTTAAAATAATTGA
AAAAAAAAGAAGCCTTAAAAGTTTGGATATACAAGTGTATAAAGACAAATAGATATGAACATGA
GATATACTCTTTAGAATATGGGACAGAGCTTTCAGAACTAATAGGACAAAAATATACAAAAGGT
CTTACAGAAAGTGAAGCTAGTAGATTCATAAAAGAGGCCCTTCTAATAAATCCATATATATTAG
AAGTAAACGTAAAAAGTGCTAACTTTAACAGAGACGTATTGAGTGCAAATGTAAAAGTATCCAC
TATCTATGGGGAGGTGGAAATAAATGTATAGTGACCAGACATATGAAGTAATAAAAAATAGAAC
TCTTGAAAATATTAATCTTGATATTTATAAAGGAGAAGGTTCTTTTCTAAACAACATGGTATCT
GGAAATAATCTAGAACTTTCGAAGATATATCTAGAACTTTCAAAGATACATAAAATGGCTTTTA
TACAAGACACATATAACCAGTTTCTTGATAAAAGAGTCAATGAATTTGGTGTATATAGAAAGTT
AGGTACAGAGTCAAATGGAGAAGTTGAATTTATTGGAGAGAAAGGAACTGTAATAAATAATGGC
ACAATAATATCATATAGAGATTTACTATTTGTAGTAATAAAAGATGTAACTATTGGTAGTGAAG
AAGGTGACAATAGCCCAGTTCAAGCTCTGGAAGTTGGTAAGAAATATAATTTACCTACAAATTG
TGAATTTAAACTAGTTGATAATATATCTGGAGTAACAAAGATTACTAACACAAGAAGTTTTGAA
GGTGGTACAGATATAGAGACAGATGAAGAACTAAAAGAAAGATTTTATAAAATCCAAAGAAATC
AAGCTACAAGTGGAAATAAAGCTCACTATGAAGAATGGGCTTTGGAAGTAGATGGAGTCTATAA
TGTTAAGGTTTATCCAAGATGGGATGGTCCAGGAACAGTTAAGGTCTTGATATTTGGGGAAAAT
AATCAAGCTGTTGATACAGAAACGATTGAAAGGTGTCAGCAACATATAGATGAAGAGAAGCCTA
TTGGACCAACTATAACAGTTGTGACACCATTACCAATAGAAATAAGTATAAGTGCAGTAATGAA
ACTAGAAGATGGATATACATTAGACAATGTAAAAGAATCTTTCCTAGAAAGTATAAATACATAC
TTTAGAGATATTAGAGGAGAGATAATCTATACAAAAGTCATGGGAATACTTATAAATACTACTG
GTGTACACGATTTAAGTAATCTACTTATAAATGGAAGTACAGATAATATAACTATTAATGAAGA
TAAAATACCTAGTGTAACAACTGTTAATTTTAGTGAGGTGGAAAATCAATGAAGCTAATTGATA
AACTACCATCATTTGATAGAAATTACATTGTAGAGGAGATACAAGGTGCATACGATACAGAATT
AAATATTCTTAAAGAAGATATTGATGATACCTTTAACCAATTATTTGTTGATACAGCGACATGG
GGATTAGATATGTGGGAAGACATACTCTGCATTGaAAAAAAAGAACTTGATTTTGACACAAGAC
GTAGCAATATAAAAGCTAAAATGAGAAGCAGAGGTACTAGTACTATTGAAGTTATAAAAAGTAT
ATGTGAGGCATATACAAAATCAGAAACAGATATAAAAGTTTATAGTGATGAATTTACATTCGTA
TTGAGTTTTATAGCAAATAACTGTGACTATAAAACTCTTTTAGATTGTAGCGAGATGATTGAAA
GAGTAAAACCTGCTCACTTATTACACTATTTAGAACCAATAATACTAGATAAAAGTATGGTCTA
TTGTGGTGGAGGTATGGTATGTAGTGAAGAGGTAAAAGTTCATCCATACTTTGAACCAATTATA
AAATGTAGTGCTGTTGTAAACTGTGGAGCTGGAATGTTAAGTAGAGAAGAAATAAAGGTTTATC
CTTTAAGCATTAAATGCATTGAAAATAATTGTAAGATTAATATAGCTATTGCAAATGATACAGG
CGTAGAAAATGTAGTAGTTTATCCTAAATCGGAGGTGGTATAATTGGAAGAAAAATTTTATATA
ATATTAACCAAAATTGGTAGAGAAAAAATAGCAAATGCAACTGCACTAGGAGAGCTTGTTGGAT
TAACCAAGTTTCAAGTTGGAGATAGTAATGGAGAATATTATGAGCCAACAGAGGAACAAACTGC
TTTAAAGAATGTAGTTTGGGAAGGAAATATAAATTCTCTAAGAATTGATGAAAAAAATCCTAAT
TGGATAGTTATAGAGACTATTTTACCAGGAACAGTTGGTGGATTTATGATAAGAGAAGCTGCTG
TTCTGGATAATGAGAATAATATAATAGCTATWGGTAAGTATCCAGAGACGTATAAGCCACGTGC
TGAAGATGGCAGTATTAAAGATTTGGTTGTAAAAATGATTTTACAATTGTCCAATACTTCAAAT
GTTACATTAGAAGTAGACCCGACGTTGGTTTTTGTAACTCAAAAGGATATTCAAGATTTAGATG

Figure 1P

ATAAGTTTGATAAAAATATAAAAGAAATAAAAGTAAAAATTGGAGATACAGATATATTAACTAC
AGATTCTAAAGATTTATCAGGAGCTATAAATGAGGTAGTTAAAAAAATAGAAAATATATCTTTT
GATGATGTTATAAGTGGTCAAATACAAACTGATATATCAGTATTAAAAAATAGCTATAACAAAT
TATCTGAAAAAGTGCTAGATATATTAATATACCTAGAATTAGAGTCAGAAGTAACTGTAGATGA
GGCTGGTTATTGGTATGATACATTAGCAAATGGAAATAACATAGTAGCTATAGAAGGGCTTAAG
TTAGATTTAAATAGAAAATGTATAACAGGTGAAATTGGTAATGTGATTTTTAGAGATGTAGTAT
TACCATTTAGTGCAAATAGAGTTAGATATATACATGATATGGATAATAACTTTGTTGAGACAAA
ATCTAGTAACACTTATTTAAAAGAACAAAAAGATATAACTCTAAGTAAATATTCATATGAAATA
AGATAAATAAAGGAGGTAGTACTAATAATGAAGCAAAATAAACTTTTACAGCGTGGTGCTTATT
TTAATGATAAGAACATATTGATTGATGATTTTGATAAAAGATATAATGATTATGATTTTGTAGA
ATTTTTTACTGGTATAAGTAATAGTACCTTTGGTTTAAAATCAGATGGTAATTTATATGCTTGT
GGCGATAATACAGGTTTTCAACTAGGACTTGGAAAAGATTCGTCAGAGAGAAGGATGTTTAGTA
AAGTAAAAATTGATAATGTAAAATATGTATCTTGTGGTTCAAAACACAGTGTAGCAGTAACTAA
AGATGGATTTGCATATGGAGCAGGAACAAGTAATGTAGGTCAATTAGGTGTAATTGAGTCTACA
GTATATTATGAATTTACTAAGCTACCAATAGATGATGTAAAAACTGTTGCATGTGGTTATGACT
TTACATTTGTGCTTAAAAATGATGGAACATTATATTCAGCAGGTTTAAACTCAAGTGGTCAACT
TGGACTAGGTGATACTAACAATAGAGCTACTTTTACTAAAGTAAATATAGATAGTGTGAAAGAT
GTAGTGACTTATAATCAATCTGTATTTATCATAAAAATGGATGGGACAGCACATGCATGTGGAT
TAAATTCAAATGGGCAGTTGGGAATTAATAGTACTTTAAATAAAAGTGTATTTAATAAAATAGA
AGGTATGGATAATGTAAAACAGATAGCGTGTGGTAGTAGTCATACAATTCTTATTAAGAATGAT
GGAACTATGTATACTACAGGCTATAATGGAGTTGGTCAGCTTGGTACAGGAAATAATAATAATT
CAATTGTATTTACTCTTTCTAGTATAAATAATGTTAAGTATGCTTCTTGTGGAAATAATCATAC
TATGATATTAAAATACGATAATACACTGTTTAGTACAGGACAAAACAATTATGGTCAACTAGCC
AATGCCAATAAAGATGTAGCATCAAGAAATACTTTTGCTAAGGTTAATGTAGAAAATATAAAAG
ATATTAAATGTGGTTCTCAATTTAATTTTTtAATAAATGGTTCAAAAGAGATATTTGTATCTGG
CTGTAATTTAGCAGGTCAACTTGGTTCATTTTTTCATACAACTTTTCTGTATGAGTTTTCAAAT
GTGCAATCTTCAAATTTAGATAATTATTCAGGTTTATTGGTTAATGATGATTATTTATATGTTA
CAAAGGACAATAGTGAATTTTTAAATGTAAAGTTAAGTGATAATTTTCAAGATTATAAGAAGAT
AGAGTTAACAGATAGCAATATGTTTATTGTTATGAATGATGGTACATTGTATGCTTGTGGTTTA
AATAATTATGGACAGTTAGGATTGGGAGATACTGTTAACAGGTCAGTTATGACTAAGGTGGATA
TAGATAATGTTTTGGATATAAAAGGAAACGGAAACTCAACTTTTGTGCTTAAGAATAATGGAAC
ATTATATTCATGTGGTTTAAATAGTAATGGACAATTGGGTTTAAGAGATGAAGTTAATAGAAAT
ATATTTACAAAAATAGAAATAGAGAATGTAAAGGATTTTTGTGTAGGAAGCAATTATGTCATAG
CTTTAAATCACTCAAAAGAAGTATATGGATGGGGAAATAATCCTTATAATAATATAGAAAAAAC
TTCTAATTATCCATATAAGCAGGGAATAAGTAATATTGAAAAGATAGCAGCATATGATTATTCT
GTATATATGATAAACAGTGAAGGGAAACTATATGTTTCTGGATACAATTATAATTATCAATTAG
GTAAAGGAAATAATAGTAACCAAAGCAAAGCATTAGTATCTCAATGTAGAACAAATTCAACATC
TTCTACATCAAATGGACTTAGAACGTTACCTAAAATAACTAATGTTTTtCCTTTTTATGATGGT
TGTGCAATAATTGACGAAGGAGGTTATGTTTATTTAACAGGATATCATGGATATTTAAGAACAT
TAAATAGCAGTCCAAGTATATCTGATTATTCAAGATATGGAACTTTTATTGAGGCTACAAATTC
AAATCATAATACTTATTTTATACAAGAGACTGATTTTAGTGGAATTGAAAAAGTAATAGGGATG
TCAAATAATATATTATTTTTTAAGAAAGGAAGTTCATATATTACTGGATATCCAAAAACATTTG
GCTCAACCATTACTGGACATAGAAGTTATACTAGTATTAATTCTGAGAGTTCTAATTTAGGAAG
TAATTTTATAATATATCATAGTAATTCCAAGTTATATGGAAAAGGGATTGCTAATAGTGGGCAA
TTTGGG

Figure 1Q

SEQ ID NO:34 3′ fragment

AATTCAACAAATATAGATGGCACAAGTAACTATGATACAGGATTAAAAGACATAAAAGATATAA
TTGTAAAAGGAAATACTGTAGTAGTAGTAGATAAAAATAACAATATATATGTAACAGGAATGAA
TCAGAATAACAAACTTGGGATAGGGGAATATAACAACGAACCAGTAAAAAAATTCACAAATATA
ACTGAACAATCAAACTCATTTATATTTATGGATGATATAAAAGAAATTACAACATCAAGAAATA
CAATGTTTATAGTAAAAAATGATGGAACAGCCTATGCCACAGGAAATAATAGTTCTGGACAATT
AGGATTAGGTGACACAATAAATAGAAATAAGTTCACTCAGATAAACCTTGATAATATAAAGAAA
ATATCAACAAGTATAGATGGTAACACAACATTTGCAATTAGAAATGATGGAACACTATACTCCA
CAGGATTAAATACCAAAGGACAACTGGGATTAGGTGATATAGTAAATAGAAATACATTTACCAA
AGTAAACATCCAAAATGTAAGAGATGTTGTTTTAGGGACTACTCACTCGCATGCAATCAAAGAT
GATAACACATTATATTCATGTGGAGaAAACACTCATGGGCAACTGGGCTTAGGAAGCGAAAGCA
ACCATCCAGACGTATTGACATTTACTGTAAACAATATAACTAATGTAAGAGATGTGTACTGCTC
AGATACAACAACATTTATTGTAAAGGACACAAACATTGCATATTGTTGTGGATACAATAATAAT
TCACAACTAGGTATGGGAAATACTACTGACCAGTATAGTTTTATAAAGTGTATGGAAAATGTAA
AAGAAGTTATACCAAATGAAATAAATACCTATATAATAACAATCTATAATACTGCATATAGTAC
AGGTTTAAATACTGATTATTGCTTAGGTCTAAATAGTAATAGCAATCAAAGTTCATTTTCTGAA
ATTCCAATTTCAAATGTAGTAAAAGTAGCTCCAAACAGAAATAATGCAGTACTTTTACTTACAA
GTGAAGGGGATGTATATACTGCAGGCAAATGTAGTAATGGTTCAGGTACAGGAAGTGAGACTCC
AGAGAAGATTAAAAAAATAGCATCAAAGGCAAAGGATATTGGAATGAATTATAGATGTGGACAT
TATGTAAGTGATAATGGAGACCTATATGGTACAGGTTTTAATAATAATGGACAATTAGGTGTTG
GTGATGTAACAAAAAGAGATACATTTATAAAAACCAATACAAGAGTAAAGAAAATACTTCCTTT
AGAATATGCAAATATAGCAATAAAAGATACTAATGATATATATATTTGTGGATTAAATAACTAT
GGACAATTAGGTGTTGGAAATAGATACGATAGTAGAAATAATGATAATAGAATATTTAATTATA
AGCATATGAATTTTGTAATGGGTGATTTGACATCTATTAAAAACAGACATAACTTTATACTTCT
AAACAATAAGATAGTGATACCTACCACAAAAGACATAGATTATGGTTTAGTATTAGGAAATTTA
TACAAAGGAGACCTTTATACTGAGCTTCCATATGAAGATATAAAAGAAGTATCTATTTCTAAGA
CTCATATTATTATATTACTTAATGATGGAACAATGTATGGATGTGGTACAAACTACCATGGAGA
ATTATTGCAAGACTTGTCTATAAATCAAGTGGATGAATTTGTGCAGATTAATGTATCAGATGTA
AAGCATGTTTCATGTGGAGATAACTTTACTTATTTTATAAAATCTGATGATAGTCTTTGGTCTA
TTGGTAAAAATTCCGAATATCAATTAGGTATAGGTCACAATAATCCAGTTACTGAATTACAAAG
AATTACAACTATATCTAGCTGTAAAGAAGTACATTGTGGTAAAAACTATACATTAGTAGTAACT
ACAGGTAATGAATTATTTGTACAAGGATATAATGATAAGGGAGCTTTAGGATTAGGAAGCGATA
GTGAAAATACTATAATTAAGTTCTTTACAAAAGCACTAACAGACATAAGAGAAATAAAATCTTA
TGGAAGTGACCATATATTAGTACTTAAAAATGATAATTCAGTATGGGTTACTGGAAAAAATAGG
GATGTATATAAAATTGAACAACCAGTAGAATTTTTAAAAGAATTTACTATAGTACCTATTTCTG
AAGATGTAAATACAGTAAAGGATGTACTTGCAACAGACAATACATTATATATTATATCAGAAGT
AGGAACGACAAATGCTGCTATAGAAATTACTGAAAAATCAATTTCATCAATTAAGATAAAAATA
CAAGACCCTAATAAAGATATAAGTAGAATAGAAATGCTTATAAATGGTGAAAGTGTAAAATCTG
TAAGTGATTTAACTACTGAAAAAATATCCTTTGAAGTACCACCAGATAAAATTAAAATAGGAGA
GAATAAGATACTATTTAGAGCTTATTGTAAAGGTGATGATTTATATGCATCTTTATTTATTTTT
AAAGAGAGTACTGGAAATTCTATAATTAAAGATTCTTATGTTATGATAGGTAATAGAATGTACA
AGGTAGTTAATACAACATCTAATGAACAAGATATTACAATTACACTAGATAGAGGACTTGAAGA
AGATTTAAATCTTGGAGACCCTATATATCAATTAATAAATAAAACTAAAGTTCAAGTAAAAATA
AATAAATCTGACTTATTCAAAGACATGAAACTAGTTGAAATCAAAAAATCAGACTCAAGTTATC
AAGAAATCTATGAATTAGAAGAAGCCAACATAAAAAGTGCTCAGCCTAAAATCATAGTAGAAAA
AGGAGATAAATGGACAGCTATAAAACGTCCATCTATGATTTTTAGATATGATGCTGAAAACAAC
GAGCCACAAGCTTAAAATGGAGGTGTAAAAATTGTTTAAATTCGATAAAAATAAAATAGAACAA

Figure 1R

ATCAAACAAGGTAGAAAAGTAGAAATGCAGTATAAAGACATTTCAGACATAAGTATAGGTCAAG
CAAAGCAAGATGATGATATAACAAATAATTTTATAGCAAATGCAGAAATATATGAGATGTTGTT
AAGTCAAAGTTCTGTCAATGAAGCAAGTAATATAAGCACTTTTAGTGTAAGAAAATCTGGAGGT
GAGAGTGGAATGGTAGAAGTATATGTAGCTTTAATTTTAAGAGGCAGAAAAACAATAGAAGAAG
TACCAGCAGTAATTAGAGAGCAAGTTAGAATTAGATGTAAAGAATTAGAAATACCAGTTGAATA
GTAAATTTAGAATAACTATGTATTAGTTAtTTTTTTTATGTAAAGTACAAGGTCTTAACTTTAA
TAAGTAAGCCTTGTACTTATTTTTTGTTATATTAGAAATTGTATATATATTTATTATTTATTCA
ATCTATAAATTAAACCTACAATTTAAAGTACAGAAGATTAAATTGATAATCCTGAAAATATAAT
ATTGCATGATGTAAGAATATAACAAAAATTAAAGCTATAAGTATAAAAAATTTAGACAATAGGA
GGCTATAATGGATAAATTAATAACCGAATTGAGTAGTCTGGGGGCAATAGGTATACTATGTGCT
CTATTATTTAAAAATACTATGCAGGAGAAAAAAGAAGATAGAGACATGTATAAAAAAACTGTAG
AAAATTTTATAGAATTATCTACACAACAACAAGAAATAAACAAAAATATACTTGTTCAAATGGG
AATAATGAAAACAGATGTAGAGGAAATTAAGGAAGATGTTACTGATATAAAAGGTATGTTACAA
AACGGTGTATAACATGAAAGTAGCAGTAGCACCAGATTATATATTATTAGGAAAAGATAAAGTA
GTATTGTAGATAGTGCCCTATTTTATTGAGAAGGATTTTATATTTTAAAATATTAATTAAAAAA
AGTAATAAAAATAATATATAAAAATAACATATAAAAATTCAAAAAGGAGTTAAGCTTAAATTTG
ATTAGAAAAAATCAATTTTAAGACAACTCCTTTTTTTtATTAAATTATTGTCTATTAACCAAAA
TAGCTATTTTAGCATCTGGATTATAACTTATCTGAACCATTTGATTTTTCTTAACATGTTCAAG
GTCTTCACCACCATAAGCTATTTGTAACTTAACTGGTAACTTACCTTGTTTTATAATAGCAACG
TACTCTTTTTTACCTTTTTCTCTAAACTAATCAAATTGCCAACATAAGGTTTAAAGTTCTGATA
CTTTTTACTAGAATTTCTTATGTAGAAGAAAGCACCAACAGCAATAACTAAATTTATGCCAAGT
GTAACCCAAGAATTGATTTTAAGCATAGCTCCAGCGATTATTATCACGAACATTAAAACGATAG
GTAATATAGCTTTCTTAAGAAGCAATTTACCCATTATTTCATTAGCCTTTTTCTCAGGGCCACT
CATAGTTTTTGATCTAGCAAATGATTGCGCGAATTTGTCTCTTAAGCCCATTTTATCCTCCTAA
TTTTAATAAATATTTAGTTATAATAACGAGATATTACTTGAAACTAAAAATTTACTACATTTAT
ATTATGTTTGACTTTTGTATAAATAATTACATTCAAGTAAAGCAAAATATACTAATTATTTTAT
CATAAAATTATAAAAAAGAAAATAAATGAAATAAAAATATTAGAACAAAGAAATGATGTAAAAT
CGTATCAAAAGCAACATAAAAATTATTTATCTATTTTCTCATCTTTATTTTTGTTATACTCAAT
TTTTCCTAAATCCTTCTCTTTTTCATATTCATGAAGTTTTAATTCAATCATACCTTCTATTTTG
GCTTTATCATAATCATTTAACTTTCTAAAGTTGTTTAAAAGCTTTATTTCATTAGAGTTTATGC
TATTAAGTGGATAGTTTGAGGAGGAATCGCAAATTAAATCTGATTTATGTGATAGATTATCTCC
ATTTAATAGCCAGTCTACTGAAACATTAAATATCTCAGCTATAGATTTTAATATTTCATAATTT
GGTTTTCTAATGTTTCTCTCAAATTTACTTAAGTTGTCACAGCCTAACATTTCTTCTAGTTCAT
ATTGTTTAAGGTTTTTTGCTTTTCTCAAATAAACAATTCTTTCTCCTAAAGTATCCATAAACAC
TCTCCATTCAATTAATGTCAAAAAGACTTTTTAAGATGTAAATAGTTTCAAATTAAAGGTCAAA
ATGACATAAAAACCATTGACTTAAGGTCAAAATGACTTTATAATTAACTTAATGATACGAATTT
ACATCCTAATTTTAGCACAAAGTAATCAAAAAATCTTATTTAGTATTAAATAAATTTATATACT
TAATATGTGTACATATTAAAAATATATACTAAATAGAGGGGGTGCGTAAGCTAAAGTAATATAA
AAGTAAATATAAATCACTTAGAAAGGAAGTTGATAAATGGATGCTCGAAAAAAATGGATACCTT
TTTTGGGAGTGCAAGTCAAGCAAAGACTTATTGAATTAAATATGACTCAAAGGGAATTAGCGAA
GAAAATAGGTGTTAATGAAAACTATTTGTCAGCTATTTTAAATGGAAGAAGAACAGGTAAAAAA
TATAAATCATCAATTTATCAATTACTTAATATAGAATATTCAGAAGATGATTAATAAATAGTAT
ATAAAGTAGGTGAATATTCTTGTGTGCAAATTGGATTCAGATGGGGTTATAGAGTGTTGTAGAG
CAATTGATGATTTTATTACAGCACTTAGTAATATAAAAAGCTTAAATATGGAAAGATTAAATAC
TTTAACTAAATATTCTAGTACATGTTCAATCCTTCTTAAAGAGGGGAATTATGAAGGATGTACA
ATTGTGTATAGAAAGATGTTGGAAGAATTAAAAACATGAGTAATGCATTTCTTAGGAATATAAA
TTATACATAGAAATGTATTATATTTTTCAAAGTACTTAAACTAAAATATGGATAAGATAATCTA

Figure 1S

AATATTATAAATGTGCTTGAAATTAGACTATACTTGTTTTTAAATAATCCAATATCCATATTTT
AGTAATATACTACAAAAAAAGAAGGTTAATAGATGATGTAAAATCGTATCAAATTATGTATGTT
TAAACCATTTTATCTTCATTATTATTAGAGGAATGCTTTTTTAAGTCTTTATATTCAGATATCT
TAAGTTCAAGTATTCCTTCTATTTTTATTTTATCACGTTCGTTTAGTTGTCTGTATAGATTTAA
TATCATCATTTCATCATTAGTAACATGTAAGTAATCTTCTTTATCTTCTTTTACACTACTATTG
ACATTTACCTTCTCTTTACCATAGAGAAGCCAGTCAGTCGTAACATTAAAATAATCAGCTATTG
ACATTAGTATATCACAATTAGGTTTTCTATCTCCTGTTTCATACTTGCCTAAGTTTTCAAATTT
TAAAATATCCATAAGTTTGCGCTGAGTAAGTTTTTTGGAGTTTCTCAAATAAGCAATTCTTTTT
CCTAAAGTATCCACAAAATACACTCCTTTCTTTTTATGAGTAATGTCTAAATGACATTTGAAAT
TAAAAATATATAAATTTATAATATAAAACTACTAAATTAAAGTCTAAATGACATTTTGCTTAAA
TTAATATGCTCATAATATGATTTTAACATATTATAGTTGAAAATATATGGTTTATTTTGATTTG
TATATATAACAATAGATTTAATTGTTATAAAAATGTAAAGGGGTGTATGAATAGATTGTATAAA
TTTATTTCGATAAACTAAGATTGCTTTTTGATTGTCTGTAAAAGAGAAAAAGATTAAGATAAAA
ATAGTATTATATTGTAATTTATATTAATCAATTACAAAGATTTTATGAATTTATTCTTTAGGGT
AAAATATTTAAGAATAAGATAAATTTACAATATAATACTATAACACTCTTTTATCTAGTTTTAT
TTTCTTTATAGAACAATAATATTATAAATGCTAGTAGATTTACACAGAATACTGTTATATACAT
CTGTTTGAATCCTGAGTTTAGAGTAGATTGTAGTGtGGATCCGG

SEQ ID NO:35 >AV1368
ttttttGCGGCCGCaatacccactacaccttcgtc

SEQ ID NO:36 >AV1289
Tatacatctcgagtcccatctctttc

SEQ ID NO:37 >AV1288
gaagaaagagatgggactcgagatg

SEQ ID NO:38 >AV1366
CTTGTGCCATCTATATTTGTTG

SEQ ID NO:39 >AV1367
GGAAAAGGGATTGCTAATAGTG

SEQ ID NO:40 >AV1300
tcccccGGATCCacactacaatctactctaaactcagg

SEQ ID NO:41 >DG1
GGCGCGCCACTAGTACCGGTGCCATGGCGGCCGC

SEQ ID NO:42 >DG2
AGCTGCGGCCGCCATGGCACCGGTACTAGTGGCGCGCCCATG

SEQ ID NO:43 >DG9
ttccttggtctcAcgcgAACAAAATTCTCCAGTCTTC

SEQ ID NO:44 >DG10
ttccttggtctcAggccGTCGCGACTAAGAAAATGCC

Figure 1T

SEQ ID NO:45 >DG13
gtgagcggataacaattccc

SEQ ID NO:46 >DG14
AGATTGTAGTGtGGATCCGG

SEQ ID NO:47 >DG15
tccttcggcgcgccTCAAATTTAAGCTTAACTCC

SEQ ID NO:48 >DG16
TTTAGGGACTACTCACTCGC

SEQ ID NO:49 >CD4 Orf1374
MKRTKLLQRGNFFGDKNMVVDEFDEGYDNYDFINFFTGCCNYTFGLKNNNILYGCGDNSNFQLG
LGEDNTTRKLFTKIPNISTNIKKVACGESHAVILTSDGELLVAGINTDGQMGLGLEKVGKTVST
FEKVPEIKGVKDIACGLQSTYLLYNDGTLYVAGNNLYGQLGLGTNGASANVNTFTKVDVDNVKA
VFSYNKSAFIIKNDNKCYSTGFNNQGQLGLGDKNNRDLFSLVSINDVKTIACGSEHTVLMTYNN
DIYGCGKEKCFGNALQSSLFTKIEEVNIKTIACGHGNTMLIDNKGTLKVAGNNDIYQLGIANYS
ENIDNSFIDLKNIVAKNIFIGLSHSILIDSNNDSYCTGDNTYGQLGSFFDDMHIVEFKKMDSEK
YSYSNYINLIKSEDKLTLLKEEMEIKDIELPLDIHSVRDVVFSPYCTLVILGNGDVYGLGNNRY
KGMGSDLPSQLNELTKLSISNVKSIVASKNISGGIFYIKNDDTCYYSGPNSNSIAGVLPSNSDV
FKKISIDNVKKVVINTDLSNWFSLIVTNNKQIYTSGKSSSYVNGLSNALISQYTEISLSNVTDA
YSSYNATFIVVDEKKVYATGINTNYLLGFSTSDGSNVNLGLLSDWYYINISGSSYSRVSCTNNI
TKINNIIIYEYVTVFCTNIGSFLTGYHGTSWTKPTDSSYRVQYQGISYAGYLDSYIYNYYPTRC
TQSSSSTTFAYLYNGESSSNLKNVNPDNLLISGGSSYIHQYGRNYLNNQSSNNIAASNINSGPI
TSDKAIFLYKALLYLSSNTLYGFGNISESAKELDVSDTQDGYNATNYKKVMKNIKNIFIPPYDL
SRDKTRFAILTDKSLFICGYNSKGTHGISVNSSLNLNNKINYNKKNSSSEISSNIQEIYSHSKS
TYLLTNNNMLYSVGLNDVGQLGVGDEINRKVFTKINIDNIKSINVNRFTDNSKHAFAIKNDNTC
YAVGLNNSGQLGIGDNVNRNIFTKINVENVKYVAVYGNTSLLLTNDGLLYGAGNNGKGQLGLGD
TTSRNIFTRIPINGVRDVYLCNDVSIIVKNDNTCYVCGLVNGYFGFTEGSISTFTKINIENVKS
VVTAGSEATFFITNDNMIYTTGKKERVFFSTETNDIKGIRVINNIINAKKIVVNGYTSAILTND
NKLFVGGLSGYGSIANNNNTNSVEDVKDVFVTANNTLYIDNNNNLISSGRDTYGISDESYRDMS
VPYYKVSIKKDVDTVFSSYNTIFIKDIYGKFYSSTRDNRYNHLGIHHRYDNDKNEALEGSLHSY
FKTDNTSDKIVFNKKNEKLVMFNDKYIKTNNKYINYKNIFKDNFKYTSIILPFEVSDIDISKTH
SLAVAKDGKLYGIGSNSYKEINQTLEDIELLTLTEVNISDVKKVACGDNYSYIIKTDNTLWSYG
KNTEYQLGVGHNNDVRELQKVTGLPSVKDISIYNSMTLVLTNEGELYAQGYNTNGLFGLGESEK
DKIIRTFTKVLTNVKEIKSHNDDHILVIKNDNSLWITGKNKSMYKISISITDLYEFTKIPIPEH
LNDILDIELSDDTIYMITKVDTSKASIEIVEKSISQVRVVVQDPNNVIEKLEMFINDELISTKT
NLEINSIIFEIPQNKIVLGENKILIKASSPTGDLYSSMFIFKSETGLKVKKDSILMINNKVYSI
INITENNTDLIVTLNEGLKDDMMENNPIYQLINKTKVQVKINKSDLFKDMKLVEIKKSDSSYQE
IYELEEANIKSAQPKIIVEKGDKWTAIKRPSMIFRYDAENNEPQA

Figure 1U

SEQ ID NO:50 >CD108 Orf1374
MKQNKLLQRGAYFNDKNILIDDFDKRYNDYDFVEFFTGISNSTFGLKSDGNLYACGDNTGFQLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRVTFTKVNIDSVKDVVTYNQSVF
IIKMDGTAHACGLNSNGQLGINSTLNKSVFNKIEGMDNVKQIACGSSHTILIKNDGTMYTTGSN
GYGQLGTGNNNNSIVFTLSSINNVKYASCGNNHTMILKYDNTLFSTGQNNYGQLANANKDVASR
NTFVKVNVENIKDIKCGSQFNFLINGSKEIFVSGCNLAGQLGSFFHTTFLYEFSKVQSSNLDNY
SGLLVNDDYLYVTKDNSEFLNVKLSDNFQDYKKIELTDNNMFIVMNDGTLYACGLNNYGQLGLG
DTVNRSVMTKVDIDNVLDIKGNGNSTFVLKNNGTLYSCGYNSSGILGLKDNTNRNIFTKIEIEN
IKEFCVESNYIVALNHSKELYGWGNQSYIVYGDNRNYPYKDTRVSNVEKIATWSDTLYILDSTG
ATKTIGYSYNGSGGYPAPSSSSTYREGGYINKNTSYRTLEFYNTSKTKLVNLFAFYNGCVFVDE
NGLAYCIGENNINFRGGSTTNENNSLRFINNSGVYYTNTDGTDYTCYQWTYKLIRCSIFDSPQN
IIGNSKNILYLSKNNSTFKCTGNCITYGINSQNWYSYFSDSSNGAIALGNEFILKNYSGECLLK
GYGKATNGEFGNSTNISSISNYDTGLKDIKDIIVKNNTVVVVDKNNNIYVTGANQFNKLGIGEY
NNQPIRKFTNITEQSNSFIFMDDIKEITTSRNTMFIVKNDGTAYATGNNSSGQLGLGDTINRNK
FTQINLDNIKKISTSIDGNTTFAIRNDGTLYSTGLNTKGQLGLGDIVNRNTFTKVNIQNVRDVV
LGTTHSHAIKDDNTLYSCGENTHGQLGLGSESNHPDVLTFTVNNITNVRDVYCSDTTTFIVKDT
NIAYCCGYNNNSQLGMGNTTDQYSFIKCMENVKEVIPNEINTYIITIYNTAYSTGLNTDYCLGL
NSNSNQSSFSEIPISNVVKVAPNRNNAVLLLTSEGDVYTAGKCSNGSGTGSETPEKIKKIASKA
KDIGMNYRCGHYVSDNGDLYGTGFNDCGQLGVGNVTKRDTFIKTNTRVKKILPLEYANIAIKDT
NDIYICGLNNYGQLGVGNRYDSRNNDNRIFNYKHMNFVMGDLTSIKNRHNFILLNNKIVIPTTK
DIDYGLVLGNLYKGDLYTELPYEDIKEVSISKTHIIILLNDGTMYGCGTNYHGELLQDLSINQV
DEFVQINVSDVKHVSCGDNFTYFIKSDDSLWSIGKNSEYQLGIGHNNPVTELQRITTISSCKEV
HCGKNYTLVVTTSNELFVQGYNDKGALGLGSDSENTIIKFFTKALTDIREIKSYGSDHILVLKN
DNSVWVTGKNRDVYKIEQPVEFLKEFTIVPISEDVNTVKDVLATDNTLYIISEVGTTNAAIEIT
EKSISSIKIKIQDPNKDISRIEMLINGESVKSVSDLITEKISFEVPPDKIKIGENKILFRAYCK
GDDLYASLFIFKESTGNSIIKDSYVMIGNRMYKVVNTTSNEQDITITLDRGLEEDLNLGDPIYQ
LINKTKVQVKINKSDLFKDMKLVEIKKSDSSYQEIYELEEANIKSAQPKIIVEKGDKWTAIKRP
SMIFRYDAENNEPQA

SEQ ID NO:51 >CD123 Orf1374
MKRTKLLQRGNFFGDKNMVVDEFDEGYDNYDFINFFTGCCNYTFGLKNNNILYGCGDNSNFQLG
LGEDNTTRKLFTKIPNISTNIKKVACGESHAVILTSDGELLVAGINTDGQMGLGLEKVGKTVST
FEKVPEIKGVKDIACGLQSTYLLYNDGTLYVAGNNLYGQLGLGTNGASANVNTFTKVDVDNVKA
VFSYNKSAFIIKNDNKCYSTGFNNQGQLGLGDKNNRDLFSLVSINDVKTIACGSEHTVLMTYNN
DIYGCGKEKCFGNALQSSLFTKIEEVNIKTIACGHGNTMLIDNKGTLKVAGNNDIYQLGIANYS
ENIDNSFIDLKNIVAKNIFIGLSHSILIDSNNDSYCTGDNTYGQLGSFFDDMHIVEFKKMDSEK
YSYSNYINLIKSEDKLTLLKEEMEIKDIELPLDIHSVRDVVFSPYCTLVILGNGDVYGLGNNRY
KGMGSDLPSQLNELTKLSISNVKSIVASKNISGGIFYIKNDDTCYYSGPNSNSIAGVLPSNSDV
FKKISIDNVKKVVINTDLSNWFSLIVTNNKQIYTSGKSSSYVNGLSNALISQYTEISLSNVTDA
YSSYNATFIVVDEKKVYATGINTNYLLGFSTSDGSNVNLGLLSDWYYINISGSSYSRVSCTNNI
TKINNIIIYEYVTVFCTNIGSFLTGYHGTSWTKPTDSSYRVQYQGISYAGYLDSYIYNYYPTRC
TQSSSSTTFAYLYNGESSSNLKNVNPDNLLISGGSSYIHQYGRNYLNNQSSNNIAASNINSGPI
TSDKAIFLYKALLYLSSNTLYGFGNISESAKELDVSDTQDGYNATNYKKVMKNIKNIFIPPYDL
SRDKTRFAILTDKSLFICGYNSKGTHGISVNSSLNLNNKINYHKKNSSSEISSNIQEIYSHSKS
TYLLTNNNMLYSVGLNDVGQLGVGDEINRKVFTKINIDNIKSINVNRFTDNSKHAFAIKNDNTC
YAVGLNNSGQLGIGDNVNRNIFTKINVENVKYVAVYGNTSLLLTNDGLLYGAGNNGKGQLGLGD

Figure 1V

TTSRNIFTRIPINGVRDVYLCNDVSIIVKNDNTCYVCGLVNGYFGFTEGSISTFTKINIENVKS
VVTAGSEATFFITNDNMIYTTGKKERVFFSTETNDIKGIRVINNIINAKKIVVNGYTSAILTND
NKLFVGGLSGYGSIANNNNTNSVEDVKDVFVTANNTLYIDNNNNLISSGRDTYGISDESYRDMS
VPYYKVSIKKDVDTVFSSYNTIFIKDIYGKFYSSTRDNRYNHLGIHHRYDNDKNEALEGSLHSY
FKTDNTSDKIVFNKKNEKLVMFNDKYIKTNNKYINYKNIFKDNFKYTSIILPFEVSDIDISKTH
SLAVAKDGKLYGIGSNSYKEINQTLEDIELLTLTEVNISDVKKVACGDNYSYIIKTDNTLWSYG
KNTEYQLGVGHNNDVRELQKVTGLPSVKDISIYNSMTLVLTNEGELYAQGYNTNGLFGLGESEK
DKIIRTFTKVLTNVKEIKSHNDDHILVIKNDNSLWITGKNKSMYKISISITDLYEFTKIPIPEH
LNDILDIELSDDTIYMITKVDTSKASIEIVEKSISQVRVVVQDPNNVIEKLEMFINDELISTKT
NLEINSIIFEIPQNKIVLGENKILIKASSPTGDLYSSMFIFKSETGLKVKKDSILMINNKVYSI
INITENNTDLIVTLNEGLKDDMMENNPIYQLINKTKVQVKINKSDLFKDMKLVEIKKSDSSYQE
IYELEEANIKSAQPKIIVEKGDKWTAIKRPSMIFRYDAENNEPQA

SEQ ID NO:52 >CD126 Orf1374
MKQNKLLQRGAYFNDKNILIDDFDKRYNDYDFVEFFTGISNSTFGLKSDGNLYACGDNTGFPLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN
GVGQLGTGNNNNSIVFTLSSINNVKYASCGNNHTMILKYDNTLFSTGQNNYGQLANANKDVASR
NTFAKVNVENIKDIKCGSQFNFLINGSKEIFVSGCNLAGQLGSFFHTTFLYEFSNVQSSNLDNY
SGLLVNDDYLYVTKDNSEFLNVKLSDNFQDYKKIELTDSNMFIVMNDGTLYACGLNNYGQLGLG
DTVNRSVMTKVDIDNVLDIKGNGNSTFVLKNNGTLYSCGLNSNGQLGLRDEVNRNIFTKIEIEN
VKDFCVGSNYVIALNHSKEVYGWGNNPYNNIEKTSNYPYKQGISNIEKIAAYDYSVYMINSEGK
LYVSGYNYNYQLGKGNNSNQSKALVSQCRTNSTSSTSNGLRTLPKITNVFPFYDGCAIIDEGGY
VYLTGYHGYLRTLNSSPSISDYSRYGTFIEATNSNHNTYFIQETDFSGIEKVIGMSNNILFFKK
GSSYITGYPKTFGSTITGHRSYTSINSESSNLGSNFIIYHSNSKLYGKGIANSGQFGNSTNIDG
TSNYDTGLKDIKDIIVKGNTVVVVDKNNNIYVTGMNQNNKLGIGEYNNEPVKKFTNITEQSNSF
IFMDDIKEITTSRNTMFIVKNDGTAYATGNNSSGQLGLGDTINRNKFTQINLDNIKKISTSIDG
NTTFAIRNDGTLYSTGLNTKGQLGLGDIVNRNTFTKVNIQNVRDVVLGTTHSHAIKDDNTLYSC
GENTHGQLGLGSESNHPDVLTFTVNNITNVRDVYCSDTTTFIVKDTNIAYCCGYNNNSQLGMGN
TTDQYSFIKCMENVKEVIPNEINTYIITIYNTAYSTGLNTDYCLGLNSNSNQSSFSEIPISNVV
KVAPNRNNAVLLLTSEGDVYTAGKCSNGSGTGSETPEKIKKIASKAKDIGMNYRCGHYVSDNGD
LYGTGFNNNGQLGVGDVTKRDTFIKTNTRVKKILPLEYANIAIKDTNDIYICGLNNYGQLGVGN
RYDSRNNDNRIFNYKHMNFVMGDLTSIKNRHNFILLNNKIVIPTTKDIDYGLVLGNLYKGDLYT
ELPYEDIKEVSISKTHIIILLNDGTMYGCGTNYHGELLQDLSINQVDEFVQINVSDVKHVSCGD
NFTYFIKSDDSLWSIGKNSEYQLGIGHNNPVTELQRITTISSCKEVHCGKNYTLVVTTGNELFV
QGYNDKGALGLGSDSENTIIKFFTKALTDIREIKSYGSDHILVLKNDNSVWVTGKNRDVYKIEQ
PVEFLKEFTIVPISEDVNTVKDVLATDNTLYIISEVGTTNAAIEITEKSISSIKIKIQDPNKDI
SRIEMLINGESVKSVSDLTTEKISFEVPPDKIKIGENKILFRAYCKGDDLYASLFIFKESTGNS
IIKDSYVMIGNRMYKVVNTTSNEQDITITLDRGLEEDLNLGDPIYQLINKTKVQVKINKSDLFK
DMKLVEIKKSDSSYQEIYELEEANIKSAQPKIIVEKGDKWTAIKRPSMIFRYDAENNEPQA

SEQ ID NO:53 >43593 Orf1374
MKQNKLLQRGAYFNDKNILIDDFDKRYNDYDFVEFFTGISNSTFGLKSDGNLYACGNNTGFPLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN

Figure 1W

GVGQLGTGNNNNSIVFTLSSINNVKYASCGNNHTMILKYDNTLFSTGQNTYGQLANANKDVASR
NTFAKVNVENIKDIKCGSQFNFLINGSKEIFVSGCNLAGQLGSFFHTTFLYEFSKVQSSNLDNY
SGLLVNDDYLYVTKDNSEFLNVKLSDNFQDYKKIELTDNNMFIVMNDGTLYACGLNNYGQLGLG
DTVNRSVMTKVDIDNVLDIKGNGNSTFVLKNNGTLYSCGYNSSGILGLKDNTNRNIFTKIEIEN
VKAFCVESNYIVVLNHSKELYGWGNESYIVYGNSRNYPYKDTRVSNVEKIATWSDTLYILDSTG
ATKTIGYSYNGSGGYPAPSSSSTYRDGGYINKNTSYRTLEFYNTSKTKLVNLFAFYNGCVFVDE
NGLAYCIGENNINFRGNSTTNENNSLRFINNSGVYYTNTDGTDYTCYQWTYKLIRCSIFDSPQN
IIGNSKNILYLSKNNSTFKCTGNCITYGINSQNWYSYFSDSSNGAIALGNEFILKNYSGECLLK
GYGKATNGEFGNSTNISSISNYDTGLKDIKDIIVKNNTVVVVDKNNNIYVTGANQFNKLGIGEY
NNQPIKKFTNITEQSNSFIFMDDIKEITTSRNTMFIVKNDGTAYATGNNSSGQLGLGDTINRNK
FTQINLDNIKKISTSIDGNTTFAIRNDGTLYSTGLNTKGQLGLGDIVNRNTFTKVNIQNVRDVV
LGTTHSHAIKDDNTLYSCGENTHGQLGLGSESNHPDVLTFTVNNITNVRDVYCSDTTTFIVKDT
NIAYCCGYNNNSQLGMGNTTDQYSFIKCMENVKEVIPNEINTYIITIYNTAYSTGLNTDYCLGL
NSNSNQSSFSEIPISNVVKVAPNRNNAVLLLTSEGDVYTAGKCSNGSGTGSETPEKIKKIASKA
KDIGMNYRCGHYVSDNGDLYGTGFNDCGQLGVGDVTKRDTFIKTNTRVKKILPLEYANIAIKDT
NDIYICGLNNYGQLGVGNRYDSRNNDNRIFNYKHMNFVMGDLTSIKNRHNFILLNNKIVIPTTK
DIDYGLVLGNLYKGDLYTELPYEDIKEVSISKTHIIILLNDGTMYGCGTNYHGELLQDLSINQV
DEFVQINVSDVKHVSCGDNFTYFIKSDDSLWSIGKNSEYQLGIGHNNPVTELQRITTISSCKEV
HCGKNYTLVVTTGNELFVQGYNDKGALGLGSDSENTIIKFFTKALTDIREIKSYGSDHILVLKN
DNSVWVTGKNRDVYKIEQPVEFLKEFTIIPISEDVNTVKDVLATDNTLYIISEVGTTNAAIEIT
EKSISSIKIKIQDPNKDISRIEMLINGESVKSVSDLITEKISFEVPPDKIKIGENKILFRAYCK
GDDLYASLFIFKESTGNSIIKDSYVMIGNRMYKVVNTTSNEQDITITLDRGLEEDLNLGDPIYQ
LINKTKVQVKINKSDLFKDMKLVEIKKSDSSYQEIYELEEANIKSAQPKIIVEKGDKWTAIKRP
SMIFRYDAENNEPQA

SEQ ID NO:54 >ΦC2 Orf1373
MAIDKSYYTIITDVGKAKIANASVTGNKVGFVKIQLGDGGGSEYTPTESQTALKNVVWEGNIGN
TTTDETAPNCIILESLIPSSVGGFMIREIGYLDDENNLIAISKYKECYKPSIEQGAVVDMKVKT
VLIVSNVNNIELKIDPTIIFATLKDIQDLETKIGTVNTKIDTTKTELTSNIETTKTELNTRIDT
ENEKQNIKIDQLIAGGSNVASTQIITIDDWVEDAENGFKATVTHSLLTQRIVVNIIDATTKENV
VTNFKIIDDNSIEIRSEVKVELNVYVINGNAETHFINATVDDNRVSEMTTYSSKKIEDRLVNIE
EKVNGGLSNIATSVNELITYC

SEQ ID NO:55 >ΦCD119 Orf1373
MAEQQYFTLVTDIGKAAIANASVTGEKVDFAKIKVGDGGGSSYTPNESQTALKNVVWESTLEHA
QVDKDNPNWVVIQKFIPGDVGGFEIREVGLFDSKDQLLAVSSYPTTYKPESRFGDCKRTINKSN
ISCI

SEQ ID NO:56 >ΦCD27 Orf1373
MPNELNFNNEIEEYLITTPAHANEFNNRQQKLLDNDKYLNNKIDTTKTELNTRIDTENEKQNIK
IDQLIAGGSNVAYTQRVAIDDWVEDAENGFKATVTHSLLTQRIVVNIIDATTKENVVTNFKIID
DNSIEIRSETRSELNVYVINGNAETHFINATVDDNRVSEMTTYSSKKIEDRLVNIEEKVNGGLS
NIATSVNELITYC

SEQ ID NO:57 >DG211
ggccgcctcgaggg

Figure 1X

SEQ ID NO:58 >DG212
cgcgccctcgaggc

SEQ ID NO:59 >DG210
TGAAGTACCATGGTATCCAG

SEQ ID NO:60 >DG209
ACTGGATACCATGGTACTTC

SEQ ID NO:61 >Dif4 Locus without orf1377-1379
GCAATACCCACTACACCTTCGTCATCTTTAAATTTAAGAGTTTTTACTATTGAATAATAAAGGT
ATATTCCAGTAAAAATAATCTTTAAATACAAGAAAAATAAACTCTTTGGGTATATTAAAAAGCT
AAAAAGTGTAAATATAAAAGCAAGTAGAGTACTTATCCTGTAAAAGAAATCTATTTGTGTAATG
TCTTTATATTTTATCATAAACACCGAATATAAAATGATGAAAACAATTGCGACGATTGCATATA
TGGTAAATAACATATTTTCAAGAGTACCATTTGAAATTACTATCCACTTATACCACATAATTGG
CCAAAATAATAGTGCTAAGAACTTAAAATAATTATCAAACAACTTTTCTTTATACATTCATCAA
ACAACCTTTCTTAACAAAAGCATATATTTGTTTTTAGAATTTTAAATAATATGATATCATTATT
ATATATTAATATTGAATTTATAGAAACCAAAATTTGTTAAAATAAATATATAGATTTTACTGTT
AAGCCAGTTAAAATTACTACTATTTTTATTATGAAATTGGATCAAATATGTAGAAATACGGCAA
ATTAGTTAATATTAAATATTTATTATTTCCAAGTTGTAAAGACTGTTTTTTTAATGATAGAAAT
TCTAATCTTTTTTGAAAGAAAGTAATATCCACATTAAGTATGTCTGCCATTTCATAAACGCAAG
TGATGCCAGAGTTAATTATGTTTATTATATCTTCTTCAGTAATTAAGAACTCACAAGCCCATTT
TAAGGCTTTATTTTCGCACTTATCTATAATAATTTTTGTATAATAATCGTTATAAGAGGATACA
TAGTATCCAAGGCTAGTGAAATGATGTCCAAGTTCTTCAGCTAAGATGGATGTCAATTTTTTTG
AGTTTTGTTTTAAATTACTGAGTAATGATATAATTTTAATACCATGTTTGTTTATATATAGTCC
TTCTAAATCACCTGCAATATAAGTGGTATAATGAATTATTATCTCTTCTTGAGAAGCTAATTCA
AAAAGCTTATCCAAATTATTCATAAAAATCCCCCTAAAATAGAATGTATGTTTGCCTTTAAATT
ATATTAAAAGAGCAGAAAAATAGACTGCTCATCATATGGTTTATTTTTTTTTATATTTATTTAG
TAAAAATTCTATATAATCATTAAGTTGTTCTTGTGCTTCTTCAGGTAACTCTTCATGTGGATTT
TTTCTATGTGCAGCTACTGTATCAATATTTTCCTTAACTAAGGTTCTTCCAAGAAGGTAATCAA
CTGATACATTAAATACATCAGCCAATTTATTTAAAATGTGTTCATCAGGAAATCTGTTTTCTGT
TTCATAGTACCCTAAGACTCTTTGGGAAACGCCTACTTTTTCTCCAAGTTCTCTTTGAGTCAAT
CCAAATTCCTTTCTAAGTTCTCTTAATCTTTTGGCAAACATTATAACACCACCTTATGTATAGA
TTATAACAAATTGTTCTAAAAAATAAAACTAATAAAATATAAAAGAATATTTTTTTCTAAAATC
TATTGATAAAGAACAAATAATTCTATATAATCTAAGTGAGGAAGAACAAAATATTCTTAATAGT
AATGGAGGTATAAAACAATGTTTAAAAATAACTTGAAATATTATAGAAAATGCAAAGGTATGAC
ACAAATTCAACTTGCCAGAAAGGCTGGAATTACAAATGATTATATATCTCAAATAGAAAGAGGT
ATAAAAAATCCTGGACTTCTTATGGCTAAGAAGATTTCTAGTATTTTAGAACAAAATATAGAAG
AAGTTTTTTTTATACAGTTATAGAACAATATGTTCTTGAAAGTTGTGAGATTAGTAAAAAACTG
TGCACTAAAGAGATTATTGTAAATTTGAAGCTAATAATAAGTATATAAAAAAGGGGAAGTACTA
TGGAAAACAAAAAAGATATATTATTTAAAGAAACAGATAAAAGATTACATAATTATAAGTATTT
GGATATAAAGATAAAGAATATTAACTTGGACATAAAAAGATGTGAGAATGAATACTCTGGATGT
GGAGCAATGGTATATACAGAAAAGACTAGTAACACATATAACATAAGCTCTTCTGTGGAAAATG
AGGTGTTAAAAAGAGAGGAAAGATTAAGAAAATTAAAAATGGAAAAAGAAGATATAGAAATAGA
AAAAGAGAAGATAGAAAATGCTCTAACGTGTCTAAATGATATAGAAATGGAATTTTTTAATCTT
TTTTATAATAGTAAGACAAAAAACAATATGACATATATTTCTATGAAACTACACTTAGATAGAA

Figure 1Y

CATCTTGCTACAATTTAAAGAAAAAGATGATATTTAAATTGAGTGAGATATTATAAAAAATAGG
ACAATTTTACAACACTTTATATACACCATTGCAACAATAGGCAATAAAATATGTGAGATAATGT
TATTGTGAAAGAAATCCATATTGAAGGAGGTGATAGATTGAAAAGAATAATATTACCTAAAAAT
ATAGAAGATACTTGACAGGAATAAATGAGATATATATTTAAAAATGACTTATATCATTTATAGT
AAGATTATCAGATTAAGCAAGAATATTTAGTGATAGTGTGGTGATTATTTGCTTAAATACAAGG
AAATATTAGAAACAATTATTGAGATTCTCAAAAAAAACTTTACTGAAAGTATTTTTATTGATGA
TGAAAGTGTGCAAGGCTCTGAAGGGTCTTGTTTTTTTGTAAGTATACTATCAGTTATTTGTACA
CCTGTAATGTTAAATACGAATAACAAAGATATTGTTATCTCTATAAAATACTTACCAAAACCAC
AGTCAAAGAGTATTAGAATGTATGAAATTTCAGATGAATTAAATAAGCTATTTAACAGAAATAT
AAAGGTAACAGACAGAAAATTAAATATAACAAAGCTAGAACAAAGTATTAAAAAAGAAGAGTCA
ATTTATGTATTGAACTTTACATTTACACTAAACTATCTGGATAGTGTATATGAAGAAGATGTAG
TATATGAAAATATGAAAGAAATCAATTTAAATTTAGGAGAGTGATAGTATGGCTATAGGATTAC
CAAGTATCAACATATCATTTAAGGAGCTAGCTACAACTGTTAAAGAACGTTCAGCTAGAGGAAT
AATTGCAATGGTACTTAAAGATGCTAAGGCACTAGGTCTTAATGAAATACATGAAAAAGAGGAT
ATACCAGTTGATTTATCTGCTGAAAATAAAGAATATATAAATTTAGCTTTGATGGGAAATGTTA
ACACTCCAAATAAATTATTAGTTTATGTAATAGAAGGAGAAGCAGATATTCAAACTGCATTAGA
TTTTTTAGAGACTAAGGAATTTAATTATCTATGTATGCCAAAAGCAGTAGAAGCTGATAAGACT
GCTATAAAAAATTGGATAATTAAACTTAGAGATATAGATAAGGTTAAGGTTAAAGCTGTATTAG
GAAAAGTTGTAGGAAATCATGAAGGGATAATTAATTTTACTACAGAAGATGTGTTAGTTGGAGA
AAAGAAATACAGTGTTGATGAGTTTACAAGCAGGGTGGCTGGACTTATAGCAGGTACACCTTTA
AGTCAATCAGTAACTTATACTAAACTTAGTGATGTAGTCGATATACCTAAGATGACGAAAGTTG
ATGCAGAATCAAGGGTTAATAAAGGAGAGCTTATACTTATTAAAGAAGCAGGAGCTATAAGAAT
TGCTAGAGGAGTAAATTCTTTAACTGAATTAACAGCAGAAAAAGGAGAAATGTTCCAGAAAATA
AAAATAGTTGACACTTTAGATATTATACATAGTGACATAAGAAAGGTGATAATAGATGACTATA
TAGGAAAGGTTACTAACAGTTATGACAACAAATGTTTATTGATAGTAGCTATAAAAAGTTATTT
AGAAGAATTAGAAAAATCAGCACTTATAGAATCTGATTCTACTGTTGAAATAGATTTTGAAGCA
CAAAAATCGTATTTAAAATCAAAAGGAGTAGATTTATCTTATATGACATTACAAGAAATAAAAG
AAGCTAACACAGGTTCTAAAGTATTTTTAAAAGCAAAAATAAAAGTACTTGATGCTATGGAAGA
TATAGATTTATCAATAGAAATATAGGAGGATTATTAATATGGCAAATATGGAAGCTAGAAATGT
AATGAGTGGTACTTGGGGAGAACTTTGGCTTGATGGAAACAAAGTAGCAGAAGTAAAGAAATTT
CAAGCAAAGATGGAATTTACAAAAGAAGATATTATAATAGCAGGTCAAATGGGTACTGATACAA
AGTATATGGGATATAAAGGAAAAGGCTCAATAACTCTATACCACGTTAGTTCAAGAATGCACAA
GTTAATTGGAGAAAAGATAAAGAGAGGTTCTGAACCTAGATTTGTTGCTATATCAAAATTAAAT
GACCCAGATTCTTATGGAGCAGAAAGAATAGCAGTAAAAAATATAGCATTTGATGATTTAACTT
TAGCTGATTGGGAGGTTGGAGTAAAAGGAGAGATAGAAGCTCCTTTCACATTTACTGAGTATGA
TTTTCTTGATATAATTTAGTTTTATATTTAGTTTTATACTGATATTTAGTAAGTATATACTTAA
TAAATTCAGATAGTTAATAAGTAAAAAAGTTAGTTGATTGAATTTGATTGATAAAGGAGCAAAT
AATAATGAGTGAAAATGGATTATCAAAAAATATAAACATAGTAGATTTACTTTTAAATTCAGAT
ACAGAAAACTTAGAAAGACCAAGTACTATAGTTGAACTTAAGAGATTATCAACTATATTTGGGC
AGGAATTTAAAGTAATGTGTAGAGCTTTAACAATAAGTAAAGATGAAGAAATACAAAATACTTG
TCTTAAAATTGATGAAAATATGAAAACGGATATAGACTTACCGGAGATGCAGATGCTTACAATT
ATAGAAGGTGTTTGTGATTTGGATGGAAAGCTTTTATTTAAAAATAAGGAGCTAATGGATAAAT
TTAAGGCTCCAACACCAAAAGAATTAGCAAGAAAATTATTATTACCAGGTGAAATTACCAACTT
ATATAGAATACTTCAAGATGTTATGGGTTATGGTAAAAATGCAGTGATAGAAGAGGTAAAAAAC
TAATAGGGACGGATACCAGGACTACAATAATGTACTATTATTGGAAGAAAAAAGGTATAAGACC
GTCCCTTTTTTATGCAATGGATAAAGGCGAATTAAAGCTTATTGAAGCTTTTTTCGCCTTAGAA
ATTGAGGAAGAAGTTGAAAAAATGAAACATGGATATGGAGTGTGTCCTTTGACAGGAGGTGGTA

Figure 1Z

TGTAATGGGAAATGTGAGAGAAGAAGGTATAAATATGTACCTTACAGATAATTACACACCAAAA
ATGAATCAAATTATATCAGTAACTGATAATTTTAGGAGAGCAACTGTGGCTGTTTCACTTTCCA
CTAATGTAATGGCTAGTAGCATAAAAAATTCTATTGGAAGTGCAAGTAATAGAGTAAACAGTTT
AAATTCCTCGTTAAGAAAAGTTCAAACTACTGCTAGTAGTGTAAGTTCAACTATGACAAAATTA
AGTTCTAGCATAAATGCTGTTTCAGGAGTTATTGGAAGTTTAAATGGAAGTATTATGAGACTAG
CAATAACTATAGCTATGATTATTGATTATTTTAATAAGTTGATTCAAAAGAAAAATGAGTTTAA
TTCAAATATTATGATTATATTAATATTTAAAGCTAAAAGTGATGAAGTAGAAAAAACTAAAAAT
AAATTACTTGGAAATTTAAAAAAGATTGGTGGCAAGATTTGGAATATCGTAATAAAAGCAAAAG
ATATGACTAAGAGAGTGATAAGTAGTATCTTGGGAAAATTAAAACAAGTAGAGAAACGTCCTTA
TCAAGGAAGTATTAATCTTAAAGATATGGTGAGTAGTGCTATGGGTAGAATTTTGCCTAAGTTA
ATGTTGTTTAAAAATACTTTTTGGAGTGGTGTAATAGCTATAAAAGATATGGCAAGTGGCATTA
TAAGTAAAGTATTTCCCAAATTGAGATTATTTGCAGGTAAGGTATGGAGTGGTGCAATAGCTGT
AAAGGATATGGCAAGTGGAATACTTGGTTCGATAAAAGGGAAGATATCTGATTTGACAAATGGT
GCTACTATAGGTGTCGCTGTGAAAAAGGGTGTTGATTTACTTGGTCAGGAACAAAATCAGAAAG
TTGTTCTAGAAAGTGTAATGAAAAGAAATACTGGAAAAGTTAATCAAATAGATGTTGATGATTA
TTATGGCAGTTTAGTAAGAATGGCAAATGATACGCCTTTTGACCCTGAAGATGTTGTTGCAATG
GGAACTAAAGCTAAAATGATTAGTAATATTACTGGTGGCAAAAAAGAAAAAGATATAACTCAAG
CTATGGTAGATGTTAGAGCTTTAAATATGAATACAAGTAGTGAACAAGATGTATCAGCAGCTTT
CTTAAGTGCAGCAAAAGGAAACATGGAATCTCTTAATACTCTGGTAGGAGAAAATTATAAAACT
TTTGATGAAGCATTGGAAGGCATAAGTGTAAAGCAGATGGGGTTAGCTAAAGAAATGAGTAATA
CAATACCAGGTATAATATCAGGAGCTCAAACAAGCATTAACAATGGCTTGAAGAGTATTGTTAA
ACCTTTTGATGATATTTTAGGTCAAGGACTAAAGAAAATAAAAACTTTTATAGAAAGTGGATTA
GGCAATTTAGCTGGCTTATCTGAAAAAATGGCTGGTAAAATAGGCAATGTAATGAATGGTAAGA
TAATTATTGGCAACAAATATGACCAGATGCAATCTAGAAGTGTAAAAAATGGAAAAGAGTTTTC
TGATTCTACTCAATATCGAATTTCTAATGAGGCTGAAAAGCGTAAAATGATGGTTGAAAATAAG
CAAGAACGTTTTGAAAATCATGCAGCAACAATGATAGGGAATGCACCAAAAGCAATTGTTAACG
CAGGAAGTACACTATTACAAAATATCGATTTTACAGCATTAATAGATTCATTACTTCCAGTAGT
AAACTTAGTAAATAATTTACTAGATAGTATAAACAATAAATCACCAATTGCACAAGGATTAATA
AGTATATTTGGTACAATAGTAACTACAGCATTCCAACTAATCGGACCTGTAGTTGAAGCTGTTA
GTCCTATTATCACAAGAATTTTTACTTTTTTAGGTGAATATGCACCTCAAATAAACAATTTTAT
AGAGACACTGGGTGTTATTTGGAAAACTGTATGGGAGACCTTAGGACCTCTGTTGGAAACTGGA
TGGAAAATTATAGAGCCAATATTGGGAGCTTTTTTTAACATATTAGATAAAGTATGTAAAATAG
TTAAAGATATATGTAAATGGTGGCAAACTATGATTAATAAGATAAAAAATGGAAGCATCACAGG
AACAGTTTTAAATCTAGTGGAAAAGAGTAAAAAAAATTACAAAGATAATCCATATGCTGGAACA
AAGGCTGGTGATTCTGGTAAAGCTTATTCAGGTAAGAAAGGTAATAATGCATTTGGATTGAACT
ATGTTCCTTATAATGACTATCAAACCAGACTCCATGAAGGTGAAATGGTTTTAACTAAACAAGA
AGCAAATCAATATAGAAGCAGAAAAAATGGTGGAAATATAAACATAGCTAAGTTAGCTGATACA
ATAGTGATTAGAGAAGAAGCTGATATAGAAAAGATAACATCAAAATTAGTTGCAAGTATCCAAT
TGGCACAGTTAGGGGGTGTCTTATAATGGAAATGTGGCTTAGACAAGCTGAAGATAGATTTAGA
TTTCCAGTATTTCCATCTTCCTTTAGTATTAATGGAAAAGCTGCTGTAAACTCTTCTAGTATAC
TCAAAATAGGTGAAATAGCAACTTTTGGTGGTGTAGCTCTTAAAAGCATTTCAATATCAAGTTT
TTTTCCAAATAAAGACTATACTTTCTGTGACTATACAGGTTTTCCATCACCATATGATTGTGTA
AATAAGATAGAAAAATGGATGAAGGAAGGTTTATATTAAGATTTACAATTACGGAAACAAATA
TAAATATGGAAGTCATAATTGAAGGGTTTAGTTATGAAGAAAGAGATGGGACTCGAGATGTATA
TTTTACATTAGATTTAAAAGAGTATAAAAGAATAAAGATACCAAAAGTAACTCCAAAACAATAA
CTATTATAGATAATAAGTTATAAATAACTGCTGATAGAATTAAATGAAAAGGCAGGTGATTTTT
TATTATTAAGATTTGGGTACACATAAAAAACGGAAGTATATATGACATAACTGACATAGTAGAC

Figure 1AA

AAGGTATCATGGTCAGGTGATTATAAATCTCCATCAAGGACACTAGAGTTTTCAATAATACAAT
CATCATTTGATGTAAATTTCCAACAAATCGATATACCAATAGCTAGTACAGTCTGTTTCTATGT
AGATGAGAAAGAACTCTTTAGAGGAATGATAATTAATAGGTCTAAAGATTCAAGCAGTAATGAA
ATTAGTTTTGTATCTAAAGATATGGGATTTTTACTTACACAAAGTGAAGTGTCATACAATTTTA
AAGATAAGTTAGTTGAAGACATAGCAAAGCAAGTATTTGCTGAAAATAGGCTTTCAGTTGGAAT
AATAGCAAAGACCAATGTCAAGTATACAAAGATGTTTATAGGAGTAAATGGTTATGACACAATA
ATGAGTGCATATACAGAAGCAAGTAAAAAGACAAAGAAAAAGTATATGATAGAGGCCAATTTAG
ATAAGTTTAATGTTATTGAAAAAGGAACTGTTACATTAAGTGTTATGTTTGAAGAGGGATTTAA
TATTATAAATACCACCTTTTCGGAGAGCATGGAAAATGTAAAAAATAAAGTAATAGTGGTAGAC
CAGTATGGAAGCAAGATTAGCGAAAAAATAGATAATGAAATTTTTAAGGAAGTAAATGTAATAA
TGCAAAAAGTAATTCAGCAACAAGAAAATCAAGATGTAGATATTGATAGCGAGTTTAATGGGAT
AGAAAAAAGCTGTTCTCTTAAAGGTTATGGAGATGTAAGTTGTATAACTGGTAGAGGAGTAAAA
GTTAAAGATTCTTATACAAAGCTTGTAGGACTATTTTATATAGATACAGACAAACATACTTGGC
AAAATGGAGAATATCAAATTGAGCTTGAACTTAATTTTCAAAATCTTATGGATGAAAAGTCAGC
AGGACAGGATGAACCTAAGGAAGAAAGTAATTTAGGGGGAGAAGATTATGCAGGAGGAAAAGAG
TTTACAGCAGAATTTACAGCTTACTGTCCTAGAAAAGAAGAAGGTGGAGATACAGATTGTAGAA
AGAAAAAACTTGACCCATCTAAAAAAACTTGCGCTGCTCCTATGGTTGGTAAATATGAGCAAAC
TTATTATACAAAAGAGTTTTTAAATAAACATCCTTTATTAAACTATGGAGATGAAATACAGGTA
ATTACAGGAGTTTCTGGTCGTGATGGAGTCTATAAAGTAAATGACGTAGGACCTGCAATAACTA
TAGAAAAGAATGGAACATACCATATAGATATTTTATTTGGAAATGTTGAAGAAGCTAGTAAATT
TGGAAGAAGAAAAGGAAAAATTATTATTGGTGGTTATTCTGGTAATGTATCTGATAAAGCTAAA
ATAGTAATATCAGAAGCAAAAAAACATCTAGGTAAACCTTATAAATGGGGTGGAAATGGACCAA
GTAGTTTTGACTGTTCTGGTTTAATGGTCTATTGTTTTAAAAAAGTTAATGTTAGTTTGCCAAG
AACGTCAAATCAACAATCTAAAAAAGGCAAGAAAGTAGAACAAAAAAATCTTCAAGCAGGAGAT
TTAGTATTTTTTCATAATCCAGTCAGCCATGTTGGATTATATATAGGTAATGGAGAATTTTTAC
ATGCTCCACAAAAAGGTGATGTAGTTAAAATAAGTAAGTTAAGTAGTAGAAGAGATTTTAACAC
AGCTAGGAGAGTATTATAAAAGGATGGTGATATAATGGCTAATCCAATAAATGAATTTATAGGA
ATAATAAGAGAAGAAGGAAAGTATCATAATCAACCTTCTTTTTTTATTGGAAAAATTAAAAGTA
AATTACCAGATTTAAAAATAGAGACAAATAACATCATATTAGAAAAAGAAGATATTTTGATAGA
TAGTTGGATGATTGATAGACAGCTAGAAACATTTGACACAGAAACAAATCAAGAACACCAGCAT
GAAGTAAAAAATCCTTTTATAGATAACTTTGAATCTGGGGATATGGTAATAATGTTTAGAATAG
GCGAAAAATTTGCTGTTGTAAGTAAGTTGGTGAGCTTATAATGAGTACAATATTTCCTTTTATA
GGTGTCCCAGAGGATTATATCTTACCTAAAACAGAAGAATTGCCAATCTTTCGTGAAGTGGCAT
GGGATTTTGAAAAAGATGAACCTATTTTAGAAAAAGGTGACTTTAAAATAATTGAAAAAAAAGA
AGCCTTAAAAGTTTGGATATACAAGTGTATAAAGACAAATAGATATGAACATGAGATATACTCT
TTAGAATATGGGACAGAGCTTTCAGAACTAATAGGACAAAAATATACAAAAGGTCTTACAGAAA
GTGAAGCTAGTAGATTCATAAAAGAGGCCCTTCTAATAAATCCATATATATTAGAAGTAAACGT
AAAAAGTGCTAACTTTAACAGAGACATATTGAGTGCAAATGTAAAAGTATCCACTATCTATGGG
GAGGTGGAAATAAATGTATAGTGACCAGACATATGAAGTAATAAAAAATAGAACTCTTGAAAAT
ATTAATCTTGATATTTATAAAGGAGAAGGTTCTTTTCTAAACAACATGGTATCTGGAAATAATC
TAGAACTTTCGAAGATATATCTAGAACTTTCAAAGATGCATAAAATGGCTTTTATACAAGACAC
ATATAACCAGTTTCTTGATAAAAGAGTCAATGAATTTGGTGTATATAGAAAGTTAGGTACAGAG
TCAAATGGAGAAGTTGAATTTATTGGAGAGAAAGGTACTGTAATAAATAATGGCACAATAATAT
CATATAGAGATTTACTATTTGTAGTAATAAAAGATGTAACTATTGGTAGTGAAGAAGGTGACAA
TAGCCCAGTTCAAGCTCTGGAAGTTGGTAAGAAATATAATTTACCTACAAATTGTGAATTTAAA
CTAGTTGATAATATATCTGGAGTAACAAAGATTACTAACACAAGAAGTTTTGAAGGTGGTACAG
ATATAGAGACAGATGAAGAACTAAAAGAAAGATTTTATAAAATCCAAAGAAATCAAGCTACAAG

Figure 1AB

TGGAAATAAAGCTCACTATGAAGAATGGGCTTTGGAAGTAGATGGAGTCTATAATGTTAAGGTT
TATCCAAGATGGGATGGTCCGGGAACAGTTAAGGTCTTGATATTTGGGAAAAATAATCAAGCTG
TTGATACAGAAACAATTGAAAGGTGTCAGCAACATATAGATGAAGAGAAGCCTATTGGACCAAC
TATAACAGTTGTGACACCATTACCAATAGAAATAAGTATAAGTGCAGTAATGAAACTAGAAGAT
GGATATACATTAGACAATGTAAAAGAATCTTTCCTAGAAAGTATAAATACATACTTTAGAGATA
TTAGAGGAGAGATAATCTATACAAAAGTAATGGGAATACTTATAAATACTACTGGTGTACACGA
TTTAAGTAACCTACTTATAAATGGAAGTACAGATAATATAACTATTAATGAAGATAAAATACCT
AGTGTAACAACTGTTAATTTTAGTGAGGTGGAAAATCAATGAAGCTAATTGATAAACTACCATC
ATTTGATAGAAATTACATTGTAGAGGAGATACAAGGTGCATACGATACAGAATTAAATATTCTT
AAAGAAGATATTGATGATACCTTTAACCAATTATTTGTTGACACTGCAACATGGGGATTAGATA
TGTGGGAAGACATACTCTGCATTGAAAAAAAAGAACTTGATTTTGACACAAGACGTAGCAATAT
AAAAGCTAAAATGAGAAGCAGAGGTACTAGTACTATTGAAGTTATAAAAAGTATATGTGAGGCA
TATACAAAATCAGAAACAGATATAAAAGTTTATAGTGATGAATTTACATTCGTATTGAGTTTTA
TAGCAAATAACTGTGACTATAAAACTCTTTTAGATTGTAGCGATATGATTGAAAGAGTAAAACC
TGCTCACTTATTACACTATTTAGAACCAATAATACTAGATAAAAGTATGGTCTATTGTGGTGGA
GGTATGGTATGTAGTGAAGAGGTAAAAGTTCATCCATACTTTGAACCAATTATAAAATGTAGTG
CTGTTGTAAACTGTGGAGCTGGAATGATAAGTAGAGAAGAAATAAAGGTTTATCCTTTAAGCAT
TAAATGCATTGAAAATAATTGTAAGATTAATATAGCTATTGCAAATGATACAGGTGTAGAAAAT
GTAGTAGTTTATCCTAAATCGGAGGTGGTATAATTGGAAGAAAAATTTTATATAATATTAACCA
AAATTGGTAGAGAAAAAATAGCAAATGCAACTGCACTAGGAGAGCTTGTTGGATTAACCAAGTT
TCAAGTTGGAGATAGTAATGGAGAATATTATGAGCCAACAGAGGAACAAACTGCTTTAAAGAAT
GTAGTTTGGGAAGGAAATATAAATTCTCTAAGAATTGATGAAAAAAATCCTAATTGGATAGTTA
TAGAGACTATTTTACCAGGAACAGTTGGTGGATTTATGATAAGAGAAGCTGCTGTTCTGGATAA
TGAGAATAATATAATAGCTATAGGTAAGTATCCAGAGACGTATAAGCCACGTGCTGAAGATGGC
AGTATTAAAGATTTGGTTGTAAAAATGATTTTACAATTGTCCAATACTTCAAATGTTACATTAG
AAGTAGACCCGACGTTGGTTTTTGTAACTCAAAAGGATATTCAAGATTTAGATGATAAGTTTGA
TAAAAATATAAAAGAAATAAAAGTAAAAATTGGCGAAGAACTCTTATCTACAGAAGCTAAAAAC
TTATCAGGAGCTATAAATGAGGTAGTAGAAAAAATTAAAAATATATCTATTGATGATGTAATAG
GAGGTCAAATACAAACTGAACTATCTGTATTAAAAAATAGTTACAATAAATTATCTGAAAAAGT
ATTAGATATCTTAATATACTTAGAATTAGAGTCAGAAATAGATGTAGATGAAGCTGGATATTGG
TATGATACCTTAACTAATGCTAAAAACATAATAGCTATAGAAGGCCTTAAGTTAGATTTAAATA
GAAAGTGTATAACTGGAGAACTTGGTAGTGTTACATTTAAGAATGTGGTGCTACCATTTAATGC
AAATAGAGTTAGATATATACATGAAATGGATAATAACTTTGTTGAAACAAAATCTAATAGGGCA
TATTCAATTGGTCAGACAGATATAACTTTAAATAAATATTCGTATGAAATAAGATAATTAGGAG
GTTTTTATAATGAAAAGAACTAAACTACTTCAAAGAGGTAATTTCTTTGGCGATAAAAATATGG
TAGTTGATGAATTTGATGAAGGGTATGATAATTATGACTTTATTAATTTTTTTACTGGATGTTG
TAACTATACATTTGGTCTAAAAAATAATAATATCTTGTATGGATGTGGAGATAATAGTAACTTT
CAACTTGGATTGGGAGAAGACAATACAACAAGAAAATTATTTACGAAAATACCAAATATATCTA
CCAATATTAAAAAAGTTGCATGTGGAGAATCTCATGCAGTTATACTTACTTCAGATGGAGAATT
ACTTGTCGCAGGTATAAATACAGATGGTCAAATGGGATTGGGATTAGAAAAAGTAGGGAAAACA
GTTTCTACATTTGAGAAGGTTCCAGAAATAAAAGGCGTAAAGGATATTGCATGTGGACTTCAAT
CAACATATCTTTTATACAATGATGGAACTTTATATGTTGCTGGAAATAATTTGTATGGTCAATT
AGGTCTAGGAACTAATGGAGCATCTGCAAATGTAAATACATTTACAAAAGTAGATGTTGACAAT
GTAAAGGCTGTATTTTCATATAATAAATCAGCTTTTATAATAAAGAATGACAATAAATGCTATT
CTACTGGTTTTAATAATCAAGGTCAACTAGGTTTAGGAGATAAGAATAATAGAGATTTATTTAG
TTTAGTTTCTATTAATGATGTTAAGACTATAGCTTGTGGTTCTGAACACACTGTGTTAATGACG
TATAATAATGATATATATGGTTGTGGAAAGGAAAAATGTTTTGGAAATGCACTTCAATCATCAC

Figure 1AC

TATTTACTAAGATAGAAGAAGTAAATATAAAAACTATTGCATGTGGTCATGGTAACACTATGCT
TATAGATAACAAAGGTACTTTAAAGGTTGCTGGAAATAATGATATATATCAGTTAGGTATAGCA
AATTACTCTGAGAATATAGATAATTCATTTATAGATTTAAAAAATATTGTAGCTAAGAATATTT
TCATTGGTTTATCACATAGCATACTAATTGATTCAAATAATGATTCATATTGTACAGGAGATAA
TACTTATGGACAATTAGGTTCGTTTTTTGATGATATGCACATTGTAGAATTTAAGAAAATGGAT
AGTGAAAAATATAGTTATAGTAATTATATAAATTTAATTAAATCTGAGGATAAATTAACTTTAT
TAAAAGAAGAAATGGAAATAAAGGATATTGAACTTCCACTAGATATACATTCTGTAAGAGATGT
CGTTTTTAGTCCTTATTGTACTCTGGTTATTTTAGGGAATGGAGATGTATATGGTCTAGGAAAT
AATAGATACAAAGGAATGGGTTCTGACTTACCAAGTCAATTAAATGAGTTGACAAAATTAAGTA
TCTCTAATGTAAAGTCTATAGTAGCATCAAAAAATATTTCTGGAGGAATATTCTACATTAAAAA
TGATGATACTTGTTATTATTCTGGACCAAATAGTAACTCAATAGCAGGTGTTCTTCCTTCTAAT
TCAGATGTATTTAAGAAAATATCTATAGATAATGTAAAAAAAGTTGTTATAAATACTGATTTAT
CAAACTGGTTTTCATTAATTGTAACTAATAATAAGCAAATATACACTTCTGGAAAGAGTTCAAG
TTATGTTAATGGACTTAGTAATGCATTAATAAGTCAATATACTGAGATTAGCCTTAGTAATGTA
ACTGATGCTTATAGTTCATATAATGCAACATTTATTGTAGTTGATGAAAAAAAGGTATATGCAA
CTGGTATAAATACAAATTACCTGTTAGGTTTAGTACTTCTGATGGATCTAATGTAAATCTAGG
TTTATTAAGTGATTGGTATTATATAAATATATCAGGGTCAAGTTATAGTAGAGTTTCATGCACG
AATAATATTACTAAAATTAATAATATTATCATATATGAGTATGTAACTGTATTTTGTACAAACA
TTGGATCTTTTCTAACTGGATACCATGGTACTTCATGGACAAAACCAACTGATTCAAGCTATAG
AGTTCAATATCAGGGAATTTCATATGCAGGATATCTTGATTCTTATATATATAATTATTATCCT
ACAAGATGTACACAATCATCATCTTCTACAACTTTTGCTTATTTATATAATGGGGAATCGTCAA
GTAATTTAAAAAATGTCAATCCAGATAATTTACTTATTTCTGGAGGTTCATCTTATATACATCA
ATATGGAAGGAATTATCTTAACAATCAATCATCTAATAATATTGCAGCATCTAATATAAATTCA
GGTCCTATTACCTCTGATAAAGCCATATTTTTATATAAAGCTCTATTGTATTTATCTTCTAACA
CGCTATATGGTTTTGGGAATATATCTGAAAGTGCAAAAGAACTAGATGTTTCAGATACACAAGA
TGGATATAATGCCACTAATTATAAAAAGGTAATGAAAAATATAAAAAATATATTTATACCTCCT
TATGATTTAAGTAGAGATAAAACTAGATTTGCAATATTAACTGATAAGAGCTTATTTATATGTG
GATATAACTCTAAGGGTACGCATGGTATATCAGTTAATAGTAGTTTAAATTTAAATAATAAGAT
AAATTACAATAAAAAGAATAGCAGTAGTGAAATATCTTCTAATATACAAGAAATATATAGCCAT
TCAAAGTCTACATATTTATTAACTAATAATAATATGCTTTACAGTGTTGGTTTAAATGATGTAG
GTCAATTAGGAGTGGGAGATGAGATAAATAGAAAGGTATTTACTAAAATAAATATTGATAATAT
AAAATCTATAAATGTAAATAGATTTACTGACAATAGTAAACATGCATTTGCGATAAAAAATGAT
AATACCTGTTATGCTGTTGGTTTAAATAATTCTGGTCAGTTAGGAATAGGAGATAATGTAAATA
GAAATATATTTACTAAAATAAATGTTGAAAATGTAAAATATGTAGCTGTATATGGAAACACATC
TCTATTATTAACTAATGATGGTCTTTTATATGGAGCAGGTAATAATGGAAAAGGACAGTTAGGA
TTGGGTGATACTACAAGTAGGAATATATTTACACGTATACCTATAAATGGTGTTAGAGATGTAT
ATCTATGTAATGATGTATCAATCATTGTTAAAAATGATAATACATGCTATGTATGTGGACTTGT
AAATGGCTATTTTGGGTTTACTGAAGGAAGTATAAGTACATTTACAAAAATAAATATTGAGAAT
GTAAAATCTGTTGTGACAGCAGGAAGTGAAGCTACATTTTTTATAACAAATGACAATATGATTT
ATACTACAGGGAAAAAAGAGAGGGTATTCTTTTCAACAGAGACTAATGATATAAAGGGGATACG
AGTAATTAATAATATTATAAATGCAAAAAAAATAGTAGTTAATGGATATACTTCAGCCATTTTA
ACAAATGACAATAAACTATTTGTTGGAGGTCTTAGTGGATATGGAAGTATAGCAAATAATAATA
ATACAAATAGTGTGGAAGATGTTAAAGATGTTTTTGTAACAGCTAATAATACACTTTATATAGA
TAATAATAACAATTTGATATCATCAGGTAGAGATACTTATGGTATATCTGATGAATCTTATAGG
GATATGTCAGTTCCATATTATAAAGTATCTATAAAGAAAGATGTTGATACTGTATTTTCTAGTT
ACAATACTATATTTATTAAAGATATATATGGAAAATTTTATTCTTCAACAAGAGATAATAGATA
TAATCATTTAGGTATTCACCATAGATATGATAATGATAAAAATGAAGCTCTTGAAGGTTCCCTA

Figure 1AD

CATTCATATTTTAAAACAGATAACACATCAGATAAAATAGTTTTTAATAAGAAAAATGAAAAGC
TAGTAATGTTTAATGATAAGTATATAAAAACAAATAATAAGTATATAAATTATAAAAACATATT
TAAAGATAATTTTAAGTATACTTCAATAATATTGCCATTTGAGGTATCTGATATTGATATATCA
AAAACACATTCATTGGCTGTTGCTAAGGATGGCAAGTTATATGGAATAGGAAGTAATTCATATA
AAGAAATTAATCAAACCCTTGAAGATATAGAATTATTAACTCTTACTGAAGTAAATATATCAGA
TGTCAAAAAAGTTGCTTGTGGAGATAACTACTCCTATATTATTAAGACAGATAATACTCTATGG
TCATATGGAAAGAATACTGAGTACCAATTGGGAGTTGGCCACAATAATGATGTAAGAGAGTTAC
AAAAGGTTACTGGATTACCTTCTGTTAAAGATATAAGTATATATAACTCAATGACACTTGTTTT
AACTAATGAGGGAGAGTTGTACGCTCAAGGGTACAATACAAATGGATTATTTGGACTAGGAGAA
AGTGAAAAAGATAAGATAATAAGAACTTTTACTAAAGTATTAACTAATGTTAAAGAAATTAAGT
CACATAATGATGACCACATACTAGTAATTAAAAATGATAATAGTCTATGGATAACTGGTAAAAA
TAAATCTATGTATAAAATATCTATATCAATTACTGATTTATATGAATTTACTAAAATACCAATT
CCTGAACATCTAAATGATATTTTAGATATAGAGCTTTCAGATGATACAATATACATGATAACAA
AAGTAGATACAAGTAAAGCATCTATAGAAATAGTTGAAAAATCAATATCTCAAGTGAGAGTTGT
AGTACAAGACCCTAATAATGTTATAGAAAAACTTGAAATGTTTATAAATGATGAATTAATATCT
ACTAAGACTAATTTGGAAATAAATAGCATTATATTTGAGATACCACAAAATAAAATAGTATTAG
GAGAAAATAAGATACTGATTAAAGCCAGTAGTCCTACAGGCGATTTATATTCAAGTATGTTTAT
ATTTAAATCAGAAACAGGGCTTAAAGTAAAAAAGGATTCTATTTTAATGATAAACAATAAAGTA
TATTCAATCATAAACATTACTGAAAATAACACTGACTTAATAGTAACATTAAATGAGGGATTAA
AGGATGATATGATGGAAAACAATCCTATATATCAATTAATAAATAAAACTAAAGTTCAAGTAAA
AATAAATAAATCTGACTTATTCAAAGACATGAAACTAGTTGAAATCAAAAAATCAGACTCAAGT
TACCAAGAAATCTATGAATTAGAAGAAGCCAACATAAAAAGTGCTCAGCCTAAAATCATAGTAG
AAAAAGGAGATAAATGGACAGCTATAAAACGTCCATCTATGATTTTTAGATATGATGCTGAAAA
CAACGAGCCACAAGCTTAAAATGGAGGTGTGAAAATTGTTTAAATTCGATAAAAATAAAATAGA
ACAAATCAAACAAGGTAGAAAAGTAGAAATGCAGTATAAAGACATTTCAGACATAAGTATAGGT
CAAGTAAAGCAAGATGATGATATAACAAATAATTTTATAGCAAATGTAGAAATATATGAGATGT
TGTTAAATCAAAGTTCTGTCAATGAAGCAAGTAATATAAGCACTTTTAGTGTAAGAAAATCTGG
AGGTGAGAGTGGAATGGTAGAAGTATATGTAGCTTTAATTTTAAGAGGCAAAAAAACAATAGAA
GAAGTACCAGCAGTAATTAGAGAGCAAGTTAGAATTAGATGTAAAGAATTAGAAATACCAGTTG
AATAGTAAATTTAGAATAACTATGTATTAGTTATTTTTTTTATGTAAAGTACAAGGTCTTAACT
TTAATAAGTAAGCCTTGTACTTATTTTTTGTTACATTAGAACTTGTATATATATTTATTATTTA
TTCAATCTATAAATTACACCTACAATTTAAAGTACAGAAGATTAAATTGATAATCCTGAAAATA
TAATATTGCATGATGTAAGAATACAACAAAAATTAAAGCTATAAGTATAAAAAATTTAGACAAT
AGGAGGCTATAATGGATAAATTAATAACCGAATTGAGTAGTCTAGGGGCAATAGGTATACTATG
TGCTCTATTATTTAAAAATACTATGCAGGAGAAAAAAGAAGATAGAGACATGTATAAAAAAACT
GTAGAAAATTTTATAGAATTATCTACACAACAACAAGAAATAAACAAAAATATACTTGTTCAAA
TGGGTATAATGAAAACAGATGTAGAGGAAATTAAGGAAGATGTTACTGATATAAAAGGTATGTT
ACAAAATGGTGTATAACATGAAAGAGTAGCACCAGATTATATATTGTTAGGAAAAGATAAAGTA
GTATTGTAGATAGTTCACTATTTTATTGAGAAGGATTTAATATTTAAAATATTAATTAAAAAAA
GTAATAAAAATAACATATAAAAATTAAAAAAGGAGTTAAGCTTAAATTTGAGGCGCG

SEQ ID NO:62 >CD4-1359
MNNLDKLFELASQEEIIIHYTTYIAGDLEGLYINKHGIKIISLLSNLKQNSKKLTSILAEELGH
HFTSLGYYVSSYNDYYTKIIIDKCENKALKWACEFLITEEDIINIINSGITCVYEMADILNVDI
TFFQKRLEFLSLKKQSLQLGNNKYLILTNLPYFYIFDPIS

Figure 1AE

SEQ ID NO:63 >CD4-1360
MFAKRLRELRKEFGLTQRELGEKVGVSQRVLGYYETENRFPDEHILNKLADVFNVSVDYLLGRT
LVKENIDTVAAHRKNPHEELPEEAQEQLNDYIEFLLNKYKKK

SEQ ID NO:64 >CD4-1360A
MFKNNLKYYRKCKGMTQIQLARKAGITNDYISQIERGIKNPGLLMAKKISSILEQNIEEVFFIQ
L

SEQ ID NO:65 >CD4-1361
MENKKDILFKETDKRLHNYKYLDIKIKNINLDIKRCENEYSGCGAMVYTEKTSNTYNISSSVEN
EVLKREERLRKLKMEKEDIEIEKEKIENALTCLNDIEMEFFNLFYNSKTKNNMTYISMKLHLDR
TSCYNLKKKMIFKLSEIL

SEQ ID NO:66 >CD4-1362
LLKYKEILETIIEILKKNFTESIFIDDESVQGSEGSCFFVSILSVICTPVMLNTNNKDIVISIK
YLPKPQSKSIRMYEISDELNKLFNRNIKVTDRKLNITKLEQSIKKEESIYVLNFTFTLNYLDSV
YEEDVVYENMKEINLNLGE

SEQ ID NO:67 >CD4-1363
MAIGLPSINISFKELATTVKERSARGIIAMVLKDAKALGLNEIHEKEDIPVDLSAENKEYINLA
LMGNVNTPNKLLVYVIEGEADIQTALDFLETKEFNYLCMPKAVEADKTAIKNWIIKLRDIDKVK
VKAVLGKVVGNHEGIINFTTEDVLVGEKKYSVDEFTSRVAGLIAGTPLSQSVTYTKLSDVVDIP
KMTKVDAESRVNKGELILIKEAGAIRIARGVNSLTELTAEKGEMFQKIKIVDTLDIIHSDIRKV
IIDDYIGKVTNSYDNKCLLIVAIKSYLEELEKSALIESDSTVEIDFEAQKSYLKSKGVDLSYMT
LQEIKEANTGSKVFLKAKIKVLDAMEDIDLSIEI

SEQ ID NO:68 >CD4-1364
MANMEARNVMSGTWGELWLDGNKVAEVKKFQAKMEFTKEDIIIAGQMGTDTKYMGYKGKGSITL
YHVSSRMHKLIGEKIKRGSEPRFVAISKLNDPDSYGAERIAVKNIAFDDLTLADWEVGVKGEIE
APFTFTEYDFLDII

SEQ ID NO:69 >CD4-1365
MSENGLSKNINIVDLLLNSDTENLERPSTIVELKRLSTIFGQEFKVMCRALTISKDEEIQNTCL
KIDENMKTDIDLPEMQMLTIIEGVCDLDGKLLFKNKELMDKFKAPTPKELARKLLLPGEITNLY
RILQDVMGYGKNAVIEEVKN

SEQ ID NO:70 >CD4-1365A
MYYYWKKKGIRPSLFYAMDKGELKLIEAFFALEIEEEVEKMKHGYGVCPLTGGGM

SEQ ID NO:71 >CD4-1366
MGNVREEGINMYLTDNYTPKMNQIISVTDNFRRATVAVSLSTNVMASSIKNSIGSASNRVNSLN
SSLRKVQTTASSVSSTMTKLSSSINAVSGVIGSLNGSIMRLAITIAMIIDYFNKLIQKKNEFNS
NIMIILIFKAKSDEVEKTKNKLLGNLKKIGGKIWNIVIKAKDMTKRVISSILGKLKQVEKRPYQ
GSINLKDMVSSAMGRILPKLMLFKNTFWSGVIAIKDMASGIISKVFPKLRLFAGKVWSGAIAVK
DMASGILGSIKGKISDLTNGATIGVAVKKGVDLLGQEQNQKVVLESVMKRNTGKVNQIDVDDYY
GSLVRMANDTPFDPEDVVAMGTKAKMISNITGGKKEKDITQAMVDVRALNMNTSSEQDVSAAFL
SAAKGNMESLNTLVGENYKTFDEALEGISVKQMGLAKEMSNTIPGIISGAQTSINNGLKSIVKP

Figure 1AF

FDDILGQGLKKIKTFIESGLGNLAGLSEKMAGKIGNVMNGKIIIGNKYDQMQSRSVKNGKEFSD
STQYRISNEAEKRKMMVENKQERFENHAATMIGNAPKAIVNAGSTLLQNIDFTALIDSLLPVVN
LVNNLLDSINNKSPIAQGLISIFGTIVTTAFQLIGPVVEAVSPIITRIFTFLGEYAPQINNFIE
TLGVIWKTVWETLGPLLETGWKIIEPILGAFFNILDKVCKIVKDICKWWQTMINKIKNGSITGT
VLNLVEKSKKNYKDNPYAGTKAGDSGKAYSGKKGNNAFGLNYVPYNDYQTRLHEGEMVLTKQEA
NQYRSRKNGGNINIAKLADTIVIREEADIEKITSKLVASIQLAQLGGVL

SEQ ID NO:72 >CD4-1367
MEMWLRQAEDRFRFPVFPSSFSINGKAAVNSSSILKIGEIATFGGVALKSISISSFFPNKDYTF
CDYTGFPSPYDCVNKIEKWMKEGFILRFTITETNINMEVIIEGFSYEERDGTRDVYFTLDLKEY
KRIKIPKVTPKQ

SEQ ID NO:73 >CD4-1368
MIINRSKDSSSNEISFVSKDMGFLLTQSEVSYNFKDKLVEDIAKQVFAENRLSVGIIAKTNVKY
TKMFIGVNGYDTIMSAYTEASKKTKKKYMIEANLDKFNVIEKGTVTLSVMFEEGFNIINTTFSE
SMENVKNKVIVVDQYGSKISEKIDNEIFKEVNVIMQKVIQQQENQDVDIDSEFNGIEKSCSLKG
YGDVSCITGRGVKVKDSYTKLVGLFYIDTDKHTWQNGEYQIELELNFQNLMDEKSAGQDEPKEE
SNLGGEDYAGGKEFTAEFTAYCPRKEEGGDTDCRKKKLDPSKKTCAAPMVGKYEQTYYTKEFLN
KHPLLNYGDEIQVITGVSGRDGVYKVNDVGPAITIEKNGTYHIDILFGNVEEASKFGRRKGKII
IGGYSGNVSDKAKIVISEAKKHLGKPYKWGGNGPSSFDCSGLMVYCFKKVNVSLPRTSNQQSKK
GKKVEQKNLQAGDLVFFHNPVSHVGLYIGNGEFLHAPQKGDVVKISKLSSRRDFNTARRVL

SEQ ID NO:74 >CD4-1369
MANPINEFIGIIREEGKYHNQPSFFIGKIKSKLPDLKIETNNIILEKEDILIDSWMIDRQLETF
DTETNQEHQHEVKNPFIDNFESGDMVIMFRIGEKFAVVSKLVSL

SEQ ID NO:75 >CD4-1370
MSTIFPFIGVPEDYILPKTEELPIFREVAWDFEKDEPILEKGDFKIIEKKEALKVWIYKCIKTN
RYEHEIYSLEYGTELSELIGQKYTKGLTESEASRFIKEALLINPYILEVNVKSANFNRDILSAN
VKVSTIYGEVEINV

SEQ ID NO:76 >CD4-1371
MYSDQTYEVIKNRTLENINLDIYKGEGSFLNNMVSGNNLELSKIYLELSKMHKMAFIQDTYNQF
LDKRVNEFGVYRKLGTESNGEVEFIGEKGTVINNGTIISYRDLLFVVIKDVTIGSEEGDNSPVQ
ALEVGKKYNLPTNCEFKLVDNISGVTKITNTRSFEGGTDIETDEELKERFYKIQRNQATSGNKA
HYEEWALEVDGVYNVKVYPRWDGPGTVKVLIFGKNNQAVDTETIERCQQHIDEEKPIGPTITVV
TPLPIEISISAVMKLEDGYTLDNVKESFLESINTYFRDIRGEIIYTKVMGILINTTGVHDLSNL
LINGSTDNITINEDKIPSVTTVNFSEVENQ

SEQ ID NO:77 >CD4-1372
MKLIDKLPSFDRNYIVEEIQGAYDTELNILKEDIDDTFNQLFVDTATWGLDMWEDILCIEKKEL
DFDTRRSNIKAKMRSRGTSTIEVIKSICEAYTKSETDIKVYSDEFTFVLSFIANNCDYKTLLDC
SDMIERVKPAHLLHYLEPIILDKSMVYCGGGMVCSEEVKVHPYFEPIIKCSAVVNCGAGMISRE
EIKVYPLSIKCIENNCKINIAIANDTGVENVVVYPKSEVV

Figure 1AG

SEQ ID NO:78 >CD4-1373
LEEKFYIILTKIGREKIANATALGELVGLTKFQVGDSNGEYYEPTEEQTALKNVVWEGNINSLR
IDEKNPNWIVIETILPGTVGGFMIREAAVLDNENNIIAIGKYPETYKPRAEDGSIKDLVVKMIL
QLSNTSNVTLEVDPTLVFVTQKDIQDLDDKFDKNIKEIKVKIGEELLSTEAKNLSGAINEVVEK
IKNISIDDVIGGQIQTELSVLKNSYNKLSEKVLDILIYLELESEIDVDEAGYWYDTLTNAKNII
AIEGLKLDLNRKCITGELGSVTFKNVVLPFNANRVRYIHEMDNNFVETKSNRAYSIGQTDITLN
KYSYEIR

SEQ ID NO:79 >CD4-1375
MQYKDISDISIGQVKQDDDITNNFIANVEIYEMLLNQSSVNEASNISTFSVRKSGGESGMVEVY
VALILRGKKTIEEVPAVIREQVRIRCKELEIPVE

SEQ ID NO:80 >CD4-1376
MDKLITELSSLGAIGILCALLFKNTMQEKKEDRDMYKKTVENFIELSTQQQEINKNILVQMGIM
KTDVEEIKEDVTDIKGMLQNGV

Figure 1AH

Diffocin 16

```
CD108        MKQNKLLQRGAYFNDKNILIDDFDKRYNDYDFVEFFTGISNSTFGLKSDGNLYACGDNTG 60
43593        MKQNKLLQRGAYFNDKNILIDDFDKRYNDYDFVEFFTGISNSTFGLKSDGNLYACGNNTG 60
CD16         MKQNKLLQRGAYFNDKNILIDDFDKRYNDYDFVEFFTGISNSTFGLKSDGNLYACGDNTG 60
CD126        MKQNKLLQRGAYFNDKNILIDDFDKRYNDYDFVEFFTGISNSTFGLKSDGNLYACGDNTG 60
CD4          MKRTKLLQRGNFFGDKNMVVDEFDEGYDNYDFINFFTGCCNYTFGLKNNNILYGCGDNSN 60
CD123        MKRTKLLQRGNFFGDKNMVVDEFDEGYDNYDFINFFTGCCNYTFGLKNNNILYGCGDNSN 60
             **:.****** :*.***:::*:**: *::***::**** .* *****.:. **.**:*:.

CD108        FQLGLGKDSSERRMFSKVK--IDNVKYVSCGSKHSVAVTKDGFAYGAGTSNVGQLGVIES 118
43593        FPLGLGKDSSERRMFSKVK--IDNVKYVSCGSKHSVAVTKDGFAYGAGTSNVGQLGVIES 118
CD16         FQLGLGKDSSERRMFSKVK--IDNVKYVSCGSKHSVAVTKDGFAYGAGTSNVGQLGVIES 118
CD126        FPLGLGKDSSERRMFSKVK--IDNVKYVSCGSKHSVAVTKDGFAYGAGTSNVGQLGVIES 118
CD4          FQLGLGEDNTTRKLFTKIPNISTNIKKVACGESHAVILTSDGELLVAGINTDGQMGLGLE 120
CD123        FQLGLGEDNTTRKLFTKIPNISTNIKKVACGESHAVILTSDGELLVAGINTDGQMGLGLE 120
             * ****:*.: *::*:*:     *:* *:**..*:* :*.**    ** .. **:*:  .

CD108        TV---YYEFTKLP-IDDVKTVACGYDFTFVLKNDGTLYSAGLNSSGQLGLG---DTNNRV 171
43593        TV---YYEFTKLP-IDDVKTVACGYDFTFVLKNDGTLYSAGLNSSGQLGLG---DTNNRA 171
CD16         TV---YYEFTKLP-IDDVKTVACGYDFTFVLKNDGTLYSAGLNSSGQLGLG---DTNNRA 171
CD126        TV---YYEFTKLP-IDDVKTVACGYDFTFVLKNDGTLYSAGLNSSGQLGLG---DTNNRA 171
CD4          KVGKTVSTFEKVPEIKGVKDIACGLQSTYLLYNDGTLYVAGNNLYGQLGLGTNGASANVN 180
CD123        KVGKTVSTFEKVPEIKGVKDIACGLQSTYLLYNDGTLYVAGNNLYGQLGLGTNGASANVN 180
             .*      * *:* *..** :*** : *::* ****** ** *  ******    : *

CD108        TFTKVNIDSVKDVVTYNQSVFIIKMDGTAHACGLNSNGQLGINSTLNKSVFNKIEGMDNV 231
43593        TFTKVNIDSVKDVVTYNQSVFIIKMDGTAHACGLNSNGQLGINSTLNKSVFNKIEGMDNV 231
CD16         TFTKVNIDSVKDVVTYNQSVFIIKMDGTAHACGLNSNGQLGINSTLNKSVFNKIEGMDNV 231
CD126        TFTKVNIDSVKDVVTYNQSVFIIKMDGTAHACGLNSNGQLGINSTLNKSVFNKIEGMDNV 231
CD4          TFTKVDVDNVKAVFSYNKSAFIIKNDNKCYSTGFNNQGQLGLGDKNNRDLFSLVS-INDV 239
CD123        TFTKVDVDNVKAVFSYNKSAFIIKNDNKCYSTGFNNQGQLGLGDKNNRDLFSLVS-INDV 239
             *****::*.** *.:**:*.**** *...:: *:*.:****:... *:.:*. :. :::*

CD108        KQIACGSSHTILIKNDGTMYTTGSNGYGQLGTGNNNNSIVFTLSSINNVKYASCGNNHTM 291
43593        KQIACGSSHTILIKNDGTMYTTGYNGVGQLGTGNNNNSIVFTLSSINNVKYASCGNNHTM 291
CD16         KQIACGSSHTILIKNDGTMYTTGYNGVGQLGTGNNNNSIVFTLSSINNVKYASCGNNHTM 291
CD126        KQIACGSSHTILIKNDGTMYTTGYNGVGQLGTGNNNNSIVFTLSSINNVKYASCGNNHTM 291
CD4          KTIACGSEHTVLMTYNNDIYGCGK----EKCFGNALQSSLFTKIEEVNIKTIACGHGNTM 295
CD123        KTIACGSEHTVLMTYNNDIYGCGK----EKCFGNALQSSLFTKIEEVNIKTIACGHGNTM 295
             * *****.**:*:. :. :*  *     :   **  :* :**  .  *:*  :**:.:**

CD108        ILKYDNTLFSTGQNNYGQLANANKDVASRNTFVKVNVENIKDIKCGSQFNFLINGSKEIF 351
43593        ILKYDNTLFSTGQNTYGQLANANKDVASRNTFAKVNVENIKDIKCGSQFNFLINGSKEIF 351
CD16         ILKYDNTLFSTGQNNYGQLANANKDVASRNTFAKVNVENIKDIKCGSQFNFLINGSKEIF 351
CD126        ILKYDNTLFSTGQNNYGQLANANKDVASRNTFAKVNVENIKDIKCGSQFNFLINGSKEIF 351
CD4          LIDNKGTLKVAGNNDIYQLGIANYSENIDNSFIDLKNIVAKNIFIGLSHSILIDSNNDSY 355
CD123        LIDNKGTLKVAGNNDIYQLGIANYSENIDNSFIDLKNIVAKNIFIGLSHSILIDSNNDSY 355
             ::. ..**  :*:*   **. ** .    *:* .::    *:*  * ...:**:..:: :

CD108        VSGCNLAGQLGSFFHTTFLYEFSKVQSS--NLDNYSGLLVNDDYLYVTKDNSEFLNVKLS 409
43593        VSGCNLAGQLGSFFHTTFLYEFSKVQSS--NLDNYSGLLVNDDYLYVTKDNSEFLNVKLS 409
CD16         VSGCNLAGQLGSFFHTTFLYEFSNVQSS--NLDNYSGLLVNDDYLYVTKDNSEFLNVKLS 409
CD126        VSGCNLAGQLGSFFHTTFLYEFSNVQSS--NLDNYSGLLVNDDYLYVTKDNSEFLNVKLS 409
CD4          CTGDNTYGQLGSFFDDMHIVEFKKMDSEKYSYSNYINLIKSEDKLTLLKEEMEIKDIELP 415
CD123        CTGDNTYGQLGSFFDDMHIVEFKKMDSEKYSYSNYINLIKSEDKLTLLKEEMEIKDIELP 415
              :* *  *******.  .: **.:::*.  . .** .*: .:* * : *:: *: :::*.
```

Figure 8A

```
CD108           DNFQDYKKIELTDNNMFIVMNDGTLYACGLNNYGQLGLGDTVNRSVMTKVDIDNVLDIKG 469
43593           DNFQDYKKIELTDNNMFIVMNDGTLYACGLNNYGQLGLGDTVNRSVMTKVDIDNVLDIKG 469
CD16            DNFQDYKKIELTDSNMFIVMNDGTLYACGLNNYGQLGLGDTVNRSVMTKVDIDNVLDIKG 469
CD126           DNFQDYKKIELTDSNMFIVMNDGTLYACGLNNYGQLGLGDTVNRSVMTKVDIDNVLDIKG 469
CD4             LDIHSVRDVVFSPYCTLVILGNGDVYGLGNNRYKGMGSDLPSQLNELTKLSISNVKSIVA 475
CD123           LDIHSVRDVVFSPYCTLVILGNGDVYGLGNNRYKGMGSDLPSQLNELTKLSISNVKSIVA 475
                 :::. :.: ::    ::::.:* :*. * *.*  :* . . : . :**:.*.** .* .

CD108           NGNST---FVLKNNGTLYSCGYNSSGILGLKDNTNRNIFTKIEIENIKEFCVESN----Y 522
43593           NGNST---FVLKNNGTLYSCGYNSSGILGLKDNTNRNIFTKIEIENVKAFCVESN----Y 522
CD16            NGNST---FVLKNNGTLYSCGLNSNGQLGLRDEVNRNIFTKIEIENVKDFCVGSN----Y 522
CD126           NGNST---FVLKNNGTLYSCGLNSNGQLGLRDEVNRNIFTKIEIENVKDFCVGSN----Y 522
CD4             SKNISGGIFYIKNDDTCYYSGPNSNSIAGVLP-SNSDVFKKISIDNVKKVVINTDLSNWF 534
CD123           SKNISGGIFYIKNDDTCYYSGPNSNSIAGVLP-SNSDVFKKISIDNVKKVVINTDLSNWF 534
                . * :   * :**:.* * .* **..  *:    * ::*.**.*:*:* . : ::    :

CD108           IVALNHSKELYGWGNQS--YIVYGDNRNYPYKDTRVSNVEKIATWSDTLYILDSTGATKT 580
43593           IVVLNHSKELYGWGNES--YIVYGNSRNYPYKDTRVSNVEKIATWSDTLYILDSTGATKT 580
CD16            VIALNHSKEVYGWGNNP--YNNIEKTSNYPYKQG-ISNIEKIAAYDYSVYMINSEGKLYV 579
CD126           VIALNHSKEVYGWGNNP--YNNIEKTSNYPYKQG-ISNIEKIAAYDYSVYMINSEGKLYV 579
CD4             SLIVTNNKQIYTSGKSSSYVNGLSNALISQYTEISLSNVTDAYSSYNATFIVVDEKKVYA 594
CD123           SLIVTNNKQIYTSGKSSSYVNGLSNALISQYTEISLSNVTDAYSSYNATFIVVDEKKVYA 594
                 : :.:.*::*  *:..       .     *.:  :**: .  :    : ::: .     .

CD108           IGYSYNGSGGYPAPSSSSTYR----EGGYINKNTSYRTLEFYNTSKTKLVNLFAFYNGCV 636
43593           IGYSYNGSGGYPAPSSSSTYR----DGGYINKNTSYRTLEFYNTSKTKLVNLFAFYNGCV 636
CD16            SGYNYNYQLGKGNNSNQSKAL----VSQCRTNSTSSTSNGLR--TLPKITNVFPFYDGCA 633
CD126           SGYNYNYQLGKGNNSNQSKAL----VSQCRTNSTSSTSNGLR--TLPKITNVFPFYDGCA 633
CD4             TGINTNYLLGFSTSDGSNVNLGLLSDWYYINISGSSYSRVSCTNNITKINNIIIYEYVTV 654
CD123           TGINTNYLLGFSTSDGSNVNLGLLSDWYYINISGSSYSRVSCTNNITKINNIIIYEYVTV 654
                 * . *   *    ....            . . *  :      . .*: *:: :     .

CD108           FVDENGLAYCIGENNINFRGGSTTNENNSLRFINNSGVVYYT--------NTDGTDYTCYQ 688
43593           FVDENGLAYCIGENNINFRGNSTTNENNSLRFINNSGVVYYT--------NTDGTDYTCYQ 688
CD16            IIDEGGYVYLTG-----YHGYLRT--LNSSPSISDYSRYGT--------FIEATNSNHNT 678
CD126           IIDEGGYVYLTG-----YHGYLRT--LNSSPSISDYSRYGT--------FIEATNSNHNT 678
CD4             FCTNIG-SFLTG-----YHGTSWTKPTDSSYRVQYQGISYAGYLDSYIYNYYPTRCTQSS 708
CD123           FCTNIG-SFLTG-----YHGTSWTKPTDSSYRVQYQGISYAGYLDSYIYNYYPTRCTQSS 708
                :  : *  :  *     ::*    *    :*   :.  .   :             *  .

CD108           WTYKLIRCSIFDSPQNIIGNSKNILYLSKNNSTFKCTGNCITYGINSQNWYSYFS----- 743
43593           WTYKLIRCSIFDSPQNIIGNSKNILYLSKNNSTFKCTGNCITYGINSQNWYSYFS----- 743
CD16            Y---FIQETDFSGIEKVIGMSNNILFFKKGSS--YITGYPKTFGSTITGHRSYTS----- 728
CD126           Y---FIQETDFSGIEKVIGMSNNILFFKKGSS--YITGYPKTFGSTITGHRSYTS----- 728
CD4             SSTTFAYLYNGESSSNLKNVNPDNLLISGGSS--YIHQYGRNYLNNQSSNNIAASNINSG 766
CD123           SSTTFAYLYNGESSSNLKNVNPDNLLISGGSS--YIHQYGRNYLNNQSSNNIAASNINSG 766
                    :       .. .:: . . : * :. ..*          .:  .  .      *

CD108           -DSSNGAIALGNEFILKNYSGECLLKGYG----KATNGEFGNSTNISSISNYDTGLKDIK 798
43593           -DSSNGAIALGNEFILKNYSGECLLKGYG----KATNGEFGNSTNISSISNYDTGLKDIK 798
CD16            -INSE-SSNLGSNFIIYHSN--SKLYGKG----IANSGQFGNSTNIDGTSNYDTGLKDIK 780
CD126           -INSE-SSNLGSNFIIYHSN--SKLYGKG----IANSGQFGNSTNIDGTSNYDTGLKDIK 780
CD4             PITSDKAIFLYKALLYLSSN---TLYGFGNISESAKELDVSDTQDGYNATNYKKVMKNIK 823
CD123           PITSDKAIFLYKALLYLSSN---TLYGFGNISESAKELDVSDTQDGYNATNYKKVMKNIK 823
                  .*: :   * . ::     .     * * *     *.. :..:: :  . :**.. :*:**
```

Figure 8B

```
CD108       DIIV------KNNTVVVVDKNNNIYVTGANQFNKLGIGEYNNQPIRKFTNITEQSNSFIF 852
43593       DIIV------KNNTVVVVDKNNNIYVTGANQFNKLGIGEYNNQPIKKFTNITEQSNSFIF 852
CD16        DIIV------KGNTVVVVDKNNNIYVTGMNQNNKLGIGEYNNEPVKKFTNITEQSNSFIF 834
CD126       DIIV------KGNTVVVVDKNNNIYVTGMNQNNKLGIGEYNNEPVKKFTNITEQSNSFIF 834
CD4         NIFIPPYDLSRDKTRFAILTDKSLFICGYNSKGTHGISVNSSLNLNNKINYNKKNSSSEI 883
CD123       NIFIPPYDLSRDKTRFAILTDKSLFICGYNSKGTHGISVNSSLNLNNKINYHKKNSSSEI 883
            :*::      :.:* ..: .::.::: * *. .. **.  ..  :.:  *  ::..*  :

CD108       MDDIKEITTSRNTMFIVKNDGTAYATGNNSSGQLGLGDTINRNKFTQINLDNIKKIST-- 910
43593       MDDIKEITTSRNTMFIVKNDGTAYATGNNSSGQLGLGDTINRNKFTQINLDNIKKIST-- 910
CD16        MDDIKEITTSRNTMFIVKNDGTAYATGNNSSGQLGLGDTINRNKFTQINLDNIKKIST-- 892
CD126       MDDIKEITTSRNTMFIVKNDGTAYATGNNSSGQLGLGDTINRNKFTQINLDNIKKIST-- 892
CD4         SSNIQEIYSHSKSTYLLTNNNMLYSVGLNDVGQLGVGDEINRKVFTKINIDNIKSINVNR 943
CD123       SSNIQEIYSHSKSTYLLTNNNMLYSVGLNDVGQLGVGDEINRKVFTKINIDNIKSINVNR 943
             .:*:** :  :: :::.*:.  *:.* *. ****:** ***: **:**:****.*..

CD108       -SIDGNTTFAIRNDGTLYSTGLNTKGQLGLGDIVNRNTFTKVNIQNVRDVVLGTTHSHAI 969
43593       -SIDGNTTFAIRNDGTLYSTGLNTKGQLGLGDIVNRNTFTKVNIQNVRDVVLGTTHSHAI 969
CD16        -SIDGNTTFAIRNDGTLYSTGLNTKGQLGLGDIVNRNTFTKVNIQNVRDVVLGTTHSHAI 951
CD126       -SIDGNTTFAIRNDGTLYSTGLNTKGQLGLGDIVNRNTFTKVNIQNVRDVVLGTTHSHAI 951
CD4         FTDNSKHAFAIKNDNTCYAVGLNNSGQLGIGDNVNRNIFTKINVENVKYVAVYGNTSLLL 1003
CD123       FTDNSKHAFAIKNDNTCYAVGLNNSGQLGIGDNVNRNIFTKINVENVKYVAVYGNTSLLL 1003
             : :.: :***:**.* *:.***..****:** **** ***:*::**: *.:  . *  :

CD108       KDDNTLYSCGENTHGQLGLGSESNHPDVLTFTVNNITNVRDVYCSDTTTFIVKDTNIAYC 1029
43593       KDDNTLYSCGENTHGQLGLGSESNHPDVLTFTVNNITNVRDVYCSDTTTFIVKDTNIAYC 1029
CD16        KDDNTLYSCGENTHGQLGLGSESNHPDVLTFTVNNITNVRDVYCSDTTTFIVKDTNIAYC 1011
CD126       KDDNTLYSCGENTHGQLGLGSESNHPDVLTFTVNNITNVRDVYCSDTTTFIVKDTNIAYC 1011
CD4         TNDGLLYGAGNNGKGQLGLGDTTSRN---IFTRIPINGVRDVYLCNDVSIIVKNDNTCYV 1060
CD123       TNDGLLYGAGNNGKGQLGLGDTTSRN---IFTRIPINGVRDVYLCNDVSIIVKNDNTCYV 1060
            .:*. **..*:* :******. :.:    **   *..***** .: .::***: * .*

CD108       CGYNNNSQLGMGNTTDQYSFIKCMENVKEVIPN-EINTYIITIYNTAYSTGLNTDYCLGL 1088
43593       CGYNNNSQLGMGNTTDQYSFIKCMENVKEVIPN-EINTYIITIYNTAYSTGLNTDYCLGL 1088
CD16        CGYNNNSQLGMGNTTDQYSFIKCMENVKEVIPN-EINTYIITIYNTAYSTGLNTDYCLGL 1070
CD126       CGYNNNSQLGMGNTTDQYSFIKCMENVKEVIPN-EINTYIITIYNTAYSTGLNTDYCLGL 1070
CD4         CGLVNGYFGFTEGSISTFTKIN-IENVKSVVTAGSEATFFITNDNMIYTTGKKERVFFST 1119
CD123       CGLVNGYFGFTEGSISTFTKIN-IENVKSVVTAGSEATFFITNDNMIYTTGKKERVFFST 1119
            **  *.      .: . :: *: :****.*:.  .  *::**  *  *:** :    :.

CD108       NSNSNQSSFSEIPISNVVKVAPNRNNAVLLLTSEGDVYTAGKCSNGSGTGSETPEKIKKI 1148
43593       NSNSNQSSFSEIPISNVVKVAPNRNNAVLLLTSEGDVYTAGKCSNGSGTGSETPEKIKKI 1148
CD16        NSNSNQSSFSEIPISNVVKVAPNRNNAVLLLTSEGDVYTAGKCSNGSGTGSETPEKIKKI 1130
CD126       NSNSNQSSFSEIPISNVVKVAPNRNNAVLLLTSEGDVYTAGKCSNGSGTGSETPEKIKKI 1130
CD4         ETNDIKGIRVINNIINAKKIVVN-GYTSAILTNDNKLFVGG----LSGYGSIANNNNTNS 1174
CD123       ETNDIKGIRVINNIINAKKIVVN-GYTSAILTNDNKLFVGG----LSGYGSIANNNNTNS 1174
            ::*. :.      * *. *:. * . :  :**.:..::..*     ** ** : :: .:

CD108       ASKAKDIGMNYRCGHYVSDNGDLYGTGFNDCGQLGVGNVTKRDTFIKTNTR-VKKILPLE 1207
43593       ASKAKDIGMNYRCGHYVSDNGDLYGTGFNDCGQLGVGDVTKRDTFIKTNTR-VKKILPLE 1207
CD16        ASKAKDIGMNYRCGHYVSDNGDLYGTGFNNNGQLGVGDVTKRDTFIKTNTR-VKKILPLE 1189
CD126       ASKAKDIGMNYRCGHYVSDNGDLYGTGFNNNGQLGVGDVTKRDTFIKTNTR-VKKILPLE 1189
CD4         VEDVKDVFVTANNTLYIDNNNNLISSGRDTYGISDESYRDMSVPYYKVSIKKDVDTVFSS 1234
CD123       VEDVKDVFVTANNTLYIDNNNNLISSGRDTYGISDESYRDMSVPYYKVSIKKDVDTVFSS 1234
            ....**: :. .   *:.:*.:* .:* :  *  . .      .: *.. :   . :  .
```

Figure 8C

```
CD108     YANIAIKDTN-DIYICGLNN-YGQLGVGNRYDSRNN---DNRIFNYKHMNFVMGDLTSIK 1262
43593     YANIAIKDTN-DIYICGLNN-YGQLGVGNRYDSRNN---DNRIFNYKHMNFVMGDLTSIK 1262
CD16      YANIAIKDTN-DIYICGLNN-YGQLGVGNRYDSRNN---DNRIFNYKHMNFVMGDLTSIK 1244
CD126     YANIAIKDTN-DIYICGLNN-YGQLGVGNRYDSRNN---DNRIFNYKHMNFVMGDLTSIK 1244
CD4       YNTIFIKDIYGKFYSSTRDNRYNHLGIHHRYDNDKNEALEGSLHSYFKTDNTSDKIVFNK 1294
CD123     YNTIFIKDIYGKFYSSTRDNRYNHLGIHHRYDNDKNEALEGSLHSYFKTDNTSDKIVFNK 1294
          * .* ***   .:* .  :* *.:**: :***. :*   :. :..* : : . ..:.  *

CD108     NRHNFILLNNKIVIPTTKDIDYGLVLGNLYKGDLYTELPYEDIKEVSISKTHIIILLNDG 1322
43593     NRHNFILLNNKIVIPTTKDIDYGLVLGNLYKGDLYTELPYEDIKEVSISKTHIIILLNDG 1322
CD16      NRHNFILLNNKIVIPTTKDIDYGLVLGNLYKGDLYTELPYEDIKEVSISKTHIIILLNDG 1304
CD126     NRHNFILLNNKIVIPTTKDIDYGLVLGNLYKGDLYTELPYEDIKEVSISKTHIIILLNDG 1304
CD4       KNEKLVMFNDKYIKTNNKYINYKNIFKDNFK--YTSIILPFEVSDIDISKTHSLAVAKDG 1352
CD123     KNEKLVMFNDKYIKTNNKYINYKNIFKDNFK--YTSIILPFEVSDIDISKTHSLAVAKDG 1352
          :..:::::*:* : ...* *:*  :: : :*    : :   ::.::.***** : : :**

CD108     TMYGCGTNYHGELLQDLSINQVDEFVQINVSDVKHVSCGDNFTYFIKSDDSLWSIGKNSE 1382
43593     TMYGCGTNYHGELLQDLSINQVDEFVQINVSDVKHVSCGDNFTYFIKSDDSLWSIGKNSE 1382
CD16      TMYGCGTNYHGELLQDLSINQVDEFVQINVSDVKHVSCGDNFTYFIKSDDSLWSIGKNSE 1364
CD126     TMYGCGTNYHGELLQDLSINQVDEFVQINVSDVKHVSCGDNFTYFIKSDDSLWSIGKNSE 1364
CD4       KLYGIGSNSYKEINQTLEDIELLTLTEVNISDVKKVACGDNYSYIIKTDNTLWSYGKNTE 1412
CD123     KLYGIGSNSYKEINQTLEDIELLTLTEVNISDVKKVACGDNYSYIIKTDNTLWSYGKNTE 1412
          .:** *:* : *: * *.  ::  :.::*:****:*:****::*:**:*::*** ***:*

CD108     YQLGIGHNNPVTELQRITTISSCKEVHCGKNYTLVVTTSNELFVQGYNDKGALGLGSDSE 1442
43593     YQLGIGHNNPVTELQRITTISSCKEVHCGKNYTLVVTTGNELFVQGYNDKGALGLGSDSE 1442
CD16      YQLGIGHNNPVTELQRITTISSCKEVHCGKNYTLVVTTGNELFVQGYNDKGALGLGSDSE 1424
CD126     YQLGIGHNNPVTELQRITTISSCKEVHCGKNYTLVVTTGNELFVQGYNDKGALGLGSDSE 1424
CD4       YQLGVGHNNDVRELQKVTGLPSVKDISIYNSMTLVLTNEGELYAQGYNTNGLFGLGESEK 1472
CD123     YQLGVGHNNDVRELQKVTGLPSVKDISIYNSMTLVLTNEGELYAQGYNTNGLFGLGESEK 1472
          ****:**** * ***::* :.* *::   :. ***:*. .**:.**** :* :***...:

CD108     NTIIKFFTKALTDIREIKSYGSDHILVLKNDNSVWVTGKNRDVYKIEQPVEFLKEFTIVP 1502
43593     NTIIKFFTKALTDIREIKSYGSDHILVLKNDNSVWVTGKNRDVYKIEQPVEFLKEFTIIP 1502
CD16      NTIIKFFTKALTDIREIKSYGSDHILVLKNDNSVWVTGKNRDVYKIEQPVEFLKEFTIVP 1484
CD126     NTIIKFFTKALTDIREIKSYGSDHILVLKNDNSVWVTGKNRDVYKIEQPVEFLKEFTIVP 1484
CD4       DKIIRTFTKVLTNVKEIKSHNDDHILVIKNDNSLWITGKNKSMYKISISITDLYEFTKIP 1532
CD123     DKIIRTFTKVLTNVKEIKSHNDDHILVIKNDNSLWITGKNKSMYKISISITDLYEFTKIP 1532
          :.**: ***.**:::****:..*****:*****:*:****:.:***. .:  * *** :*

CD108     ISEDVNTVKDVLATDNTLYIISEVGTTNAAIEITEKSISSIKIKIQDPNKDISRIEMLIN 1562
43593     ISEDVNTVKDVLATDNTLYIISEVGTTNAAIEITEKSISSIKIKIQDPNKDISRIEMLIN 1562
CD16      ISEDVNTVKDVLATDNTLYIISEVGTTNAAIEITEKSISSIKIKIQDPNKDISRIEMLIN 1544
CD126     ISEDVNTVKDVLATDNTLYIISEVGTTNAAIEITEKSISSIKIKIQDPNKDISRIEMLIN 1544
CD4       IPEHLNDILDIELSDDTIYMITKVDTSKASIEIVEKSISQVRVVVQDPNNVIEKLEMFIN 1592
CD123     IPEHLNDILDIELSDDTIYMITKVDTSKASIEIVEKSISQVRVVVQDPNNVIEKLEMFIN 1592
          *.*.:* : *:  :*:*:*:*::*.*::*:***.*****.::: :****: *.::**:**

CD108     GESVKSVSDLITEKISFEVPPDKIKIGENKILFRAYCKGDDLYASLFIFKESTGNSIIKD 1622
43593     GESVKSVSDLITEKISFEVPPDKIKIGENKILFRAYCKGDDLYASLFIFKESTGNSIIKD 1622
CD16      GESVKSVSDLTTEKISFEVPPDKIKIGENKILFRAYCKGDDLYASLFIFKESTGNSIIKD 1604
CD126     GESVKSVSDLTTEKISFEVPPDKIKIGENKILFRAYCKGDDLYASLFIFKESTGNSIIKD 1604
CD4       DELISTKTNLEINSIIFEIPQNKIVLGENKILIKASSPTGDLYSSMFIFKSETGLKVKKD 1652
CD123     DELISTKTNLEINSIIFEIPQNKIVLGENKILIKASSPTGDLYSSMFIFKSETGLKVKKD 1652
          .* :.: ::*  :.* **:* :** :******::* .  .***:*:****..** .: **
```

Figure 8D

```
CD108            SYVMIGNRMYKVVNTTSNEQDITITLDRGLEEDLNLGDPIYQLINKTKVQVKINKSDLFK 1682
43593            SYVMIGNRMYKVVNTTSNEQDITITLDRGLEEDLNLGDPIYQLINKTKVQVKINKSDLFK 1682
CD16             SYVMIGNRMYKVVNTTSNEQDITITLDRGLEEDLNLGDPIYQLINKTKVQVKINKSDLFK 1664
CD126            SYVMIGNRMYKVVNTTSNEQDITITLDRGLEEDLNLGDPIYQLINKTKVQVKINKSDLFK 1664
CD4              SILMINNKVYSIINITENNTDLIVTLNEGLKDDMMENNPIYQLINKTKVQVKINKSDLFK 1712
CD123            SILMINNKVYSIINITENNTDLIVTLNEGLKDDMMENNPIYQLINKTKVQVKINKSDLFK 1712
                 * :**.*::*.::* *.*: *: :**:.**::*:  .:**********************

CD108            DMKLVEIKKSDSSYQEIYELEEANIKSAQPKIIVEKGDKWTAIKRPSMIFRYDAENNEPQ 1742
43593            DMKLVEIKKSDSSYQEIYELEEANIKSAQPKIIVEKGDKWTAIKRPSMIFRYDAENNEPQ 1742
CD16             DMKLVEIKKSDSSYQEIYELEEANIKSAQPKIIVEKGDKWTAIKRPSMIFRYDAENNEPQ 1724
CD126            DMKLVEIKKSDSSYQEIYELEEANIKSAQPKIIVEKGDKWTAIKRPSMIFRYDAENNEPQ 1724
CD4              DMKLVEIKKSDSSYQEIYELEEANIKSAQPKIIVEKGDKWTAIKRPSMIFRYDAENNEPQ 1772
CD123            DMKLVEIKKSDSSYQEIYELEEANIKSAQPKIIVEKGDKWTAIKRPSMIFRYDAENNEPQ 1772
                 ************************************************************
```

Figure 8E

SEQUENCE LISTING

```
<160> NUMBER OF SEQ ID NOS: 86

<210> SEQ ID NO 1
<211> LENGTH: 22825
<212> TYPE: DNA
<213> ORGANISM: Clostridium difficile

<400> SEQUENCE: 1

ggccgcaata cccactacac cttcgtcatc tttaaattta agagttttta ctattgaata      60

ataaaggtat attccagtaa aaataatctt taaatacaag aaaaataaac tctttgggta     120

tattaaaaag ctaaaaagtg taaatataaa agcaagtaga gtacttatcc tgtaaaagaa     180

atctatttgt gtaatgtctt tatattttat cataaacacc gaatataaaa tgatgaaaat     240

aattgcgacg attgcatata tggtaaataa catattttca agagtaccat ttgaaattac     300

tatccactta taccacataa ttggccaaaa taatagtgct aagaacttaa aataattatc     360

aaacaacttt tctttataca ttcatcaaac aacctttctt aacaaaagca tatatttgtt     420

tttagaattt taaataatat gatatcatta ttatatatta atattgaatt tatagaaacc     480

aaaatttgtt aaaataaata tatagatttt actgttaagc cagttaaaat tactactatt     540

tttattatga aattggatca aatatgtaga aatacggcaa attagttaat attaaatatt     600

tattatttcc aagttgtaaa gactgttttt ttaatgataa aaattctaat cttttttgaa     660

agaaagtaat atccacatta agtatgtctg ccatttcata aacgcaagtg atgccagaat     720

taattatgtt tattatatct tcttcagtaa ttaagaactc acaagcccat tttaaggctt     780
```

-continued

```
tattttcgca cttatctata ataatttttg tataataatc gttataagag gatacatagt    840
atccaaggct agtgaaatga tgtccaagtt cttcagctaa gatggatgtc aatttttttg    900
agttttgttt taaattactg agtaatgata taattttaat accatgtttg tttatatata    960
gcccttctaa atcacctgca atataagtgg tataatgaat tattatctct tcttgagaag   1020
ctaattcaaa aagcttatcc aaattattca taaaaatccc cctaaaatag aatgtatgtt   1080
tgcctttaaa ttatattaaa agagcagaaa aatagactgc tcatcatatg gtttattttt   1140
ttttatattt atttagtaaa aattctatat aatcattaag ttgttcttgt gcttcttcag   1200
gtaactcttc atgtggattt tttctatgtg cagctactgt atcaatattt tccttaacta   1260
aggttcttcc aagaaggtaa tcaactgata cattaaatac atcagccaat ttgtttaaaa   1320
tgtgttcatc aggaaatctg ttttctgttt catagtaccc taagactctt tgggaaacgc   1380
ctactttttc tccaagttct ctttgagtca atccaaattc ctttctaagt tctcttaatc   1440
ttttggcaaa cattataaca ccaccttatg tatagattat aacaaattgt tctaaaaaat   1500
aaaactaata aaatataaaa gaatattttt tctaaaatct attgataaag aacaaatgat   1560
tctatataat ctaagtgtgg aagaacaaaa tattcttaat ggtaatggag gtataaaaca   1620
atgtttaaaa ataacttgaa atattataga aaatgcaaag gtatgacaca aattcaactt   1680
gccagaaagg ctggaattac aaatgactat atatctcaaa tagaaagagg tataaaaaat   1740
cctggtcttc ttatggctaa gaagatttct agtattttag aacaaaatat agaagaagtt   1800
tttttatac agttatagaa caatatgttc ttgaaagttg tgagattagt aaaaaactgt   1860
gcactaaaga gattattgta aatttgaagc taataataag tatataaaaa aggagaagta   1920
ctatggaaaa caaaaaagat atattattta aagaaacaga tgaaagatta cataattata   1980
agtatttgga tataaagata aagaatatta atttggacat aaaaagatgt gagaatgaat   2040
actctggatg tggagcaatg gtatatacag aaaagactag taacacatat aacataagtt   2100
cttctgtgga aaatgaggtg ttaaaaagag aggaaagatt aagaaaatta aaaatggaaa   2160
aagaagatat agaaatagaa aaagagaaga tagaaaatgc tctaacatgt ctaaatgata   2220
tagaaatgga attttttaat ctttttttata atagtaagac aaaaaacaat atgacatata   2280
tttctatgaa actacactta gatagaacat cttgctacaa tttaaagaaa aaaatgatat   2340
ttaaattgag tgagatatta taaaaaatat gacaacttta caacacttta tatacactat   2400
tgcaacacta ggcaataaaa tatgtgagat aatgttattg tgaaagaaat ccatattgaa   2460
ggaggtgata aattgaaaag aataatatta cctaaaaata tagaagatat ttgacaggaa   2520
taaatgagat gtatatttaa aaatgactta tatcatttat agtaagatta tcagattaag   2580
caagaatatt tagtgatagt gtggtgatta tttgcttaaa tacaaggaaa tattagaaac   2640
aattattgag attctcaaaa aaaactttac tgaaagtatt tttattgatg atgaaagtgt   2700
gcaaggctct gaagggtctt gtttttttgt aagtatacta tcagttattt gtacacctat   2760
aatgttaaat acgaataata aagatattgt tatctctata aaatacttac caaaaccaca   2820
gtcaaagagt attagaatgt atgaaatttc agatgaatta aataagttat tcaacagaaa   2880
tataaaggta acagacagaa aattaaatat aacaaagcta gaacaaagta ttaaaaaaga   2940
agagtcaatt tatgtattga actttacaat tacactaaat tatctggata gtgtatatga   3000
agaagatgta gtatatgaaa atatggaaga aatcaattta aatttaggag agtgatagta   3060
tggctatagg attaccaagt atcaacatat catttaagga gctagctaca actgttaaag   3120
aacgttcagc tagaggaata attgcaatgg tgcttaaaga tgctaaggca ctaggtctta   3180
```

-continued

```
atgaaataca tgaaaaagag gatataccag ttgatttatc tgctgaaaat aaagagtata   3240
taaatttagc tttgatggga aatgttaaca ctccaaataa attattagtt tatgtaatag   3300
aaggagaagc agatattcaa actgcattag attttttaga gactaaggaa tttaattatc   3360
tatgtatgcc aaaagcagta gaagctgata agactgctat aaaaaattgg ataattaaac   3420
ttagagatat agataaggtt aaggttaaag ctgtattagg aaaagttgta ggaaatcatg   3480
aagggataat taattttact acagaagatg tgttagttgg agaaaagaaa tacagtgttg   3540
atgagtttac aagtagggtg gctggactta tagcaggaac acctttaagt caatcagtaa   3600
cttatactaa gcttagtgat gtagttgata tacctaagat gacgaaagtt gatgcagaat   3660
caagggttaa taaaggagag cttatactta ttaaggaagc aggggctata agaattgcaa   3720
gaggagtaaa ttctttaact gagttaacag aagaaaaagg agaaatgttc cagaaaataa   3780
aaatagttga cactttagat attatacata gtgacataag aaaggtgata atagatgact   3840
atataggaaa ggttactaac agttatgaca acaaatgttt attgatagta gctataaaaa   3900
gttatttaga agaattagaa aagtcagcac ttatagaatc tgattctact gttgaaatag   3960
attttgaagc acaaaaatcg tatttaaaat caaaaggagt agatttatct tatatgacat   4020
tacaagaaat aaaagaagct aacacaggtt ctaaagtatt tttaaaagca aaaataaaag   4080
tacttgatgc tatggaagat atagatttat caatagaaat ataggaggat tattaatatg   4140
gcaaatatgg aagctagaaa tgtaatgagt ggtacttggg gagaactttg gcttgatgga   4200
aacaaagtag cagaagtaaa gaagtttcaa gcaaagatgg aatttacaaa agaggatatt   4260
ataatagcag gtcaaatggg tactgataca aagtatatgg gatataaagg aaaaggttca   4320
ataactctat accatgttag ttcaagaatg cacaagttaa ttggagaaaa gataaagaga   4380
ggttctgaac ctagatttgt tgctatatct aaattaaatg acccagattc ttatggagca   4440
gaaagaatag cagtaaaaaa tatagcattt gatgatttaa ctttagctga ttgggaggtt   4500
ggagtaaaag gagagataga agcacctttc acatttactg agtatgattt tcttgatata   4560
atttagtttt atatttggtt ttatactgat atttagtaga tatatactta ataaatttag   4620
gtagttaata agtaaaaaag ttagttgatt gaatttgatt gataaaggag caaataataa   4680
tgaatgaaaa tggattatca aaaaatataa acatagtaga tttactttta aatgcagata   4740
cagaaaactt agaaagacca agtactatag ttgaacttaa gagattatca actatatttg   4800
ggcaggaatt taaagtaatg tgtagagctt taacaataag taaagatgaa gagatacaaa   4860
atacttgtct taaaattgat gaaaatatga aaacggatat agacttaccg gagatgcaga   4920
tgcttacaat tatagaaggt gtttgtgatt tggatggaaa gcttttattt aaaaataagg   4980
aactaatgga taaatttaag gctccaacac caaaagaatt ggcaagaaaa ctattattac   5040
caggtgaaat taccaaccta tatagaatac ttcaagatgt tatgggttat ggtaaaaatg   5100
cagtgataga agaggtaaaa aactaatagg gacggatacc aagactacaa taatgtacta   5160
ttattggaag aaaaaaggta taagaccgtc cctttttttat gcaatggata aaggcgaatt   5220
aaagcttatt gaagcttttt tcgccttaga aattgaggaa gaagttgaaa aaatgaaaca   5280
tggatatgga gtgtgtcctt tgacaggagg tggtatgtaa tgggaaatgt gagagaagaa   5340
ggtataaata tgtatcttac agataattac acaccaaaaa tgaaccaaat tatatcagta   5400
actgataatt ttaggagagc aactgtggct gtttcacttt ccactaatgt aatggctagt   5460
agcataaaaa attctattgg aagtgcaagt agtagagtaa acagtttaaa ttcctcgtta   5520
agaaaagttc aaactactgc tagtagtgta agttcaacta tggcaaaatt aagttctagc   5580
```

-continued

```
ataaatgctg tttcaggagt tattggaagt ttaaatggaa gtattatgag actagcaata   5640
actatagcta tgattattga ttattttaat aagttgattc aaaagaaaaa tgagtttaat   5700
tcaaatatta tgattatatt aatatttaaa gctaaaagtg atgaagtaga aaaaactaaa   5760
aataaattac ttggaaattt aaaaaagatt ggtggcaaga tttggaatat cgtaataaaa   5820
gcaaaagata tgactaagag agtgataagt agtatcttgg gaaaattaaa acgagtagag   5880
aaacgtcctt atcaaggaag tattaatctt aaagatatgg taagtagtgc tatggctaga   5940
attttgccta agttaatgtt gtttaaaaat actttttgga gtggtgtaat agctataaaa   6000
gatatggcaa gtagcattat aagtaaagta tttcccaaat tgagattgtt tgcaggtaag   6060
gtatggagtg gtgcaatagc tgtaaaggat atggcaagtg gaatacttgg ttcgataaaa   6120
gggaagatat ctgatttgac aaatggtgct actataggtg tcgctgtgaa aaagggtgtt   6180
gacttacttg gtcaggaaca aaatcagaaa gttgttctag aaagtgtaat gaaaagaaat   6240
actggaaaaa ctagccaaaa agatgttgat aagtattatg acagtttagt aaatatggca   6300
aatgatacgc cttttgaccc tgaagatgtt gttgcaatgg gaactaaagc taaaatgatt   6360
agtaatatta ctggtggcaa aaaagaaaaa gatataactc aagctatggt agatgttaga   6420
gctttaaata tgaatacaag tagtgaacaa gatgtatcag cagctttctt aagtgcagca   6480
aaaggaaata tggaatctct taatactctg gtaggagaaa attataaaac ttttgatgaa   6540
gcattggaag gcataagtgt aaagcagatg gggttagcta aagaaatgag taatacaata   6600
ccaggtataa tatcaggagc tcaaacaagc attaacaatg gtttgaagag tattgttaaa   6660
ccttttgatg atattttagg tcaaggacta aagaaaataa aaacttttat agaaagtgga   6720
ttagggaatt tagctggctt atctgaaaaa atggctggta aaataggcaa tgtaatgaat   6780
ggtaagataa ttattggcaa caaatatgac cagatgcaat ctagaagtgt aaaaaatgga   6840
aaagagtttt ctgattctac tcaatatcga atttctaatg aggctgaaaa gcgtaaaatg   6900
atggttgaaa ataagcaaga acgttttgaa aatcatgcag caacaatgat agggaatgca   6960
ccaaaagcaa ttgttaacgc aggaagtaca ctattacaaa atattgattt tacagcatta   7020
atagattcac tacttccagt agtaaactta gtaaataatt tactagatag tataaacaat   7080
aaatcaccaa ttgcacaagg attaataagt atatttggta caatagtaac tacagcattc   7140
caactaatcg gacctgtagt tgaagctgtt agtcctatta tcacaagaat tttactttt    7200
ttaggtgaat atgcacctca aataaacaat tttatagaga cactgggtgt tatttggaaa   7260
actgtatggg agaccttagg acctctgttg gaaactggat ggaaaattat agagccaata   7320
ttgggagctt tttttaacat attagataaa gtatgtaaaa tagttaaaga tatatgcaaa   7380
tggtggcaaa ctatgattaa taagataaaa aatggaagca tcacaggaac agttttaaat   7440
ctagtggaaa agagtaaaaa aaattacaaa gataatccat atgctggaac aaaggctggt   7500
gattctggta aagcttattc aagtaagaaa ggtaataatg catttggatt gaactatgtt   7560
ccttataatg actatcaaac cagactccat gaaggtgaaa tggttttaac taaacaagaa   7620
gcaaatcaat atagaagcag aaaaaatggt ggaaatataa acatagctaa gttagctgat   7680
acaatagtga ttagagaaga agctgatata gaaaagataa catcaaaatt agttgcaagt   7740
atccaattgg cacagttagg gggtgtctta taatggaaat gtggcttaga caagcagaag   7800
atagatttag atttccagta tttccatctt cctttagtat taatggaaaa gctgctgtaa   7860
actcttctag tatactcaaa ataggtgaag tagcaacttt tggtggtgta gctcttaaaa   7920
gcatttcaat atcaagtttt tttccaaata aagactacac tttctgtgac tatacaggtt   7980
```

-continued

```
ttccatcacc atatgattgt gtaaataaga tagaaaaatg gatgaaggaa ggttttatat   8040
taagatttac aattacggaa acaaatataa atatggaagt cataattgaa gggtttagtt   8100
atgaagaaag agatgggact cgagatgtat attttacatt agatttaaaa gagtataaaa   8160
gaataaagat accaaaagta actccaaaac aataactatt atagataata agttgtaagt   8220
aactgctgat agaattaaat gaaaaggcag gtgatttttt attattaaga tttgggtaca   8280
cataaaaaac ggaagtatat atgacataac tgacatagta gacaaggtat catggtcagg   8340
tgattataaa tctccatcaa ggacactaga gttttcaata atacaatcat catttgatgt   8400
aaatttccaa caaatcgata taccaatagc tagtacagtc tgtttctatg tagatgagaa   8460
agaactcttt agaggaatga taattaatag gtctaaagat tcaagcagta atgaaattag   8520
ttttgtatct aaagatatgg gatttttact tacacaaagt gaagtgtcat acaattttaa   8580
agataagtta gttgaagaca tagcaaagca agtatttgct gaaaataggc tttcagttgg   8640
aacaatagca aagaccaatg tcaagtatac aaagatgttt ataggagtaa atggttatga   8700
cacaataatg agtgcatata cagaggcaag taaaaagaca aagaaaaagt atatgataga   8760
ggctaattta gataagttta atgttattga aaaaggaact gttacattaa gtgttatgtt   8820
tgaagaggga tttaatatta taaataccac cttttcggag agcatggaaa atgtaaaaaa   8880
taaagtaata gtggtagacc agtatggaag caagattagc gaaaaaatag ataatgaaat   8940
ttttaaggaa gtaaatgtaa taatgcaaaa agtaattcag caacaagaaa atcaagatgt   9000
agatattgat agcgagttta atgggataga aaaaagctgt tctcttaaag gttatggaga   9060
tgtaagttgt ataactggta gaggagtaaa agttaaagat tcttatacaa agcttgtagg   9120
actattttat atagatacag acaaacatac ttggcaaaat ggagaatatc aaattgagct   9180
tgaacttaat tttcaaaatc ttatggatga aaagtcagca ggacaggatg aacctaagga   9240
agaaagtaat ttagggggag aagattatgc aggaggaaaa gagtttacag cagaatttac   9300
agcttactgt cctagaaaag aagaaggtgg agatacagat tgtagaaaga aaaaacttga   9360
cccatctaaa aaacttgcgc tgctcctatg gttggtaaat atgagcaaac ttattataca   9420
aaagagtttt taaataaaca tcctttattg aactatggag atgaaataca ggtaattaca   9480
ggagtttctg gtcgtgatgg agtctataaa gtaaatgacg taggacctgc aataactata   9540
gaaaaaaatg gaacatacca tatagatatt ttatttggaa atgttgaaga agctagtaaa   9600
tttggaagaa gaaaaggaaa aattattatt ggtggttatt ctggtaatgt atctgataaa   9660
gctaaaatag taatatcaga ggcaaaaaaa catctaggta aaccttataa atggggtgga   9720
aatggaccaa gtagttttga ctgttctggt ttaatggtct actgttttaa aaaagttaat   9780
gttagtttgc caagaacgtc aaatcaacaa tctaaaaaag gcaagaaagt agaacaaaaa   9840
aatcttcaag caggagattt agtatttttt cataatccag tcagccatgt tggattatat   9900
ataggtaatg gagaattttt acatgctcca caaaaaggtg atgtagttaa aataagtaag   9960
ttaagtagta gaagagattt taatacagct aggagagtat tataaaagga tggtgatata  10020
atggctaatc caataaatga atttatagga ataataagag aagaaggaaa gtatcataat  10080
caaccttctt ttttattgga aaattaaaag taaattacca gatttaaaaa tagagacaaa  10140
taacatcata ttagaaaaag aagatatttt gatagatagt tggatgattg atagacagct  10200
agaaacattt gacacagaaa caaatcaaga acaccagcat gaagtaaaaa atccttttat  10260
agataacttt gaatctgggg atatggtaat aatgtttaga ataggcgaaa aatttgctgt  10320
tgtaagtaag ttggtgagct tataatgagt acaatatttc cttttatagg tgtcccagag  10380
```

-continued

```
gattatatct tacctaaaac agaagaattg ccaatctttc gtgaagtggc atgggatttt  10440
gaaaaagatg aacctatttt agaaaaaggt gactttaaaa taattgaaaa aaaaagaagc  10500
cttaaaagtt tggatataca agtgtataaa gacaaataga tatgaacatg agatatactc  10560
tttagaatat gggacagagc tttcagaact aataggacaa aaatatacaa aaggtcttac  10620
agaaagtgaa gctagtagat tcataaaaga ggcccttcta ataaatccat atatattaga  10680
agtaaacgta aaaagtgcta actttaacag agacgtattg agtgcaaatg taaaagtatc  10740
cactatctat ggggaggtgg aaataaatgt atagtgacca gacatatgaa gtaataaaaa  10800
atagaactct tgaaaatatt aatcttgata tttataaagg agaaggttct tttctaaaca  10860
acatggtatc tggaaataat ctagaacttt cgaagatata tctagaactt tcaaagatac  10920
ataaaatggc ttttatacaa gacacatata accagtttct tgataaaaga gtcaatgaat  10980
ttggtgtata tagaaagtta ggtacagagt caaatggaga agttgaattt attggagaga  11040
aaggaactgt aataaataat ggcacaataa tatcatatag agatttacta tttgtagtaa  11100
taaaagatgt aactattggt agtgaagaag gtgacaatag cccagttcaa gctctggaag  11160
ttggtaagaa atataattta cctacaaatt gtgaatttaa actagttgat aatatatctg  11220
gagtaacaaa gattactaac acaagaagtt ttgaaggtgg tacagatata gagacagatg  11280
aagaactaaa agaaagattt tataaaatcc aaagaaatca agctacaagt ggaaataaag  11340
ctcactatga agaatgggct ttggaagtag atggagtcta taatgttaag gtttatccaa  11400
gatgggatgg tccaggaaca gttaaggtct tgatatttgg ggaaaataat caagctgttg  11460
atacagaaac gattgaaagg tgtcagcaac atatagatga agagaagcct attggaccaa  11520
ctataacagt tgtgacacca ttaccaatag aaataagtat aagtgcagta atgaaactag  11580
aagatggata tacattagac aatgtaaaag aatctttcct agaaagtata aatacatact  11640
ttagagatat tagaggagag ataatctata caaaagtcat gggaatactt ataaatacta  11700
ctggtgtaca cgatttaagt aatctactta taaatggaag tacagataat ataactatta  11760
atgaagataa aatacctagt gtaacaactg ttaattttag tgaggtggaa aatcaatgaa  11820
gctaattgat aaactaccat catttgatag aaattacatt gtagaggaga tacaaggtgc  11880
atacgataca gaattaaata ttcttaaaga agatattgat gataccttta accaattatt  11940
tgttgataca gcgacatggg gattagatat gtgggaagac atactctgca ttgaaaaaaa  12000
agaacttgat tttgacacaa gacgtagcaa tataaaagct aaaatgagaa gcagaggtac  12060
tagtactatt gaagttataa aaagtatatg tgaggcatat acaaaatcag aaacagatat  12120
aaaagtttat agtgatgaat ttacattcgt attgagtttt atagcaaata actgtgacta  12180
taaaactctt ttagattgta gcgagatgat tgaaagagta aaacctgctc acttattaca  12240
ctatttagaa ccaataatac tagataaaag tatggtctat tgtggtggag gtatggtatg  12300
tagtgaagag gtaaaagttc atccatactt tgaaccaatt ataaaatgta gtgctgttgt  12360
aaactgtgga gctggaatgt taagtagaga agaaataaag gtttatcctt taagcattaa  12420
atgcattgaa aataattgta agattaatat agctattgca aatgatacag gcgtagaaaa  12480
tgtagtagtt tatcctaaat cggaggtggt ataattggaa gaaaaatttt atataatatt  12540
aaccaaaatt ggtagagaaa aaatagcaaa tgcaactgca ctaggagagc ttgttggatt  12600
aaccaagttt caagttggag atagtaatgg agaatattat gagccaacag aggaacaaac  12660
tgctttaaag aatgtagttt gggaaggaaa tataaattct ctaagaattg atgaaaaaaa  12720
tcctaattgg atagttatag agactatttt accaggaaca gttggtggat ttatgataag  12780
```

-continued

```
agaagctgct gttctggata atgagaataa tataatagct atwggtaagt atccagagac  12840
gtataagcca cgtgctgaag atggcagtat taaagatttg gttgtaaaaa tgattttaca  12900
attgtccaat acttcaaatg ttacattaga agtagacccg acgttggttt ttgtaactca  12960
aaaggatatt caagatttag atgataagtt tgataaaaat ataaaagaaa taaaagtaaa  13020
aattggagat acagatatat taactacaga ttctaaagat ttatcaggag ctataaatga  13080
ggtagttaaa aaaatagaaa atatatcttt tgatgatgtt ataagtggtc aaatacaaac  13140
tgatatatca gtattaaaaa atagctataa caaattatct gaaaaagtgc tagatatatt  13200
aatataccta gaattagagt cagaagtaac tgtagatgag gctggttatt ggtatgatac  13260
attagcaaat ggaaataaca tagtagctat agaagggctt aagttagatt taaatagaaa  13320
atgtataaca ggtgaaattg gtaatgtgat ttttagagat gtagtattac catttagtgc  13380
aaatagagtt agatatatac atgatatgga taataacttt gttgagacaa aatctagtaa  13440
cacttattta aaagaacaaa aagatataac tctaagtaaa tattcatatg aaataagata  13500
aataaaggag gtagtactaa taatgaagca aaataaactt ttacagcgtg gtgcttattt  13560
taatgataag aacatattga ttgatgattt tgataaaaga tataatgatt atgattttgt  13620
agaattttt actggtataa gtaatagtac ctttggttta aaatcagatg gtaatttata  13680
tgcttgtggc gataatacag gttttcaact aggacttgga aaagattcgt cagagagaag  13740
gatgtttagt aaagtaaaaa ttgataatgt aaaatatgta tcttgtggtt caaaacacag  13800
tgtagcagta actaaagatg gatttgcata tggagcagga acaagtaatg taggtcaatt  13860
aggtgtaatt gagtctacag tatattatga atttactaag ctaccaatag atgatgtaaa  13920
aactgttgca tgtggttatg actttacatt tgtgcttaaa aatgatggaa cattatattc  13980
agcaggttta aactcaagtg gtcaacttgg actaggtgat actaacaata gagctacttt  14040
tactaaagta aatatagata gtgtgaaaga tgtagtgact tataatcaat ctgtatttat  14100
cataaaaatg gatgggacag cacatgcatg tggattaaat tcaaatgggc agttgggaat  14160
taatagtact ttaaataaaa gtgtatttaa taaaatagaa ggtatggata atgtaaaaca  14220
gatagcgtgt ggtagtagtc atacaattct tattaagaat gatggaacta tgtatactac  14280
aggctataat ggagttggtc agcttggtac aggaaataat aataattcaa ttgtatttac  14340
tctttctagt ataaataatg ttaagtatgc ttcttgtgga aataatcata ctatgatatt  14400
aaaatacgat aatacactgt ttagtacagg acaaaacaat tatggtcaac tagccaatgc  14460
caataaagat gtagcatcaa gaaatacttt tgctaaggtt aatgtagaaa atataaaaga  14520
tattaaatgt ggttctcaat ttaatttttt aataaatggt tcaaaagaga tatttgtatc  14580
tggctgtaat ttagcaggtc aacttggttc atttttcat acaacttttc tgtatgagtt  14640
ttcaaatgtg caatcttcaa atttagataa ttattcaggt ttattggtta atgatgatta  14700
tttatatgtt acaaaggaca atagtgaatt tttaaatgta aagttaagtg ataattttca  14760
agattataag aagatagagt taacagatag caatatgttt attgttatga atgatggtac  14820
attgtatgct tgtggtttaa ataattatgg acagttagga ttgggagata ctgttaacag  14880
gtcagttatg actaaggtgg atatagataa tgttttggat ataaaaggaa acggaaactc  14940
aacttttgtg cttaagaata atggaacatt atattcatgt ggtttaaata gtaatggaca  15000
attgggttta agagatgaag ttaatagaaa tatatttaca aaaatagaaa tagagaatgt  15060
aaaggatttt tgtgtaggaa gcaattatgt catagcttta aatcactcaa aagaagtata  15120
tggatgggga aataatcctt ataataatat agaaaaaact tctaattatc catataagca  15180
```

-continued

```
gggaataagt aatattgaaa agatagcagc atatgattat tctgtatata tgataaacag  15240
tgaagggaaa ctatatgttt ctggatacaa ttataattat caattaggta aaggaaataa  15300
tagtaaccaa agcaaagcat tagtatctca atgtagaaca aattcaacat cttctacatc  15360
aaatggactt agaacgttac ctaaaataac taatgttttt cctttttatg atggttgtgc  15420
aataattgac gaaggaggtt atgtttattt aacaggatat catggatatt taagaacatt  15480
aaatagcagt ccaagtatat ctgattattc aagatatgga acttttattg aggctacaaa  15540
ttcaaatcat aatacttatt ttatacaaga gactgatttt agtggaattg aaaaagtaat  15600
agggatgtca aataatatat tattttttaa gaaaggaagt tcatatatta ctggatatcc  15660
aaaaacattt ggctcaacca ttactggaca tagaagttat actagtatta attctgagag  15720
ttctaattta ggaagtaatt ttataaatata tcatagtaat tccaagttat atggaaaagg  15780
gattgctaat agtgggcaat ttgggaattc aacaaatata gatggcacaa gtaactatga  15840
tacaggatta aaagacataa aagatataat tgtaaaagga aatactgtag tagtagtaga  15900
taaaaataac aatatatatg taacaggaat gaatcagaat aacaaacttg ggataggga  15960
atataacaac gaaccagtaa aaaaattcac aaatataact gaacaatcaa actcatttat  16020
atttatggat gatataaaag aaattacaac atcaagaaat acaatgttta tagtaaaaaa  16080
tgatggaaca gcctatgcca caggaaataa tagttctgga caattaggat taggtgacac  16140
aataaataga aataagttca ctcagataaa ccttgataat ataaagaaaa tatcaacaag  16200
tatagatggt aacacaacat ttgcaattag aaatgatgga acactatact ccacaggatt  16260
aaataccaaa ggacaactgg gattaggtga tatagtaaat agaaatacat ttaccaaagt  16320
aaacatccaa aatgtaagag atgttgtttt agggactact cactcgcatg caatcaaaga  16380
tgataacaca ttatattcat gtggagaaaa cactcatggg caactgggct taggaagcga  16440
aagcaaccat ccagacgtat tgacatttac tgtaaacaat ataactaatg taagagatgt  16500
gtactgctca gatacaacaa catttattgt aaaggacaca aacattgcat attgttgtgg  16560
atacaataat aattcacaac taggtatggg aaatactact gaccagtata gttttataaa  16620
gtgtatggaa aatgtaaaag aagttatacc aaatgaaata aatacctata taataacaat  16680
ctataatact gcatatagta caggtttaaa tactgattat tgcttaggtc taaatagtaa  16740
tagcaatcaa agttcatttt ctgaaattcc aatttcaaat gtagtaaaag tagctccaaa  16800
cagaaataat gcagtacttt tacttacaag tgaaggggat gtatatactg caggcaaatg  16860
tagtaatggt tcaggtacag gaagtgagac tccagagaag attaaaaaaa tagcatcaaa  16920
ggcaaaggat attggaatga attatagatg tggacattat gtaagtgata atggagacct  16980
atatggtaca ggttttaata ataatggaca attaggtgtt ggtgatgtaa caaaaagaga  17040
tacatttata aaaaccaata caagagtaaa gaaaatactt cctttagaat atgcaaatat  17100
agcaataaaa gatactaatg atatatatat ttgtggatta aataactatg gacaattagg  17160
tgttggaaat agatacgata gtagaaataa tgataataga atatttaatt ataagcatat  17220
gaattttgta atgggtgatt tgacatctat taaaaacaga cataacttta tacttctaaa  17280
caataagata gtgatacct a ccacaaaaga catagattat ggtttagtat taggaaattt  17340
atacaaagga gacctttata ctgagcttcc atatgaagat ataaaagaag tatctatttc  17400
taagactcat attattatat tacttaatga tggaacaatg tatggatgtg gtacaaacta  17460
ccatggagaa ttattgcaag acttgtctat aaatcaagtg gatgaatttg tgcagattaa  17520
tgtatcagat gtaaagcatg tttcatgtgg agataacttt acttatttta taaaatctga  17580
```

-continued

```
tgatagtctt tggtctattg gtaaaaattc cgaatatcaa ttaggtatag gtcacaataa  17640
tccagttact gaattacaaa gaattacaac tatatctagc tgtaaagaag tacattgtgg  17700
taaaaactat acattagtag taactacagg taatgaatta tttgtacaag gatataatga  17760
taagggagct ttaggattag gaagcgatag tgaaaatact ataattaagt tctttacaaa  17820
agcactaaca gacataagag aaataaaatc ttatggaagt gaccatatat tagtacttaa  17880
aaatgataat tcagtatggg ttactggaaa aaatagggat gtatataaaa ttgaacaacc  17940
agtagaattt ttaaaagaat ttactatagt acctatttct gaagatgtaa atacagtaaa  18000
ggatgtactt gcaacagaca atacattata tattatatca gaagtaggaa cgacaaatgc  18060
tgctatagaa attactgaaa aatcaatttc atcaattaag ataaaaatac aagaccctaa  18120
taaagatata agtagaatag aaatgcttat aaatggtgaa agtgtaaaat ctgtaagtga  18180
tttaactact gaaaaaatat cctttgaagt accaccagat aaaattaaaa taggagagaa  18240
taagatacta tttagagctt attgtaaagg tgatgattta tatgcatctt tatttatttt  18300
taaagagagt actggaaatt ctataattaa agattcttat gttatgatag gtaatagaat  18360
gtacaaggta gttaatacaa catctaatga acaagatatt acaattacac tagatagagg  18420
acttgaagaa gatttaaatc ttggagaccc tatatatcaa ttaataaata aaactaaagt  18480
tcaagtaaaa ataaataaat ctgacttatt caaagacatg aaactagttg aaatcaaaaa  18540
atcagactca agttatcaag aaatctatga attagaagaa gccaacataa aaagtgctca  18600
gcctaaaatc atagtagaaa aaggagataa atggacagct ataaaacgtc catctatgat  18660
ttttagatat gatgctgaaa acaacgagcc acaagcttaa aatggaggtg taaaaattgt  18720
ttaaattcga taaaaataaa atagaacaaa tcaaacaagg tagaaaagta gaaatgcagt  18780
ataaagacat ttcagacata agtataggtc aagcaaagca agatgatgat ataacaaata  18840
attttatagc aaatgcagaa atatatgaga tgttgttaag tcaaagttct gtcaatgaag  18900
caagtaatat aagcactttt agtgtaagaa aatctggagg tgagagtgga atggtagaag  18960
tatatgtagc tttaatttta agaggcagaa aaacaataga agaagtacca gcagtaatta  19020
gagagcaagt tagaattaga tgtaaagaat tagaaatacc agttgaatag taaatttaga  19080
ataactatgt attagttatt ttttttatgt aaagtacaag gtcttaactt taataagtaa  19140
gccttgtact tattttttgt tatattagaa attgtatata tatttattat ttattcaatc  19200
tataaattaa acctacaatt taaagtacag aagattaaat tgataatcct gaaaatataa  19260
tattgcatga tgtaagaata taacaaaaat taaagctata agtataaaaa atttagacaa  19320
taggaggcta taatggataa attaataacc gaattgagta gtctgggggc aataggtata  19380
ctatgtgctc tattatttaa aaatactatg caggagaaaa aagaagatag agacatgtat  19440
aaaaaaactg tagaaaattt tatagaatta tctacacaac aacaagaaat aaacaaaaat  19500
atacttgttc aaatgggaat aatgaaaaca gatgtagagg aaattaagga agatgttact  19560
gatataaaag gtatgttaca aaacggtgta taacatgaaa gtagcagtag caccagatta  19620
tatattatta ggaaaagata aagtagtatt gtagatagtg ccctatttta ttgagaagga  19680
ttttatattt taaaatatta attaaaaaaa gtaataaaaa taatatataa aaataacata  19740
taaaaattca aaaaggagtt aagcttaaat ttgattagaa aaaatcaatt ttaagacaac  19800
tccttttttt tattaaatta ttgtctatta accaaaatag ctattttagc atctggatta  19860
taacttatct gaaccatttg atttttctta acatgttcaa ggtcttcacc accataagct  19920
atttgtaact taactggtaa cttaccttgt tttataatag caacgtactc tttttacct  19980
```

-continued

```
ttttctctaa actaatcaaa ttgccaacat aaggtttaaa gttctgatac tttttactag  20040
aatttcttat gtagaagaaa gcaccaacag caataactaa atttatgcca agtgtaaccc  20100
aagaattgat tttaagcata gctccagcga ttattatcac gaacattaaa acgataggta  20160
atatagcttt cttaagaagc aatttaccca ttatttcatt agcctttttc tcagggccac  20220
tcatagtttt tgatctagca aatgattgcg cgaatttgtc tcttaagccc attttatcct  20280
cctaatttta ataaatattt agttataata acgagatatt acttgaaact aaaaatttac  20340
tacatttata ttatgtttga cttttgtata aataattaca ttcaagtaaa gcaaaatata  20400
ctaattattt tatcataaaa ttataaaaaa gaaaataaat gaaataaaaa tattagaaca  20460
aagaaatgat gtaaaatcgt atcaaaagca acataaaaat tatttatcta ttttctcatc  20520
tttatttttg ttatactcaa tttttcctaa atccttctct ttttcatatt catgaagttt  20580
taattcaatc ataccttcta ttttggcttt atcataatca tttaactttc taaagttgtt  20640
taaaagcttt atttcattag agtttatgct attaagtgga tagtttgagg aggaatcgca  20700
aattaaatct gatttatgtg atagattatc tccatttaat agccagtcta ctgaaacatt  20760
aaatatctca gctatagatt ttaatatttc ataatttggt tttctaatgt ttctctcaaa  20820
tttacttaag ttgtcacagc ctaacatttc ttctagttca tattgtttaa ggtttttttgc  20880
ttttctcaaa taaacaattc tttctcctaa agtatccata aacactctcc attcaattaa  20940
tgtcaaaaag actttttaag atgtaaatag tttcaaatta aaggtcaaaa tgacataaaa  21000
accattgact taaggtcaaa atgactttat aattaactta atgatacgaa tttacatcct  21060
aattttagca caaagtaatc aaaaaatctt atttagtatt aaataaattt atatacttaa  21120
tatgtgtaca tattaaaaat atatactaaa tagagggggt gcgtaagcta aagtaatata  21180
aaagtaaata taaatcactt agaaaggaag ttgataaatg gatgctcgaa aaaaatggat  21240
acctttttttg ggagtgcaag tcaagcaaag acttattgaa ttaaatatga ctcaaaggga  21300
attagcgaag aaaataggtg ttaatgaaaa ctatttgtca gctattttaa atggaagaag  21360
aacaggtaaa aaatataaat catcaattta tcaattactt aatatagaat attcagaaga  21420
tgattaataa atagtatata aagtaggtga atattcttgt gtgcaaattg gattcagatg  21480
gggttataga gtgttgtaga gcaattgatg attttattac agcacttagt aatataaaaa  21540
gcttaaatat ggaaagatta aatactttaa ctaaatattc tagtacatgt tcaatccttc  21600
ttaaagaggg gaattatgaa ggatgtacaa ttgtgtatag aaagatgttg gaagaattaa  21660
aaacatgagt aatgcatttc ttaggaatat aaattataca tagaaatgta ttatattttt  21720
caaagtactt aaactaaaat atggataaga taatctaaat attataaatg tgcttgaaat  21780
tagactatac ttgtttttaa ataatccaat atccatattt tagtaatata ctacaaaaaa  21840
agaaggttaa tagatgatgt aaaatcgtat caaattatgt atgtttaaac cattttatct  21900
tcattattat tagaggaatg ctttttaag tctttatatt cagatatctt aagttcaagt  21960
attccttcta tttttatttt atcacgttcg tttagttgtc tgtatagatt taatatcatc  22020
atttcatcat tagtaacatg taagtaatct tctttatctt cttttacact actattgaca  22080
tttaccttct ctttaccata gagaagccag tcagtcgtaa cattaaaata atcagctatt  22140
gacattagta tatcacaatt aggttttcta tctcctgttt catacttgcc taagttttca  22200
aattttaaaa tatccataag tttgcgctga gtaagttttt tggagtttct caaataagca  22260
attctttttc ctaaagtatc cacaaaatac actcctttct ttttatgagt aatgtctaaa  22320
tgacatttga aattaaaaat atataaattt ataatataaa actactaaat taaagtctaa  22380
```

-continued

```
atgacatttt gcttaaatta atatgctcat aatatgattt taacatatta tagttgaaaa  22440

tatatggttt attttgattt gtatatataa caatagattt aattgttata aaaatgtaaa  22500

ggggtgtatg aatagattgt ataaatttat ttcgataaac taagattgct ttttgattgt  22560

ctgtaaaaga gaaaaagatt aagataaaaa tagtattata ttgtaattta tattaatcaa  22620

ttacaaagat tttatgaatt tattctttag ggtaaaatat ttaagaataa gataaattta  22680

caatataata ctataacact cttttatcta gttttatttt ctttatagaa caataatatt  22740

ataaatgcta gtagatttac acagaatact gttatataca tctgtttgaa tcctgagttt  22800

agagtagatt gtagtgtgga tccgg                                        22825


<210> SEQ ID NO 2
<211> LENGTH: 65
<212> TYPE: PRT
<213> ORGANISM: Clostridium difficile

<400> SEQUENCE: 2

Met Phe Lys Asn Asn Leu Lys Tyr Tyr Arg Lys Cys Lys Gly Met Thr
1               5                   10                  15

Gln Ile Gln Leu Ala Arg Lys Ala Gly Ile Thr Asn Asp Tyr Ile Ser
            20                  25                  30

Gln Ile Glu Arg Gly Ile Lys Asn Pro Gly Leu Leu Met Ala Lys Lys
        35                  40                  45

Ile Ser Ser Ile Leu Glu Gln Asn Ile Glu Glu Val Phe Phe Ile Gln
    50                  55                  60

Leu
65


<210> SEQ ID NO 3
<211> LENGTH: 146
<212> TYPE: PRT
<213> ORGANISM: Clostridium difficile

<400> SEQUENCE: 3

Met Glu Asn Lys Lys Asp Ile Leu Phe Lys Glu Thr Asp Glu Arg Leu
1               5                   10                  15

His Asn Tyr Lys Tyr Leu Asp Ile Lys Ile Lys Asn Ile Asn Leu Asp
            20                  25                  30

Ile Lys Arg Cys Glu Asn Glu Tyr Ser Gly Cys Gly Ala Met Val Tyr
        35                  40                  45

Thr Glu Lys Thr Ser Asn Thr Tyr Asn Ile Ser Ser Ser Val Glu Asn
    50                  55                  60

Glu Val Leu Lys Arg Glu Glu Arg Leu Arg Lys Leu Lys Met Glu Lys
65                  70                  75                  80

Glu Asp Ile Glu Ile Glu Lys Glu Lys Ile Glu Asn Ala Leu Thr Cys
                85                  90                  95

Leu Asn Asp Ile Glu Met Glu Phe Phe Asn Leu Phe Tyr Asn Ser Lys
            100                 105                 110

Thr Lys Asn Asn Met Thr Tyr Ile Ser Met Lys Leu His Leu Asp Arg
        115                 120                 125

Thr Ser Cys Tyr Asn Leu Lys Lys Lys Met Ile Phe Lys Leu Ser Glu
    130                 135                 140

Ile Leu
145


<210> SEQ ID NO 4
<211> LENGTH: 130
```

<212> TYPE: PRT
<213> ORGANISM: Clostridium difficile

<400> SEQUENCE: 4

```
Asn Phe Thr Glu Ser Ile Phe Ile Asp Asp Glu Ser Val Gln Gly Ser
1               5                   10                  15

Glu Gly Ser Cys Phe Phe Val Ser Ile Leu Ser Val Ile Cys Thr Pro
            20                  25                  30

Ile Met Leu Asn Thr Asn Asn Lys Asp Ile Val Ile Ser Ile Lys Tyr
        35                  40                  45

Leu Pro Lys Pro Gln Ser Lys Ser Ile Arg Met Tyr Glu Ile Ser Asp
    50                  55                  60

Glu Leu Asn Lys Leu Phe Asn Arg Asn Ile Lys Val Thr Asp Arg Lys
65                  70                  75                  80

Leu Asn Ile Thr Lys Leu Glu Gln Ser Ile Lys Lys Glu Glu Ser Ile
                85                  90                  95

Tyr Val Leu Asn Phe Thr Ile Thr Leu Asn Tyr Leu Asp Ser Val Tyr
            100                 105                 110

Glu Glu Asp Val Val Tyr Glu Asn Met Glu Glu Ile Asn Leu Asn Leu
        115                 120                 125

Gly Glu
    130
```

<210> SEQ ID NO 5
<211> LENGTH: 354
<212> TYPE: PRT
<213> ORGANISM: Clostridium difficile

<400> SEQUENCE: 5

```
Met Ala Ile Gly Leu Pro Ser Ile Asn Ile Ser Phe Lys Glu Leu Ala
1               5                   10                  15

Thr Thr Val Lys Glu Arg Ser Ala Arg Gly Ile Ile Ala Met Val Leu
            20                  25                  30

Lys Asp Ala Lys Ala Leu Gly Leu Asn Glu Ile His Glu Lys Glu Asp
        35                  40                  45

Ile Pro Val Asp Leu Ser Ala Glu Asn Lys Glu Tyr Ile Asn Leu Ala
    50                  55                  60

Leu Met Gly Asn Val Asn Thr Pro Asn Lys Leu Leu Val Tyr Val Ile
65                  70                  75                  80

Glu Gly Glu Ala Asp Ile Gln Thr Ala Leu Asp Phe Leu Glu Thr Lys
                85                  90                  95

Glu Phe Asn Tyr Leu Cys Met Pro Lys Ala Val Glu Ala Asp Lys Thr
            100                 105                 110

Ala Ile Lys Asn Trp Ile Ile Lys Leu Arg Asp Ile Asp Lys Val Lys
        115                 120                 125

Val Lys Ala Val Leu Gly Lys Val Val Gly Asn His Glu Gly Ile Ile
    130                 135                 140

Asn Phe Thr Thr Glu Asp Val Leu Val Gly Glu Lys Lys Tyr Ser Val
145                 150                 155                 160

Asp Glu Phe Thr Ser Arg Val Ala Gly Leu Ile Ala Gly Thr Pro Leu
                165                 170                 175

Ser Gln Ser Val Thr Tyr Thr Lys Leu Ser Asp Val Val Asp Ile Pro
            180                 185                 190

Lys Met Thr Lys Val Asp Ala Glu Ser Arg Val Asn Lys Gly Glu Leu
        195                 200                 205

Ile Leu Ile Lys Glu Ala Gly Ala Ile Arg Ile Ala Arg Gly Val Asn
```

```
    210                 215                 220

Ser Leu Thr Glu Leu Thr Glu Glu Lys Gly Glu Met Phe Gln Lys Ile
225                 230                 235                 240

Lys Ile Val Asp Thr Leu Asp Ile Ile His Ser Asp Ile Arg Lys Val
                245                 250                 255

Ile Ile Asp Asp Tyr Ile Gly Lys Val Thr Asn Ser Tyr Asp Asn Lys
            260                 265                 270

Cys Leu Leu Ile Val Ala Ile Lys Ser Tyr Leu Glu Glu Leu Glu Lys
        275                 280                 285

Ser Ala Leu Ile Glu Ser Asp Ser Thr Val Glu Ile Asp Phe Glu Ala
    290                 295                 300

Gln Lys Ser Tyr Leu Lys Ser Lys Gly Val Asp Leu Ser Tyr Met Thr
305                 310                 315                 320

Leu Gln Glu Ile Lys Glu Ala Asn Thr Gly Ser Lys Val Phe Leu Lys
                325                 330                 335

Ala Lys Ile Lys Val Leu Asp Ala Met Glu Asp Ile Asp Leu Ser Ile
            340                 345                 350

Glu Ile


<210> SEQ ID NO 6
<211> LENGTH: 142
<212> TYPE: PRT
<213> ORGANISM: Clostridium difficile

<400> SEQUENCE: 6

Met Ala Asn Met Glu Ala Arg Asn Val Met Ser Gly Thr Trp Gly Glu
1               5                   10                  15

Leu Trp Leu Asp Gly Asn Lys Val Ala Glu Val Lys Lys Phe Gln Ala
            20                  25                  30

Lys Met Glu Phe Thr Lys Glu Asp Ile Ile Ile Ala Gly Gln Met Gly
        35                  40                  45

Thr Asp Thr Lys Tyr Met Gly Tyr Lys Gly Lys Gly Ser Ile Thr Leu
    50                  55                  60

Tyr His Val Ser Ser Arg Met His Lys Leu Ile Gly Glu Lys Ile Lys
65                  70                  75                  80

Arg Gly Ser Glu Pro Arg Phe Val Ala Ile Ser Lys Leu Asn Asp Pro
                85                  90                  95

Asp Ser Tyr Gly Ala Glu Arg Ile Ala Val Lys Asn Ile Ala Phe Asp
            100                 105                 110

Asp Leu Thr Leu Ala Asp Trp Glu Val Gly Val Lys Gly Glu Ile Glu
        115                 120                 125

Ala Pro Phe Thr Phe Thr Glu Tyr Asp Phe Leu Asp Ile Ile
    130                 135                 140


<210> SEQ ID NO 7
<211> LENGTH: 148
<212> TYPE: PRT
<213> ORGANISM: Clostridium difficile

<400> SEQUENCE: 7

Met Asn Glu Asn Gly Leu Ser Lys Asn Ile Asn Ile Val Asp Leu Leu
1               5                   10                  15

Leu Asn Ala Asp Thr Glu Asn Leu Glu Arg Pro Ser Thr Ile Val Glu
            20                  25                  30

Leu Lys Arg Leu Ser Thr Ile Phe Gly Gln Glu Phe Lys Val Met Cys
        35                  40                  45
```

-continued

```
Arg Ala Leu Thr Ile Ser Lys Asp Glu Glu Ile Gln Asn Thr Cys Leu
    50                  55                  60

Lys Ile Asp Glu Asn Met Lys Thr Asp Ile Asp Leu Pro Glu Met Gln
65                  70                  75                  80

Met Leu Thr Ile Ile Glu Gly Val Cys Asp Leu Asp Gly Lys Leu Leu
                85                  90                  95

Phe Lys Asn Lys Glu Leu Met Asp Lys Phe Lys Ala Pro Thr Pro Lys
            100                 105                 110

Glu Leu Ala Arg Lys Leu Leu Leu Pro Gly Glu Ile Thr Asn Leu Tyr
        115                 120                 125

Arg Ile Leu Gln Asp Val Met Gly Tyr Gly Lys Asn Ala Val Ile Glu
    130                 135                 140

Glu Val Lys Asn
145


<210> SEQ ID NO 8
<211> LENGTH: 55
<212> TYPE: PRT
<213> ORGANISM: Clostridium difficile

<400> SEQUENCE: 8

Met Tyr Tyr Tyr Trp Lys Lys Lys Gly Ile Arg Pro Ser Leu Phe Tyr
1               5                   10                  15

Ala Met Asp Lys Gly Glu Leu Lys Leu Ile Glu Ala Phe Phe Ala Leu
            20                  25                  30

Glu Ile Glu Glu Glu Val Glu Lys Met Lys His Gly Tyr Gly Val Cys
        35                  40                  45

Pro Leu Thr Gly Gly Gly Met
    50                  55


<210> SEQ ID NO 9
<211> LENGTH: 817
<212> TYPE: PRT
<213> ORGANISM: Clostridium difficile

<400> SEQUENCE: 9

Met Gly Asn Val Arg Glu Glu Gly Ile Asn Met Tyr Leu Thr Asp Asn
1               5                   10                  15

Tyr Thr Pro Lys Met Asn Gln Ile Ile Ser Val Thr Asp Asn Phe Arg
            20                  25                  30

Arg Ala Thr Val Ala Val Ser Leu Ser Thr Asn Val Met Ala Ser Ser
        35                  40                  45

Ile Lys Asn Ser Ile Gly Ser Ala Ser Ser Arg Val Asn Ser Leu Asn
    50                  55                  60

Ser Ser Leu Arg Lys Val Gln Thr Thr Ala Ser Ser Val Ser Ser Thr
65                  70                  75                  80

Met Ala Lys Leu Ser Ser Ser Ile Asn Ala Val Ser Gly Val Ile Gly
                85                  90                  95

Ser Leu Asn Gly Ser Ile Met Arg Leu Ala Ile Thr Ile Ala Met Ile
            100                 105                 110

Ile Asp Tyr Phe Asn Lys Leu Ile Gln Lys Lys Asn Glu Phe Asn Ser
        115                 120                 125

Asn Ile Met Ile Ile Leu Ile Phe Lys Ala Lys Ser Asp Glu Val Glu
    130                 135                 140

Lys Thr Lys Asn Lys Leu Leu Gly Asn Leu Lys Lys Ile Gly Gly Lys
145                 150                 155                 160

Ile Trp Asn Ile Val Ile Lys Ala Lys Asp Met Thr Lys Arg Val Ile
```

-continued

```
                165                 170                 175

Ser Ser Ile Leu Gly Lys Leu Lys Arg Val Glu Lys Arg Pro Tyr Gln
            180                 185                 190

Gly Ser Ile Asn Leu Lys Asp Met Val Ser Ser Ala Met Ala Arg Ile
        195                 200                 205

Leu Pro Lys Leu Met Leu Phe Lys Asn Thr Phe Trp Ser Gly Val Ile
    210                 215                 220

Ala Ile Lys Asp Met Ala Ser Ser Ile Ile Ser Lys Val Phe Pro Lys
225                 230                 235                 240

Leu Arg Leu Phe Ala Gly Lys Val Trp Ser Gly Ala Ile Ala Val Lys
                245                 250                 255

Asp Met Ala Ser Gly Ile Leu Gly Ser Ile Lys Gly Lys Ile Ser Asp
            260                 265                 270

Leu Thr Asn Gly Ala Thr Ile Gly Val Ala Val Lys Lys Gly Val Asp
        275                 280                 285

Leu Leu Gly Gln Glu Gln Asn Gln Lys Val Val Leu Glu Ser Val Met
    290                 295                 300

Lys Arg Asn Thr Gly Lys Thr Ser Gln Lys Asp Val Asp Lys Tyr Tyr
305                 310                 315                 320

Asp Ser Leu Val Asn Met Ala Asn Asp Thr Pro Phe Asp Pro Glu Asp
                325                 330                 335

Val Val Ala Met Gly Thr Lys Ala Lys Met Ile Ser Asn Ile Thr Gly
            340                 345                 350

Gly Lys Lys Glu Lys Asp Ile Thr Gln Ala Met Val Asp Val Arg Ala
        355                 360                 365

Leu Asn Met Asn Thr Ser Ser Glu Gln Asp Val Ser Ala Ala Phe Leu
    370                 375                 380

Ser Ala Ala Lys Gly Asn Met Glu Ser Leu Asn Thr Leu Val Gly Glu
385                 390                 395                 400

Asn Tyr Lys Thr Phe Asp Glu Ala Leu Glu Gly Ile Ser Val Lys Gln
                405                 410                 415

Met Gly Leu Ala Lys Glu Met Ser Asn Thr Ile Pro Gly Ile Ile Ser
            420                 425                 430

Gly Ala Gln Thr Ser Ile Asn Asn Gly Leu Lys Ser Ile Val Lys Pro
        435                 440                 445

Phe Asp Asp Ile Leu Gly Gln Gly Leu Lys Lys Ile Lys Thr Phe Ile
    450                 455                 460

Glu Ser Gly Leu Gly Asn Leu Ala Gly Leu Ser Glu Lys Met Ala Gly
465                 470                 475                 480

Lys Ile Gly Asn Val Met Asn Gly Lys Ile Ile Ile Gly Asn Lys Tyr
                485                 490                 495

Asp Gln Met Gln Ser Arg Ser Val Lys Asn Gly Lys Glu Phe Ser Asp
            500                 505                 510

Ser Thr Gln Tyr Arg Ile Ser Asn Glu Ala Glu Lys Arg Lys Met Met
        515                 520                 525

Val Glu Asn Lys Gln Glu Arg Phe Glu Asn His Ala Ala Thr Met Ile
    530                 535                 540

Gly Asn Ala Pro Lys Ala Ile Val Asn Ala Gly Ser Thr Leu Leu Gln
545                 550                 555                 560

Asn Ile Asp Phe Thr Ala Leu Ile Asp Ser Leu Leu Pro Val Val Asn
                565                 570                 575

Leu Val Asn Asn Leu Leu Asp Ser Ile Asn Asn Lys Ser Pro Ile Ala
            580                 585                 590
```

Gln Gly Leu Ile Ser Ile Phe Gly Thr Ile Val Thr Thr Ala Phe Gln
595 600 605

Leu Ile Gly Pro Val Val Glu Ala Val Ser Pro Ile Ile Thr Arg Ile
610 615 620

Phe Thr Phe Leu Gly Glu Tyr Ala Pro Gln Ile Asn Asn Phe Ile Glu
625 630 635 640

Thr Leu Gly Val Ile Trp Lys Thr Val Trp Glu Thr Leu Gly Pro Leu
645 650 655

Leu Glu Thr Gly Trp Lys Ile Ile Glu Pro Ile Leu Gly Ala Phe Phe
660 665 670

Asn Ile Leu Asp Lys Val Cys Lys Ile Val Lys Asp Ile Cys Lys Trp
675 680 685

Trp Gln Thr Met Ile Asn Lys Ile Lys Asn Gly Ser Ile Thr Gly Thr
690 695 700

Val Leu Asn Leu Val Glu Lys Ser Lys Lys Asn Tyr Lys Asp Asn Pro
705 710 715 720

Tyr Ala Gly Thr Lys Ala Gly Asp Ser Gly Lys Ala Tyr Ser Ser Lys
725 730 735

Lys Gly Asn Asn Ala Phe Gly Leu Asn Tyr Val Pro Tyr Asn Asp Tyr
740 745 750

Gln Thr Arg Leu His Glu Gly Glu Met Val Leu Thr Lys Gln Glu Ala
755 760 765

Asn Gln Tyr Arg Ser Arg Lys Asn Gly Gly Asn Ile Asn Ile Ala Lys
770 775 780

Leu Ala Asp Thr Ile Val Ile Arg Glu Glu Ala Asp Ile Glu Lys Ile
785 790 795 800

Thr Ser Lys Leu Val Ala Ser Ile Gln Leu Ala Gln Leu Gly Gly Val
805 810 815

Leu

<210> SEQ ID NO 10
<211> LENGTH: 140
<212> TYPE: PRT
<213> ORGANISM: Clostridium difficile

<400> SEQUENCE: 10

Met Glu Met Trp Leu Arg Gln Ala Glu Asp Arg Phe Arg Phe Pro Val
1 5 10 15

Phe Pro Ser Ser Phe Ser Ile Asn Gly Lys Ala Ala Val Asn Ser Ser
20 25 30

Ser Ile Leu Lys Ile Gly Glu Val Ala Thr Phe Gly Gly Val Ala Leu
35 40 45

Lys Ser Ile Ser Ile Ser Ser Phe Phe Pro Asn Lys Asp Tyr Thr Phe
50 55 60

Cys Asp Tyr Thr Gly Phe Pro Ser Pro Tyr Asp Cys Val Asn Lys Ile
65 70 75 80

Glu Lys Trp Met Lys Glu Gly Phe Ile Leu Arg Phe Thr Ile Thr Glu
85 90 95

Thr Asn Ile Asn Met Glu Val Ile Ile Glu Gly Phe Ser Tyr Glu Glu
100 105 110

Arg Asp Gly Thr Arg Asp Val Tyr Phe Thr Leu Asp Leu Lys Glu Tyr
115 120 125

Lys Arg Ile Lys Ile Pro Lys Val Thr Pro Lys Gln
130 135 140

<210> SEQ ID NO 11
<211> LENGTH: 509
<212> TYPE: PRT
<213> ORGANISM: Clostridium difficile

<400> SEQUENCE: 11

Met Ile Ile Asn Arg Ser Lys Asp Ser Ser Ser Asn Glu Ile Ser Phe
1 5 10 15

Val Ser Lys Asp Met Gly Phe Leu Leu Thr Gln Ser Glu Val Ser Tyr
20 25 30

Asn Phe Lys Asp Lys Leu Val Glu Asp Ile Ala Lys Gln Val Phe Ala
35 40 45

Glu Asn Arg Leu Ser Val Gly Thr Ile Ala Lys Thr Asn Val Lys Tyr
50 55 60

Thr Lys Met Phe Ile Gly Val Asn Gly Tyr Asp Thr Ile Met Ser Ala
65 70 75 80

Tyr Thr Glu Ala Ser Lys Lys Thr Lys Lys Lys Tyr Met Ile Glu Ala
85 90 95

Asn Leu Asp Lys Phe Asn Val Ile Glu Lys Gly Thr Val Thr Leu Ser
100 105 110

Val Met Phe Glu Glu Gly Phe Asn Ile Ile Asn Thr Thr Phe Ser Glu
115 120 125

Ser Met Glu Asn Val Lys Asn Lys Val Ile Val Val Asp Gln Tyr Gly
130 135 140

Ser Lys Ile Ser Glu Lys Ile Asp Asn Glu Ile Phe Lys Glu Val Asn
145 150 155 160

Val Ile Met Gln Lys Val Ile Gln Gln Gln Glu Asn Gln Asp Val Asp
165 170 175

Ile Asp Ser Glu Phe Asn Gly Ile Glu Lys Ser Cys Ser Leu Lys Gly
180 185 190

Tyr Gly Asp Val Ser Cys Ile Thr Gly Arg Gly Val Lys Val Lys Asp
195 200 205

Ser Tyr Thr Lys Leu Val Gly Leu Phe Tyr Ile Asp Thr Asp Lys His
210 215 220

Thr Trp Gln Asn Gly Glu Tyr Gln Ile Glu Leu Glu Leu Asn Phe Gln
225 230 235 240

Asn Leu Met Asp Glu Lys Ser Ala Gly Gln Asp Glu Pro Lys Glu Glu
245 250 255

Ser Asn Leu Gly Gly Glu Asp Tyr Ala Gly Gly Lys Glu Phe Thr Ala
260 265 270

Glu Phe Thr Ala Tyr Cys Pro Arg Lys Glu Glu Gly Gly Asp Thr Asp
275 280 285

Cys Arg Lys Lys Lys Leu Asp Pro Ser Lys Lys Thr Cys Ala Ala Pro
290 295 300

Met Val Gly Lys Tyr Glu Gln Thr Tyr Tyr Thr Lys Glu Phe Leu Asn
305 310 315 320

Lys His Pro Leu Leu Asn Tyr Gly Asp Glu Ile Gln Val Ile Thr Gly
325 330 335

Val Ser Gly Arg Asp Gly Val Tyr Lys Val Asn Asp Val Gly Pro Ala
340 345 350

Ile Thr Ile Glu Lys Asn Gly Thr Tyr His Ile Asp Ile Leu Phe Gly
355 360 365

Asn Val Glu Glu Ala Ser Lys Phe Gly Arg Arg Lys Gly Lys Ile Ile
370 375 380

Ile Gly Gly Tyr Ser Gly Asn Val Ser Asp Lys Ala Lys Ile Val Ile

-continued

```
385                 390                 395                 400

Ser Glu Ala Lys Lys His Leu Gly Lys Pro Tyr Lys Trp Gly Gly Asn
                405                 410                 415

Gly Pro Ser Ser Phe Asp Cys Ser Gly Leu Met Val Tyr Cys Phe Lys
            420                 425                 430

Lys Val Asn Val Ser Leu Pro Arg Thr Ser Asn Gln Gln Ser Lys Lys
        435                 440                 445

Gly Lys Lys Val Glu Gln Lys Asn Leu Gln Ala Gly Asp Leu Val Phe
    450                 455                 460

Phe His Asn Pro Val Ser His Val Gly Leu Tyr Ile Gly Asn Gly Glu
465                 470                 475                 480

Phe Leu His Ala Pro Gln Lys Gly Asp Val Val Lys Ile Ser Lys Leu
                485                 490                 495

Ser Ser Arg Arg Asp Phe Asn Thr Ala Arg Arg Val Leu
            500                 505


<210> SEQ ID NO 12
<211> LENGTH: 108
<212> TYPE: PRT
<213> ORGANISM: Clostridium difficile

<400> SEQUENCE: 12

Met Ala Asn Pro Ile Asn Glu Phe Ile Gly Ile Ile Arg Glu Glu Gly
1               5                   10                  15

Lys Tyr His Asn Gln Pro Ser Phe Phe Ile Gly Lys Ile Lys Ser Lys
            20                  25                  30

Leu Pro Asp Leu Lys Ile Glu Thr Asn Asn Ile Ile Leu Glu Lys Glu
        35                  40                  45

Asp Ile Leu Ile Asp Ser Trp Met Ile Asp Arg Gln Leu Glu Thr Phe
    50                  55                  60

Asp Thr Glu Thr Asn Gln Glu His Gln His Glu Val Lys Asn Pro Phe
65                  70                  75                  80

Ile Asp Asn Phe Glu Ser Gly Asp Met Val Ile Met Phe Arg Ile Gly
                85                  90                  95

Glu Lys Phe Ala Val Val Ser Lys Leu Val Ser Leu
            100                 105


<210> SEQ ID NO 13
<211> LENGTH: 142
<212> TYPE: PRT
<213> ORGANISM: Clostridium difficile

<400> SEQUENCE: 13

Met Ser Thr Ile Phe Pro Phe Ile Gly Val Pro Glu Asp Tyr Ile Leu
1               5                   10                  15

Pro Lys Thr Glu Glu Leu Pro Ile Phe Arg Glu Val Ala Trp Asp Phe
            20                  25                  30

Glu Lys Asp Glu Pro Ile Leu Glu Lys Gly Asp Phe Lys Ile Ile Glu
        35                  40                  45

Lys Lys Glu Ala Leu Lys Val Trp Ile Tyr Lys Cys Ile Lys Thr Asn
    50                  55                  60

Arg Tyr Glu His Glu Ile Tyr Ser Leu Glu Tyr Gly Thr Glu Leu Ser
65                  70                  75                  80

Glu Leu Ile Gly Gln Lys Tyr Thr Lys Gly Leu Thr Glu Ser Glu Ala
                85                  90                  95

Ser Arg Phe Ile Lys Glu Ala Leu Leu Ile Asn Pro Tyr Ile Leu Glu
            100                 105                 110
```

-continued

```
Val Asn Val Lys Ser Ala Asn Phe Asn Arg Asp Val Leu Ser Ala Asn
        115                 120                 125

Val Lys Val Ser Thr Ile Tyr Gly Glu Val Glu Ile Asn Val
    130                 135                 140


<210> SEQ ID NO 14
<211> LENGTH: 350
<212> TYPE: PRT
<213> ORGANISM: Clostridium difficile

<400> SEQUENCE: 14

Met Tyr Ser Asp Gln Thr Tyr Glu Val Ile Lys Asn Arg Thr Leu Glu
1               5                   10                  15

Asn Ile Asn Leu Asp Ile Tyr Lys Gly Glu Gly Ser Phe Leu Asn Asn
            20                  25                  30

Met Val Ser Gly Asn Asn Leu Glu Leu Ser Lys Ile Tyr Leu Glu Leu
        35                  40                  45

Ser Lys Ile His Lys Met Ala Phe Ile Gln Asp Thr Tyr Asn Gln Phe
    50                  55                  60

Leu Asp Lys Arg Val Asn Glu Phe Gly Val Tyr Arg Lys Leu Gly Thr
65                  70                  75                  80

Glu Ser Asn Gly Glu Val Glu Phe Ile Gly Glu Lys Gly Thr Val Ile
                85                  90                  95

Asn Asn Gly Thr Ile Ile Ser Tyr Arg Asp Leu Leu Phe Val Val Ile
            100                 105                 110

Lys Asp Val Thr Ile Gly Ser Glu Glu Gly Asp Asn Ser Pro Val Gln
        115                 120                 125

Ala Leu Glu Val Gly Lys Lys Tyr Asn Leu Pro Thr Asn Cys Glu Phe
    130                 135                 140

Lys Leu Val Asp Asn Ile Ser Gly Val Thr Lys Ile Thr Asn Thr Arg
145                 150                 155                 160

Ser Phe Glu Gly Gly Thr Asp Ile Glu Thr Asp Glu Glu Leu Lys Glu
                165                 170                 175

Arg Phe Tyr Lys Ile Gln Arg Asn Gln Ala Thr Ser Gly Asn Lys Ala
            180                 185                 190

His Tyr Glu Glu Trp Ala Leu Glu Val Asp Gly Val Tyr Asn Val Lys
        195                 200                 205

Val Tyr Pro Arg Trp Asp Gly Pro Gly Thr Val Lys Val Leu Ile Phe
    210                 215                 220

Gly Glu Asn Asn Gln Ala Val Asp Thr Glu Thr Ile Glu Arg Cys Gln
225                 230                 235                 240

Gln His Ile Asp Glu Glu Lys Pro Ile Gly Pro Thr Ile Thr Val Val
                245                 250                 255

Thr Pro Leu Pro Ile Glu Ile Ser Ile Ser Ala Val Met Lys Leu Glu
            260                 265                 270

Asp Gly Tyr Thr Leu Asp Asn Val Lys Glu Ser Phe Leu Glu Ser Ile
        275                 280                 285

Asn Thr Tyr Phe Arg Asp Ile Arg Gly Glu Ile Ile Tyr Thr Lys Val
    290                 295                 300

Met Gly Ile Leu Ile Asn Thr Thr Gly Val His Asp Leu Ser Asn Leu
305                 310                 315                 320

Leu Ile Asn Gly Ser Thr Asp Asn Ile Thr Ile Asn Glu Asp Lys Ile
                325                 330                 335

Pro Ser Val Thr Thr Val Asn Phe Ser Glu Val Glu Asn Gln
            340                 345                 350
```

<210> SEQ ID NO 15
<211> LENGTH: 232
<212> TYPE: PRT
<213> ORGANISM: Clostridium difficile

<400> SEQUENCE: 15

```
Met Lys Leu Ile Asp Lys Leu Pro Ser Phe Asp Arg Asn Tyr Ile Val
1               5                   10                  15

Glu Glu Ile Gln Gly Ala Tyr Asp Thr Glu Leu Asn Ile Leu Lys Glu
            20                  25                  30

Asp Ile Asp Asp Thr Phe Asn Gln Leu Phe Val Asp Thr Ala Thr Trp
        35                  40                  45

Gly Leu Asp Met Trp Glu Asp Ile Leu Cys Ile Glu Lys Lys Glu Leu
    50                  55                  60

Asp Phe Asp Thr Arg Arg Ser Asn Ile Lys Ala Lys Met Arg Ser Arg
65                  70                  75                  80

Gly Thr Ser Thr Ile Glu Val Ile Lys Ser Ile Cys Glu Ala Tyr Thr
                85                  90                  95

Lys Ser Glu Thr Asp Ile Lys Val Tyr Ser Asp Glu Phe Thr Phe Val
            100                 105                 110

Leu Ser Phe Ile Ala Asn Asn Cys Asp Tyr Lys Thr Leu Leu Asp Cys
        115                 120                 125

Ser Glu Met Ile Glu Arg Val Lys Pro Ala His Leu Leu His Tyr Leu
    130                 135                 140

Glu Pro Ile Ile Leu Asp Lys Ser Met Val Tyr Cys Gly Gly Gly Met
145                 150                 155                 160

Val Cys Ser Glu Glu Val Lys Val His Pro Tyr Phe Glu Pro Ile Ile
                165                 170                 175

Lys Cys Ser Ala Val Val Asn Cys Gly Ala Gly Met Leu Ser Arg Glu
            180                 185                 190

Glu Ile Lys Val Tyr Pro Leu Ser Ile Lys Cys Ile Glu Asn Asn Cys
        195                 200                 205

Lys Ile Asn Ile Ala Ile Ala Asn Asp Thr Gly Val Glu Asn Val Val
    210                 215                 220

Val Tyr Pro Lys Ser Glu Val Val
225                 230
```

<210> SEQ ID NO 16
<211> LENGTH: 328
<212> TYPE: PRT
<213> ORGANISM: Clostridium difficile

<400> SEQUENCE: 16

```
Met Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95
```

-continued

```
Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Asp Asp Lys Phe Asp
145                 150                 155                 160

Lys Asn Ile Lys Glu Ile Lys Val Lys Ile Gly Asp Thr Asp Ile Leu
                165                 170                 175

Thr Thr Asp Ser Lys Asp Leu Ser Gly Ala Ile Asn Glu Val Val Lys
            180                 185                 190

Lys Ile Glu Asn Ile Ser Phe Asp Asp Val Ile Ser Gly Gln Ile Gln
        195                 200                 205

Thr Asp Ile Ser Val Leu Lys Asn Ser Tyr Asn Lys Leu Ser Glu Lys
    210                 215                 220

Val Leu Asp Ile Leu Ile Tyr Leu Glu Leu Glu Ser Glu Val Thr Val
225                 230                 235                 240

Asp Glu Ala Gly Tyr Trp Tyr Asp Thr Leu Ala Asn Gly Asn Asn Ile
                245                 250                 255

Val Ala Ile Glu Gly Leu Lys Leu Asp Leu Asn Arg Lys Cys Ile Thr
            260                 265                 270

Gly Glu Ile Gly Asn Val Ile Phe Arg Asp Val Val Leu Pro Phe Ser
        275                 280                 285

Ala Asn Arg Val Arg Tyr Ile His Asp Met Asp Asn Asn Phe Val Glu
    290                 295                 300

Thr Lys Ser Ser Asn Thr Tyr Leu Lys Glu Gln Lys Asp Ile Thr Leu
305                 310                 315                 320

Ser Lys Tyr Ser Tyr Glu Ile Arg
                325
```

<210> SEQ ID NO 17
<211> LENGTH: 1725
<212> TYPE: PRT
<213> ORGANISM: Clostridium difficile

<400> SEQUENCE: 17

```
Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140
```

-continued

```
Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Asn Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Asn Pro Tyr Asn Asn Ile Glu
    530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
                565                 570                 575
```

-continued

```
Leu Tyr Val Ser Gly Tyr Asn Tyr Asn Tyr Gln Leu Gly Lys Gly Asn
            580                 585                 590

Asn Ser Asn Gln Ser Lys Ala Leu Val Ser Gln Cys Arg Thr Asn Ser
        595                 600                 605

Thr Ser Ser Thr Ser Asn Gly Leu Arg Thr Leu Pro Lys Ile Thr Asn
    610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
                645                 650                 655

Pro Ser Ile Ser Asp Tyr Ser Arg Tyr Gly Thr Phe Ile Glu Ala Thr
            660                 665                 670

Asn Ser Asn His Asn Thr Tyr Phe Ile Gln Glu Thr Asp Phe Ser Gly
        675                 680                 685

Ile Glu Lys Val Ile Gly Met Ser Asn Asn Ile Leu Phe Phe Lys Lys
    690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
                725                 730                 735

Gly Ser Asn Phe Ile Ile Tyr His Ser Asn Ser Lys Leu Tyr Gly Lys
            740                 745                 750

Gly Ile Ala Asn Ser Gly Gln Phe Gly Asn Ser Thr Asn Ile Asp Gly
        755                 760                 765

Thr Ser Asn Tyr Asp Thr Gly Leu Lys Asp Ile Lys Asp Ile Ile Val
    770                 775                 780

Lys Gly Asn Thr Val Val Val Val Asp Lys Asn Asn Asn Ile Tyr Val
785                 790                 795                 800

Thr Gly Met Asn Gln Asn Asn Lys Leu Gly Ile Gly Glu Tyr Asn Asn
                805                 810                 815

Glu Pro Val Lys Lys Phe Thr Asn Ile Thr Glu Gln Ser Asn Ser Phe
            820                 825                 830

Ile Phe Met Asp Asp Ile Lys Glu Ile Thr Thr Ser Arg Asn Thr Met
        835                 840                 845

Phe Ile Val Lys Asn Asp Gly Thr Ala Tyr Ala Thr Gly Asn Asn Ser
    850                 855                 860

Ser Gly Gln Leu Gly Leu Gly Asp Thr Ile Asn Arg Asn Lys Phe Thr
865                 870                 875                 880

Gln Ile Asn Leu Asp Asn Ile Lys Lys Ile Ser Thr Ser Ile Asp Gly
                885                 890                 895

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
        915                 920                 925

Thr Phe Thr Lys Val Asn Ile Gln Asn Val Arg Asp Val Val Leu Gly
    930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
                965                 970                 975

Pro Asp Val Leu Thr Phe Thr Val Asn Asn Ile Thr Asn Val Arg Asp
            980                 985                 990

Val Tyr Cys Ser Asp Thr Thr Thr  Phe Ile Val Lys Asp  Thr Asn Ile
```

-continued

```
        995                 1000                1005

Ala Tyr  Cys Cys Gly Tyr Asn  Asn Asn Ser Gln Leu  Gly Met Gly
    1010                 1015                 1020

Asn Thr  Thr Asp Gln Tyr Ser  Phe Ile Lys Cys Met  Glu Asn Val
    1025                 1030                 1035

Lys Glu  Val Ile Pro Asn Glu  Ile Asn Thr Tyr Ile  Ile Thr Ile
    1040                 1045                 1050

Tyr Asn  Thr Ala Tyr Ser Thr  Gly Leu Asn Thr Asp  Tyr Cys Leu
    1055                 1060                 1065

Gly Leu  Asn Ser Asn Ser Asn  Gln Ser Ser Phe Ser  Glu Ile Pro
    1070                 1075                 1080

Ile Ser  Asn Val Val Lys Val  Ala Pro Asn Arg Asn  Asn Ala Val
    1085                 1090                 1095

Leu Leu  Leu Thr Ser Glu Gly  Asp Val Tyr Thr Ala  Gly Lys Cys
    1100                 1105                 1110

Ser Asn  Gly Ser Gly Thr Gly  Ser Glu Thr Pro Glu  Lys Ile Lys
    1115                 1120                 1125

Lys Ile  Ala Ser Lys Ala Lys  Asp Ile Gly Met Asn  Tyr Arg Cys
    1130                 1135                 1140

Gly His  Tyr Val Ser Asp Asn  Gly Asp Leu Tyr Gly  Thr Gly Phe
    1145                 1150                 1155

Asn Asn  Asn Gly Gln Leu Gly  Val Gly Asp Val Thr  Lys Arg Asp
    1160                 1165                 1170

Thr Phe  Ile Lys Thr Asn Thr  Arg Val Lys Lys Ile  Leu Pro Leu
    1175                 1180                 1185

Glu Tyr  Ala Asn Ile Ala Ile  Lys Asp Thr Asn Asp  Ile Tyr Ile
    1190                 1195                 1200

Cys Gly  Leu Asn Asn Tyr Gly  Gln Leu Gly Val Gly  Asn Arg Tyr
    1205                 1210                 1215

Asp Ser  Arg Asn Asn Asp Asn  Arg Ile Phe Asn Tyr  Lys His Met
    1220                 1225                 1230

Asn Phe  Val Met Gly Asp Leu  Thr Ser Ile Lys Asn  Arg His Asn
    1235                 1240                 1245

Phe Ile  Leu Leu Asn Asn Lys  Ile Val Ile Pro Thr  Thr Lys Asp
    1250                 1255                 1260

Ile Asp  Tyr Gly Leu Val Leu  Gly Asn Leu Tyr Lys  Gly Asp Leu
    1265                 1270                 1275

Tyr Thr  Glu Leu Pro Tyr Glu  Asp Ile Lys Glu Val  Ser Ile Ser
    1280                 1285                 1290

Lys Thr  His Ile Ile Ile Leu  Leu Asn Asp Gly Thr  Met Tyr Gly
    1295                 1300                 1305

Cys Gly  Thr Asn Tyr His Gly  Glu Leu Leu Gln Asp  Leu Ser Ile
    1310                 1315                 1320

Asn Gln  Val Asp Glu Phe Val  Gln Ile Asn Val Ser  Asp Val Lys
    1325                 1330                 1335

His Val  Ser Cys Gly Asp Asn  Phe Thr Tyr Phe Ile  Lys Ser Asp
    1340                 1345                 1350

Asp Ser  Leu Trp Ser Ile Gly  Lys Asn Ser Glu Tyr  Gln Leu Gly
    1355                 1360                 1365

Ile Gly  His Asn Asn Pro Val  Thr Glu Leu Gln Arg  Ile Thr Thr
    1370                 1375                 1380

Ile Ser  Ser Cys Lys Glu Val  His Cys Gly Lys Asn  Tyr Thr Leu
    1385                 1390                 1395
```

-continued

Val Val Thr Thr Gly Asn Glu Leu Phe Val Gln Gly Tyr Asn Asp
1400 1405 1410

Lys Gly Ala Leu Gly Leu Gly Ser Asp Ser Glu Asn Thr Ile Ile
1415 1420 1425

Lys Phe Phe Thr Lys Ala Leu Thr Asp Ile Arg Glu Ile Lys Ser
1430 1435 1440

Tyr Gly Ser Asp His Ile Leu Val Leu Lys Asn Asp Asn Ser Val
1445 1450 1455

Trp Val Thr Gly Lys Asn Arg Asp Val Tyr Lys Ile Glu Gln Pro
1460 1465 1470

Val Glu Phe Leu Lys Glu Phe Thr Ile Val Pro Ile Ser Glu Asp
1475 1480 1485

Val Asn Thr Val Lys Asp Val Leu Ala Thr Asp Asn Thr Leu Tyr
1490 1495 1500

Ile Ile Ser Glu Val Gly Thr Thr Asn Ala Ala Ile Glu Ile Thr
1505 1510 1515

Glu Lys Ser Ile Ser Ser Ile Lys Ile Lys Ile Gln Asp Pro Asn
1520 1525 1530

Lys Asp Ile Ser Arg Ile Glu Met Leu Ile Asn Gly Glu Ser Val
1535 1540 1545

Lys Ser Val Ser Asp Leu Thr Thr Glu Lys Ile Ser Phe Glu Val
1550 1555 1560

Pro Pro Asp Lys Ile Lys Ile Gly Glu Asn Lys Ile Leu Phe Arg
1565 1570 1575

Ala Tyr Cys Lys Gly Asp Asp Leu Tyr Ala Ser Leu Phe Ile Phe
1580 1585 1590

Lys Glu Ser Thr Gly Asn Ser Ile Ile Lys Asp Ser Tyr Val Met
1595 1600 1605

Ile Gly Asn Arg Met Tyr Lys Val Val Asn Thr Thr Ser Asn Glu
1610 1615 1620

Gln Asp Ile Thr Ile Thr Leu Asp Arg Gly Leu Glu Glu Asp Leu
1625 1630 1635

Asn Leu Gly Asp Pro Ile Tyr Gln Leu Ile Asn Lys Thr Lys Val
1640 1645 1650

Gln Val Lys Ile Asn Lys Ser Asp Leu Phe Lys Asp Met Lys Leu
1655 1660 1665

Val Glu Ile Lys Lys Ser Asp Ser Ser Tyr Gln Glu Ile Tyr Glu
1670 1675 1680

Leu Glu Glu Ala Asn Ile Lys Ser Ala Gln Pro Lys Ile Ile Val
1685 1690 1695

Glu Lys Gly Asp Lys Trp Thr Ala Ile Lys Arg Pro Ser Met Ile
1700 1705 1710

Phe Arg Tyr Asp Ala Glu Asn Asn Glu Pro Gln Ala
1715 1720 1725

<210> SEQ ID NO 18
<211> LENGTH: 98
<212> TYPE: PRT
<213> ORGANISM: Clostridium difficile

<400> SEQUENCE: 18

Met Gln Tyr Lys Asp Ile Ser Asp Ile Ser Ile Gly Gln Ala Lys Gln
1 5 10 15

Asp Asp Asp Ile Thr Asn Asn Phe Ile Ala Asn Ala Glu Ile Tyr Glu
20 25 30

Met Leu Leu Ser Gln Ser Ser Val Asn Glu Ala Ser Asn Ile Ser Thr
        35                  40                  45

Phe Ser Val Arg Lys Ser Gly Gly Glu Ser Gly Met Val Glu Val Tyr
    50                  55                  60

Val Ala Leu Ile Leu Arg Gly Arg Lys Thr Ile Glu Glu Val Pro Ala
65                  70                  75                  80

Val Ile Arg Glu Gln Val Arg Ile Arg Cys Lys Glu Leu Glu Ile Pro
                85                  90                  95

Val Glu

<210> SEQ ID NO 19
<211> LENGTH: 86
<212> TYPE: PRT
<213> ORGANISM: Clostridium difficile

<400> SEQUENCE: 19

Met Asp Lys Leu Ile Thr Glu Leu Ser Ser Leu Gly Ala Ile Gly Ile
1               5                   10                  15

Leu Cys Ala Leu Leu Phe Lys Asn Thr Met Gln Glu Lys Lys Glu Asp
            20                  25                  30

Arg Asp Met Tyr Lys Lys Thr Val Glu Asn Phe Ile Glu Leu Ser Thr
        35                  40                  45

Gln Gln Gln Glu Ile Asn Lys Asn Ile Leu Val Gln Met Gly Ile Met
    50                  55                  60

Lys Thr Asp Val Glu Glu Ile Lys Glu Asp Val Thr Asp Ile Lys Gly
65                  70                  75                  80

Met Leu Gln Asn Gly Val
                85

<210> SEQ ID NO 20
<211> LENGTH: 151
<212> TYPE: PRT
<213> ORGANISM: Clostridium difficile

<400> SEQUENCE: 20

Met Gly Leu Arg Asp Lys Phe Ala Gln Ser Phe Ala Arg Ser Lys Thr
1               5                   10                  15

Met Ser Gly Pro Glu Lys Lys Ala Asn Glu Ile Met Gly Lys Leu Leu
            20                  25                  30

Leu Lys Lys Ala Ile Leu Pro Ile Val Leu Met Phe Val Ile Ile Ile
        35                  40                  45

Ala Gly Ala Met Leu Lys Ile Asn Ser Trp Val Thr Leu Gly Ile Asn
    50                  55                  60

Leu Val Ile Ala Val Gly Ala Phe Phe Tyr Ile Arg Asn Ser Ser Lys
65                  70                  75                  80

Lys Tyr Gln Asn Phe Lys Pro Tyr Val Gly Asn Leu Ile Ser Leu Glu
                85                  90                  95

Lys Lys Gly Lys Lys Glu Tyr Val Ala Ile Ile Lys Gln Gly Lys Leu
            100                 105                 110

Pro Val Lys Leu Gln Ile Ala Tyr Gly Gly Glu Asp Leu Glu His Val
        115                 120                 125

Lys Lys Asn Gln Met Val Gln Ile Ser Tyr Asn Pro Asp Ala Lys Ile
    130                 135                 140

Ala Ile Leu Val Asn Arg Gln
145                 150

<210> SEQ ID NO 21

<211> LENGTH: 139
<212> TYPE: PRT
<213> ORGANISM: Clostridium difficile

<400> SEQUENCE: 21

```
Met Asp Thr Leu Gly Glu Arg Ile Val Tyr Leu Arg Lys Ala Lys Asn
1               5                   10                  15

Leu Lys Gln Tyr Glu Leu Glu Glu Met Leu Gly Cys Asp Asn Leu Ser
            20                  25                  30

Lys Phe Glu Arg Asn Ile Arg Lys Pro Asn Tyr Glu Ile Leu Lys Ser
        35                  40                  45

Ile Ala Glu Ile Phe Asn Val Ser Val Asp Trp Leu Leu Asn Gly Asp
    50                  55                  60

Asn Leu Ser His Lys Ser Asp Leu Ile Cys Asp Ser Ser Ser Asn Tyr
65                  70                  75                  80

Pro Leu Asn Ser Ile Asn Ser Asn Glu Ile Lys Leu Leu Asn Asn Phe
                85                  90                  95

Arg Lys Leu Asn Asp Tyr Asp Lys Ala Lys Ile Glu Gly Met Ile Glu
            100                 105                 110

Leu Lys Leu His Glu Tyr Glu Lys Glu Lys Asp Leu Gly Lys Ile Glu
        115                 120                 125

Tyr Asn Lys Asn Lys Asp Glu Lys Ile Asp Lys
    130                 135
```

<210> SEQ ID NO 22
<211> LENGTH: 69
<212> TYPE: PRT
<213> ORGANISM: Clostridium difficile

<400> SEQUENCE: 22

```
Met Asp Ala Arg Lys Lys Trp Ile Pro Phe Leu Gly Val Gln Val Lys
1               5                   10                  15

Gln Arg Leu Ile Glu Leu Asn Met Thr Gln Arg Glu Leu Ala Lys Lys
            20                  25                  30

Ile Gly Val Asn Glu Asn Tyr Leu Ser Ala Ile Leu Asn Gly Arg Arg
        35                  40                  45

Thr Gly Lys Lys Tyr Lys Ser Ser Ile Tyr Gln Leu Leu Asn Ile Glu
    50                  55                  60

Tyr Ser Glu Asp Asp
65
```

<210> SEQ ID NO 23
<211> LENGTH: 132
<212> TYPE: PRT
<213> ORGANISM: Clostridium difficile

<400> SEQUENCE: 23

```
Val Asp Thr Leu Gly Lys Arg Ile Ala Tyr Leu Arg Asn Ser Lys Lys
1               5                   10                  15

Leu Thr Gln Arg Lys Leu Met Asp Ile Leu Lys Phe Glu Asn Leu Gly
            20                  25                  30

Lys Tyr Glu Thr Gly Asp Arg Lys Pro Asn Cys Asp Ile Leu Met Ser
        35                  40                  45

Ile Ala Asp Tyr Phe Asn Val Thr Thr Asp Trp Leu Leu Tyr Gly Lys
    50                  55                  60

Glu Lys Val Asn Val Asn Ser Ser Val Lys Glu Asp Lys Glu Asp Tyr
65                  70                  75                  80

Leu His Val Thr Asn Asp Glu Met Met Ile Leu Asn Leu Tyr Arg Gln
```

-continued

```
                85                  90                  95

Leu Asn Glu Arg Asp Lys Ile Lys Ile Glu Gly Ile Leu Glu Leu Lys
            100                 105                 110

Ile Ser Glu Tyr Lys Asp Leu Lys Lys His Ser Ser Asn Asn Asn Glu
        115                 120                 125

Asp Lys Met Val
    130


<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

tttcttgaag accatcgaag caccaccacc accaccactg                           40


<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

ttttttgaag acaatcgaag ggcttcgccc tgtcgctcga c                         41


<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

ttccttgaag acctaatttg gggcaatccc gcaaggag                             38


<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

ccccttgaag acccaatttc gtatggcaat gaaagacgg                            39


<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

aattgcggcc gcagctcgct agcggtacct cgaggatatc ttcgaagaag acacatccg      59


<210> SEQ ID NO 29
<211> LENGTH: 36
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 29
aattccggga tgcatgcctc taggatccgg cgcgcc 36

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
agctggcgcg ccggatccta gaggcatgca tcccggaatt cggatgtgtc ttctt 55

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
cgaagatatc ctcgaggtac cgctagcgag ctgcggccgc 40

<210> SEQ ID NO 32
<211> LENGTH: 8119
<212> TYPE: DNA
<213> ORGANISM: Clostridium difficile

<400> SEQUENCE: 32
ggccgcaata cccactacac cttcgtcatc tttaaattta agagttttta ctattgaata 60
ataaaggtat attccagtaa aaataatctt taaatacaag aaaaataaac tctttgggta 120
tattaaaaag ctaaaaagtg taaatataaa agcaagtaga gtacttatcc tgtaaaagaa 180
atctatttgt gtaatgtctt tatattttat cataaacacc gaatataaaa tgatgaaaat 240
aattgcgacg attgcatata tggtaaataa catattttca agagtaccat ttgaaattac 300
tatccactta taccacataa ttggccaaaa taatagtgct aagaacttaa aataattatc 360
aaacaacttt tctttataca ttcatcaaac aacctttctt aacaaaagca tatatttgtt 420
tttagaattt taaataatat gatatcatta ttatatatta atattgaatt tatagaaacc 480
aaaatttgtt aaaataaata tatagatttt actgttaagc cagttaaaat tactactatt 540
tttattatga aattggatca aatatgtaga aatacggcaa attagttaat attaaatatt 600
tattatttcc aagttgtaaa gactgttttt ttaatgataa aaattctaat ctttttttgaa 660 agaaagtaat atccacatta agtatgtctg ccatttcata aacgcaagtg atgccagaat 720
taattatgtt tattatatct tcttcagtaa ttaagaactc acaagcccat tttaaggctt 780
tattttcgca cttatctata ataatttttg tataataatc gttataagag gatacatagt 840
atccaaggct agtgaaatga tgtccaagtt cttcagctaa gatggatgtc aattttttttg 900 agttttgttt taaattactg agtaatgata taattttaat accatgtttg tttatatata 960
gcccttctaa atcacctgca atataagtgg tataatgaat tattatctct tcttgagaag 1020
ctaattcaaa aagcttatcc aaattattca taaaaatccc cctaaaatag aatgtatgtt 1080
tgcctttaaa ttatattaaa agagcagaaa aatagactgc tcatcatatg gtttattttt 1140

-continued

```
ttttatattt atttagtaaa aattctatat aatcattaag ttgttcttgt gcttcttcag   1200
gtaactcttc atgtggattt tttctatgtg cagctactgt atcaatattt tccttaacta   1260
aggttcttcc aagaaggtaa tcaactgata cattaaatac atcagccaat ttgtttaaaa   1320
tgtgttcatc aggaaatctg ttttctgttt catagtaccc taagactctt tgggaaacgc   1380
ctactttttc tccaagttct ctttgagtca atccaaattc ctttctaagt tctcttaatc   1440
ttttggcaaa cattataaca ccaccttatg tatagattat aacaaattgt tctaaaaaat   1500
aaaactaata aaatataaaa gaatattttt tctaaaatct attgataaag aacaaatgat   1560
tctatataat ctaagtgtgg aagaacaaaa tattcttaat ggtaatggag gtataaaaca   1620
atgtttaaaa ataacttgaa atattataga aaatgcaaag gtatgacaca aattcaactt   1680
gccagaaagg ctggaattac aaatgactat atatctcaaa tagaaagagg tataaaaaat   1740
cctggtcttc ttatggctaa gaagatttct agtattttag aacaaaatat agaagaagtt   1800
tttttatac agttatagaa caatatgttc ttgaaagttg tgagattagt aaaaaactgt   1860
gcactaaaga gattattgta aatttgaagc taataataag tatataaaaa aggagaagta   1920
ctatggaaaa caaaaaagat atattattta aagaaacaga tgaaagatta cataattata   1980
agtatttgga tataaagata aagaatatta atttggacat aaaaagatgt gagaatgaat   2040
actctggatg tggagcaatg gtatatacag aaaagactag taacacatat aacataagtt   2100
cttctgtgga aaatgaggtg ttaaaaagag aggaaagatt aagaaaatta aaaatggaaa   2160
aagaagatat agaaatagaa aaagagaaga tagaaaatgc tctaacatgt ctaaatgata   2220
tagaaatgga atttttaat ctttttata atagtaagac aaaaaacaat atgacatata   2280
tttctatgaa actacactta gatagaacat cttgctacaa tttaaagaaa aaaatgatat   2340
ttaaattgag tgagatatta taaaaaatat gacaacttta caacacttta tatacactat   2400
tgcaacacta ggcaataaaa tatgtgagat aatgttattg tgaaagaaat ccatattgaa   2460
ggaggtgata aattgaaaag aataatatta cctaaaaata tagaagatat ttgacaggaa   2520
taaatgagat gtatatttaa aaatgactta tatcatttat agtaagatta tcagattaag   2580
caagaatatt tagtgatagt gtggtgatta tttgcttaaa tacaaggaaa tattagaaac   2640
aattattgag attctcaaaa aaaactttac tgaaagtatt tttattgatg atgaaagtgt   2700
gcaaggctct gaagggtctt gtttttttgt aagtatacta tcagttattt gtacacctat   2760
aatgttaaat acgaataata aagatattgt tatctctata aaatacttac caaaaccaca   2820
gtcaaagagt attagaatgt atgaaatttc agatgaatta aataagttat tcaacagaaa   2880
tataaaggta acagacagaa aattaaatat aacaaagcta gaacaaagta ttaaaaaaga   2940
agagtcaatt tatgtattga actttacaat tacactaaat tatctggata gtgtatatga   3000
agaagatgta gtatatgaaa atatggaaga aatcaattta aatttaggag agtgatagta   3060
tggctatagg attaccaagt atcaacatat catttaagga gctagctaca actgttaaag   3120
aacgttcagc tagaggaata attgcaatgg tgcttaaaga tgctaaggca ctaggtctta   3180
atgaaataca tgaaaaagag gatataccag ttgatttatc tgctgaaaat aaagagtata   3240
taaatttagc tttgatggga aatgttaaca ctccaaataa attattagtt tatgtaatag   3300
aaggagaagc agatattcaa actgcattag atttttaga gactaaggaa tttaattatc   3360
tatgtatgcc aaaagcagta gaagctgata agactgctat aaaaaattgg ataattaaac   3420
ttagagatat agataaggtt aaggttaaag ctgtattagg aaaagttgta ggaaatcatg   3480
aagggataat taattttact acagaagatg tgttagttgg agaaaagaaa tacagtgttg   3540
```

-continued

```
atgagtttac aagtagggtg gctggactta tagcaggaac acctttaagt caatcagtaa   3600
cttatactaa gcttagtgat gtagttgata tacctaagat gacgaaagtt gatgcagaat   3660
caagggttaa taaaggagag cttatactta ttaaggaagc aggggctata agaattgcaa   3720
gaggagtaaa ttctttaact gagttaacag aagaaaaagg agaaatgttc cagaaaataa   3780
aaatagttga cactttagat attatacata gtgacataag aaaggtgata atagatgact   3840
atataggaaa ggttactaac agttatgaca acaaatgttt attgatagta gctataaaaa   3900
gttatttaga agaattagaa aagtcagcac ttatagaatc tgattctact gttgaaatag   3960
attttgaagc acaaaaatcg tatttaaaat caaaaggagt agatttatct tatatgacat   4020
tacaagaaat aaaagaagct aacacaggtt ctaaagtatt tttaaaagca aaaataaaag   4080
tacttgatgc tatggaagat atagatttat caatagaaat ataggaggat tattaatatg   4140
gcaaatatgg aagctagaaa tgtaatgagt ggtacttggg gagaactttg gcttgatgga   4200
aacaaagtag cagaagtaaa gaagtttcaa gcaaagatgg aatttacaaa agaggatatt   4260
ataatagcag gtcaaatggg tactgataca aagtatatgg gatataaagg aaaaggttca   4320
ataactctat accatgttag ttcaagaatg cacaagttaa ttggagaaaa gataaagaga   4380
ggttctgaac ctagatttgt tgctatatct aaattaaatg acccagattc ttatggagca   4440
gaaagaatag cagtaaaaaa tatagcattt gatgatttaa ctttagctga ttgggaggtt   4500
ggagtaaaag gagagataga agcacctttc acatttactg agtatgattt tcttgatata   4560
atttagtttt atatttggtt ttatactgat atttagtaga tatatactta ataaatttag   4620
gtagttaata agtaaaaaag ttagttgatt gaatttgatt gataaaggag caaataataa   4680
tgaatgaaaa tggattatca aaaaatataa acatagtaga tttactttta aatgcagata   4740
cagaaaactt agaaagacca agtactatag ttgaacttaa gagattatca actatatttg   4800
ggcaggaatt taaagtaatg tgtagagctt taacaataag taaagatgaa gagatacaaa   4860
atacttgtct taaaattgat gaaaatatga aaacggatat agacttaccg gagatgcaga   4920
tgcttacaat tatagaaggt gtttgtgatt tggatggaaa gcttttattt aaaaataagg   4980
aactaatgga taaatttaag gctccaacac caaaagaatt ggcaagaaaa ctattattac   5040
caggtgaaat taccaaccta tatagaatac ttcaagatgt tatgggttat ggtaaaaatg   5100
cagtgataga agaggtaaaa aactaatagg gacggatacc aagactacaa taatgtacta   5160
ttattggaag aaaaaaggta taagaccgtc ccttttttat gcaatggata aaggcgaatt   5220
aaagcttatt gaagcttttt tcgccttaga aattgaggaa gaagttgaaa aaatgaaaca   5280
tggatatgga gtgtgtcctt tgacaggagg tggtatgtaa tgggaaatgt gagagaagaa   5340
ggtataaata tgtatcttac agataattac acaccaaaaa tgaaccaaat tatatcagta   5400
actgataatt ttaggagagc aactgtggct gtttcacttt ccactaatgt aatggctagt   5460
agcataaaaa attctattgg aagtgcaagt agtagagtaa acagtttaaa ttcctcgtta   5520
agaaaagttc aaactactgc tagtagtgta agttcaacta tggcaaaatt aagttctagc   5580
ataaatgctg tttcaggagt tattggaagt ttaaatggaa gtattatgag actagcaata   5640
actatagcta tgattattga ttattttaat aagttgattc aaaagaaaaa tgagtttaat   5700
tcaaatatta tgattatatt aatatttaaa gctaaaagtg atgaagtaga aaaaactaaa   5760
aataaattac ttggaaattt aaaaaagatt ggtggcaaga tttggaatat cgtaataaaa   5820
gcaaaagata tgactaagag agtgataagt agtatcttgg gaaaattaaa acgagtagag   5880
aaacgtcctt atcaaggaag tattaatctt aaagatatgg taagtagtgc tatggctaga   5940
```

```
attttgccta agttaatgtt gtttaaaaat actttttgga gtggtgtaat agctataaaa   6000
gatatggcaa gtagcattat aagtaaagta tttcccaaat tgagattgtt tgcaggtaag   6060
gtatggagtg gtgcaatagc tgtaaaggat atggcaagtg gaatacttgg ttcgataaaa   6120
gggaagatat ctgatttgac aaatggtgct actataggtg tcgctgtgaa aaagggtgtt   6180
gacttacttg gtcaggaaca aaatcagaaa gttgttctag aaagtgtaat gaaaagaaat   6240
actggaaaaa ctagccaaaa agatgttgat aagtattatg acagtttagt aaatatggca   6300
aatgatacgc cttttgaccc tgaagatgtt gttgcaatgg gaactaaagc taaaatgatt   6360
agtaatatta ctggtggcaa aaaagaaaaa gatataactc aagctatggt agatgttaga   6420
gctttaaata tgaatacaag tagtgaacaa gatgtatcag cagctttctt aagtgcagca   6480
aaaggaaata tggaatctct taatactctg gtaggagaaa attataaaac ttttgatgaa   6540
gcattggaag gcataagtgt aaagcagatg gggttagcta aagaaatgag taatacaata   6600
ccaggtataa tatcaggagc tcaaacaagc attaacaatg gtttgaagag tattgttaaa   6660
ccttttgatg atattttagg tcaaggacta aagaaaataa aaacttttat agaaagtgga   6720
ttagggaatt tagctggctt atctgaaaaa atggctggta aaataggcaa tgtaatgaat   6780
ggtaagataa ttattggcaa caaatatgac cagatgcaat ctagaagtgt aaaaaatgga   6840
aaagagtttt ctgattctac tcaatatcga atttctaatg aggctgaaaa gcgtaaaatg   6900
atggttgaaa ataagcaaga acgttttgaa aatcatgcag caacaatgat agggaatgca   6960
ccaaaagcaa ttgttaacgc aggaagtaca ctattacaaa atattgattt tacagcatta   7020
atagattcac tacttccagt agtaaactta gtaaataatt tactagatag tataaacaat   7080
aaatcaccaa ttgcacaagg attaataagt atatttggta caatagtaac tacagcattc   7140
caactaatcg gacctgtagt tgaagctgtt agtcctatta tcacaagaat tttactttt    7200
ttaggtgaat atgcacctca aataaacaat tttatagaga cactgggtgt tatttggaaa   7260
actgtatggg agaccttagg acctctgttg gaaactggat ggaaaattat agagccaata   7320
ttgggagctt tttttaacat attagataaa gtatgtaaaa tagttaaaga tatatgcaaa   7380
tggtggcaaa ctatgattaa taagataaaa aatggaagca tcacaggaac agttttaaat   7440
ctagtggaaa agagtaaaaa aaattacaaa gataatccat atgctggaac aaaggctggt   7500
gattctggta aagcttattc aagtaagaaa ggtaataatg catttggatt gaactatgtt   7560
ccttataatg actatcaaac cagactccat gaaggtgaaa tggttttaac taaacaagaa   7620
gcaaatcaat atagaagcag aaaaaatggt ggaaatataa acatagctaa gttagctgat   7680
acaatagtga ttagagaaga agctgatata gaaaagataa catcaaaatt agttgcaagt   7740
atccaattgg cacagttagg gggtgtctta taatggaaat gtggcttaga caagcagaag   7800
atagatttag atttccagta tttccatctt cctttagtat taatggaaaa gctgctgtaa   7860
actcttctag tatactcaaa ataggtgaag tagcaacttt tggtggtgta gctcttaaaa   7920
gcatttcaat atcaagtttt tttccaaata aagactacac tttctgtgac tatacaggtt   7980
ttccatcacc atatgattgt gtaaataaga tagaaaaatg gatgaaggaa ggttttatat   8040
taagatttac aattacggaa acaaatataa atatggaagt cataattgaa gggtttagtt   8100
atgaagaaag agatgggac                                                8119
```

<210> SEQ ID NO 33
<211> LENGTH: 7686
<212> TYPE: DNA
<213> ORGANISM: Clostridium difficile

<400> SEQUENCE: 33

```
tcgagatgta tattttacat tagatttaaa agagtataaa agaataaaga taccaaaagt     60
aactccaaaa caataactat tatagataat aagttgtaag taactgctga tagaattaaa    120
tgaaaaggca ggtgattttt tattattaag atttgggtac acataaaaaa cggaagtata    180
tatgacataa ctgacatagt agacaaggta tcatggtcag gtgattataa atctccatca    240
aggacactag agttttcaat aatacaatca tcatttgatg taaatttcca acaaatcgat    300
ataccaatag ctagtacagt ctgtttctat gtagatgaga aagaactctt tagaggaatg    360
ataattaata ggtctaaaga ttcaagcagt aatgaaatta gttttgtatc taaagatatg    420
ggatttttac ttacacaaag tgaagtgtca tacaatttta aagataagtt agttgaagac    480
atagcaaagc aagtatttgc tgaaaatagg ctttcagttg gaacaatagc aaagaccaat    540
gtcaagtata caaagatgtt tataggagta aatggttatg acacaataat gagtgcatat    600
acagaggcaa gtaaaaagac aaagaaaaag tatatgatag aggctaattt agataagttt    660
aatgttattg aaaaaggaac tgttacatta agtgttatgt ttgaagaggg atttaatatt    720
ataaatacca ccttttcgga gagcatggaa aatgtaaaaa ataaagtaat agtggtagac    780
cagtatggaa gcaagattag cgaaaaaata gataatgaaa tttttaagga agtaaatgta    840
ataatgcaaa aagtaattca gcaacaagaa aatcaagatg tagatattga tagcgagttt    900
aatgggatag aaaaaagctg ttctcttaaa ggttatggag atgtaagttg tataactggt    960
agaggagtaa aagttaaaga ttcttataca aagcttgtag gactatttta tatagataca   1020
gacaaacata cttggcaaaa tggagaatat caaattgagc ttgaacttaa ttttcaaaat   1080
cttatggatg aaaagtcagc aggacaggat gaacctaagg aagaaagtaa tttaggggga   1140
gaagattatg caggaggaaa agagtttaca gcagaattta cagcttactg tcctagaaaa   1200
gaagaaggtg gagatacaga ttgtagaaag aaaaaacttg acccatctaa aaaacttgcg   1260
ctgctcctat ggttggtaaa tatgagcaaa cttattatac aaaagagttt ttaaataaac   1320
atcctttatt gaactatgga gatgaaatac aggtaattac aggagtttct ggtcgtgatg   1380
gagtctataa agtaaatgac gtaggacctg caataactat agaaaaaaat ggaacatacc   1440
atatagatat tttatttgga aatgttgaag aagctagtaa atttggaaga agaaaaggaa   1500
aaattattat tggtggttat tctggtaatg tatctgataa agctaaaata gtaatatcag   1560
aggcaaaaaa acatctaggt aaaccttata aatggggtgg aaatggacca agtagttttg   1620
actgttctgg tttaatggtc tactgtttta aaaaagttaa tgttagtttg ccaagaacgt   1680
caaatcaaca atctaaaaaa ggcaagaaag tagaacaaaa aaatcttcaa gcaggagatt   1740
tagtattttt tcataatcca gtcagccatg ttggattata tataggtaat ggagaatttt   1800
tacatgctcc acaaaaaggt gatgtagtta aaataagtaa gttaagtagt agaagagatt   1860
ttaatacagc taggagagta ttataaaagg atggtgatat aatggctaat ccaataaatg   1920
aatttatagg aataataaga gaagaaggaa agtatcataa tcaaccttct tttttattgg   1980
aaaattaaaa gtaaattacc agatttaaaa atagagacaa ataacatcat attagaaaaa   2040
gaagatattt tgatagatag ttggatgatt gatagacagc tagaaacatt tgacacagaa   2100
acaaatcaag aacaccagca tgaagtaaaa aatcctttta tagataactt tgaatctggg   2160
gatatggtaa taatgtttag aataggcgaa aaatttgctg ttgtaagtaa gttggtgagc   2220
ttataatgag tacaatattt ccttttatag gtgtcccaga ggattatatc ttacctaaaa   2280
cagaagaatt gccaatcttt cgtgaagtgg catgggattt tgaaaaagat gaacctattt   2340
```

```
tagaaaaagg tgactttaaa ataattgaaa aaaaaagaag ccttaaaagt ttggatatac   2400
aagtgtataa agacaaatag atatgaacat gagatatact ctttagaata tgggacagag   2460
ctttcagaac taataggaca aaaatataca aaaggtctta cagaaagtga agctagtaga   2520
ttcataaaag aggcccttct aataaatcca tatatattag aagtaaacgt aaaaagtgct   2580
aactttaaca gagacgtatt gagtgcaaat gtaaaagtat ccactatcta tggggaggtg   2640
gaaataaatg tatagtgacc agacatatga agtaataaaa aatagaactc ttgaaaatat   2700
taatcttgat atttataaag gagaaggttc ttttctaaac aacatggtat ctggaaataa   2760
tctagaactt tcgaagatat atctagaact ttcaaagata cataaaatgg cttttataca   2820
agacacatat aaccagtttc ttgataaaag agtcaatgaa tttggtgtat atagaaagtt   2880
aggtacagag tcaaatggag aagttgaatt tattggagag aaaggaactg taataaataa   2940
tggcacaata atatcatata gagatttact atttgtagta ataaaagatg taactattgg   3000
tagtgaagaa ggtgacaata gcccagttca agctctggaa gttggtaaga aatataattt   3060
acctacaaat tgtgaattta aactagttga taatatatct ggagtaacaa agattactaa   3120
cacaagaagt tttgaaggtg gtacagatat agagacagat gaagaactaa aagaaagatt   3180
ttataaaatc caaagaaatc aagctacaag tggaaataaa gctcactatg aagaatgggc   3240
tttggaagta gatggagtct ataatgttaa ggtttatcca agatgggatg gtccaggaac   3300
agttaaggtc ttgatatttg gggaaaataa tcaagctgtt gatacagaaa cgattgaaag   3360
gtgtcagcaa catatagatg aagagaagcc tattggacca actataacag ttgtgacacc   3420
attaccaata gaaataagta taagtgcagt aatgaaacta gaagatggat atacattaga   3480
caatgtaaaa gaatctttcc tagaaagtat aaatacatac tttagagata ttagaggaga   3540
gataatctat acaaaagtca tggaatact tataaatact actggtgtac acgatttaag   3600
taatctactt ataaatggaa gtacagataa tataactatt aatgaagata aaatacctag   3660
tgtaacaact gttaatttta gtgaggtgga aaatcaatga agctaattga taaactacca   3720
tcatttgata gaaattacat tgtagaggag atacaaggtg catacgatac agaattaaat   3780
attcttaaag aagatattga tgataccttt aaccaattat ttgttgatac agcgacatgg   3840
ggattagata tgtgggaaga catactctgc attgaaaaaa aagaacttga ttttgacaca   3900
agacgtagca atataaaagc taaaatgaga agcagaggta ctagtactat tgaagttata   3960
aaaagtatat gtgaggcata tacaaaatca gaaacagata taaaagttta tagtgatgaa   4020
tttacattcg tattgagttt tatagcaaat aactgtgact ataaaactct tttagattgt   4080
agcgagatga ttgaaagagt aaaacctgct cacttattac actatttaga accaataata   4140
ctagataaaa gtatggtcta ttgtggtgga ggtatggtat gtagtgaaga ggtaaaagtt   4200
catccatact ttgaaccaat tataaaatgt agtgctgttg taaactgtgg agctggaatg   4260
ttaagtagag aagaaataaa ggtttatcct ttaagcatta aatgcattga aaataattgt   4320
aagattaata tagctattgc aaatgataca ggcgtagaaa atgtagtagt ttatcctaaa   4380
tcggaggtgg tataattgga agaaaaattt tatataatat taaccaaaat tggtagagaa   4440
aaaatagcaa atgcaactgc actaggagag cttgttggat taaccaagtt tcaagttgga   4500
gatagtaatg gagaatatta tgagccaaca gaggaacaaa ctgctttaaa gaatgtagtt   4560
tgggaaggaa atataaattc tctaagaatt gatgaaaaaa atcctaattg gatagttata   4620
gagactattt taccaggaac agttggtgga tttatgataa gagaagctgc tgttctggat   4680
aatgagaata atataatagc tatwggtaag tatccagaga cgtataagcc acgtgctgaa   4740
```

-continued

```
gatggcagta ttaaagattt ggttgtaaaa atgattttac aattgtccaa tacttcaaat   4800
gttacattag aagtagaccc gacgttggtt tttgtaactc aaaaggatat tcaagattta   4860
gatgataagt ttgataaaaa tataaaagaa ataaaagtaa aaattggaga tacagatata   4920
ttaactacag attctaaaga tttatcagga gctataaatg aggtagttaa aaaaatagaa   4980
aatatatctt ttgatgatgt tataagtggt caaatacaaa ctgatatatc agtattaaaa   5040
aatagctata acaaattatc tgaaaaagtg ctagatatat taatatacct agaattagag   5100
tcagaagtaa ctgtagatga ggctggttat tggtatgata cattagcaaa tggaaataac   5160
atagtagcta tagaagggct taagttagat ttaaatagaa aatgtataac aggtgaaatt   5220
ggtaatgtga tttttagaga tgtagtatta ccatttagtg caaatagagt tagatatata   5280
catgatatgg ataataactt tgttgagaca aaatctagta acacttattt aaaagaacaa   5340
aaagatataa ctctaagtaa atattcatat gaaataagat aaataaagga ggtagtacta   5400
ataatgaagc aaaataaact tttacagcgt ggtgcttatt ttaatgataa gaacatattg   5460
attgatgatt ttgataaaag atataatgat tatgattttg tagaattttt tactggtata   5520
agtaatagta cctttggttt aaaatcagat ggtaatttat atgcttgtgg cgataataca   5580
ggttttcaac taggacttgg aaaagattcg tcagagagaa ggatgtttag taaagtaaaa   5640
attgataatg taaaatatgt atcttgtggt tcaaaacaca gtgtagcagt aactaaagat   5700
ggatttgcat atggagcagg aacaagtaat gtaggtcaat taggtgtaat tgagtctaca   5760
gtatattatg aatttactaa gctaccaata gatgatgtaa aaactgttgc atgtggttat   5820
gactttacat ttgtgcttaa aaatgatgga acattatatt cagcaggttt aaactcaagt   5880
ggtcaacttg gactaggtga tactaacaat agagctactt ttactaaagt aaatatagat   5940
agtgtgaaag atgtagtgac ttataatcaa tctgtattta tcataaaaat ggatgggaca   6000
gcacatgcat gtggattaaa ttcaaatggg cagttgggaa ttaatagtac tttaaataaa   6060
agtgtattta ataaaataga aggtatggat aatgtaaaac agatagcgtg tggtagtagt   6120
catacaattc ttattaagaa tgatggaact atgtatacta caggctataa tggagttggt   6180
cagcttggta caggaaataa taataattca attgtattta ctctttctag tataaataat   6240
gttaagtatg cttcttgtgg aaataatcat actatgatat taaaatacga taatacactg   6300
tttagtacag gacaaaacaa ttatggtcaa ctagccaatg ccaataaaga tgtagcatca   6360
agaaatactt ttgctaaggt taatgtagaa aatataaaag atattaaatg tggttctcaa   6420
tttaattttt taataaatgg ttcaaaagag atatttgtat ctggctgtaa tttagcaggt   6480
caacttggtt catttttca tacaactttt ctgtatgagt tttcaaatgt gcaatcttca   6540
aatttagata attattcagg tttattggtt aatgatgatt atttatatgt tacaaaggac   6600
aatagtgaat ttttaaatgt aaagttaagt gataattttc aagattataa gaagatagag   6660
ttaacagata gcaatatgtt tattgttatg aatgatggta cattgtatgc ttgtggttta   6720
aataattatg gacagttagg attgggagat actgttaaca ggtcagttat gactaaggtg   6780
gatatagata atgttttgga tataaaagga aacggaaact caacttttgt gcttaagaat   6840
aatggaacat tatattcatg tggtttaaat agtaatggac aattgggttt aagagatgaa   6900
gttaatagaa atatatttac aaaaatagaa atagagaatg taaaggattt ttgtgtagga   6960
agcaattatg tcatagcttt aaatcactca aaagaagtat atggatgggg aaataatcct   7020
tataataata tagaaaaaac ttctaattat ccatataagc agggaataag taatattgaa   7080
aagatagcag catatgatta ttctgtatat atgataaaca gtgaagggaa actatatgtt   7140
```

-continued

```
tctggataca attataatta tcaattaggt aaaggaaata atagtaacca aagcaaagca   7200

ttagtatctc aatgtagaac aaattcaaca tcttctacat caaatggact tagaacgtta   7260

cctaaaataa ctaatgtttt tcctttttat gatggttgtg caataattga cgaaggaggt   7320

tatgtttatt taacaggata tcatggatat ttaagaacat taaatagcag tccaagtata   7380

tctgattatt caagatatgg aacttttatt gaggctacaa attcaaatca taatacttat   7440

tttatacaag agactgattt tagtggaatt gaaaaagtaa tagggatgtc aaataatata   7500

ttattttta agaaaggaag ttcatatatt actggatatc caaaaacatt tggctcaacc   7560

attactggac atagaagtta tactagtatt aattctgaga gttctaattt aggaagtaat   7620

tttataatat atcatagtaa ttccaagtta tatggaaaag ggattgctaa tagtgggcaa   7680

tttggg                                                              7686
```

<210> SEQ ID NO 34
<211> LENGTH: 7020
<212> TYPE: DNA
<213> ORGANISM: Clostridium difficile

<400> SEQUENCE: 34

```
aattcaacaa atatagatgg cacaagtaac tatgatacag gattaaaaga cataaaagat     60

ataattgtaa aaggaaatac tgtagtagta gtagataaaa ataacaatat atatgtaaca    120

ggaatgaatc agaataacaa acttgggata ggggaatata acaacgaacc agtaaaaaaa    180

ttcacaaata taactgaaca atcaaactca tttatattta tggatgatat aaaagaaatt    240

acaacatcaa gaaatacaat gtttatagta aaaaatgatg gaacagccta tgccacagga    300

aataatagtt ctggacaatt aggattaggt gacacaataa atagaaataa gttcactcag    360

ataaaccttg ataatataaa gaaaatatca acaagtatag atggtaacac aacatttgca    420

attagaaatg atggaacact atactccaca ggattaaata ccaaaggaca actgggatta    480

ggtgatatag taaatagaaa tacatttacc aaagtaaaca tccaaaatgt aagagatgtt    540

gttttaggga ctactcactc gcatgcaatc aaagatgata acacattata ttcatgtgga    600

gaaaacactc atgggcaact gggcttagga agcgaaagca accatccaga cgtattgaca    660

tttactgtaa acaatataac taatgtaaga gatgtgtact gctcagatac aacaacattt    720

attgtaaagg acacaaacat tgcatattgt tgtggataca ataataattc acaactaggt    780

atgggaaata ctactgacca gtatagtttt ataaagtgta tggaaaatgt aaaagaagtt    840

ataccaaatg aaataaatac ctatataata acaatctata atactgcata tagtacaggt    900

ttaaatactg attattgctt aggtctaaat agtaatagca atcaaagttc attttctgaa    960

attccaattt caaatgtagt aaaagtagct ccaaacagaa ataatgcagt acttttactt   1020

acaagtgaag ggatgtata tactgcaggc aaatgtagta atggttcagg tacaggaagt   1080

gagactccag agaagattaa aaaaatagca tcaaaggcaa aggatattgg aatgaattat   1140

agatgtggac attatgtaag tgataatgga gacctatatg gtacaggttt taataataat   1200

ggacaattag gtgttggtga tgtaacaaaa agagatacat ttataaaaac caatacaaga   1260

gtaaagaaaa tacttccttt agaatatgca aatatagcaa taaaagatac taatgatata   1320

tatatttgtg gattaaataa ctatggacaa ttaggtgttg gaaatagata cgatagtaga   1380

aataatgata atagaatatt taattataag catatgaatt ttgtaatggg tgatttgaca   1440

tctattaaaa acagacataa ctttatactt ctaaacaata agatagtgat acctaccaca   1500

aaagacatag attatggttt agtattagga aatttataca aaggagacct ttatactgag   1560
```

-continued

```
cttccatatg aagatataaa agaagtatct atttctaaga ctcatattat tatattactt   1620
aatgatggaa caatgtatgg atgtggtaca aactaccatg gagaattatt gcaagacttg   1680
tctataaatc aagtggatga atttgtgcag attaatgtat cagatgtaaa gcatgtttca   1740
tgtggagata actttactta ttttataaaa tctgatgata gtctttggtc tattggtaaa   1800
aattccgaat atcaattagg tataggtcac aataatccag ttactgaatt acaaagaatt   1860
acaactatat ctagctgtaa agaagtacat tgtggtaaaa actatacatt agtagtaact   1920
acaggtaatg aattatttgt acaaggatat aatgataagg gagctttagg attaggaagc   1980
gatagtgaaa atactataat taagttcttt acaaaagcac taacagacat aagagaaata   2040
aaatcttatg gaagtgacca tatattagta cttaaaaatg ataattcagt atgggttact   2100
ggaaaaaata gggatgtata taaaattgaa caaccagtag aatttttaaa agaatttact   2160
atagtaccta tttctgaaga tgtaaataca gtaaaggatg tacttgcaac agacaataca   2220
ttatatatta tatcagaagt aggaacgaca aatgctgcta tagaaattac tgaaaaatca   2280
atttcatcaa ttaagataaa aatacaagac cctaataaag atataagtag aatagaaatg   2340
cttataaatg gtgaaagtgt aaaatctgta agtgatttaa ctactgaaaa aatatccttt   2400
gaagtaccac cagataaaat taaaatagga gagaataaga tactatttag agcttattgt   2460
aaaggtgatg atttatatgc atctttattt atttttaaag agagtactgg aaattctata   2520
attaaagatt cttatgttat gataggtaat agaatgtaca aggtagttaa tacaacatct   2580
aatgaacaag atattacaat tacactagat agaggacttg aagaagattt aaatcttgga   2640
gaccctatat atcaattaat aaataaaact aaagttcaag taaaaataaa taaatctgac   2700
ttattcaaag acatgaaact agttgaaatc aaaaaatcag actcaagtta tcaagaaatc   2760
tatgaattag aagaagccaa cataaaaagt gctcagccta aaatcatagt agaaaaagga   2820
gataaatgga cagctataaa acgtccatct atgattttta gatatgatgc tgaaaacaac   2880
gagccacaag cttaaaatgg aggtgtaaaa attgtttaaa ttcgataaaa ataaaataga   2940
acaaatcaaa caaggtagaa aagtagaaat gcagtataaa gacatttcag acataagtat   3000
aggtcaagca aagcaagatg atgatataac aaataatttt atagcaaatg cagaaatata   3060
tgagatgttg ttaagtcaaa gttctgtcaa tgaagcaagt aatataagca cttttagtgt   3120
aagaaaatct ggaggtgaga gtggaatggt agaagtatat gtagctttaa ttttaagagg   3180
cagaaaaaca atagaagaag taccagcagt aattagagag caagttagaa ttagatgtaa   3240
agaattagaa ataccagttg aatagtaaat ttagaataac tatgtattag ttattttttt   3300
tatgtaaagt acaaggtctt aactttaata agtaagcctt gtacttattt tttgttatat   3360
tagaaattgt atatatattt attatttatt caatctataa attaaaccta caatttaaag   3420
tacagaagat taaattgata atcctgaaaa tataatattg catgatgtaa gaatataaca   3480
aaaattaaag ctataagtat aaaaaattta gacaatagga ggctataatg gataaattaa   3540
taaccgaatt gagtagtctg gggcaatag gtatactatg tgctctatta tttaaaaata   3600
ctatgcagga gaaaaaagaa gatagagaca tgtataaaaa aactgtagaa aattttatag   3660
aattatctac acaacaacaa gaaataaaca aaaatatact tgttcaaatg ggaataatga   3720
aaacagatgt agaggaaatt aaggaagatg ttactgatat aaaaggtatg ttacaaaacg   3780
gtgtataaca tgaaagtagc agtagcacca gattatatat tattaggaaa agataaagta   3840
gtattgtaga tagtgcccta ttttattgag aaggatttta tattttaaaa tattaattaa   3900
aaaaagtaat aaaaataata tataaaaata acatataaaa attcaaaaag gagttaagct   3960
```

taaatttgat tagaaaaaat caattttaag acaactcctt ttttttatta aattattgtc 4020
tattaaccaa aatagctatt ttagcatctg gattataact tatctgaacc atttgatttt 4080
tcttaacatg ttcaaggtct tcaccaccat aagctatttg taacttaact ggtaacttac 4140
cttgttttat aatagcaacg tactcttttt tacctttttc tctaaactaa tcaaattgcc 4200
aacataaggt ttaaagttct gatacttttt actagaattt cttatgtaga agaaagcacc 4260
aacagcaata actaaattta tgccaagtgt aacccaagaa ttgattttaa gcatagctcc 4320
agcgattatt atcacgaaca ttaaaacgat aggtaatata gctttcttaa gaagcaattt 4380
acccattatt tcattagcct ttttctcagg gccactcata gtttttgatc tagcaaatga 4440
ttgcgcgaat ttgtctctta agcccatttt atcctcctaa ttttaataaa tatttagtta 4500
taataacgag atattacttg aaactaaaaa tttactacat ttatattatg tttgactttt 4560
gtataaataa ttacattcaa gtaaagcaaa atatactaat tattttatca taaaattata 4620
aaaaagaaaa taaatgaaat aaaaatatta gaacaaagaa atgatgtaaa atcgtatcaa 4680
aagcaacata aaaattattt atctattttc tcatctttat ttttgttata ctcaattttt 4740
cctaaatcct tctcttttc atattcatga agttttaatt caatcatacc ttctattttg 4800
gctttatcat aatcatttaa ctttctaaag ttgtttaaaa gctttatttc attagagttt 4860
atgctattaa gtggatagtt tgaggaggaa tcgcaaatta aatctgattt atgtgataga 4920
ttatctccat ttaatagcca gtctactgaa acattaaata tctcagctat agattttaat 4980
atttcataat ttggttttct aatgtttctc tcaaatttac ttaagttgtc acagcctaac 5040
atttcttcta gttcatattg tttaaggttt tttgcttttc tcaaataaac aattctttct 5100
cctaaagtat ccataaacac tctccattca attaatgtca aaaagacttt ttaagatgta 5160
aatagtttca aattaaaggt caaaatgaca taaaaaccat tgacttaagg tcaaaatgac 5220
tttataatta acttaatgat acgaatttac atcctaattt tagcacaaag taatcaaaaa 5280
atcttattta gtattaaata aatttatata cttaatatgt gtacatatta aaaatatata 5340
ctaaatagag ggggtgcgta agctaaagta atataaaagt aaatataaat cacttagaaa 5400
ggaagttgat aaatggatgc tcgaaaaaaa tggatacctt ttttgggagt gcaagtcaag 5460
caaagactta ttgaattaaa tatgactcaa agggaattag cgaagaaaat aggtgttaat 5520
gaaaactatt tgtcagctat tttaaatgga agaagaacag gtaaaaaata taaatcatca 5580
atttatcaat tacttaatat agaatattca gaagatgatt aataaatagt atataaagta 5640
ggtgaatatt cttgtgtgca aattggattc agatggggtt atagagtgtt gtagagcaat 5700
tgatgatttt attacagcac ttagtaatat aaaaagctta aatatggaaa gattaaatac 5760
tttaactaaa tattctagta catgttcaat ccttcttaaa gaggggaatt atgaaggatg 5820
tacaattgtg tatagaaaga tgttggaaga attaaaaaca tgagtaatgc atttcttagg 5880
aatataaatt atacatagaa atgtattata tttttcaaag tacttaaact aaaatatgga 5940
taagataatc taaatattat aaatgtgctt gaaattagac tatacttgtt tttaaataat 6000
ccaatatcca tattttagta atatactaca aaaaaagaag gttaatagat gatgtaaaat 6060
cgtatcaaat tatgtatgtt taaaccattt tatcttcatt attattagag gaatgctttt 6120
ttaagtcttt atattcagat atcttaagtt caagtattcc ttctattttt attttatcac 6180
gttcgtttag ttgtctgtat agatttaata tcatcatttc atcattagta acatgtaagt 6240
aatcttcttt atcttctttt acactactat tgacatttac cttctcttta ccatagagaa 6300
gccagtcagt cgtaacatta aaataatcag ctattgacat tagtatatca caattaggtt 6360
ttctatctcc tgtttcatac ttgcctaagt tttcaaattt taaaatatcc ataagtttgc 6420
gctgagtaag ttttttggag tttctcaaat aagcaattct ttttcctaaa gtatccacaa 6480
aatacactcc tttcttttta tgagtaatgt ctaaatgaca tttgaaatta aaaatatata 6540
aatttataat ataaaactac taaattaaag tctaaatgac attttgctta aattaatatg 6600
ctcataatat gattttaaca tattatagtt gaaaatatat ggtttatttt gatttgtata 6660
tataacaata gatttaattg ttataaaaat gtaaaggggt gtatgaatag attgtataaa 6720
tttatttcga taaactaaga ttgctttttg attgtctgta aaagagaaaa agattaagat 6780
aaaaatagta ttatattgta atttatatta atcaattaca aagattttat gaatttattc 6840
tttagggtaa aatatttaag aataagataa atttacaata taatactata acactctttt 6900
atctagtttt attttcttta tagaacaata atattataaa tgctagtaga tttacacaga 6960
atactgttat atacatctgt ttgaatcctg agtttagagt agattgtagt gtggatccgg 7020

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 35 tttttgcgg ccgcaatacc cactacacct tcgtc 35

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tatacatctc gagtcccatc tctttc 26

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gaagaaagag atgggactcg agatg 25

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cttgtgccat ctatatttgt tg 22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
ggaaaaggga ttgctaatag tg 22

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
tcccccggat ccacactaca atctactcta aactcagg 38

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
ggcgcgccac tagtaccggt gccatggcgg ccgc 34

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
agctgcggcc gccatggcac cggtactagt ggcgcgccca tg 42

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ttccttggtc tcacgcgaac aaaattctcc agtcttc 37

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
ttccttggtc tcaggccgtc gcgactaaga aaatgcc 37

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gtgagcggat aacaattccc 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
agattgtagt gtggatccgg 20

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tccttcggcg cgcctcaaat ttaagcttaa ctcc 34

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tttagggact actcactcgc 20

<210> SEQ ID NO 49
<211> LENGTH: 1773
<212> TYPE: PRT
<213> ORGANISM: Clostridium difficile

<400> SEQUENCE: 49

```
Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
            20                  25                  30

Ile Asn Phe Phe Thr Gly Cys Cys Asn Tyr Thr Phe Gly Leu Lys Asn
        35                  40                  45

Asn Asn Ile Leu Tyr Gly Cys Gly Asp Asn Ser Asn Phe Gln Leu Gly
    50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140
```

```
Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205

Cys Tyr Ser Thr Gly Phe Asn Asn Gln Gly Gln Leu Gly Leu Gly Asp
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
            260                 265                 270

Ser Ser Leu Phe Thr Lys Ile Glu Glu Val Asn Ile Lys Thr Ile Ala
        275                 280                 285

Cys Gly His Gly Asn Thr Met Leu Ile Asp Asn Lys Gly Thr Leu Lys
    290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
            340                 345                 350

Asp Ser Tyr Cys Thr Gly Asp Asn Thr Tyr Gly Gln Leu Gly Ser Phe
        355                 360                 365

Phe Asp Asp Met His Ile Val Glu Phe Lys Lys Met Asp Ser Glu Lys
    370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480

Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Ser Tyr Val Asn Gly Leu Ser Asn Ala
545                 550                 555                 560

Leu Ile Ser Gln Tyr Thr Glu Ile Ser Leu Ser Asn Val Thr Asp Ala
                565                 570                 575
```

```
Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
625                 630                 635                 640

Thr Lys Ile Asn Asn Ile Ile Ile Tyr Glu Tyr Val Thr Val Phe Cys
                645                 650                 655

Thr Asn Ile Gly Ser Phe Leu Thr Gly Tyr His Gly Thr Ser Trp Thr
            660                 665                 670

Lys Pro Thr Asp Ser Ser Tyr Arg Val Gln Tyr Gln Gly Ile Ser Tyr
        675                 680                 685

Ala Gly Tyr Leu Asp Ser Tyr Ile Tyr Asn Tyr Tyr Pro Thr Arg Cys
    690                 695                 700

Thr Gln Ser Ser Ser Ser Thr Thr Phe Ala Tyr Leu Tyr Asn Gly Glu
705                 710                 715                 720

Ser Ser Ser Asn Leu Lys Asn Val Asn Pro Asp Asn Leu Leu Ile Ser
                725                 730                 735

Gly Gly Ser Ser Tyr Ile His Gln Tyr Gly Arg Asn Tyr Leu Asn Asn
            740                 745                 750

Gln Ser Ser Asn Asn Ile Ala Ala Ser Asn Ile Asn Ser Gly Pro Ile
        755                 760                 765

Thr Ser Asp Lys Ala Ile Phe Leu Tyr Lys Ala Leu Leu Tyr Leu Ser
    770                 775                 780

Ser Asn Thr Leu Tyr Gly Phe Gly Asn Ile Ser Glu Ser Ala Lys Glu
785                 790                 795                 800

Leu Asp Val Ser Asp Thr Gln Asp Gly Tyr Asn Ala Thr Asn Tyr Lys
                805                 810                 815

Lys Val Met Lys Asn Ile Lys Asn Ile Phe Ile Pro Pro Tyr Asp Leu
            820                 825                 830

Ser Arg Asp Lys Thr Arg Phe Ala Ile Leu Thr Asp Lys Ser Leu Phe
        835                 840                 845

Ile Cys Gly Tyr Asn Ser Lys Gly Thr His Gly Ile Ser Val Asn Ser
    850                 855                 860

Ser Leu Asn Leu Asn Asn Lys Ile Asn Tyr Asn Lys Lys Asn Ser Ser
865                 870                 875                 880

Ser Glu Ile Ser Ser Asn Ile Gln Glu Ile Tyr Ser His Ser Lys Ser
                885                 890                 895

Thr Tyr Leu Leu Thr Asn Asn Asn Met Leu Tyr Ser Val Gly Leu Asn
            900                 905                 910

Asp Val Gly Gln Leu Gly Val Gly Asp Glu Ile Asn Arg Lys Val Phe
        915                 920                 925

Thr Lys Ile Asn Ile Asp Asn Ile Lys Ser Ile Asn Val Asn Arg Phe
    930                 935                 940

Thr Asp Asn Ser Lys His Ala Phe Ala Ile Lys Asn Asp Asn Thr Cys
945                 950                 955                 960

Tyr Ala Val Gly Leu Asn Asn Ser Gly Gln Leu Gly Ile Gly Asp Asn
                965                 970                 975

Val Asn Arg Asn Ile Phe Thr Lys Ile Asn Val Glu Asn Val Lys Tyr
            980                 985                 990

Val Ala Val Tyr Gly Asn Thr Ser  Leu Leu Leu Thr Asn  Asp Gly Leu
```

-continued

```
        995                 1000                1005

Leu Tyr  Gly Ala Gly Asn Asn  Gly Lys Gly Gln Leu  Gly Leu Gly
    1010                 1015                 1020

Asp Thr  Thr Ser Arg Asn Ile  Phe Thr Arg Ile Pro  Ile Asn Gly
    1025                 1030                 1035

Val Arg  Asp Val Tyr Leu Cys  Asn Asp Val Ser Ile  Ile Val Lys
    1040                 1045                 1050

Asn Asp  Asn Thr Cys Tyr Val  Cys Gly Leu Val Asn  Gly Tyr Phe
    1055                 1060                 1065

Gly Phe  Thr Glu Gly Ser Ile  Ser Thr Phe Thr Lys  Ile Asn Ile
    1070                 1075                 1080

Glu Asn  Val Lys Ser Val Val  Thr Ala Gly Ser Glu  Ala Thr Phe
    1085                 1090                 1095

Phe Ile  Thr Asn Asp Asn Met  Ile Tyr Thr Thr Gly  Lys Lys Glu
    1100                 1105                 1110

Arg Val  Phe Phe Ser Thr Glu  Thr Asn Asp Ile Lys  Gly Ile Arg
    1115                 1120                 1125

Val Ile  Asn Asn Ile Ile Asn  Ala Lys Lys Ile Val  Val Asn Gly
    1130                 1135                 1140

Tyr Thr  Ser Ala Ile Leu Thr  Asn Asp Asn Lys Leu  Phe Val Gly
    1145                 1150                 1155

Gly Leu  Ser Gly Tyr Gly Ser  Ile Ala Asn Asn Asn  Asn Thr Asn
    1160                 1165                 1170

Ser Val  Glu Asp Val Lys Asp  Val Phe Val Thr Ala  Asn Asn Thr
    1175                 1180                 1185

Leu Tyr  Ile Asp Asn Asn Asn  Asn Leu Ile Ser Ser  Gly Arg Asp
    1190                 1195                 1200

Thr Tyr  Gly Ile Ser Asp Glu  Ser Tyr Arg Asp Met  Ser Val Pro
    1205                 1210                 1215

Tyr Tyr  Lys Val Ser Ile Lys  Lys Asp Val Asp Thr  Val Phe Ser
    1220                 1225                 1230

Ser Tyr  Asn Thr Ile Phe Ile  Lys Asp Ile Tyr Gly  Lys Phe Tyr
    1235                 1240                 1245

Ser Ser  Thr Arg Asp Asn Arg  Tyr Asn His Leu Gly  Ile His His
    1250                 1255                 1260

Arg Tyr  Asp Asn Asp Lys Asn  Glu Ala Leu Glu Gly  Ser Leu His
    1265                 1270                 1275

Ser Tyr  Phe Lys Thr Asp Asn  Thr Ser Asp Lys Ile  Val Phe Asn
    1280                 1285                 1290

Lys Lys  Asn Glu Lys Leu Val  Met Phe Asn Asp Lys  Tyr Ile Lys
    1295                 1300                 1305

Thr Asn  Asn Lys Tyr Ile Asn  Tyr Lys Asn Ile Phe  Lys Asp Asn
    1310                 1315                 1320

Phe Lys  Tyr Thr Ser Ile Ile  Leu Pro Phe Glu Val  Ser Asp Ile
    1325                 1330                 1335

Asp Ile  Ser Lys Thr His Ser  Leu Ala Val Ala Lys  Asp Gly Lys
    1340                 1345                 1350

Leu Tyr  Gly Ile Gly Ser Asn  Ser Tyr Lys Glu Ile  Asn Gln Thr
    1355                 1360                 1365

Leu Glu  Asp Ile Glu Leu Leu  Thr Leu Thr Glu Val  Asn Ile Ser
    1370                 1375                 1380

Asp Val  Lys Lys Val Ala Cys  Gly Asp Asn Tyr Ser  Tyr Ile Ile
    1385                 1390                 1395
```

-continued

```
Lys Thr  Asp Asn Thr Leu Trp  Ser Tyr Gly Lys Asn  Thr Glu Tyr
    1400                 1405                 1410

Gln Leu  Gly Val Gly His Asn  Asn Asp Val Arg Glu  Leu Gln Lys
    1415                 1420                 1425

Val Thr  Gly Leu Pro Ser Val  Lys Asp Ile Ser Ile  Tyr Asn Ser
    1430                 1435                 1440

Met Thr  Leu Val Leu Thr Asn  Glu Gly Glu Leu Tyr  Ala Gln Gly
    1445                 1450                 1455

Tyr Asn  Thr Asn Gly Leu Phe  Gly Leu Gly Glu Ser  Glu Lys Asp
    1460                 1465                 1470

Lys Ile  Ile Arg Thr Phe Thr  Lys Val Leu Thr Asn  Val Lys Glu
    1475                 1480                 1485

Ile Lys  Ser His Asn Asp Asp  His Ile Leu Val Ile  Lys Asn Asp
    1490                 1495                 1500

Asn Ser  Leu Trp Ile Thr Gly  Lys Asn Lys Ser Met  Tyr Lys Ile
    1505                 1510                 1515

Ser Ile  Ser Ile Thr Asp Leu  Tyr Glu Phe Thr Lys  Ile Pro Ile
    1520                 1525                 1530

Pro Glu  His Leu Asn Asp Ile  Leu Asp Ile Glu Leu  Ser Asp Asp
    1535                 1540                 1545

Thr Ile  Tyr Met Ile Thr Lys  Val Asp Thr Ser Lys  Ala Ser Ile
    1550                 1555                 1560

Glu Ile  Val Glu Lys Ser Ile  Ser Gln Val Arg Val  Val Val Gln
    1565                 1570                 1575

Asp Pro  Asn Asn Val Ile Glu  Lys Leu Glu Met Phe  Ile Asn Asp
    1580                 1585                 1590

Glu Leu  Ile Ser Thr Lys Thr  Asn Leu Glu Ile Asn  Ser Ile Ile
    1595                 1600                 1605

Phe Glu  Ile Pro Gln Asn Lys  Ile Val Leu Gly Glu  Asn Lys Ile
    1610                 1615                 1620

Leu Ile  Lys Ala Ser Ser Pro  Thr Gly Asp Leu Tyr  Ser Ser Met
    1625                 1630                 1635

Phe Ile  Phe Lys Ser Glu Thr  Gly Leu Lys Val Lys  Lys Asp Ser
    1640                 1645                 1650

Ile Leu  Met Ile Asn Asn Lys  Val Tyr Ser Ile Ile  Asn Ile Thr
    1655                 1660                 1665

Glu Asn  Asn Thr Asp Leu Ile  Val Thr Leu Asn Glu  Gly Leu Lys
    1670                 1675                 1680

Asp Asp  Met Met Glu Asn Asn  Pro Ile Tyr Gln Leu  Ile Asn Lys
    1685                 1690                 1695

Thr Lys  Val Gln Val Lys Ile  Asn Lys Ser Asp Leu  Phe Lys Asp
    1700                 1705                 1710

Met Lys  Leu Val Glu Ile Lys  Lys Ser Asp Ser Ser  Tyr Gln Glu
    1715                 1720                 1725

Ile Tyr  Glu Leu Glu Glu Ala  Asn Ile Lys Ser Ala  Gln Pro Lys
    1730                 1735                 1740

Ile Ile  Val Glu Lys Gly Asp  Lys Trp Thr Ala Ile  Lys Arg Pro
    1745                 1750                 1755

Ser Met  Ile Phe Arg Tyr Asp  Ala Glu Asn Asn Glu  Pro Gln Ala
    1760                 1765                 1770
```

<210> SEQ ID NO 50
<211> LENGTH: 1743
<212> TYPE: PRT
<213> ORGANISM: Clostridium difficile

<400> SEQUENCE: 50

```
Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Val Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Ser Asn
                245                 250                 255

Gly Tyr Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Val Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Lys Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415
```

```
Lys Ile Glu Leu Thr Asp Asn Asn Met Phe Ile Val Met Asn Asp Gly
            420                 425                 430

Thr Leu Tyr Ala Cys Gly Leu Asn Asn Tyr Gly Gln Leu Gly Leu Gly
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Tyr Asn Ser Ser Gly Ile Leu Gly Leu
                485                 490                 495

Lys Asp Asn Thr Asn Arg Asn Ile Phe Thr Lys Ile Glu Ile Glu Asn
            500                 505                 510

Ile Lys Glu Phe Cys Val Glu Ser Asn Tyr Ile Val Ala Leu Asn His
        515                 520                 525

Ser Lys Glu Leu Tyr Gly Trp Gly Asn Gln Ser Tyr Ile Val Tyr Gly
    530                 535                 540

Asp Asn Arg Asn Tyr Pro Tyr Lys Asp Thr Arg Val Ser Asn Val Glu
545                 550                 555                 560

Lys Ile Ala Thr Trp Ser Asp Thr Leu Tyr Ile Leu Asp Ser Thr Gly
                565                 570                 575

Ala Thr Lys Thr Ile Gly Tyr Ser Tyr Asn Gly Ser Gly Gly Tyr Pro
            580                 585                 590

Ala Pro Ser Ser Ser Ser Thr Tyr Arg Glu Gly Gly Tyr Ile Asn Lys
        595                 600                 605

Asn Thr Ser Tyr Arg Thr Leu Glu Phe Tyr Asn Thr Ser Lys Thr Lys
    610                 615                 620

Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
                645                 650                 655

Gly Ser Thr Thr Asn Glu Asn Asn Ser Leu Arg Phe Ile Asn Asn Ser
            660                 665                 670

Gly Val Tyr Tyr Thr Asn Thr Asp Gly Thr Asp Tyr Thr Cys Tyr Gln
        675                 680                 685

Trp Thr Tyr Lys Leu Ile Arg Cys Ser Ile Phe Asp Ser Pro Gln Asn
    690                 695                 700

Ile Ile Gly Asn Ser Lys Asn Ile Leu Tyr Leu Ser Lys Asn Asn Ser
705                 710                 715                 720

Thr Phe Lys Cys Thr Gly Asn Cys Ile Thr Tyr Gly Ile Asn Ser Gln
                725                 730                 735

Asn Trp Tyr Ser Tyr Phe Ser Asp Ser Ser Asn Gly Ala Ile Ala Leu
            740                 745                 750

Gly Asn Glu Phe Ile Leu Lys Asn Tyr Ser Gly Glu Cys Leu Leu Lys
        755                 760                 765

Gly Tyr Gly Lys Ala Thr Asn Gly Glu Phe Gly Asn Ser Thr Asn Ile
    770                 775                 780

Ser Ser Ile Ser Asn Tyr Asp Thr Gly Leu Lys Asp Ile Lys Asp Ile
785                 790                 795                 800

Ile Val Lys Asn Asn Thr Val Val Val Val Asp Lys Asn Asn Asn Ile
                805                 810                 815

Tyr Val Thr Gly Ala Asn Gln Phe Asn Lys Leu Gly Ile Gly Glu Tyr
            820                 825                 830

Asn Asn Gln Pro Ile Arg Lys Phe Thr Asn Ile Thr Glu Gln Ser Asn
```

-continued

```
        835                 840                 845

Ser Phe Ile Phe Met Asp Asp Ile Lys Glu Ile Thr Thr Ser Arg Asn
    850                 855                 860

Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
                885                 890                 895

Phe Thr Gln Ile Asn Leu Asp Asn Ile Lys Lys Ile Ser Thr Ser Ile
            900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
    930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asp Asn Thr Leu Tyr
                965                 970                 975

Ser Cys Gly Glu Asn Thr His Gly Gln Leu Gly Leu Gly Ser Glu Ser
            980                 985                 990

Asn His Pro Asp Val Leu Thr Phe  Thr Val Asn Asn Ile  Thr Asn Val
        995                 1000                 1005

Arg Asp  Val Tyr Cys Ser Asp  Thr Thr Thr Phe Ile  Val Lys Asp
    1010                 1015                 1020

Thr Asn  Ile Ala Tyr Cys Cys  Gly Tyr Asn Asn Asn  Ser Gln Leu
    1025                 1030                 1035

Gly Met  Gly Asn Thr Thr Asp  Gln Tyr Ser Phe Ile  Lys Cys Met
    1040                 1045                 1050

Glu Asn  Val Lys Glu Val Ile  Pro Asn Glu Ile Asn  Thr Tyr Ile
    1055                 1060                 1065

Ile Thr  Ile Tyr Asn Thr Ala  Tyr Ser Thr Gly Leu  Asn Thr Asp
    1070                 1075                 1080

Tyr Cys  Leu Gly Leu Asn Ser  Asn Ser Asn Gln Ser  Ser Phe Ser
    1085                 1090                 1095

Glu Ile  Pro Ile Ser Asn Val  Val Lys Val Ala Pro  Asn Arg Asn
    1100                 1105                 1110

Asn Ala  Val Leu Leu Leu Thr  Ser Glu Gly Asp Val  Tyr Thr Ala
    1115                 1120                 1125

Gly Lys  Cys Ser Asn Gly Ser  Gly Thr Gly Ser Glu  Thr Pro Glu
    1130                 1135                 1140

Lys Ile  Lys Lys Ile Ala Ser  Lys Ala Lys Asp Ile  Gly Met Asn
    1145                 1150                 1155

Tyr Arg  Cys Gly His Tyr Val  Ser Asp Asn Gly Asp  Leu Tyr Gly
    1160                 1165                 1170

Thr Gly  Phe Asn Asp Cys Gly  Gln Leu Gly Val Gly  Asn Val Thr
    1175                 1180                 1185

Lys Arg  Asp Thr Phe Ile Lys  Thr Asn Thr Arg Val  Lys Lys Ile
    1190                 1195                 1200

Leu Pro  Leu Glu Tyr Ala Asn  Ile Ala Ile Lys Asp  Thr Asn Asp
    1205                 1210                 1215

Ile Tyr  Ile Cys Gly Leu Asn  Asn Tyr Gly Gln Leu  Gly Val Gly
    1220                 1225                 1230

Asn Arg  Tyr Asp Ser Arg Asn  Asn Asp Asn Arg Ile  Phe Asn Tyr
    1235                 1240                 1245
```

```
Lys His Met Asn Phe Val Met Gly Asp Leu Thr Ser Ile Lys Asn
    1250                1255                1260

Arg His Asn Phe Ile Leu Leu Asn Asn Lys Ile Val Ile Pro Thr
    1265                1270                1275

Thr Lys Asp Ile Asp Tyr Gly Leu Val Leu Gly Asn Leu Tyr Lys
    1280                1285                1290

Gly Asp Leu Tyr Thr Glu Leu Pro Tyr Glu Asp Ile Lys Glu Val
    1295                1300                1305

Ser Ile Ser Lys Thr His Ile Ile Ile Leu Leu Asn Asp Gly Thr
    1310                1315                1320

Met Tyr Gly Cys Gly Thr Asn Tyr His Gly Glu Leu Leu Gln Asp
    1325                1330                1335

Leu Ser Ile Asn Gln Val Asp Glu Phe Val Gln Ile Asn Val Ser
    1340                1345                1350

Asp Val Lys His Val Ser Cys Gly Asp Asn Phe Thr Tyr Phe Ile
    1355                1360                1365

Lys Ser Asp Asp Ser Leu Trp Ser Ile Gly Lys Asn Ser Glu Tyr
    1370                1375                1380

Gln Leu Gly Ile Gly His Asn Asn Pro Val Thr Glu Leu Gln Arg
    1385                1390                1395

Ile Thr Thr Ile Ser Ser Cys Lys Glu Val His Cys Gly Lys Asn
    1400                1405                1410

Tyr Thr Leu Val Val Thr Thr Ser Asn Glu Leu Phe Val Gln Gly
    1415                1420                1425

Tyr Asn Asp Lys Gly Ala Leu Gly Leu Gly Ser Asp Ser Glu Asn
    1430                1435                1440

Thr Ile Ile Lys Phe Phe Thr Lys Ala Leu Thr Asp Ile Arg Glu
    1445                1450                1455

Ile Lys Ser Tyr Gly Ser Asp His Ile Leu Val Leu Lys Asn Asp
    1460                1465                1470

Asn Ser Val Trp Val Thr Gly Lys Asn Arg Asp Val Tyr Lys Ile
    1475                1480                1485

Glu Gln Pro Val Glu Phe Leu Lys Glu Phe Thr Ile Val Pro Ile
    1490                1495                1500

Ser Glu Asp Val Asn Thr Val Lys Asp Val Leu Ala Thr Asp Asn
    1505                1510                1515

Thr Leu Tyr Ile Ile Ser Glu Val Gly Thr Thr Asn Ala Ala Ile
    1520                1525                1530

Glu Ile Thr Glu Lys Ser Ile Ser Ser Ile Lys Ile Lys Ile Gln
    1535                1540                1545

Asp Pro Asn Lys Asp Ile Ser Arg Ile Glu Met Leu Ile Asn Gly
    1550                1555                1560

Glu Ser Val Lys Ser Val Ser Asp Leu Ile Thr Glu Lys Ile Ser
    1565                1570                1575

Phe Glu Val Pro Pro Asp Lys Ile Lys Ile Gly Glu Asn Lys Ile
    1580                1585                1590

Leu Phe Arg Ala Tyr Cys Lys Gly Asp Asp Leu Tyr Ala Ser Leu
    1595                1600                1605

Phe Ile Phe Lys Glu Ser Thr Gly Asn Ser Ile Ile Lys Asp Ser
    1610                1615                1620

Tyr Val Met Ile Gly Asn Arg Met Tyr Lys Val Val Asn Thr Thr
    1625                1630                1635

Ser Asn Glu Gln Asp Ile Thr Ile Thr Leu Asp Arg Gly Leu Glu
    1640                1645                1650
```

```
Glu Asp  Leu Asn Leu Gly Asp  Pro Ile Tyr Gln Leu  Ile Asn Lys
    1655                 1660                 1665

Thr Lys  Val Gln Val Lys Ile  Asn Lys Ser Asp Leu  Phe Lys Asp
    1670                 1675                 1680

Met Lys  Leu Val Glu Ile Lys  Lys Ser Asp Ser Ser  Tyr Gln Glu
    1685                 1690                 1695

Ile Tyr  Glu Leu Glu Glu Ala  Asn Ile Lys Ser Ala  Gln Pro Lys
    1700                 1705                 1710

Ile Ile  Val Glu Lys Gly Asp  Lys Trp Thr Ala Ile  Lys Arg Pro
    1715                 1720                 1725

Ser Met  Ile Phe Arg Tyr Asp  Ala Glu Asn Asn Glu  Pro Gln Ala
    1730                 1735                 1740


<210> SEQ ID NO 51
<211> LENGTH: 1773
<212> TYPE: PRT
<213> ORGANISM: Clostridium difficile

<400> SEQUENCE: 51

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
            20                  25                  30

Ile Asn Phe Phe Thr Gly Cys Cys Asn Tyr Thr Phe Gly Leu Lys Asn
        35                  40                  45

Asn Asn Ile Leu Tyr Gly Cys Gly Asp Asn Ser Asn Phe Gln Leu Gly
    50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205

Cys Tyr Ser Thr Gly Phe Asn Asn Gln Gly Gln Leu Gly Leu Gly Asp
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
            260                 265                 270

Ser Ser Leu Phe Thr Lys Ile Glu Glu Val Asn Ile Lys Thr Ile Ala
        275                 280                 285
```

-continued

```
Cys Gly His Gly Asn Thr Met Leu Ile Asp Asn Lys Gly Thr Leu Lys
    290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
            340                 345                 350

Asp Ser Tyr Cys Thr Gly Asp Asn Thr Tyr Gly Gln Leu Gly Ser Phe
        355                 360                 365

Phe Asp Asp Met His Ile Val Glu Phe Lys Lys Met Asp Ser Glu Lys
    370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480

Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Ser Tyr Val Asn Gly Leu Ser Asn Ala
545                 550                 555                 560

Leu Ile Ser Gln Tyr Thr Glu Ile Ser Leu Ser Asn Val Thr Asp Ala
                565                 570                 575

Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
625                 630                 635                 640

Thr Lys Ile Asn Asn Ile Ile Ile Tyr Glu Tyr Val Thr Val Phe Cys
                645                 650                 655

Thr Asn Ile Gly Ser Phe Leu Thr Gly Tyr His Gly Thr Ser Trp Thr
            660                 665                 670

Lys Pro Thr Asp Ser Ser Tyr Arg Val Gln Tyr Gln Gly Ile Ser Tyr
        675                 680                 685

Ala Gly Tyr Leu Asp Ser Tyr Ile Tyr Asn Tyr Tyr Pro Thr Arg Cys
    690                 695                 700

Thr Gln Ser Ser Ser Ser Thr Thr Phe Ala Tyr Leu Tyr Asn Gly Glu
```

```
705                 710                 715                 720

Ser Ser Ser Asn Leu Lys Asn Val Asn Pro Asp Asn Leu Leu Ile Ser
                725                 730                 735

Gly Gly Ser Ser Tyr Ile His Gln Tyr Gly Arg Asn Tyr Leu Asn Asn
            740                 745                 750

Gln Ser Ser Asn Asn Ile Ala Ala Ser Asn Ile Asn Ser Gly Pro Ile
        755                 760                 765

Thr Ser Asp Lys Ala Ile Phe Leu Tyr Lys Ala Leu Leu Tyr Leu Ser
    770                 775                 780

Ser Asn Thr Leu Tyr Gly Phe Gly Asn Ile Ser Glu Ser Ala Lys Glu
785                 790                 795                 800

Leu Asp Val Ser Asp Thr Gln Asp Gly Tyr Asn Ala Thr Asn Tyr Lys
                805                 810                 815

Lys Val Met Lys Asn Ile Lys Asn Ile Phe Ile Pro Pro Tyr Asp Leu
            820                 825                 830

Ser Arg Asp Lys Thr Arg Phe Ala Ile Leu Thr Asp Lys Ser Leu Phe
        835                 840                 845

Ile Cys Gly Tyr Asn Ser Lys Gly Thr His Gly Ile Ser Val Asn Ser
    850                 855                 860

Ser Leu Asn Leu Asn Asn Lys Ile Asn Tyr His Lys Lys Asn Ser Ser
865                 870                 875                 880

Ser Glu Ile Ser Ser Asn Ile Gln Glu Ile Tyr Ser His Ser Lys Ser
                885                 890                 895

Thr Tyr Leu Leu Thr Asn Asn Asn Met Leu Tyr Ser Val Gly Leu Asn
            900                 905                 910

Asp Val Gly Gln Leu Gly Val Gly Asp Glu Ile Asn Arg Lys Val Phe
        915                 920                 925

Thr Lys Ile Asn Ile Asp Asn Ile Lys Ser Ile Asn Val Asn Arg Phe
    930                 935                 940

Thr Asp Asn Ser Lys His Ala Phe Ala Ile Lys Asn Asp Asn Thr Cys
945                 950                 955                 960

Tyr Ala Val Gly Leu Asn Asn Ser Gly Gln Leu Gly Ile Gly Asp Asn
                965                 970                 975

Val Asn Arg Asn Ile Phe Thr Lys Ile Asn Val Glu Asn Val Lys Tyr
            980                 985                 990

Val Ala Val Tyr Gly Asn Thr Ser  Leu Leu Leu Thr Asn  Asp Gly Leu
        995                 1000                1005

Leu Tyr  Gly Ala Gly Asn Asn  Gly Lys Gly Gln Leu  Gly Leu Gly
    1010                 1015                 1020

Asp Thr  Thr Ser Arg Asn Ile  Phe Thr Arg Ile Pro  Ile Asn Gly
    1025                 1030                 1035

Val Arg  Asp Val Tyr Leu Cys  Asn Asp Val Ser Ile  Ile Val Lys
    1040                 1045                 1050

Asn Asp  Asn Thr Cys Tyr Val  Cys Gly Leu Val Asn  Gly Tyr Phe
    1055                 1060                 1065

Gly Phe  Thr Glu Gly Ser Ile  Ser Thr Phe Thr Lys  Ile Asn Ile
    1070                 1075                 1080

Glu Asn  Val Lys Ser Val Val  Thr Ala Gly Ser Glu  Ala Thr Phe
    1085                 1090                 1095

Phe Ile  Thr Asn Asp Asn Met  Ile Tyr Thr Thr Gly  Lys Lys Glu
    1100                 1105                 1110

Arg Val  Phe Phe Ser Thr Glu  Thr Asn Asp Ile Lys  Gly Ile Arg
    1115                 1120                 1125
```

-continued

```
Val Ile  Asn Asn Ile Ile Asn  Ala Lys Lys Ile Val  Val Asn Gly
    1130                 1135                 1140

Tyr Thr  Ser Ala Ile Leu Thr  Asn Asp Asn Lys Leu  Phe Val Gly
    1145                 1150                 1155

Gly Leu  Ser Gly Tyr Gly Ser  Ile Ala Asn Asn Asn  Asn Thr Asn
    1160                 1165                 1170

Ser Val  Glu Asp Val Lys Asp  Val Phe Val Thr Ala  Asn Asn Thr
    1175                 1180                 1185

Leu Tyr  Ile Asp Asn Asn Asn  Asn Leu Ile Ser Ser  Gly Arg Asp
    1190                 1195                 1200

Thr Tyr  Gly Ile Ser Asp Glu  Ser Tyr Arg Asp Met  Ser Val Pro
    1205                 1210                 1215

Tyr Tyr  Lys Val Ser Ile Lys  Lys Asp Val Asp Thr  Val Phe Ser
    1220                 1225                 1230

Ser Tyr  Asn Thr Ile Phe Ile  Lys Asp Ile Tyr Gly  Lys Phe Tyr
    1235                 1240                 1245

Ser Ser  Thr Arg Asp Asn Arg  Tyr Asn His Leu Gly  Ile His His
    1250                 1255                 1260

Arg Tyr  Asp Asn Asp Lys Asn  Glu Ala Leu Glu Gly  Ser Leu His
    1265                 1270                 1275

Ser Tyr  Phe Lys Thr Asp Asn  Thr Ser Asp Lys Ile  Val Phe Asn
    1280                 1285                 1290

Lys Lys  Asn Glu Lys Leu Val  Met Phe Asn Asp Lys  Tyr Ile Lys
    1295                 1300                 1305

Thr Asn  Asn Lys Tyr Ile Asn  Tyr Lys Asn Ile Phe  Lys Asp Asn
    1310                 1315                 1320

Phe Lys  Tyr Thr Ser Ile Ile  Leu Pro Phe Glu Val  Ser Asp Ile
    1325                 1330                 1335

Asp Ile  Ser Lys Thr His Ser  Leu Ala Val Ala Lys  Asp Gly Lys
    1340                 1345                 1350

Leu Tyr  Gly Ile Gly Ser Asn  Ser Tyr Lys Glu Ile  Asn Gln Thr
    1355                 1360                 1365

Leu Glu  Asp Ile Glu Leu Leu  Thr Leu Thr Glu Val  Asn Ile Ser
    1370                 1375                 1380

Asp Val  Lys Lys Val Ala Cys  Gly Asp Asn Tyr Ser  Tyr Ile Ile
    1385                 1390                 1395

Lys Thr  Asp Asn Thr Leu Trp  Ser Tyr Gly Lys Asn  Thr Glu Tyr
    1400                 1405                 1410

Gln Leu  Gly Val Gly His Asn  Asn Asp Val Arg Glu  Leu Gln Lys
    1415                 1420                 1425

Val Thr  Gly Leu Pro Ser Val  Lys Asp Ile Ser Ile  Tyr Asn Ser
    1430                 1435                 1440

Met Thr  Leu Val Leu Thr Asn  Glu Gly Glu Leu Tyr  Ala Gln Gly
    1445                 1450                 1455

Tyr Asn  Thr Asn Gly Leu Phe  Gly Leu Gly Glu Ser  Glu Lys Asp
    1460                 1465                 1470

Lys Ile  Ile Arg Thr Phe Thr  Lys Val Leu Thr Asn  Val Lys Glu
    1475                 1480                 1485

Ile Lys  Ser His Asn Asp Asp  His Ile Leu Val Ile  Lys Asn Asp
    1490                 1495                 1500

Asn Ser  Leu Trp Ile Thr Gly  Lys Asn Lys Ser Met  Tyr Lys Ile
    1505                 1510                 1515

Ser Ile  Ser Ile Thr Asp Leu  Tyr Glu Phe Thr Lys  Ile Pro Ile
    1520                 1525                 1530
```

```
Pro Glu  His Leu Asn Asp Ile  Leu Asp Ile Glu Leu  Ser Asp Asp
    1535                 1540                 1545

Thr Ile  Tyr Met Ile Thr Lys  Val Asp Thr Ser Lys  Ala Ser Ile
    1550                 1555                 1560

Glu Ile  Val Glu Lys Ser Ile  Ser Gln Val Arg Val  Val Val Gln
    1565                 1570                 1575

Asp Pro  Asn Asn Val Ile Glu  Lys Leu Glu Met Phe  Ile Asn Asp
    1580                 1585                 1590

Glu Leu  Ile Ser Thr Lys Thr  Asn Leu Glu Ile Asn  Ser Ile Ile
    1595                 1600                 1605

Phe Glu  Ile Pro Gln Asn Lys  Ile Val Leu Gly Glu  Asn Lys Ile
    1610                 1615                 1620

Leu Ile  Lys Ala Ser Ser Pro  Thr Gly Asp Leu Tyr  Ser Ser Met
    1625                 1630                 1635

Phe Ile  Phe Lys Ser Glu Thr  Gly Leu Lys Val Lys  Lys Asp Ser
    1640                 1645                 1650

Ile Leu  Met Ile Asn Asn Lys  Val Tyr Ser Ile Ile  Asn Ile Thr
    1655                 1660                 1665

Glu Asn  Asn Thr Asp Leu Ile  Val Thr Leu Asn Glu  Gly Leu Lys
    1670                 1675                 1680

Asp Asp  Met Met Glu Asn Asn  Pro Ile Tyr Gln Leu  Ile Asn Lys
    1685                 1690                 1695

Thr Lys  Val Gln Val Lys Ile  Asn Lys Ser Asp Leu  Phe Lys Asp
    1700                 1705                 1710

Met Lys  Leu Val Glu Ile Lys  Lys Ser Asp Ser Ser  Tyr Gln Glu
    1715                 1720                 1725

Ile Tyr  Glu Leu Glu Glu Ala  Asn Ile Lys Ser Ala  Gln Pro Lys
    1730                 1735                 1740

Ile Ile  Val Glu Lys Gly Asp  Lys Trp Thr Ala Ile  Lys Arg Pro
    1745                 1750                 1755

Ser Met  Ile Phe Arg Tyr Asp  Ala Glu Asn Asn Glu  Pro Gln Ala
    1760                 1765                 1770


<210> SEQ ID NO 52
<211> LENGTH: 1725
<212> TYPE: PRT
<213> ORGANISM: Clostridium difficile

<400> SEQUENCE: 52

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125
```

-continued

```
Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Asn Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Asn Pro Tyr Asn Asn Ile Glu
    530                 535                 540

Lys Thr Ser Asn Tyr Pro Tyr Lys Gln Gly Ile Ser Asn Ile Glu Lys
```

-continued 545 550 555 560

Ile Ala Ala Tyr Asp Tyr Ser Val Tyr Met Ile Asn Ser Glu Gly Lys
565 570 575

Leu Tyr Val Ser Gly Tyr Asn Tyr Asn Tyr Gln Leu Gly Lys Gly Asn
580 585 590

Asn Ser Asn Gln Ser Lys Ala Leu Val Ser Gln Cys Arg Thr Asn Ser
595 600 605

Thr Ser Ser Thr Ser Asn Gly Leu Arg Thr Leu Pro Lys Ile Thr Asn
610 615 620

Val Phe Pro Phe Tyr Asp Gly Cys Ala Ile Ile Asp Glu Gly Gly Tyr
625 630 635 640

Val Tyr Leu Thr Gly Tyr His Gly Tyr Leu Arg Thr Leu Asn Ser Ser
645 650 655

Pro Ser Ile Ser Asp Tyr Ser Arg Tyr Gly Thr Phe Ile Glu Ala Thr
660 665 670

Asn Ser Asn His Asn Thr Tyr Phe Ile Gln Glu Thr Asp Phe Ser Gly
675 680 685

Ile Glu Lys Val Ile Gly Met Ser Asn Asn Ile Leu Phe Phe Lys Lys
690 695 700

Gly Ser Ser Tyr Ile Thr Gly Tyr Pro Lys Thr Phe Gly Ser Thr Ile
705 710 715 720

Thr Gly His Arg Ser Tyr Thr Ser Ile Asn Ser Glu Ser Ser Asn Leu
725 730 735

Gly Ser Asn Phe Ile Ile Tyr His Ser Asn Ser Lys Leu Tyr Gly Lys
740 745 750

Gly Ile Ala Asn Ser Gly Gln Phe Gly Asn Ser Thr Asn Ile Asp Gly
755 760 765

Thr Ser Asn Tyr Asp Thr Gly Leu Lys Asp Ile Lys Asp Ile Ile Val
770 775 780

Lys Gly Asn Thr Val Val Val Val Asp Lys Asn Asn Asn Ile Tyr Val
785 790 795 800

Thr Gly Met Asn Gln Asn Asn Lys Leu Gly Ile Gly Glu Tyr Asn Asn
805 810 815

Glu Pro Val Lys Lys Phe Thr Asn Ile Thr Glu Gln Ser Asn Ser Phe
820 825 830

Ile Phe Met Asp Asp Ile Lys Glu Ile Thr Thr Ser Arg Asn Thr Met
835 840 845

Phe Ile Val Lys Asn Asp Gly Thr Ala Tyr Ala Thr Gly Asn Asn Ser
850 855 860

Ser Gly Gln Leu Gly Leu Gly Asp Thr Ile Asn Arg Asn Lys Phe Thr
865 870 875 880

Gln Ile Asn Leu Asp Asn Ile Lys Lys Ile Ser Thr Ser Ile Asp Gly
885 890 895

Asn Thr Thr Phe Ala Ile Arg Asn Asp Gly Thr Leu Tyr Ser Thr Gly
900 905 910

Leu Asn Thr Lys Gly Gln Leu Gly Leu Gly Asp Ile Val Asn Arg Asn
915 920 925

Thr Phe Thr Lys Val Asn Ile Gln Asn Val Arg Asp Val Val Leu Gly
930 935 940

Thr Thr His Ser His Ala Ile Lys Asp Asp Asn Thr Leu Tyr Ser Cys
945 950 955 960

Gly Glu Asn Thr His Gly Gln Leu Gly Leu Gly Ser Glu Ser Asn His
965 970 975

-continued

```
Pro Asp Val Leu Thr Phe Thr Val Asn Asn Ile Thr Asn Val Arg Asp
            980                 985                 990

Val Tyr Cys Ser Asp Thr Thr Thr  Phe Ile Val Lys Asp  Thr Asn Ile
        995                 1000                 1005

Ala Tyr  Cys Cys Gly Tyr Asn  Asn Asn Ser Gln Leu  Gly Met Gly
    1010                 1015                 1020

Asn Thr  Thr Asp Gln Tyr Ser  Phe Ile Lys Cys Met  Glu Asn Val
    1025                 1030                 1035

Lys Glu  Val Ile Pro Asn Glu  Ile Asn Thr Tyr Ile  Ile Thr Ile
    1040                 1045                 1050

Tyr Asn  Thr Ala Tyr Ser Thr  Gly Leu Asn Thr Asp  Tyr Cys Leu
    1055                 1060                 1065

Gly Leu  Asn Ser Asn Ser Asn  Gln Ser Ser Phe Ser  Glu Ile Pro
    1070                 1075                 1080

Ile Ser  Asn Val Val Lys Val  Ala Pro Asn Arg Asn  Asn Ala Val
    1085                 1090                 1095

Leu Leu  Leu Thr Ser Glu Gly  Asp Val Tyr Thr Ala  Gly Lys Cys
    1100                 1105                 1110

Ser Asn  Gly Ser Gly Thr Gly  Ser Glu Thr Pro Glu  Lys Ile Lys
    1115                 1120                 1125

Lys Ile  Ala Ser Lys Ala Lys  Asp Ile Gly Met Asn  Tyr Arg Cys
    1130                 1135                 1140

Gly His  Tyr Val Ser Asp Asn  Gly Asp Leu Tyr Gly  Thr Gly Phe
    1145                 1150                 1155

Asn Asn  Asn Gly Gln Leu Gly  Val Gly Asp Val Thr  Lys Arg Asp
    1160                 1165                 1170

Thr Phe  Ile Lys Thr Asn Thr  Arg Val Lys Lys Ile  Leu Pro Leu
    1175                 1180                 1185

Glu Tyr  Ala Asn Ile Ala Ile  Lys Asp Thr Asn Asp  Ile Tyr Ile
    1190                 1195                 1200

Cys Gly  Leu Asn Asn Tyr Gly  Gln Leu Gly Val Gly  Asn Arg Tyr
    1205                 1210                 1215

Asp Ser  Arg Asn Asn Asp Asn  Arg Ile Phe Asn Tyr  Lys His Met
    1220                 1225                 1230

Asn Phe  Val Met Gly Asp Leu  Thr Ser Ile Lys Asn  Arg His Asn
    1235                 1240                 1245

Phe Ile  Leu Leu Asn Asn Lys  Ile Val Ile Pro Thr  Thr Lys Asp
    1250                 1255                 1260

Ile Asp  Tyr Gly Leu Val Leu  Gly Asn Leu Tyr Lys  Gly Asp Leu
    1265                 1270                 1275

Tyr Thr  Glu Leu Pro Tyr Glu  Asp Ile Lys Glu Val  Ser Ile Ser
    1280                 1285                 1290

Lys Thr  His Ile Ile Ile Leu  Leu Asn Asp Gly Thr  Met Tyr Gly
    1295                 1300                 1305

Cys Gly  Thr Asn Tyr His Gly  Glu Leu Leu Gln Asp  Leu Ser Ile
    1310                 1315                 1320

Asn Gln  Val Asp Glu Phe Val  Gln Ile Asn Val Ser  Asp Val Lys
    1325                 1330                 1335

His Val  Ser Cys Gly Asp Asn  Phe Thr Tyr Phe Ile  Lys Ser Asp
    1340                 1345                 1350

Asp Ser  Leu Trp Ser Ile Gly  Lys Asn Ser Glu Tyr  Gln Leu Gly
    1355                 1360                 1365

Ile Gly  His Asn Asn Pro Val  Thr Glu Leu Gln Arg  Ile Thr Thr
    1370                 1375                 1380
```

```
Ile Ser  Ser Cys Lys Glu Val  His Cys Gly Lys Asn  Tyr Thr Leu
    1385                 1390                 1395

Val Val  Thr Thr Gly Asn Glu  Leu Phe Val Gln Gly  Tyr Asn Asp
    1400                 1405                 1410

Lys Gly  Ala Leu Gly Leu Gly  Ser Asp Ser Glu Asn  Thr Ile Ile
    1415                 1420                 1425

Lys Phe  Phe Thr Lys Ala Leu  Thr Asp Ile Arg Glu  Ile Lys Ser
    1430                 1435                 1440

Tyr Gly  Ser Asp His Ile Leu  Val Leu Lys Asn Asp  Asn Ser Val
    1445                 1450                 1455

Trp Val  Thr Gly Lys Asn Arg  Asp Val Tyr Lys Ile  Glu Gln Pro
    1460                 1465                 1470

Val Glu  Phe Leu Lys Glu Phe  Thr Ile Val Pro Ile  Ser Glu Asp
    1475                 1480                 1485

Val Asn  Thr Val Lys Asp Val  Leu Ala Thr Asp Asn  Thr Leu Tyr
    1490                 1495                 1500

Ile Ile  Ser Glu Val Gly Thr  Thr Asn Ala Ala Ile  Glu Ile Thr
    1505                 1510                 1515

Glu Lys  Ser Ile Ser Ser Ile  Lys Ile Lys Ile Gln  Asp Pro Asn
    1520                 1525                 1530

Lys Asp  Ile Ser Arg Ile Glu  Met Leu Ile Asn Gly  Glu Ser Val
    1535                 1540                 1545

Lys Ser  Val Ser Asp Leu Thr  Thr Glu Lys Ile Ser  Phe Glu Val
    1550                 1555                 1560

Pro Pro  Asp Lys Ile Lys Ile  Gly Glu Asn Lys Ile  Leu Phe Arg
    1565                 1570                 1575

Ala Tyr  Cys Lys Gly Asp Asp  Leu Tyr Ala Ser Leu  Phe Ile Phe
    1580                 1585                 1590

Lys Glu  Ser Thr Gly Asn Ser  Ile Ile Lys Asp Ser  Tyr Val Met
    1595                 1600                 1605

Ile Gly  Asn Arg Met Tyr Lys  Val Val Asn Thr Thr  Ser Asn Glu
    1610                 1615                 1620

Gln Asp  Ile Thr Ile Thr Leu  Asp Arg Gly Leu Glu  Glu Asp Leu
    1625                 1630                 1635

Asn Leu  Gly Asp Pro Ile Tyr  Gln Leu Ile Asn Lys  Thr Lys Val
    1640                 1645                 1650

Gln Val  Lys Ile Asn Lys Ser  Asp Leu Phe Lys Asp  Met Lys Leu
    1655                 1660                 1665

Val Glu  Ile Lys Lys Ser Asp  Ser Ser Tyr Gln Glu  Ile Tyr Glu
    1670                 1675                 1680

Leu Glu  Glu Ala Asn Ile Lys  Ser Ala Gln Pro Lys  Ile Ile Val
    1685                 1690                 1695

Glu Lys  Gly Asp Lys Trp Thr  Ala Ile Lys Arg Pro  Ser Met Ile
    1700                 1705                 1710

Phe Arg  Tyr Asp Ala Glu Asn  Asn Glu Pro Gln Ala
    1715                 1720                 1725
```

<210> SEQ ID NO 53
<211> LENGTH: 1743
<212> TYPE: PRT
<213> ORGANISM: Clostridium difficile

<400> SEQUENCE: 53

```
Met Lys Gln Asn Lys Leu Leu Gln Arg Gly Ala Tyr Phe Asn Asp Lys
1               5                   10                  15
```

```
Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asn Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Thr Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Lys Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Asn Asn Met Phe Ile Val Met Asn Asp Gly
            420                 425                 430

Thr Leu Tyr Ala Cys Gly Leu Asn Asn Tyr Gly Gln Leu Gly Leu Gly
```

-continued

```
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Tyr Asn Ser Ser Gly Ile Leu Gly Leu
                485                 490                 495

Lys Asp Asn Thr Asn Arg Asn Ile Phe Thr Lys Ile Glu Ile Glu Asn
            500                 505                 510

Val Lys Ala Phe Cys Val Glu Ser Asn Tyr Ile Val Val Leu Asn His
        515                 520                 525

Ser Lys Glu Leu Tyr Gly Trp Gly Asn Glu Ser Tyr Ile Val Tyr Gly
    530                 535                 540

Asn Ser Arg Asn Tyr Pro Tyr Lys Asp Thr Arg Val Ser Asn Val Glu
545                 550                 555                 560

Lys Ile Ala Thr Trp Ser Asp Thr Leu Tyr Ile Leu Asp Ser Thr Gly
                565                 570                 575

Ala Thr Lys Thr Ile Gly Tyr Ser Tyr Asn Gly Ser Gly Gly Tyr Pro
            580                 585                 590

Ala Pro Ser Ser Ser Ser Thr Tyr Arg Asp Gly Gly Tyr Ile Asn Lys
        595                 600                 605

Asn Thr Ser Tyr Arg Thr Leu Glu Phe Tyr Asn Thr Ser Lys Thr Lys
    610                 615                 620

Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
                645                 650                 655

Asn Ser Thr Thr Asn Glu Asn Asn Ser Leu Arg Phe Ile Asn Asn Ser
            660                 665                 670

Gly Val Tyr Tyr Thr Asn Thr Asp Gly Thr Asp Tyr Thr Cys Tyr Gln
        675                 680                 685

Trp Thr Tyr Lys Leu Ile Arg Cys Ser Ile Phe Asp Ser Pro Gln Asn
    690                 695                 700

Ile Ile Gly Asn Ser Lys Asn Ile Leu Tyr Leu Ser Lys Asn Asn Ser
705                 710                 715                 720

Thr Phe Lys Cys Thr Gly Asn Cys Ile Thr Tyr Gly Ile Asn Ser Gln
                725                 730                 735

Asn Trp Tyr Ser Tyr Phe Ser Asp Ser Ser Asn Gly Ala Ile Ala Leu
            740                 745                 750

Gly Asn Glu Phe Ile Leu Lys Asn Tyr Ser Gly Glu Cys Leu Leu Lys
        755                 760                 765

Gly Tyr Gly Lys Ala Thr Asn Gly Glu Phe Gly Asn Ser Thr Asn Ile
    770                 775                 780

Ser Ser Ile Ser Asn Tyr Asp Thr Gly Leu Lys Asp Ile Lys Asp Ile
785                 790                 795                 800

Ile Val Lys Asn Asn Thr Val Val Val Val Asp Lys Asn Asn Asn Ile
                805                 810                 815

Tyr Val Thr Gly Ala Asn Gln Phe Asn Lys Leu Gly Ile Gly Glu Tyr
            820                 825                 830

Asn Asn Gln Pro Ile Lys Lys Phe Thr Asn Ile Thr Glu Gln Ser Asn
        835                 840                 845

Ser Phe Ile Phe Met Asp Asp Ile Lys Glu Ile Thr Thr Ser Arg Asn
    850                 855                 860
```

-continued

```
Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
                885                 890                 895

Phe Thr Gln Ile Asn Leu Asp Asn Ile Lys Lys Ile Ser Thr Ser Ile
            900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
    930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asp Asn Thr Leu Tyr
                965                 970                 975

Ser Cys Gly Glu Asn Thr His Gly Gln Leu Gly Leu Gly Ser Glu Ser
            980                 985                 990

Asn His Pro Asp Val Leu Thr Phe  Thr Val Asn Asn Ile  Thr Asn Val
        995                 1000                 1005

Arg Asp  Val Tyr Cys Ser Asp  Thr Thr Thr Phe Ile  Val Lys Asp
    1010                 1015                 1020

Thr Asn  Ile Ala Tyr Cys Cys  Gly Tyr Asn Asn Asn  Ser Gln Leu
    1025                 1030                 1035

Gly Met  Gly Asn Thr Thr Asp  Gln Tyr Ser Phe Ile  Lys Cys Met
    1040                 1045                 1050

Glu Asn  Val Lys Glu Val Ile  Pro Asn Glu Ile Asn  Thr Tyr Ile
    1055                 1060                 1065

Ile Thr  Ile Tyr Asn Thr Ala  Tyr Ser Thr Gly Leu  Asn Thr Asp
    1070                 1075                 1080

Tyr Cys  Leu Gly Leu Asn Ser  Asn Ser Asn Gln Ser  Ser Phe Ser
    1085                 1090                 1095

Glu Ile  Pro Ile Ser Asn Val  Val Lys Val Ala Pro  Asn Arg Asn
    1100                 1105                 1110

Asn Ala  Val Leu Leu Leu Thr  Ser Glu Gly Asp Val  Tyr Thr Ala
    1115                 1120                 1125

Gly Lys  Cys Ser Asn Gly Ser  Gly Thr Gly Ser Glu  Thr Pro Glu
    1130                 1135                 1140

Lys Ile  Lys Lys Ile Ala Ser  Lys Ala Lys Asp Ile  Gly Met Asn
    1145                 1150                 1155

Tyr Arg  Cys Gly His Tyr Val  Ser Asp Asn Gly Asp  Leu Tyr Gly
    1160                 1165                 1170

Thr Gly  Phe Asn Asp Cys Gly  Gln Leu Gly Val Gly  Asp Val Thr
    1175                 1180                 1185

Lys Arg  Asp Thr Phe Ile Lys  Thr Asn Thr Arg Val  Lys Lys Ile
    1190                 1195                 1200

Leu Pro  Leu Glu Tyr Ala Asn  Ile Ala Ile Lys Asp  Thr Asn Asp
    1205                 1210                 1215

Ile Tyr  Ile Cys Gly Leu Asn  Asn Tyr Gly Gln Leu  Gly Val Gly
    1220                 1225                 1230

Asn Arg  Tyr Asp Ser Arg Asn  Asn Asp Asn Arg Ile  Phe Asn Tyr
    1235                 1240                 1245

Lys His  Met Asn Phe Val Met  Gly Asp Leu Thr Ser  Ile Lys Asn
    1250                 1255                 1260

Arg His  Asn Phe Ile Leu Leu  Asn Asn Lys Ile Val  Ile Pro Thr
    1265                 1270                 1275
```

```
Thr Lys  Asp Ile Asp Tyr Gly  Leu Val Leu Gly Asn  Leu Tyr Lys
    1280                 1285                 1290

Gly Asp  Leu Tyr Thr Glu Leu  Pro Tyr Glu Asp Ile  Lys Glu Val
    1295                 1300                 1305

Ser Ile  Ser Lys Thr His Ile  Ile Ile Leu Leu Asn  Asp Gly Thr
    1310                 1315                 1320

Met Tyr  Gly Cys Gly Thr Asn  Tyr His Gly Glu Leu  Leu Gln Asp
    1325                 1330                 1335

Leu Ser  Ile Asn Gln Val Asp  Glu Phe Val Gln Ile  Asn Val Ser
    1340                 1345                 1350

Asp Val  Lys His Val Ser Cys  Gly Asp Asn Phe Thr  Tyr Phe Ile
    1355                 1360                 1365

Lys Ser  Asp Asp Ser Leu Trp  Ser Ile Gly Lys Asn  Ser Glu Tyr
    1370                 1375                 1380

Gln Leu  Gly Ile Gly His Asn  Asn Pro Val Thr Glu  Leu Gln Arg
    1385                 1390                 1395

Ile Thr  Thr Ile Ser Ser Cys  Lys Glu Val His Cys  Gly Lys Asn
    1400                 1405                 1410

Tyr Thr  Leu Val Val Thr Thr  Gly Asn Glu Leu Phe  Val Gln Gly
    1415                 1420                 1425

Tyr Asn  Asp Lys Gly Ala Leu  Gly Leu Gly Ser Asp  Ser Glu Asn
    1430                 1435                 1440

Thr Ile  Ile Lys Phe Phe Thr  Lys Ala Leu Thr Asp  Ile Arg Glu
    1445                 1450                 1455

Ile Lys  Ser Tyr Gly Ser Asp  His Ile Leu Val Leu  Lys Asn Asp
    1460                 1465                 1470

Asn Ser  Val Trp Val Thr Gly  Lys Asn Arg Asp Val  Tyr Lys Ile
    1475                 1480                 1485

Glu Gln  Pro Val Glu Phe Leu  Lys Glu Phe Thr Ile  Ile Pro Ile
    1490                 1495                 1500

Ser Glu  Asp Val Asn Thr Val  Lys Asp Val Leu Ala  Thr Asp Asn
    1505                 1510                 1515

Thr Leu  Tyr Ile Ile Ser Glu  Val Gly Thr Thr Asn  Ala Ala Ile
    1520                 1525                 1530

Glu Ile  Thr Glu Lys Ser Ile  Ser Ser Ile Lys Ile  Lys Ile Gln
    1535                 1540                 1545

Asp Pro  Asn Lys Asp Ile Ser  Arg Ile Glu Met Leu  Ile Asn Gly
    1550                 1555                 1560

Glu Ser  Val Lys Ser Val Ser  Asp Leu Ile Thr Glu  Lys Ile Ser
    1565                 1570                 1575

Phe Glu  Val Pro Pro Asp Lys  Ile Lys Ile Gly Glu  Asn Lys Ile
    1580                 1585                 1590

Leu Phe  Arg Ala Tyr Cys Lys  Gly Asp Asp Leu Tyr  Ala Ser Leu
    1595                 1600                 1605

Phe Ile  Phe Lys Glu Ser Thr  Gly Asn Ser Ile Ile  Lys Asp Ser
    1610                 1615                 1620

Tyr Val  Met Ile Gly Asn Arg  Met Tyr Lys Val Val  Asn Thr Thr
    1625                 1630                 1635

Ser Asn  Glu Gln Asp Ile Thr  Ile Thr Leu Asp Arg  Gly Leu Glu
    1640                 1645                 1650

Glu Asp  Leu Asn Leu Gly Asp  Pro Ile Tyr Gln Leu  Ile Asn Lys
    1655                 1660                 1665

Thr Lys  Val Gln Val Lys Ile  Asn Lys Ser Asp Leu  Phe Lys Asp
```

-continued

```
    1670                1675                1680

Met Lys  Leu Val Glu Ile Lys  Lys Ser Asp Ser Ser  Tyr Gln Glu
    1685                1690                1695

Ile Tyr  Glu Leu Glu Glu Ala  Asn Ile Lys Ser Ala  Gln Pro Lys
    1700                1705                1710

Ile Ile  Val Glu Lys Gly Asp  Lys Trp Thr Ala Ile  Lys Arg Pro
    1715                1720                1725

Ser Met  Ile Phe Arg Tyr Asp  Ala Glu Asn Asn Glu  Pro Gln Ala
    1730                1735                1740


<210> SEQ ID NO 54
<211> LENGTH: 341
<212> TYPE: PRT
<213> ORGANISM: Clostridium phage

<400> SEQUENCE: 54

Met Ala Ile Asp Lys Ser Tyr Tyr Thr Ile Ile Thr Asp Val Gly Lys
1               5                   10                  15

Ala Lys Ile Ala Asn Ala Ser Val Thr Gly Asn Lys Val Gly Phe Val
            20                  25                  30

Lys Ile Gln Leu Gly Asp Gly Gly Gly Ser Glu Tyr Thr Pro Thr Glu
        35                  40                  45

Ser Gln Thr Ala Leu Lys Asn Val Val Trp Glu Gly Asn Ile Gly Asn
    50                  55                  60

Thr Thr Thr Asp Glu Thr Ala Pro Asn Cys Ile Ile Leu Glu Ser Leu
65                  70                  75                  80

Ile Pro Ser Ser Val Gly Gly Phe Met Ile Arg Glu Ile Gly Tyr Leu
                85                  90                  95

Asp Asp Glu Asn Asn Leu Ile Ala Ile Ser Lys Tyr Lys Glu Cys Tyr
            100                 105                 110

Lys Pro Ser Ile Glu Gln Gly Ala Val Val Asp Met Lys Val Lys Thr
        115                 120                 125

Val Leu Ile Val Ser Asn Val Asn Asn Ile Glu Leu Lys Ile Asp Pro
    130                 135                 140

Thr Ile Ile Phe Ala Thr Leu Lys Asp Ile Gln Asp Leu Glu Thr Lys
145                 150                 155                 160

Ile Gly Thr Val Asn Thr Lys Ile Asp Thr Thr Lys Thr Glu Leu Thr
                165                 170                 175

Ser Asn Ile Glu Thr Thr Lys Thr Glu Leu Asn Thr Arg Ile Asp Thr
            180                 185                 190

Glu Asn Glu Lys Gln Asn Ile Lys Ile Asp Gln Leu Ile Ala Gly Gly
        195                 200                 205

Ser Asn Val Ala Ser Thr Gln Ile Ile Thr Ile Asp Asp Trp Val Glu
    210                 215                 220

Asp Ala Glu Asn Gly Phe Lys Ala Thr Val Thr His Ser Leu Leu Thr
225                 230                 235                 240

Gln Arg Ile Val Val Asn Ile Ile Asp Ala Thr Thr Lys Glu Asn Val
                245                 250                 255

Val Thr Asn Phe Lys Ile Ile Asp Asp Asn Ser Ile Glu Ile Arg Ser
            260                 265                 270

Glu Val Lys Val Glu Leu Asn Val Tyr Val Ile Asn Gly Asn Ala Glu
        275                 280                 285

Thr His Phe Ile Asn Ala Thr Val Asp Asp Asn Arg Val Ser Glu Met
    290                 295                 300

Thr Thr Tyr Ser Ser Lys Lys Ile Glu Asp Arg Leu Val Asn Ile Glu
```

```
305                 310                 315                 320

Glu Lys Val Asn Gly Gly Leu Ser Asn Ile Ala Thr Ser Val Asn Glu
                325                 330                 335

Leu Ile Thr Tyr Cys
            340


<210> SEQ ID NO 55
<211> LENGTH: 132
<212> TYPE: PRT
<213> ORGANISM: Clostridium phage

<400> SEQUENCE: 55

Met Ala Glu Gln Gln Tyr Phe Thr Leu Val Thr Asp Ile Gly Lys Ala
1               5                   10                  15

Ala Ile Ala Asn Ala Ser Val Thr Gly Glu Lys Val Asp Phe Ala Lys
            20                  25                  30

Ile Lys Val Gly Asp Gly Gly Gly Ser Ser Tyr Thr Pro Asn Glu Ser
        35                  40                  45

Gln Thr Ala Leu Lys Asn Val Val Trp Glu Ser Thr Leu Glu His Ala
    50                  55                  60

Gln Val Asp Lys Asp Asn Pro Asn Trp Val Val Ile Gln Lys Phe Ile
65                  70                  75                  80

Pro Gly Asp Val Gly Gly Phe Glu Ile Arg Glu Val Gly Leu Phe Asp
                85                  90                  95

Ser Lys Asp Gln Leu Leu Ala Val Ser Ser Tyr Pro Thr Thr Tyr Lys
            100                 105                 110

Pro Glu Ser Arg Phe Gly Asp Cys Lys Arg Thr Ile Asn Lys Ser Asn
        115                 120                 125

Ile Ser Cys Ile
    130


<210> SEQ ID NO 56
<211> LENGTH: 205
<212> TYPE: PRT
<213> ORGANISM: Clostridium phage

<400> SEQUENCE: 56

Met Pro Asn Glu Leu Asn Phe Asn Asn Glu Ile Glu Glu Tyr Leu Ile
1               5                   10                  15

Thr Thr Pro Ala His Ala Asn Glu Phe Asn Asn Arg Gln Gln Lys Leu
            20                  25                  30

Leu Asp Asn Asp Lys Tyr Leu Asn Asn Lys Ile Asp Thr Thr Lys Thr
        35                  40                  45

Glu Leu Asn Thr Arg Ile Asp Thr Glu Asn Glu Lys Gln Asn Ile Lys
    50                  55                  60

Ile Asp Gln Leu Ile Ala Gly Gly Ser Asn Val Ala Tyr Thr Gln Arg
65                  70                  75                  80

Val Ala Ile Asp Asp Trp Val Glu Asp Ala Glu Asn Gly Phe Lys Ala
                85                  90                  95

Thr Val Thr His Ser Leu Leu Thr Gln Arg Ile Val Val Asn Ile Ile
            100                 105                 110

Asp Ala Thr Thr Lys Glu Asn Val Val Thr Asn Phe Lys Ile Ile Asp
        115                 120                 125

Asp Asn Ser Ile Glu Ile Arg Ser Glu Thr Arg Ser Glu Leu Asn Val
    130                 135                 140

Tyr Val Ile Asn Gly Asn Ala Glu Thr His Phe Ile Asn Ala Thr Val
145                 150                 155                 160
```

```
Asp Asp Asn Arg Val Ser Glu Met Thr Thr Tyr Ser Ser Lys Lys Ile
                165                 170                 175

Glu Asp Arg Leu Val Asn Ile Glu Glu Lys Val Asn Gly Gly Leu Ser
            180                 185                 190

Asn Ile Ala Thr Ser Val Asn Glu Leu Ile Thr Tyr Cys
        195                 200                 205


<210> SEQ ID NO 57
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

ggccgcctcg aggg                                                        14


<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

cgcgccctcg aggc                                                        14


<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

tgaagtacca tggtatccag                                                  20


<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

actggatacc atggtacttc                                                  20


<210> SEQ ID NO 61
<211> LENGTH: 19897
<212> TYPE: DNA
<213> ORGANISM: Clostridium difficile

<400> SEQUENCE: 61

gcaataccca ctacaccttc gtcatcttta aatttaagag tttttactat tgaataataa      60

aggtatattc cagtaaaaat aatctttaaa tacaagaaaa ataaactctt tgggtatatt     120

aaaaagctaa aaagtgtaaa tataaaagca agtagagtac ttatcctgta aaagaaatct     180

atttgtgtaa tgtctttata ttttatcata aacaccgaat ataaaatgat gaaaacaatt     240

gcgacgattg catatatggt aaataacata ttttcaagag taccatttga aattactatc     300
```

-continued

```
cacttatacc acataattgg ccaaaataat agtgctaaga acttaaaata attatcaaac    360
aacttttctt tatacattca tcaaacaacc tttcttaaca aaagcatata tttgttttta    420
gaattttaaa taatatgata tcattattat atattaatat tgaatttata gaaaccaaaa    480
tttgttaaaa taaatatata gattttactg ttaagccagt taaaattact actattttta    540
ttatgaaatt ggatcaaata tgtagaaata cggcaaatta gttaatatta aatatttatt    600
atttccaagt tgtaaagact gtttttttaa tgatagaaat tctaatcttt tttgaaagaa    660
agtaatatcc acattaagta tgtctgccat ttcataaacg caagtgatgc cagagttaat    720
tatgtttatt atatcttctt cagtaattaa gaactcacaa gcccatttta aggctttatt    780
ttcgcactta tctataataa tttttgtata ataatcgtta taagaggata catagtatcc    840
aaggctagtg aaatgatgtc caagttcttc agctaagatg gatgtcaatt tttttgagtt    900
ttgttttaaa ttactgagta atgatataat tttaatacca tgtttgttta tatatagtcc    960
ttctaaatca cctgcaatat aagtggtata atgaattatt atctcttctt gagaagctaa   1020
ttcaaaaagc ttatccaaat tattcataaa aatcccccta aaatagaatg tatgtttgcc   1080
tttaaattat attaaaagag cagaaaaata gactgctcat catatggttt attttttttt   1140
atatttattt agtaaaaatt ctatataatc attaagttgt tcttgtgctt cttcaggtaa   1200
ctcttcatgt ggatttttttc tatgtgcagc tactgtatca atattttcct taactaaggt   1260
tcttccaaga aggtaatcaa ctgatacatt aaatacatca gccaatttat ttaaaatgtg   1320
ttcatcagga aatctgtttt ctgtttcata gtaccctaag actctttggg aaacgcctac   1380
tttttctcca agttctcttt gagtcaatcc aaattccttt ctaagttctc ttaatctttt   1440
ggcaaacatt ataacaccac cttatgtata gattataaca aattgttcta aaaaataaaa   1500
ctaataaaat ataaaagaat atttttttct aaaatctatt gataaagaac aaataattct   1560
atataatcta agtgaggaag aacaaaatat tcttaatagt aatggaggta taaaacaatg   1620
tttaaaaata acttgaaata ttatagaaaa tgcaaaggta tgacacaaat tcaacttgcc   1680
agaaaggctg gaattacaaa tgattatata tctcaaatag aaagaggtat aaaaaatcct   1740
ggacttctta tggctaagaa gatttctagt attttagaac aaaatataga agaagttttt   1800
tttatacagt tatagaacaa tatgttcttg aaagttgtga gattagtaaa aaactgtgca   1860
ctaaagagat tattgtaaat ttgaagctaa taataagtat ataaaaaagg ggaagtacta   1920
tggaaaacaa aaaagatata ttatttaaag aaacagataa aagattacat aattataagt   1980
atttggatat aaagataaag aatattaact tggacataaa aagatgtgag aatgaatact   2040
ctggatgtgg agcaatggta tatacagaaa agactagtaa cacatataac ataagctctt   2100
ctgtggaaaa tgaggtgtta aaaagagagg aaagattaag aaaattaaaa atggaaaaag   2160
aagatataga aatagaaaaa gagaagatag aaaatgctct aacgtgtcta aatgatatag   2220
aaatggaatt ttttaatctt ttttataata gtaagacaaa aaacaatatg acatatattt   2280
ctatgaaact acacttagat agaacatctt gctacaattt aaagaaaaag atgatattta   2340
aattgagtga gatattataa aaaataggac aattttacaa cactttatat acaccattgc   2400
aacaataggc aataaaatat gtgagataat gttattgtga aagaaatcca tattgaagga   2460
ggtgatagat tgaaaagaat aatattacct aaaaatatag aagatacttg acaggaataa   2520
atgagatata tatttaaaaa tgacttatat catttatagt aagattatca gattaagcaa   2580
gaatatttag tgatagtgtg gtgattattt gcttaaatac aaggaaatat tagaaacaat   2640
tattgagatt ctcaaaaaaa actttactga aagtattttt attgatgatg aaagtgtgca   2700
```

-continued

```
aggctctgaa gggtcttgtt tttttgtaag tatactatca gttatttgta cacctgtaat   2760
gttaaatacg aataacaaag atattgttat ctctataaaa tacttaccaa aaccacagtc   2820
aaagagtatt agaatgtatg aaatttcaga tgaattaaat aagctattta acagaaatat   2880
aaaggtaaca gacagaaaat taaatataac aaagctagaa caaagtatta aaaaagaaga   2940
gtcaatttat gtattgaact ttacatttac actaaactat ctggatagtg tatatgaaga   3000
agatgtagta tatgaaaata tgaaagaaat caatttaaat ttaggagagt gatagtatgg   3060
ctataggatt accaagtatc aacatatcat ttaaggagct agctacaact gttaaagaac   3120
gttcagctag aggaataatt gcaatggtac ttaaagatgc taaggcacta ggtcttaatg   3180
aaatacatga aaaagaggat ataccagttg atttatctgc tgaaaataaa gaatatataa   3240
atttagcttt gatgggaaat gttaacactc caaataaatt attagtttat gtaatagaag   3300
gagaagcaga tattcaaact gcattagatt ttttagagac taaggaattt aattatctat   3360
gtatgccaaa agcagtagaa gctgataaga ctgctataaa aaattggata attaaactta   3420
gagatataga taaggttaag gttaaagctg tattaggaaa agttgtagga aatcatgaag   3480
ggataattaa ttttactaca gaagatgtgt tagttggaga aaagaaatac agtgttgatg   3540
agtttacaag cagggtggct ggacttatag caggtacacc tttaagtcaa tcagtaactt   3600
atactaaact tagtgatgta gtcgatatac ctaagatgac gaaagttgat gcagaatcaa   3660
gggttaataa aggagagctt atacttatta aagaagcagg agctataaga attgctagag   3720
gagtaaattc tttaactgaa ttaacagcag aaaaaggaga aatgttccag aaaataaaaa   3780
tagttgacac tttagatatt atacatagtg acataagaaa ggtgataata gatgactata   3840
taggaaaggt tactaacagt tatgacaaca aatgtttatt gatagtagct ataaaaagtt   3900
atttagaaga attagaaaaa tcagcactta tagaatctga ttctactgtt gaaatagatt   3960
ttgaagcaca aaaatcgtat ttaaaatcaa aaggagtaga tttatcttat atgacattac   4020
aagaaataaa agaagctaac acaggttcta aagtattttt aaaagcaaaa ataaaagtac   4080
ttgatgctat ggaagatata gatttatcaa tagaaatata ggaggattat taatatggca   4140
aatatggaag ctagaaatgt aatgagtggt acttggggag aactttggct tgatggaaac   4200
aaagtagcag aagtaaagaa atttcaagca aagatggaat ttacaaaaga agatattata   4260
atagcaggtc aaatgggtac tgatacaaag tatatgggat ataaaggaaa aggctcaata   4320
actctatacc acgttagttc aagaatgcac aagttaattg gagaaaagat aaagagaggt   4380
tctgaaccta gatttgttgc tatatcaaaa ttaaatgacc cagattctta tggagcagaa   4440
agaatagcag taaaaaatat agcatttgat gatttaactt tagctgattg ggaggttgga   4500
gtaaaaggag agatagaagc tcctttcaca tttactgagt atgattttct tgatataatt   4560
tagttttata tttagtttta tactgatatt tagtaagtat atacttaata aattcagata   4620
gttaataagt aaaaaagtta gttgattgaa tttgattgat aaaggagcaa ataataatga   4680
gtgaaaatgg attatcaaaa aatataaaca tagtagattt acttttaaat tcagatacag   4740
aaaacttaga aagaccaagt actatagttg aacttaagag attatcaact atatttgggc   4800
aggaatttaa agtaatgtgt agagctttaa caataagtaa agatgaagaa atacaaaata   4860
cttgtcttaa aattgatgaa aatatgaaaa cggatataga cttaccggag atgcagatgc   4920
ttacaattat agaaggtgtt tgtgatttgg atggaaagct tttatttaaa aataaggagc   4980
taatggataa atttaaggct ccaacaccaa aagaattagc aagaaaatta ttattaccag   5040
gtgaaattac caacttatat agaatacttc aagatgttat gggttatggt aaaaatgcag   5100
```

-continued

```
tgatagaaga ggtaaaaaac taatagggac ggataccagg actacaataa tgtactatta   5160
ttggaagaaa aaaggtataa gaccgtccct tttttatgca atggataaag gcgaattaaa   5220
gcttattgaa gctttttttcg ccttagaaat tgaggaagaa gttgaaaaaa tgaaacatgg   5280
atatggagtg tgtcctttga caggaggtgg tatgtaatgg gaaatgtgag agaagaaggt   5340
ataaatatgt accttacaga taattacaca ccaaaaatga atcaaattat atcagtaact   5400
gataatttta ggagagcaac tgtggctgtt tcactttcca ctaatgtaat ggctagtagc   5460
ataaaaaatt ctattggaag tgcaagtaat agagtaaaca gtttaaattc ctcgttaaga   5520
aaagttcaaa ctactgctag tagtgtaagt tcaactatga caaaattaag ttctagcata   5580
aatgctgttt caggagttat tggaagttta aatggaagta ttatgagact agcaataact   5640
atagctatga ttattgatta ttttaataag ttgattcaaa agaaaaatga gtttaattca   5700
aatattatga ttatattaat atttaaagct aaaagtgatg aagtagaaaa aactaaaaat   5760
aaattacttg gaaatttaaa aaagattggt ggcaagattt ggaatatcgt aataaaagca   5820
aaagatatga ctaagagagt gataagtagt atcttgggaa aattaaaaca agtagagaaa   5880
cgtccttatc aaggaagtat taatcttaaa gatatggtga gtagtgctat gggtagaatt   5940
ttgcctaagt taatgttgtt taaaaatact ttttggagtg gtgtaatagc tataaaagat   6000
atggcaagtg gcattataag taaagtattt cccaaattga gattatttgc aggtaaggta   6060
tggagtggtg caatagctgt aaaggatatg gcaagtggaa tacttggttc gataaaaggg   6120
aagatatctg atttgacaaa tggtgctact ataggtgtcg ctgtgaaaaa gggtgttgat   6180
ttacttggtc aggaacaaaa tcagaaagtt gttctagaaa gtgtaatgaa aagaaatact   6240
ggaaaagtta atcaaataga tgttgatgat tattatggca gtttagtaag aatggcaaat   6300
gatacgcctt ttgaccctga agatgttgtt gcaatgggaa ctaaagctaa aatgattagt   6360
aatattactg gtggcaaaaa agaaaaagat ataactcaag ctatggtaga tgttagagct   6420
ttaaatatga atacaagtag tgaacaagat gtatcagcag ctttcttaag tgcagcaaaa   6480
ggaaacatgg aatctcttaa tactctggta ggagaaaatt ataaaacttt tgatgaagca   6540
ttggaaggca taagtgtaaa gcagatgggg ttagctaaag aaatgagtaa tacaatacca   6600
ggtataatat caggagctca aacaagcatt aacaatggct tgaagagtat tgttaaacct   6660
tttgatgata ttttaggtca aggactaaag aaaataaaaa cttttataga aagtggatta   6720
ggcaatttag ctggcttatc tgaaaaaatg gctggtaaaa taggcaatgt aatgaatggt   6780
aagataatta ttggcaacaa atatgaccag atgcaatcta gaagtgtaaa aaatggaaaa   6840
gagttttctg attctactca atatcgaatt tctaatgagg ctgaaaagcg taaaatgatg   6900
gttgaaaata agcaagaacg ttttgaaaat catgcagcaa caatgatagg gaatgcacca   6960
aaagcaattg ttaacgcagg aagtacacta ttacaaaata tcgattttac agcattaata   7020
gattcattac ttccagtagt aaacttagta aataatttac tagatagtat aaacaataaa   7080
tcaccaattg cacaaggatt aataagtata tttggtacaa tagtaactac agcattccaa   7140
ctaatcggac ctgtagttga agctgttagt cctattatca caagaatttt tacttttta    7200
ggtgaatatg cacctcaaat aaacaatttt atagagacac tgggtgttat ttggaaaact   7260
gtatgggaga ccttaggacc tctgttggaa actggatgga aaattataga gccaatattg   7320
ggagcttttt ttaacatatt agataaagta tgtaaaatag ttaaagatat atgtaaatgg   7380
tggcaaacta tgattaataa gataaaaaat ggaagcatca caggaacagt tttaaatcta   7440
gtggaaaaga gtaaaaaaaa ttacaaagat aatccatatg ctggaacaaa ggctggtgat   7500
```

-continued

```
tctggtaaag cttattcagg taagaaaggt aataatgcat ttggattgaa ctatgttcct   7560
tataatgact atcaaaccag actccatgaa ggtgaaatgg ttttaactaa acaagaagca   7620
aatcaatata gaagcagaaa aaatggtgga aatataaaca tagctaagtt agctgataca   7680
atagtgatta gagaagaagc tgatatagaa aagataacat caaaattagt tgcaagtatc   7740
caattggcac agttaggggg tgtcttataa tggaaatgtg gcttagacaa gctgaagata   7800
gatttagatt tccagtattt ccatcttcct ttagtattaa tggaaaagct gctgtaaact   7860
cttctagtat actcaaaata ggtgaaatag caacttttgg tggtgtagct cttaaaagca   7920
tttcaatatc aagttttttt ccaaataaag actatacttt ctgtgactat acaggttttc   7980
catcaccata tgattgtgta aataagatag aaaaatggat gaaggaaggt tttatattaa   8040
gatttacaat tacggaaaca aatataaata tggaagtcat aattgaaggg tttagttatg   8100
aagaaagaga tgggactcga gatgtatatt ttacattaga tttaaaagag tataaaagaa   8160
taaagatacc aaaagtaact ccaaaacaat aactattata gataataagt tataaataac   8220
tgctgataga attaaatgaa aaggcaggtg atttttttatt attaagattt gggtacacat   8280
aaaaaacgga agtatatatg acataactga catagtagac aaggtatcat ggtcaggtga   8340
ttataaatct ccatcaagga cactagagtt ttcaataata caatcatcat ttgatgtaaa   8400
tttccaacaa atcgatatac caatagctag tacagtctgt ttctatgtag atgagaaaga   8460
actctttaga ggaatgataa ttaataggtc taaagattca agcagtaatg aaattagttt   8520
tgtatctaaa gatatgggat ttttacttac acaaagtgaa gtgtcataca attttaaaga   8580
taagttagtt gaagacatag caaagcaagt atttgctgaa aataggcttt cagttggaat   8640
aatagcaaag accaatgtca agtatacaaa gatgtttata ggagtaaatg gttatgacac   8700
aataatgagt gcatatacag aagcaagtaa aaagacaaag aaaaagtata tgatagaggc   8760
caatttagat aagtttaatg ttattgaaaa aggaactgtt acattaagtg ttatgtttga   8820
agagggattt aatattataa ataccacctt ttcggagagc atggaaaatg taaaaaataa   8880
agtaatagtg gtagaccagt atggaagcaa gattagcgaa aaaatagata atgaaatttt   8940
taaggaagta aatgtaataa tgcaaaaagt aattcagcaa caagaaaatc aagatgtaga   9000
tattgatagc gagtttaatg ggatagaaaa aagctgttct cttaaaggtt atggagatgt   9060
aagttgtata actggtagag gagtaaaagt taaagattct tatacaaagc ttgtaggact   9120
attttatata gatacagaca aacatacttg gcaaaatgga gaatatcaaa ttgagcttga   9180
acttaatttt caaaatctta tggatgaaaa gtcagcagga caggatgaac ctaaggaaga   9240
aagtaattta gggggagaag attatgcagg aggaaaagag tttacagcag aatttacagc   9300
ttactgtcct agaaaagaag aaggtggaga tacagattgt agaaagaaaa aacttgaccc   9360
atctaaaaaa acttgcgctg ctcctatggt tggtaaatat gagcaaactt attatacaaa   9420
agagttttta aataaacatc ctttattaaa ctatggagat gaaatacagg taattacagg   9480
agtttctggt cgtgatggag tctataaagt aaatgacgta ggacctgcaa taactataga   9540
aaagaatgga acataccata tagatatttt atttggaaat gttgaagaag ctagtaaatt   9600
tggaagaaga aaaggaaaaa ttattattgg tggttattct ggtaatgtat ctgataaagc   9660
taaaatagta atatcagaag caaaaaaaca tctaggtaaa ccttataaat ggggtggaaa   9720
tggaccaagt agttttgact gttctggttt aatggtctat tgttttaaaa aagttaatgt   9780
tagtttgcca agaacgtcaa atcaacaatc taaaaaaggc aagaaagtag aacaaaaaaa   9840
tcttcaagca ggagatttag tatttttttca taatccagtc agccatgttg gattatatat   9900
```

-continued

```
aggtaatgga gaatttttac atgctccaca aaaaggtgat gtagttaaaa taagtaagtt   9960
aagtagtaga agagatttta acacagctag gagagtatta taaaaggatg gtgatataat  10020
ggctaatcca ataaatgaat ttataggaat aataagagaa gaaggaaagt atcataatca  10080
accttctttt tttattggaa aaattaaaag taaattacca gatttaaaaa tagagacaaa  10140
taacatcata ttagaaaaag aagatatttt gatagatagt tggatgattg atagacagct  10200
agaaacattt gacacagaaa caaatcaaga acaccagcat gaagtaaaaa atccttttat  10260
agataacttt gaatctgggg atatggtaat aatgtttaga ataggcgaaa aatttgctgt  10320
tgtaagtaag ttggtgagct tataatgagt acaatatttc cttttatagg tgtcccagag  10380
gattatatct tacctaaaac agaagaattg ccaatctttc gtgaagtggc atgggatttt  10440
gaaaaagatg aacctatttt agaaaaaggt gactttaaaa taattgaaaa aaaagaagcc  10500
ttaaaagttt ggatatacaa gtgtataaag acaaatagat atgaacatga gatatactct  10560
ttagaatatg ggacagagct ttcagaacta ataggacaaa aatatacaaa aggtcttaca  10620
gaaagtgaag ctagtagatt cataaaagag gcccttctaa taaatccata tatattagaa  10680
gtaaacgtaa aaagtgctaa ctttaacaga gacatattga gtgcaaatgt aaaagtatcc  10740
actatctatg gggaggtgga aataaatgta tagtgaccag acatatgaag taataaaaaa  10800
tagaactctt gaaaatatta atcttgatat ttataaagga gaaggttctt ttctaaacaa  10860
catggtatct ggaaataatc tagaactttc gaagatatat ctagaacttt caaagatgca  10920
taaaatggct tttatacaag acacatataa ccagtttctt gataaaagag tcaatgaatt  10980
tggtgtatat agaaagttag gtacagagtc aaatggagaa gttgaattta ttggagagaa  11040
aggtactgta ataaataatg gcacaataat atcatataga gatttactat ttgtagtaat  11100
aaaagatgta actattggta gtgaagaagg tgacaatagc ccagttcaag ctctggaagt  11160
tggtaagaaa tataatttac ctacaaattg tgaatttaaa ctagttgata atatatctgg  11220
agtaacaaag attactaaca caagaagttt tgaaggtggt acagatatag agacagatga  11280
agaactaaaa gaaagatttt ataaaatcca aagaaatcaa gctacaagtg gaaataaagc  11340
tcactatgaa gaatgggctt tggaagtaga tggagtctat aatgttaagg tttatccaag  11400
atgggatggt ccgggaacag ttaaggtctt gatatttggg aaaaataatc aagctgttga  11460
tacagaaaca attgaaaggt gtcagcaaca tatagatgaa gagaagccta ttggaccaac  11520
tataacagtt gtgacaccat taccaataga aataagtata agtgcagtaa tgaaactaga  11580
agatggatat acattagaca atgtaaaaga atctttccta gaaagtataa atacatactt  11640
tagagatatt agaggagaga taatctatac aaaagtaatg ggaatactta taaatactac  11700
tggtgtacac gatttaagta acctacttat aaatggaagt acagataata taactattaa  11760
tgaagataaa atacctagtg taacaactgt taattttagt gaggtggaaa atcaatgaag  11820
ctaattgata aactaccatc atttgataga aattacattg tagaggagat acaaggtgca  11880
tacgatacag aattaaatat tcttaaagaa gatattgatg ataccttta ccaattattt  11940
gttgacactg caacatgggg attagatatg tgggaagaca tactctgcat tgaaaaaaaa  12000
gaacttgatt ttgacacaag acgtagcaat ataaaagcta aaatgagaag cagaggtact  12060
agtactattg aagttataaa aagtatatgt gaggcatata caaaatcaga aacagatata  12120
aaagtttata gtgatgaatt tacattcgta ttgagtttta tagcaaataa ctgtgactat  12180
aaaactcttt tagattgtag cgatatgatt gaaagagtaa aacctgctca cttattacac  12240
tatttagaac caataatact agataaaagt atggtctatt gtggtggagg tatggtatgt  12300
```

-continued

```
agtgaagagg taaaagttca tccatacttt gaaccaatta taaaatgtag tgctgttgta  12360
aactgtggag ctggaatgat aagtagagaa gaaataaagg tttatccttt aagcattaaa  12420
tgcattgaaa ataattgtaa gattaatata gctattgcaa atgatacagg tgtagaaaat  12480
gtagtagttt atcctaaatc ggaggtggta taattggaag aaaaatttta tataatatta  12540
accaaaattg gtagagaaaa aatagcaaat gcaactgcac taggagagct tgttggatta  12600
accaagtttc aagttggaga tagtaatgga gaatattatg agccaacaga ggaacaaact  12660
gctttaaaga atgtagtttg ggaaggaaat ataaattctc taagaattga tgaaaaaaat  12720
cctaattgga tagttataga gactatttta ccaggaacag ttggtggatt tatgataaga  12780
gaagctgctg ttctggataa tgagaataat ataatagcta taggtaagta tccagagacg  12840
tataagccac gtgctgaaga tggcagtatt aaagatttgg ttgtaaaaat gattttacaa  12900
ttgtccaata cttcaaatgt tacattagaa gtagacccga cgttggtttt tgtaactcaa  12960
aaggatattc aagatttaga tgataagttt gataaaaata taaaagaaat aaaagtaaaa  13020
attggcgaag aactcttatc tacagaagct aaaaacttat caggagctat aaatgaggta  13080
gtagaaaaaa ttaaaaatat atctattgat gatgtaatag gaggtcaaat acaaactgaa  13140
ctatctgtat taaaaaatag ttacaataaa ttatctgaaa aagtattaga tatcttaata  13200
tacttagaat tagagtcaga aatagatgta gatgaagctg gatattggta tgataccta  13260
actaatgcta aaaacataat agctatagaa ggccttaagt tagatttaaa tagaaagtgt  13320
ataactggag aacttggtag tgttacattt aagaatgtgg tgctaccatt taatgcaaat  13380
agagttagat atatacatga aatggataat aactttgttg aaacaaaatc taatagggca  13440
tattcaattg gtcagacaga tataacttta aataaatatt cgtatgaaat aagataatta  13500
ggaggttttt ataatgaaaa gaactaaact acttcaaaga ggtaatttct ttggcgataa  13560
aaatatggta gttgatgaat ttgatgaagg gtatgataat tatgacttta ttaatttttt  13620
tactggatgt tgtaactata catttggtct aaaaaataat aatatcttgt atggatgtgg  13680
agataatagt aactttcaac ttggattggg agaagacaat acaacaagaa aattatttac  13740
gaaaatacca aatatatcta ccaatattaa aaaagttgca tgtggagaat ctcatgcagt  13800
tatacttact tcagatggag aattacttgt cgcaggtata aatacagatg gtcaaatggg  13860
attgggatta gaaaaagtag ggaaaacagt ttctacattt gagaaggttc cagaaataaa  13920
aggcgtaaag gatattgcat gtggacttca atcaacatat cttttataca atgatggaac  13980
tttatatgtt gctggaaata atttgtatgg tcaattaggt ctaggaacta atggagcatc  14040
tgcaaatgta aatacattta caaaagtaga tgttgacaat gtaaaggctg tattttcata  14100
taataaatca gcttttataa taaagaatga caataaatgc tattctactg gttttaataa  14160
tcaaggtcaa ctaggtttag gagataagaa taatagagat ttatttagtt tagtttctat  14220
taatgatgtt aagactatag cttgtggttc tgaacacact gtgttaatga cgtataataa  14280
tgatatatat ggttgtggaa aggaaaaatg ttttggaaat gcacttcaat catcactatt  14340
tactaagata gaagaagtaa atataaaaac tattgcatgt ggtcatggta acactatgct  14400
tatagataac aaaggtactt taaaggttgc tggaaataat gatatatatc agttaggtat  14460
agcaaattac tctgagaata tagataattc atttatagat ttaaaaaata ttgtagctaa  14520
gaatattttc attggtttat cacatagcat actaattgat tcaaataatg attcatattg  14580
tacaggagat aatacttatg gacaattagg ttcgtttttt gatgatatgc acattgtaga  14640
atttaagaaa atggatagtg aaaaatatag ttatagtaat tatataaatt taattaaatc  14700
```

-continued

```
tgaggataaa ttaactttat taaaagaaga aatggaaata aaggatattg aacttccact  14760
agatatacat tctgtaagag atgtcgtttt tagtccttat tgtactctgg ttattttagg  14820
gaatggagat gtatatggtc taggaaataa tagatacaaa ggaatgggtt ctgacttacc  14880
aagtcaatta aatgagttga caaaattaag tatctctaat gtaaagtcta tagtagcatc  14940
aaaaaatatt tctggaggaa tattctacat taaaaatgat gatacttgtt attattctgg  15000
accaaatagt aactcaatag caggtgttct tccttctaat tcagatgtat ttaagaaaat  15060
atctatagat aatgtaaaaa aagttgttat aaatactgat ttatcaaact ggttttcatt  15120
aattgtaact aataataagc aaatatacac ttctggaaag agttcaagtt atgttaatgg  15180
acttagtaat gcattaataa gtcaatatac tgagattagc cttagtaatg taactgatgc  15240
ttatagttca tataatgcaa catttattgt agttgatgaa aaaaaggtat atgcaactgg  15300
tataaataca aattacctgt taggttttag tacttctgat ggatctaatg taaatctagg  15360
tttattaagt gattggtatt atataaatat atcagggtca agttatagta gagtttcatg  15420
cacgaataat attactaaaa ttaataatat tatcatatat gagtatgtaa ctgtattttg  15480
tacaaacatt ggatcttttc taactggata ccatggtact tcatggacaa aaccaactga  15540
ttcaagctat agagttcaat atcagggaat ttcatatgca ggatatcttg attcttatat  15600
atataattat tatcctacaa gatgtacaca atcatcatct tctacaactt ttgcttattt  15660
atataatggg gaatcgtcaa gtaatttaaa aaatgtcaat ccagataatt tacttatttc  15720
tggaggttca tcttatatac atcaatatgg aaggaattat cttaacaatc aatcatctaa  15780
taatattgca gcatctaata taaattcagg tcctattacc tctgataaag ccatattttt  15840
atataaagct ctattgtatt tatcttctaa cacgctatat ggttttggga atatatctga  15900
aagtgcaaaa gaactagatg tttcagatac acaagatgga tataatgcca ctaattataa  15960
aaaggtaatg aaaaatataa aaaatatatt tatacctcct tatgatttaa gtagagataa  16020
aactagattt gcaatattaa ctgataagag cttatttata tgtggatata actctaaggg  16080
tacgcatggt atatcagtta atagtagttt aaatttaaat aataagataa attacaataa  16140
aaagaatagc agtagtgaaa tatcttctaa tatacaagaa atatatagcc attcaaagtc  16200
tacatattta ttaactaata ataatatgct ttacagtgtt ggtttaaatg atgtaggtca  16260
attaggagtg ggagatgaga taaatagaaa ggtatttact aaaataaata ttgataatat  16320
aaaatctata aatgtaaata gatttactga caatagtaaa catgcatttg cgataaaaaa  16380
tgataatacc tgttatgctg ttggtttaaa taattctggt cagttaggaa taggagataa  16440
tgtaaataga aatatattta ctaaaataaa tgttgaaaat gtaaaatatg tagctgtata  16500
tggaaacaca tctctattat taactaatga tggtctttta tatggagcag gtaataatgg  16560
aaaaggacag ttaggattgg gtgatactac aagtaggaat atatttacac gtatacctat  16620
aaatggtgtt agagatgtat atctatgtaa tgatgtatca atcattgtta aaaatgataa  16680
tacatgctat gtatgtggac ttgtaaatgg ctattttggg tttactgaag gaagtataag  16740
tacatttaca aaaataaata ttgagaatgt aaaatctgtt gtgacagcag gaagtgaagc  16800
tacatttttt ataacaaatg acaatatgat ttatactaca gggaaaaaag agagggtatt  16860
cttttcaaca gagactaatg atataaaggg gatacgagta attaataata ttataaatgc  16920
aaaaaaaata gtagttaatg gatatacttc agccatttta acaaatgaca ataaactatt  16980
tgttggaggt cttagtggat atggaagtat agcaaataat aataatacaa atagtgtgga  17040
agatgttaaa gatgtttttg taacagctaa taatacactt tatatagata ataataacaa  17100
```

-continued

```
tttgatatca tcaggtagag atacttatgg tatatctgat gaatcttata gggatatgtc  17160
agttccatat tataaagtat ctataaagaa agatgttgat actgtatttt ctagttacaa  17220
tactatattt attaaagata tatatggaaa attttattct tcaacaagag ataatagata  17280
taatcattta ggtattcacc atagatatga taatgataaa aatgaagctc ttgaaggttc  17340
cctacattca tattttaaaa cagataacac atcagataaa atagttttta ataagaaaaa  17400
tgaaaagcta gtaatgttta atgataagta tataaaaaca aataataagt atataaatta  17460
taaaaacata tttaaagata attttaagta tacttcaata atattgccat ttgaggtatc  17520
tgatattgat atatcaaaaa cacattcatt ggctgttgct aaggatggca agttatatgg  17580
aataggaagt aattcatata aagaaattaa tcaaaccctt gaagatatag aattattaac  17640
tcttactgaa gtaaatatat cagatgtcaa aaaagttgct tgtggagata actactccta  17700
tattattaag acagataata ctctatggtc atatggaaag aatactgagt accaattggg  17760
agttggccac aataatgatg taagagagtt acaaaaggtt actggattac cttctgttaa  17820
agatataagt atatataact caatgacact tgttttaact aatgagggag agttgtacgc  17880
tcaagggtac aatacaaatg gattatttgg actaggagaa agtgaaaaag ataagataat  17940
aagaactttt actaaagtat taactaatgt taaagaaatt aagtcacata atgatgacca  18000
catactagta attaaaaatg ataatagtct atggataact ggtaaaaata aatctatgta  18060
taaaatatct atatcaatta ctgatttata tgaatttact aaaataccaa ttcctgaaca  18120
tctaaatgat attttagata tagagctttc agatgataca atatacatga taacaaaagt  18180
agatacaagt aaagcatcta tagaaatagt tgaaaaatca atatctcaag tgagagttgt  18240
agtacaagac cctaataatg ttatagaaaa acttgaaatg tttataaatg atgaattaat  18300
atctactaag actaatttgg aaataaatag cattatattt gagataccac aaaataaaat  18360
agtattagga gaaaataaga tactgattaa agccagtagt cctacaggcg atttatattc  18420
aagtatgttt atatttaaat cagaaacagg gcttaaagta aaaaaggatt ctattttaat  18480
gataaacaat aaagtatatt caatcataaa cattactgaa aataacactg acttaatagt  18540
aacattaaat gagggattaa aggatgatat gatggaaaac aatcctatat atcaattaat  18600
aaataaaact aaagttcaag taaaaataaa taaatctgac ttattcaaag acatgaaact  18660
agttgaaatc aaaaaatcag actcaagtta ccaagaaatc tatgaattag aagaagccaa  18720
cataaaaagt gctcagccta aaatcatagt agaaaaagga gataaatgga cagctataaa  18780
acgtccatct atgattttta gatatgatgc tgaaaacaac gagccacaag cttaaaatgg  18840
aggtgtgaaa attgtttaaa ttcgataaaa ataaaataga acaaatcaaa caaggtagaa  18900
aagtagaaat gcagtataaa gacatttcag acataagtat aggtcaagta aagcaagatg  18960
atgatataac aaataatttt atagcaaatg tagaaatata tgagatgttg ttaaatcaaa  19020
gttctgtcaa tgaagcaagt aatataagca cttttagtgt aagaaaatct ggaggtgaga  19080
gtggaatggt agaagtatat gtagctttaa ttttaagagg caaaaaaaca atagaagaag  19140
taccagcagt aattagagag caagttagaa ttagatgtaa agaattagaa ataccagttg  19200
aatagtaaat ttagaataac tatgtattag ttattttttt tatgtaaagt acaaggtctt  19260
aactttaata agtaagcctt gtacttattt tttgttacat tagaacttgt atatatattt  19320
attatttatt caatctataa attacaccta caatttaaag tacagaagat taaattgata  19380
atcctgaaaa tataatattg catgatgtaa gaatacaaca aaaattaaag ctataagtat  19440
aaaaaattta gacaatagga ggctataatg gataaattaa taaccgaatt gagtagtcta  19500
```

```
ggggcaatag gtatactatg tgctctatta tttaaaaata ctatgcagga gaaaaaagaa  19560

gatagagaca tgtataaaaa aactgtagaa aattttatag aattatctac acaacaacaa  19620

gaaataaaca aaaatatact tgttcaaatg ggtataatga aaacagatgt agaggaaatt  19680

aaggaagatg ttactgatat aaaaggtatg ttacaaaatg gtgtataaca tgaaagagta  19740

gcaccagatt atatattgtt aggaaaagat aaagtagtat tgtagatagt tcactatttt  19800

attgagaagg atttaatatt taaaatatta attaaaaaaa gtaataaaaa taacatataa  19860

aaattaaaaa aggagttaag cttaaatttg aggcgcg                           19897


<210> SEQ ID NO 62
<211> LENGTH: 168
<212> TYPE: PRT
<213> ORGANISM: Clostridium difficile

<400> SEQUENCE: 62

Met Asn Asn Leu Asp Lys Leu Phe Glu Leu Ala Ser Gln Glu Glu Ile
1               5                   10                  15

Ile Ile His Tyr Thr Thr Tyr Ile Ala Gly Asp Leu Glu Gly Leu Tyr
            20                  25                  30

Ile Asn Lys His Gly Ile Lys Ile Ile Ser Leu Leu Ser Asn Leu Lys
        35                  40                  45

Gln Asn Ser Lys Lys Leu Thr Ser Ile Leu Ala Glu Glu Leu Gly His
    50                  55                  60

His Phe Thr Ser Leu Gly Tyr Tyr Val Ser Ser Tyr Asn Asp Tyr Tyr
65                  70                  75                  80

Thr Lys Ile Ile Ile Asp Lys Cys Glu Asn Lys Ala Leu Lys Trp Ala
                85                  90                  95

Cys Glu Phe Leu Ile Thr Glu Glu Asp Ile Ile Asn Ile Ile Asn Ser
            100                 105                 110

Gly Ile Thr Cys Val Tyr Glu Met Ala Asp Ile Leu Asn Val Asp Ile
        115                 120                 125

Thr Phe Phe Gln Lys Arg Leu Glu Phe Leu Ser Leu Lys Lys Gln Ser
    130                 135                 140

Leu Gln Leu Gly Asn Asn Lys Tyr Leu Ile Leu Thr Asn Leu Pro Tyr
145                 150                 155                 160

Phe Tyr Ile Phe Asp Pro Ile Ser
                165


<210> SEQ ID NO 63
<211> LENGTH: 106
<212> TYPE: PRT
<213> ORGANISM: Clostridium difficile

<400> SEQUENCE: 63

Met Phe Ala Lys Arg Leu Arg Glu Leu Arg Lys Glu Phe Gly Leu Thr
1               5                   10                  15

Gln Arg Glu Leu Gly Glu Lys Val Gly Val Ser Gln Arg Val Leu Gly
            20                  25                  30

Tyr Tyr Glu Thr Glu Asn Arg Phe Pro Asp Glu His Ile Leu Asn Lys
        35                  40                  45

Leu Ala Asp Val Phe Asn Val Ser Val Asp Tyr Leu Leu Gly Arg Thr
    50                  55                  60

Leu Val Lys Glu Asn Ile Asp Thr Val Ala Ala His Arg Lys Asn Pro
65                  70                  75                  80

His Glu Glu Leu Pro Glu Glu Ala Gln Glu Gln Leu Asn Asp Tyr Ile
                85                  90                  95
```

```
Glu Phe Leu Leu Asn Lys Tyr Lys Lys Lys
            100                 105


<210> SEQ ID NO 64
<211> LENGTH: 65
<212> TYPE: PRT
<213> ORGANISM: Clostridium difficile

<400> SEQUENCE: 64

Met Phe Lys Asn Asn Leu Lys Tyr Tyr Arg Lys Cys Lys Gly Met Thr
1               5                   10                  15

Gln Ile Gln Leu Ala Arg Lys Ala Gly Ile Thr Asn Asp Tyr Ile Ser
            20                  25                  30

Gln Ile Glu Arg Gly Ile Lys Asn Pro Gly Leu Leu Met Ala Lys Lys
        35                  40                  45

Ile Ser Ser Ile Leu Glu Gln Asn Ile Glu Glu Val Phe Phe Ile Gln
    50                  55                  60

Leu
65


<210> SEQ ID NO 65
<211> LENGTH: 146
<212> TYPE: PRT
<213> ORGANISM: Clostridium difficile

<400> SEQUENCE: 65

Met Glu Asn Lys Lys Asp Ile Leu Phe Lys Glu Thr Asp Lys Arg Leu
1               5                   10                  15

His Asn Tyr Lys Tyr Leu Asp Ile Lys Ile Lys Asn Ile Asn Leu Asp
            20                  25                  30

Ile Lys Arg Cys Glu Asn Glu Tyr Ser Gly Cys Gly Ala Met Val Tyr
        35                  40                  45

Thr Glu Lys Thr Ser Asn Thr Tyr Asn Ile Ser Ser Ser Val Glu Asn
    50                  55                  60

Glu Val Leu Lys Arg Glu Glu Arg Leu Arg Lys Leu Lys Met Glu Lys
65                  70                  75                  80

Glu Asp Ile Glu Ile Glu Lys Glu Lys Ile Glu Asn Ala Leu Thr Cys
                85                  90                  95

Leu Asn Asp Ile Glu Met Glu Phe Phe Asn Leu Phe Tyr Asn Ser Lys
            100                 105                 110

Thr Lys Asn Asn Met Thr Tyr Ile Ser Met Lys Leu His Leu Asp Arg
        115                 120                 125

Thr Ser Cys Tyr Asn Leu Lys Lys Lys Met Ile Phe Lys Leu Ser Glu
    130                 135                 140

Ile Leu
145


<210> SEQ ID NO 66
<211> LENGTH: 147
<212> TYPE: PRT
<213> ORGANISM: Clostridium difficile

<400> SEQUENCE: 66

Leu Leu Lys Tyr Lys Glu Ile Leu Glu Thr Ile Ile Glu Ile Leu Lys
1               5                   10                  15

Lys Asn Phe Thr Glu Ser Ile Phe Ile Asp Asp Glu Ser Val Gln Gly
            20                  25                  30

Ser Glu Gly Ser Cys Phe Phe Val Ser Ile Leu Ser Val Ile Cys Thr
```

35 40 45

Pro Val Met Leu Asn Thr Asn Asn Lys Asp Ile Val Ile Ser Ile Lys
50 55 60

Tyr Leu Pro Lys Pro Gln Ser Lys Ser Ile Arg Met Tyr Glu Ile Ser
65 70 75 80

Asp Glu Leu Asn Lys Leu Phe Asn Arg Asn Ile Lys Val Thr Asp Arg
85 90 95

Lys Leu Asn Ile Thr Lys Leu Glu Gln Ser Ile Lys Lys Glu Glu Ser
100 105 110

Ile Tyr Val Leu Asn Phe Thr Phe Thr Leu Asn Tyr Leu Asp Ser Val
115 120 125

Tyr Glu Glu Asp Val Val Tyr Glu Asn Met Lys Glu Ile Asn Leu Asn
130 135 140

Leu Gly Glu
145

<210> SEQ ID NO 67
<211> LENGTH: 354
<212> TYPE: PRT
<213> ORGANISM: Clostridium difficile

<400> SEQUENCE: 67

Met Ala Ile Gly Leu Pro Ser Ile Asn Ile Ser Phe Lys Glu Leu Ala
1 5 10 15

Thr Thr Val Lys Glu Arg Ser Ala Arg Gly Ile Ile Ala Met Val Leu
20 25 30

Lys Asp Ala Lys Ala Leu Gly Leu Asn Glu Ile His Glu Lys Glu Asp
35 40 45

Ile Pro Val Asp Leu Ser Ala Glu Asn Lys Glu Tyr Ile Asn Leu Ala
50 55 60

Leu Met Gly Asn Val Asn Thr Pro Asn Lys Leu Leu Val Tyr Val Ile
65 70 75 80

Glu Gly Glu Ala Asp Ile Gln Thr Ala Leu Asp Phe Leu Glu Thr Lys
85 90 95

Glu Phe Asn Tyr Leu Cys Met Pro Lys Ala Val Glu Ala Asp Lys Thr
100 105 110

Ala Ile Lys Asn Trp Ile Ile Lys Leu Arg Asp Ile Asp Lys Val Lys
115 120 125

Val Lys Ala Val Leu Gly Lys Val Val Gly Asn His Glu Gly Ile Ile
130 135 140

Asn Phe Thr Thr Glu Asp Val Leu Val Gly Glu Lys Lys Tyr Ser Val
145 150 155 160

Asp Glu Phe Thr Ser Arg Val Ala Gly Leu Ile Ala Gly Thr Pro Leu
165 170 175

Ser Gln Ser Val Thr Tyr Thr Lys Leu Ser Asp Val Val Asp Ile Pro
180 185 190

Lys Met Thr Lys Val Asp Ala Glu Ser Arg Val Asn Lys Gly Glu Leu
195 200 205

Ile Leu Ile Lys Glu Ala Gly Ala Ile Arg Ile Ala Arg Gly Val Asn
210 215 220

Ser Leu Thr Glu Leu Thr Ala Glu Lys Gly Glu Met Phe Gln Lys Ile
225 230 235 240

Lys Ile Val Asp Thr Leu Asp Ile Ile His Ser Asp Ile Arg Lys Val
245 250 255

Ile Ile Asp Asp Tyr Ile Gly Lys Val Thr Asn Ser Tyr Asp Asn Lys

-continued

```
            260                 265                 270

Cys Leu Leu Ile Val Ala Ile Lys Ser Tyr Leu Glu Glu Leu Glu Lys
        275                 280                 285

Ser Ala Leu Ile Glu Ser Asp Ser Thr Val Glu Ile Asp Phe Glu Ala
    290                 295                 300

Gln Lys Ser Tyr Leu Lys Ser Lys Gly Val Asp Leu Ser Tyr Met Thr
305                 310                 315                 320

Leu Gln Glu Ile Lys Glu Ala Asn Thr Gly Ser Lys Val Phe Leu Lys
                325                 330                 335

Ala Lys Ile Lys Val Leu Asp Ala Met Glu Asp Ile Asp Leu Ser Ile
            340                 345                 350

Glu Ile
```

<210> SEQ ID NO 68
<211> LENGTH: 142
<212> TYPE: PRT
<213> ORGANISM: Clostridium difficile

<400> SEQUENCE: 68

```
Met Ala Asn Met Glu Ala Arg Asn Val Met Ser Gly Thr Trp Gly Glu
1               5                   10                  15

Leu Trp Leu Asp Gly Asn Lys Val Ala Glu Val Lys Lys Phe Gln Ala
            20                  25                  30

Lys Met Glu Phe Thr Lys Glu Asp Ile Ile Ile Ala Gly Gln Met Gly
        35                  40                  45

Thr Asp Thr Lys Tyr Met Gly Tyr Lys Gly Lys Gly Ser Ile Thr Leu
    50                  55                  60

Tyr His Val Ser Ser Arg Met His Lys Leu Ile Gly Glu Lys Ile Lys
65                  70                  75                  80

Arg Gly Ser Glu Pro Arg Phe Val Ala Ile Ser Lys Leu Asn Asp Pro
                85                  90                  95

Asp Ser Tyr Gly Ala Glu Arg Ile Ala Val Lys Asn Ile Ala Phe Asp
            100                 105                 110

Asp Leu Thr Leu Ala Asp Trp Glu Val Gly Val Lys Gly Glu Ile Glu
        115                 120                 125

Ala Pro Phe Thr Phe Thr Glu Tyr Asp Phe Leu Asp Ile Ile
    130                 135                 140
```

<210> SEQ ID NO 69
<211> LENGTH: 148
<212> TYPE: PRT
<213> ORGANISM: Clostridium difficile

<400> SEQUENCE: 69

```
Met Ser Glu Asn Gly Leu Ser Lys Asn Ile Asn Ile Val Asp Leu Leu
1               5                   10                  15

Leu Asn Ser Asp Thr Glu Asn Leu Glu Arg Pro Ser Thr Ile Val Glu
            20                  25                  30

Leu Lys Arg Leu Ser Thr Ile Phe Gly Gln Glu Phe Lys Val Met Cys
        35                  40                  45

Arg Ala Leu Thr Ile Ser Lys Asp Glu Glu Ile Gln Asn Thr Cys Leu
    50                  55                  60

Lys Ile Asp Glu Asn Met Lys Thr Asp Ile Asp Leu Pro Glu Met Gln
65                  70                  75                  80

Met Leu Thr Ile Ile Glu Gly Val Cys Asp Leu Asp Gly Lys Leu Leu
                85                  90                  95
```

```
Phe Lys Asn Lys Glu Leu Met Asp Lys Phe Lys Ala Pro Thr Pro Lys
            100                 105                 110

Glu Leu Ala Arg Lys Leu Leu Leu Pro Gly Glu Ile Thr Asn Leu Tyr
        115                 120                 125

Arg Ile Leu Gln Asp Val Met Gly Tyr Gly Lys Asn Ala Val Ile Glu
    130                 135                 140

Glu Val Lys Asn
145


<210> SEQ ID NO 70
<211> LENGTH: 55
<212> TYPE: PRT
<213> ORGANISM: Clostridium difficile

<400> SEQUENCE: 70

Met Tyr Tyr Tyr Trp Lys Lys Lys Gly Ile Arg Pro Ser Leu Phe Tyr
1               5                   10                  15

Ala Met Asp Lys Gly Glu Leu Lys Leu Ile Glu Ala Phe Phe Ala Leu
            20                  25                  30

Glu Ile Glu Glu Glu Val Glu Lys Met Lys His Gly Tyr Gly Val Cys
        35                  40                  45

Pro Leu Thr Gly Gly Gly Met
    50                  55


<210> SEQ ID NO 71
<211> LENGTH: 817
<212> TYPE: PRT
<213> ORGANISM: Clostridium difficile

<400> SEQUENCE: 71

Met Gly Asn Val Arg Glu Glu Gly Ile Asn Met Tyr Leu Thr Asp Asn
1               5                   10                  15

Tyr Thr Pro Lys Met Asn Gln Ile Ile Ser Val Thr Asp Asn Phe Arg
            20                  25                  30

Arg Ala Thr Val Ala Val Ser Leu Ser Thr Asn Val Met Ala Ser Ser
        35                  40                  45

Ile Lys Asn Ser Ile Gly Ser Ala Ser Asn Arg Val Asn Ser Leu Asn
    50                  55                  60

Ser Ser Leu Arg Lys Val Gln Thr Thr Ala Ser Ser Val Ser Ser Thr
65                  70                  75                  80

Met Thr Lys Leu Ser Ser Ser Ile Asn Ala Val Ser Gly Val Ile Gly
                85                  90                  95

Ser Leu Asn Gly Ser Ile Met Arg Leu Ala Ile Thr Ile Ala Met Ile
            100                 105                 110

Ile Asp Tyr Phe Asn Lys Leu Ile Gln Lys Lys Asn Glu Phe Asn Ser
        115                 120                 125

Asn Ile Met Ile Ile Leu Ile Phe Lys Ala Lys Ser Asp Glu Val Glu
    130                 135                 140

Lys Thr Lys Asn Lys Leu Leu Gly Asn Leu Lys Lys Ile Gly Gly Lys
145                 150                 155                 160

Ile Trp Asn Ile Val Ile Lys Ala Lys Asp Met Thr Lys Arg Val Ile
                165                 170                 175

Ser Ser Ile Leu Gly Lys Leu Lys Gln Val Glu Lys Arg Pro Tyr Gln
            180                 185                 190

Gly Ser Ile Asn Leu Lys Asp Met Val Ser Ser Ala Met Gly Arg Ile
        195                 200                 205

Leu Pro Lys Leu Met Leu Phe Lys Asn Thr Phe Trp Ser Gly Val Ile
```

-continued

```
    210                 215                 220

Ala Ile Lys Asp Met Ala Ser Gly Ile Ile Ser Lys Val Phe Pro Lys
225                 230                 235                 240

Leu Arg Leu Phe Ala Gly Lys Val Trp Ser Gly Ala Ile Ala Val Lys
                245                 250                 255

Asp Met Ala Ser Gly Ile Leu Gly Ser Ile Lys Gly Lys Ile Ser Asp
            260                 265                 270

Leu Thr Asn Gly Ala Thr Ile Gly Val Ala Val Lys Lys Gly Val Asp
        275                 280                 285

Leu Leu Gly Gln Glu Gln Asn Gln Lys Val Val Leu Glu Ser Val Met
    290                 295                 300

Lys Arg Asn Thr Gly Lys Val Asn Gln Ile Asp Val Asp Asp Tyr Tyr
305                 310                 315                 320

Gly Ser Leu Val Arg Met Ala Asn Asp Thr Pro Phe Asp Pro Glu Asp
                325                 330                 335

Val Val Ala Met Gly Thr Lys Ala Lys Met Ile Ser Asn Ile Thr Gly
            340                 345                 350

Gly Lys Lys Glu Lys Asp Ile Thr Gln Ala Met Val Asp Val Arg Ala
        355                 360                 365

Leu Asn Met Asn Thr Ser Ser Glu Gln Asp Val Ser Ala Ala Phe Leu
    370                 375                 380

Ser Ala Ala Lys Gly Asn Met Glu Ser Leu Asn Thr Leu Val Gly Glu
385                 390                 395                 400

Asn Tyr Lys Thr Phe Asp Glu Ala Leu Glu Gly Ile Ser Val Lys Gln
                405                 410                 415

Met Gly Leu Ala Lys Glu Met Ser Asn Thr Ile Pro Gly Ile Ile Ser
            420                 425                 430

Gly Ala Gln Thr Ser Ile Asn Asn Gly Leu Lys Ser Ile Val Lys Pro
        435                 440                 445

Phe Asp Asp Ile Leu Gly Gln Gly Leu Lys Lys Ile Lys Thr Phe Ile
    450                 455                 460

Glu Ser Gly Leu Gly Asn Leu Ala Gly Leu Ser Glu Lys Met Ala Gly
465                 470                 475                 480

Lys Ile Gly Asn Val Met Asn Gly Lys Ile Ile Ile Gly Asn Lys Tyr
                485                 490                 495

Asp Gln Met Gln Ser Arg Ser Val Lys Asn Gly Lys Glu Phe Ser Asp
            500                 505                 510

Ser Thr Gln Tyr Arg Ile Ser Asn Glu Ala Glu Lys Arg Lys Met Met
        515                 520                 525

Val Glu Asn Lys Gln Glu Arg Phe Glu Asn His Ala Ala Thr Met Ile
    530                 535                 540

Gly Asn Ala Pro Lys Ala Ile Val Asn Ala Gly Ser Thr Leu Leu Gln
545                 550                 555                 560

Asn Ile Asp Phe Thr Ala Leu Ile Asp Ser Leu Leu Pro Val Val Asn
                565                 570                 575

Leu Val Asn Asn Leu Leu Asp Ser Ile Asn Asn Lys Ser Pro Ile Ala
            580                 585                 590

Gln Gly Leu Ile Ser Ile Phe Gly Thr Ile Val Thr Thr Ala Phe Gln
        595                 600                 605

Leu Ile Gly Pro Val Val Glu Ala Val Ser Pro Ile Ile Thr Arg Ile
    610                 615                 620

Phe Thr Phe Leu Gly Glu Tyr Ala Pro Gln Ile Asn Asn Phe Ile Glu
625                 630                 635                 640
```

```
Thr Leu Gly Val Ile Trp Lys Thr Val Trp Glu Thr Leu Gly Pro Leu
                645                 650                 655

Leu Glu Thr Gly Trp Lys Ile Ile Glu Pro Ile Leu Gly Ala Phe Phe
            660                 665                 670

Asn Ile Leu Asp Lys Val Cys Lys Ile Val Lys Asp Ile Cys Lys Trp
        675                 680                 685

Trp Gln Thr Met Ile Asn Lys Ile Lys Asn Gly Ser Ile Thr Gly Thr
    690                 695                 700

Val Leu Asn Leu Val Glu Lys Ser Lys Lys Asn Tyr Lys Asp Asn Pro
705                 710                 715                 720

Tyr Ala Gly Thr Lys Ala Gly Asp Ser Gly Lys Ala Tyr Ser Gly Lys
                725                 730                 735

Lys Gly Asn Asn Ala Phe Gly Leu Asn Tyr Val Pro Tyr Asn Asp Tyr
            740                 745                 750

Gln Thr Arg Leu His Glu Gly Glu Met Val Leu Thr Lys Gln Glu Ala
        755                 760                 765

Asn Gln Tyr Arg Ser Arg Lys Asn Gly Gly Asn Ile Asn Ile Ala Lys
    770                 775                 780

Leu Ala Asp Thr Ile Val Ile Arg Glu Glu Ala Asp Ile Glu Lys Ile
785                 790                 795                 800

Thr Ser Lys Leu Val Ala Ser Ile Gln Leu Ala Gln Leu Gly Gly Val
                805                 810                 815

Leu


<210> SEQ ID NO 72
<211> LENGTH: 140
<212> TYPE: PRT
<213> ORGANISM: Clostridium difficile

<400> SEQUENCE: 72

Met Glu Met Trp Leu Arg Gln Ala Glu Asp Arg Phe Arg Phe Pro Val
1               5                   10                  15

Phe Pro Ser Ser Phe Ser Ile Asn Gly Lys Ala Ala Val Asn Ser Ser
            20                  25                  30

Ser Ile Leu Lys Ile Gly Glu Ile Ala Thr Phe Gly Gly Val Ala Leu
        35                  40                  45

Lys Ser Ile Ser Ile Ser Ser Phe Phe Pro Asn Lys Asp Tyr Thr Phe
    50                  55                  60

Cys Asp Tyr Thr Gly Phe Pro Ser Pro Tyr Asp Cys Val Asn Lys Ile
65                  70                  75                  80

Glu Lys Trp Met Lys Glu Gly Phe Ile Leu Arg Phe Thr Ile Thr Glu
                85                  90                  95

Thr Asn Ile Asn Met Glu Val Ile Ile Glu Gly Phe Ser Tyr Glu Glu
            100                 105                 110

Arg Asp Gly Thr Arg Asp Val Tyr Phe Thr Leu Asp Leu Lys Glu Tyr
        115                 120                 125

Lys Arg Ile Lys Ile Pro Lys Val Thr Pro Lys Gln
    130                 135                 140


<210> SEQ ID NO 73
<211> LENGTH: 509
<212> TYPE: PRT
<213> ORGANISM: Clostridium difficile

<400> SEQUENCE: 73

Met Ile Ile Asn Arg Ser Lys Asp Ser Ser Ser Asn Glu Ile Ser Phe
1               5                   10                  15
```

```
Val Ser Lys Asp Met Gly Phe Leu Leu Thr Gln Ser Glu Val Ser Tyr
            20                  25                  30

Asn Phe Lys Asp Lys Leu Val Glu Asp Ile Ala Lys Gln Val Phe Ala
        35                  40                  45

Glu Asn Arg Leu Ser Val Gly Ile Ile Ala Lys Thr Asn Val Lys Tyr
    50                  55                  60

Thr Lys Met Phe Ile Gly Val Asn Gly Tyr Asp Thr Ile Met Ser Ala
65                  70                  75                  80

Tyr Thr Glu Ala Ser Lys Lys Thr Lys Lys Lys Tyr Met Ile Glu Ala
                85                  90                  95

Asn Leu Asp Lys Phe Asn Val Ile Glu Lys Gly Thr Val Thr Leu Ser
            100                 105                 110

Val Met Phe Glu Glu Gly Phe Asn Ile Ile Asn Thr Thr Phe Ser Glu
        115                 120                 125

Ser Met Glu Asn Val Lys Asn Lys Val Ile Val Val Asp Gln Tyr Gly
    130                 135                 140

Ser Lys Ile Ser Glu Lys Ile Asp Asn Glu Ile Phe Lys Glu Val Asn
145                 150                 155                 160

Val Ile Met Gln Lys Val Ile Gln Gln Gln Glu Asn Gln Asp Val Asp
                165                 170                 175

Ile Asp Ser Glu Phe Asn Gly Ile Glu Lys Ser Cys Ser Leu Lys Gly
            180                 185                 190

Tyr Gly Asp Val Ser Cys Ile Thr Gly Arg Gly Val Lys Val Lys Asp
        195                 200                 205

Ser Tyr Thr Lys Leu Val Gly Leu Phe Tyr Ile Asp Thr Asp Lys His
    210                 215                 220

Thr Trp Gln Asn Gly Glu Tyr Gln Ile Glu Leu Glu Leu Asn Phe Gln
225                 230                 235                 240

Asn Leu Met Asp Glu Lys Ser Ala Gly Gln Asp Glu Pro Lys Glu Glu
                245                 250                 255

Ser Asn Leu Gly Gly Glu Asp Tyr Ala Gly Gly Lys Glu Phe Thr Ala
            260                 265                 270

Glu Phe Thr Ala Tyr Cys Pro Arg Lys Glu Glu Gly Gly Asp Thr Asp
        275                 280                 285

Cys Arg Lys Lys Lys Leu Asp Pro Ser Lys Lys Thr Cys Ala Ala Pro
    290                 295                 300

Met Val Gly Lys Tyr Glu Gln Thr Tyr Tyr Thr Lys Glu Phe Leu Asn
305                 310                 315                 320

Lys His Pro Leu Leu Asn Tyr Gly Asp Glu Ile Gln Val Ile Thr Gly
                325                 330                 335

Val Ser Gly Arg Asp Gly Val Tyr Lys Val Asn Asp Val Gly Pro Ala
            340                 345                 350

Ile Thr Ile Glu Lys Asn Gly Thr Tyr His Ile Asp Ile Leu Phe Gly
        355                 360                 365

Asn Val Glu Glu Ala Ser Lys Phe Gly Arg Arg Lys Gly Lys Ile Ile
    370                 375                 380

Ile Gly Gly Tyr Ser Gly Asn Val Ser Asp Lys Ala Lys Ile Val Ile
385                 390                 395                 400

Ser Glu Ala Lys Lys His Leu Gly Lys Pro Tyr Lys Trp Gly Gly Asn
                405                 410                 415

Gly Pro Ser Ser Phe Asp Cys Ser Gly Leu Met Val Tyr Cys Phe Lys
            420                 425                 430

Lys Val Asn Val Ser Leu Pro Arg Thr Ser Asn Gln Gln Ser Lys Lys
```

```
        435                 440                 445

Gly Lys Lys Val Glu Gln Lys Asn Leu Gln Ala Gly Asp Leu Val Phe
    450                 455                 460

Phe His Asn Pro Val Ser His Val Gly Leu Tyr Ile Gly Asn Gly Glu
465                 470                 475                 480

Phe Leu His Ala Pro Gln Lys Gly Asp Val Val Lys Ile Ser Lys Leu
                485                 490                 495

Ser Ser Arg Arg Asp Phe Asn Thr Ala Arg Arg Val Leu
            500                 505


<210> SEQ ID NO 74
<211> LENGTH: 108
<212> TYPE: PRT
<213> ORGANISM: Clostridium difficile

<400> SEQUENCE: 74

Met Ala Asn Pro Ile Asn Glu Phe Ile Gly Ile Ile Arg Glu Glu Gly
1               5                   10                  15

Lys Tyr His Asn Gln Pro Ser Phe Phe Ile Gly Lys Ile Lys Ser Lys
            20                  25                  30

Leu Pro Asp Leu Lys Ile Glu Thr Asn Asn Ile Ile Leu Glu Lys Glu
        35                  40                  45

Asp Ile Leu Ile Asp Ser Trp Met Ile Asp Arg Gln Leu Glu Thr Phe
    50                  55                  60

Asp Thr Glu Thr Asn Gln Glu His Gln His Glu Val Lys Asn Pro Phe
65                  70                  75                  80

Ile Asp Asn Phe Glu Ser Gly Asp Met Val Ile Met Phe Arg Ile Gly
                85                  90                  95

Glu Lys Phe Ala Val Val Ser Lys Leu Val Ser Leu
            100                 105


<210> SEQ ID NO 75
<211> LENGTH: 142
<212> TYPE: PRT
<213> ORGANISM: Clostridium difficile

<400> SEQUENCE: 75

Met Ser Thr Ile Phe Pro Phe Ile Gly Val Pro Glu Asp Tyr Ile Leu
1               5                   10                  15

Pro Lys Thr Glu Glu Leu Pro Ile Phe Arg Glu Val Ala Trp Asp Phe
            20                  25                  30

Glu Lys Asp Glu Pro Ile Leu Glu Lys Gly Asp Phe Lys Ile Ile Glu
        35                  40                  45

Lys Lys Glu Ala Leu Lys Val Trp Ile Tyr Lys Cys Ile Lys Thr Asn
    50                  55                  60

Arg Tyr Glu His Glu Ile Tyr Ser Leu Glu Tyr Gly Thr Glu Leu Ser
65                  70                  75                  80

Glu Leu Ile Gly Gln Lys Tyr Thr Lys Gly Leu Thr Glu Ser Glu Ala
                85                  90                  95

Ser Arg Phe Ile Lys Glu Ala Leu Leu Ile Asn Pro Tyr Ile Leu Glu
            100                 105                 110

Val Asn Val Lys Ser Ala Asn Phe Asn Arg Asp Ile Leu Ser Ala Asn
        115                 120                 125

Val Lys Val Ser Thr Ile Tyr Gly Glu Val Glu Ile Asn Val
    130                 135                 140


<210> SEQ ID NO 76
```

-continued

<211> LENGTH: 350
<212> TYPE: PRT
<213> ORGANISM: Clostridium difficile

<400> SEQUENCE: 76

```
Met Tyr Ser Asp Gln Thr Tyr Glu Val Ile Lys Asn Arg Thr Leu Glu
1               5                   10                  15

Asn Ile Asn Leu Asp Ile Tyr Lys Gly Glu Gly Ser Phe Leu Asn Asn
            20                  25                  30

Met Val Ser Gly Asn Asn Leu Glu Leu Ser Lys Ile Tyr Leu Glu Leu
        35                  40                  45

Ser Lys Met His Lys Met Ala Phe Ile Gln Asp Thr Tyr Asn Gln Phe
    50                  55                  60

Leu Asp Lys Arg Val Asn Glu Phe Gly Val Tyr Arg Lys Leu Gly Thr
65                  70                  75                  80

Glu Ser Asn Gly Glu Val Glu Phe Ile Gly Glu Lys Gly Thr Val Ile
                85                  90                  95

Asn Asn Gly Thr Ile Ile Ser Tyr Arg Asp Leu Leu Phe Val Val Ile
            100                 105                 110

Lys Asp Val Thr Ile Gly Ser Glu Glu Gly Asp Asn Ser Pro Val Gln
        115                 120                 125

Ala Leu Glu Val Gly Lys Lys Tyr Asn Leu Pro Thr Asn Cys Glu Phe
    130                 135                 140

Lys Leu Val Asp Asn Ile Ser Gly Val Thr Lys Ile Thr Asn Thr Arg
145                 150                 155                 160

Ser Phe Glu Gly Gly Thr Asp Ile Glu Thr Asp Glu Glu Leu Lys Glu
                165                 170                 175

Arg Phe Tyr Lys Ile Gln Arg Asn Gln Ala Thr Ser Gly Asn Lys Ala
            180                 185                 190

His Tyr Glu Glu Trp Ala Leu Glu Val Asp Gly Val Tyr Asn Val Lys
        195                 200                 205

Val Tyr Pro Arg Trp Asp Gly Pro Gly Thr Val Lys Val Leu Ile Phe
    210                 215                 220

Gly Lys Asn Asn Gln Ala Val Asp Thr Glu Thr Ile Glu Arg Cys Gln
225                 230                 235                 240

Gln His Ile Asp Glu Glu Lys Pro Ile Gly Pro Thr Ile Thr Val Val
                245                 250                 255

Thr Pro Leu Pro Ile Glu Ile Ser Ile Ser Ala Val Met Lys Leu Glu
            260                 265                 270

Asp Gly Tyr Thr Leu Asp Asn Val Lys Glu Ser Phe Leu Glu Ser Ile
        275                 280                 285

Asn Thr Tyr Phe Arg Asp Ile Arg Gly Glu Ile Ile Tyr Thr Lys Val
    290                 295                 300

Met Gly Ile Leu Ile Asn Thr Thr Gly Val His Asp Leu Ser Asn Leu
305                 310                 315                 320

Leu Ile Asn Gly Ser Thr Asp Asn Ile Thr Ile Asn Glu Asp Lys Ile
                325                 330                 335

Pro Ser Val Thr Thr Val Asn Phe Ser Glu Val Glu Asn Gln
            340                 345                 350
```

<210> SEQ ID NO 77
<211> LENGTH: 232
<212> TYPE: PRT
<213> ORGANISM: Clostridium difficile

<400> SEQUENCE: 77

Met Lys Leu Ile Asp Lys Leu Pro Ser Phe Asp Arg Asn Tyr Ile Val
1 5 10 15

Glu Glu Ile Gln Gly Ala Tyr Asp Thr Glu Leu Asn Ile Leu Lys Glu
20 25 30

Asp Ile Asp Asp Thr Phe Asn Gln Leu Phe Val Asp Thr Ala Thr Trp
35 40 45

Gly Leu Asp Met Trp Glu Asp Ile Leu Cys Ile Glu Lys Lys Glu Leu
50 55 60

Asp Phe Asp Thr Arg Arg Ser Asn Ile Lys Ala Lys Met Arg Ser Arg
65 70 75 80

Gly Thr Ser Thr Ile Glu Val Ile Lys Ser Ile Cys Glu Ala Tyr Thr
85 90 95

Lys Ser Glu Thr Asp Ile Lys Val Tyr Ser Asp Glu Phe Thr Phe Val
100 105 110

Leu Ser Phe Ile Ala Asn Asn Cys Asp Tyr Lys Thr Leu Leu Asp Cys
115 120 125

Ser Asp Met Ile Glu Arg Val Lys Pro Ala His Leu Leu His Tyr Leu
130 135 140

Glu Pro Ile Ile Leu Asp Lys Ser Met Val Tyr Cys Gly Gly Gly Met
145 150 155 160

Val Cys Ser Glu Glu Val Lys Val His Pro Tyr Phe Glu Pro Ile Ile
165 170 175

Lys Cys Ser Ala Val Val Asn Cys Gly Ala Gly Met Ile Ser Arg Glu
180 185 190

Glu Ile Lys Val Tyr Pro Leu Ser Ile Lys Cys Ile Glu Asn Asn Cys
195 200 205

Lys Ile Asn Ile Ala Ile Ala Asn Asp Thr Gly Val Glu Asn Val Val
210 215 220

Val Tyr Pro Lys Ser Glu Val Val
225 230

<210> SEQ ID NO 78
<211> LENGTH: 327
<212> TYPE: PRT
<213> ORGANISM: Clostridium difficile

<400> SEQUENCE: 78

Leu Glu Glu Lys Phe Tyr Ile Ile Leu Thr Lys Ile Gly Arg Glu Lys
1 5 10 15

Ile Ala Asn Ala Thr Ala Leu Gly Glu Leu Val Gly Leu Thr Lys Phe
20 25 30

Gln Val Gly Asp Ser Asn Gly Glu Tyr Tyr Glu Pro Thr Glu Glu Gln
35 40 45

Thr Ala Leu Lys Asn Val Val Trp Glu Gly Asn Ile Asn Ser Leu Arg
50 55 60

Ile Asp Glu Lys Asn Pro Asn Trp Ile Val Ile Glu Thr Ile Leu Pro
65 70 75 80

Gly Thr Val Gly Gly Phe Met Ile Arg Glu Ala Ala Val Leu Asp Asn
85 90 95

Glu Asn Asn Ile Ile Ala Ile Gly Lys Tyr Pro Glu Thr Tyr Lys Pro
100 105 110

Arg Ala Glu Asp Gly Ser Ile Lys Asp Leu Val Val Lys Met Ile Leu
115 120 125

Gln Leu Ser Asn Thr Ser Asn Val Thr Leu Glu Val Asp Pro Thr Leu
130 135 140

-continued

Val Phe Val Thr Gln Lys Asp Ile Gln Asp Leu Asp Asp Lys Phe Asp
145 150 155 160

Lys Asn Ile Lys Glu Ile Lys Val Lys Ile Gly Glu Glu Leu Leu Ser
165 170 175

Thr Glu Ala Lys Asn Leu Ser Gly Ala Ile Asn Glu Val Val Glu Lys
180 185 190

Ile Lys Asn Ile Ser Ile Asp Asp Val Ile Gly Gly Gln Ile Gln Thr
195 200 205

Glu Leu Ser Val Leu Lys Asn Ser Tyr Asn Lys Leu Ser Glu Lys Val
210 215 220

Leu Asp Ile Leu Ile Tyr Leu Glu Leu Glu Ser Glu Ile Asp Val Asp
225 230 235 240

Glu Ala Gly Tyr Trp Tyr Asp Thr Leu Thr Asn Ala Lys Asn Ile Ile
245 250 255

Ala Ile Glu Gly Leu Lys Leu Asp Leu Asn Arg Lys Cys Ile Thr Gly
260 265 270

Glu Leu Gly Ser Val Thr Phe Lys Asn Val Val Leu Pro Phe Asn Ala
275 280 285

Asn Arg Val Arg Tyr Ile His Glu Met Asp Asn Asn Phe Val Glu Thr
290 295 300

Lys Ser Asn Arg Ala Tyr Ser Ile Gly Gln Thr Asp Ile Thr Leu Asn
305 310 315 320

Lys Tyr Ser Tyr Glu Ile Arg
325

<210> SEQ ID NO 79
<211> LENGTH: 98
<212> TYPE: PRT
<213> ORGANISM: Clostridium difficile

<400> SEQUENCE: 79

Met Gln Tyr Lys Asp Ile Ser Asp Ile Ser Ile Gly Gln Val Lys Gln
1 5 10 15

Asp Asp Asp Ile Thr Asn Asn Phe Ile Ala Asn Val Glu Ile Tyr Glu
20 25 30

Met Leu Leu Asn Gln Ser Ser Val Asn Glu Ala Ser Asn Ile Ser Thr
35 40 45

Phe Ser Val Arg Lys Ser Gly Gly Glu Ser Gly Met Val Glu Val Tyr
50 55 60

Val Ala Leu Ile Leu Arg Gly Lys Lys Thr Ile Glu Glu Val Pro Ala
65 70 75 80

Val Ile Arg Glu Gln Val Arg Ile Arg Cys Lys Glu Leu Glu Ile Pro
85 90 95

Val Glu

<210> SEQ ID NO 80
<211> LENGTH: 86
<212> TYPE: PRT
<213> ORGANISM: Clostridium difficile

<400> SEQUENCE: 80

Met Asp Lys Leu Ile Thr Glu Leu Ser Ser Leu Gly Ala Ile Gly Ile
1 5 10 15

Leu Cys Ala Leu Leu Phe Lys Asn Thr Met Gln Glu Lys Lys Glu Asp
20 25 30

Arg Asp Met Tyr Lys Lys Thr Val Glu Asn Phe Ile Glu Leu Ser Thr
35 40 45

```
Gln Gln Gln Glu Ile Asn Lys Asn Ile Leu Val Gln Met Gly Ile Met
    50                  55                  60

Lys Thr Asp Val Glu Glu Ile Lys Glu Asp Val Thr Asp Ile Lys Gly
65                  70                  75                  80

Met Leu Gln Asn Gly Val
                85


<210> SEQ ID NO 81
<211> LENGTH: 1802
<212> TYPE: PRT
<213> ORGANISM: Clostridium difficile

<400> SEQUENCE: 81

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Met Lys Gln Asn
    50                  55                  60

Lys Leu Leu Gln Arg Gly Ala Tyr Phe Asn Asp Lys Asn Ile Leu Ile
65                  70                  75                  80

Asp Asp Phe Asp Lys Arg Tyr Asn Asp Tyr Asp Phe Val Glu Phe Phe
                85                  90                  95

Thr Gly Ile Ser Asn Ser Thr Phe Gly Leu Lys Ser Asp Gly Asn Leu
            100                 105                 110

Tyr Ala Cys Gly Asp Asn Thr Gly Phe Gln Leu Gly Leu Gly Lys Asp
        115                 120                 125

Ser Ser Glu Arg Arg Met Phe Ser Lys Val Lys Ile Asp Asn Val Lys
    130                 135                 140

Tyr Val Ser Cys Gly Ser Lys His Ser Val Ala Val Thr Lys Asp Gly
145                 150                 155                 160

Phe Ala Tyr Gly Ala Gly Thr Ser Asn Val Gly Gln Leu Gly Val Ile
                165                 170                 175

Glu Ser Thr Val Tyr Tyr Glu Phe Thr Lys Leu Pro Ile Asp Asp Val
            180                 185                 190

Lys Thr Val Ala Cys Gly Tyr Asp Phe Thr Phe Val Leu Lys Asn Asp
        195                 200                 205

Gly Thr Leu Tyr Ser Ala Gly Leu Asn Ser Ser Gly Gln Leu Gly Leu
    210                 215                 220

Gly Asp Thr Asn Asn Arg Val Thr Phe Thr Lys Val Asn Ile Asp Ser
225                 230                 235                 240

Val Lys Asp Val Val Thr Tyr Asn Gln Ser Val Phe Ile Ile Lys Met
                245                 250                 255

Asp Gly Thr Ala His Ala Cys Gly Leu Asn Ser Asn Gly Gln Leu Gly
            260                 265                 270

Ile Asn Ser Thr Leu Asn Lys Ser Val Phe Asn Lys Ile Glu Gly Met
        275                 280                 285

Asp Asn Val Lys Gln Ile Ala Cys Gly Ser Ser His Thr Ile Leu Ile
    290                 295                 300

Lys Asn Asp Gly Thr Met Tyr Thr Thr Gly Ser Asn Gly Tyr Gly Gln
305                 310                 315                 320

Leu Gly Thr Gly Asn Asn Asn Asn Ser Ile Val Phe Thr Leu Ser Ser
                325                 330                 335
```

```
Ile Asn Asn Val Lys Tyr Ala Ser Cys Gly Asn Asn His Thr Met Ile
        340                 345                 350

Leu Lys Tyr Asp Asn Thr Leu Phe Ser Thr Gly Gln Asn Asn Tyr Gly
    355                 360                 365

Gln Leu Ala Asn Ala Asn Lys Asp Val Ala Ser Arg Asn Thr Phe Val
    370                 375                 380

Lys Val Asn Val Glu Asn Ile Lys Asp Ile Lys Cys Gly Ser Gln Phe
385                 390                 395                 400

Asn Phe Leu Ile Asn Gly Ser Lys Glu Ile Phe Val Ser Gly Cys Asn
                405                 410                 415

Leu Ala Gly Gln Leu Gly Ser Phe Phe His Thr Thr Phe Leu Tyr Glu
            420                 425                 430

Phe Ser Lys Val Gln Ser Ser Asn Leu Asp Asn Tyr Ser Gly Leu Leu
        435                 440                 445

Val Asn Asp Asp Tyr Leu Tyr Val Thr Lys Asp Asn Ser Glu Phe Leu
    450                 455                 460

Asn Val Lys Leu Ser Asp Asn Phe Gln Asp Tyr Lys Lys Ile Glu Leu
465                 470                 475                 480

Thr Asp Asn Asn Met Phe Ile Val Met Asn Asp Gly Thr Leu Tyr Ala
                485                 490                 495

Cys Gly Leu Asn Asn Tyr Gly Gln Leu Gly Leu Gly Asp Thr Val Asn
            500                 505                 510

Arg Ser Val Met Thr Lys Val Asp Ile Asp Asn Val Leu Asp Ile Lys
        515                 520                 525

Gly Asn Gly Asn Ser Thr Phe Val Leu Lys Asn Asn Gly Thr Leu Tyr
    530                 535                 540

Ser Cys Gly Tyr Asn Ser Ser Gly Ile Leu Gly Leu Lys Asp Asn Thr
545                 550                 555                 560

Asn Arg Asn Ile Phe Thr Lys Ile Glu Ile Glu Asn Ile Lys Glu Phe
                565                 570                 575

Cys Val Glu Ser Asn Tyr Ile Val Ala Leu Asn His Ser Lys Glu Leu
            580                 585                 590

Tyr Gly Trp Gly Asn Gln Ser Tyr Ile Val Tyr Gly Asp Asn Arg Asn
        595                 600                 605

Tyr Pro Tyr Lys Asp Thr Arg Val Ser Asn Val Glu Lys Ile Ala Thr
    610                 615                 620

Trp Ser Asp Thr Leu Tyr Ile Leu Asp Ser Thr Gly Ala Thr Lys Thr
625                 630                 635                 640

Ile Gly Tyr Ser Tyr Asn Gly Ser Gly Gly Tyr Pro Ala Pro Ser Ser
                645                 650                 655

Ser Ser Thr Tyr Arg Glu Gly Gly Tyr Ile Asn Lys Asn Thr Ser Tyr
            660                 665                 670

Arg Thr Leu Glu Phe Tyr Asn Thr Ser Lys Thr Lys Leu Val Asn Leu
        675                 680                 685

Phe Ala Phe Tyr Asn Gly Cys Val Phe Val Asp Glu Asn Gly Leu Ala
    690                 695                 700

Tyr Cys Ile Gly Glu Asn Asn Ile Asn Phe Arg Gly Gly Ser Thr Thr
705                 710                 715                 720

Asn Glu Asn Asn Ser Leu Arg Phe Ile Asn Asn Ser Gly Val Tyr Tyr
                725                 730                 735

Thr Asn Thr Asp Gly Thr Asp Tyr Thr Cys Tyr Gln Trp Thr Tyr Lys
            740                 745                 750

Leu Ile Arg Cys Ser Ile Phe Asp Ser Pro Gln Asn Ile Ile Gly Asn
```

```
        755                 760                 765

Ser Lys Asn Ile Leu Tyr Leu Ser Lys Asn Asn Ser Thr Phe Lys Cys
    770                 775                 780

Thr Gly Asn Cys Ile Thr Tyr Gly Ile Asn Ser Gln Asn Trp Tyr Ser
785                 790                 795                 800

Tyr Phe Ser Asp Ser Ser Asn Gly Ala Ile Ala Leu Gly Asn Glu Phe
                805                 810                 815

Ile Leu Lys Asn Tyr Ser Gly Glu Cys Leu Leu Lys Gly Tyr Gly Lys
            820                 825                 830

Ala Thr Asn Gly Glu Phe Gly Asn Ser Thr Asn Ile Ser Ser Ile Ser
        835                 840                 845

Asn Tyr Asp Thr Gly Leu Lys Asp Ile Lys Asp Ile Ile Val Lys Asn
    850                 855                 860

Asn Thr Val Val Val Val Asp Lys Asn Asn Asn Ile Tyr Val Thr Gly
865                 870                 875                 880

Ala Asn Gln Phe Asn Lys Leu Gly Ile Gly Glu Tyr Asn Asn Gln Pro
                885                 890                 895

Ile Arg Lys Phe Thr Asn Ile Thr Glu Gln Ser Asn Ser Phe Ile Phe
            900                 905                 910

Met Asp Asp Ile Lys Glu Ile Thr Thr Ser Arg Asn Thr Met Phe Ile
        915                 920                 925

Val Lys Asn Asp Gly Thr Ala Tyr Ala Thr Gly Asn Asn Ser Ser Gly
    930                 935                 940

Gln Leu Gly Leu Gly Asp Thr Ile Asn Arg Asn Lys Phe Thr Gln Ile
945                 950                 955                 960

Asn Leu Asp Asn Ile Lys Lys Ile Ser Thr Ser Ile Asp Gly Asn Thr
                965                 970                 975

Thr Phe Ala Ile Arg Asn Asp Gly Thr Leu Tyr Ser Thr Gly Leu Asn
            980                 985                 990

Thr Lys Gly Gln Leu Gly Leu Gly  Asp Ile Val Asn Arg  Asn Thr Phe
        995                 1000                1005

Thr Lys  Val Asn Ile Gln Asn  Val Arg Asp Val Val  Leu Gly Thr
    1010                 1015                 1020

Thr His  Ser His Ala Ile Lys  Asp Asp Asn Thr Leu  Tyr Ser Cys
    1025                 1030                 1035

Gly Glu  Asn Thr His Gly Gln  Leu Gly Leu Gly Ser  Glu Ser Asn
    1040                 1045                 1050

His Pro  Asp Val Leu Thr Phe  Thr Val Asn Asn Ile  Thr Asn Val
    1055                 1060                 1065

Arg Asp  Val Tyr Cys Ser Asp  Thr Thr Thr Phe Ile  Val Lys Asp
    1070                 1075                 1080

Thr Asn  Ile Ala Tyr Cys Cys  Gly Tyr Asn Asn Asn  Ser Gln Leu
    1085                 1090                 1095

Gly Met  Gly Asn Thr Thr Asp  Gln Tyr Ser Phe Ile  Lys Cys Met
    1100                 1105                 1110

Glu Asn  Val Lys Glu Val Ile  Pro Asn Glu Ile Asn  Thr Tyr Ile
    1115                 1120                 1125

Ile Thr  Ile Tyr Asn Thr Ala  Tyr Ser Thr Gly Leu  Asn Thr Asp
    1130                 1135                 1140

Tyr Cys  Leu Gly Leu Asn Ser  Asn Ser Asn Gln Ser  Ser Phe Ser
    1145                 1150                 1155

Glu Ile  Pro Ile Ser Asn Val  Val Lys Val Ala Pro  Asn Arg Asn
    1160                 1165                 1170
```

-continued

```
Asn Ala  Val Leu Leu Leu Thr  Ser Glu Gly Asp Val  Tyr Thr Ala
    1175                 1180                 1185

Gly Lys  Cys Ser Asn Gly Ser  Gly Thr Gly Ser Glu  Thr Pro Glu
    1190                 1195                 1200

Lys Ile  Lys Lys Ile Ala Ser  Lys Ala Lys Asp Ile  Gly Met Asn
    1205                 1210                 1215

Tyr Arg  Cys Gly His Tyr Val  Ser Asp Asn Gly Asp  Leu Tyr Gly
    1220                 1225                 1230

Thr Gly  Phe Asn Asp Cys Gly  Gln Leu Gly Val Gly  Asn Val Thr
    1235                 1240                 1245

Lys Arg  Asp Thr Phe Ile Lys  Thr Asn Thr Arg Val  Lys Lys Ile
    1250                 1255                 1260

Leu Pro  Leu Glu Tyr Ala Asn  Ile Ala Ile Lys Asp  Thr Asn Asp
    1265                 1270                 1275

Ile Tyr  Ile Cys Gly Leu Asn  Asn Tyr Gly Gln Leu  Gly Val Gly
    1280                 1285                 1290

Asn Arg  Tyr Asp Ser Arg Asn  Asn Asp Asn Arg Ile  Phe Asn Tyr
    1295                 1300                 1305

Lys His  Met Asn Phe Val Met  Gly Asp Leu Thr Ser  Ile Lys Asn
    1310                 1315                 1320

Arg His  Asn Phe Ile Leu Leu  Asn Asn Lys Ile Val  Ile Pro Thr
    1325                 1330                 1335

Thr Lys  Asp Ile Asp Tyr Gly  Leu Val Leu Gly Asn  Leu Tyr Lys
    1340                 1345                 1350

Gly Asp  Leu Tyr Thr Glu Leu  Pro Tyr Glu Asp Ile  Lys Glu Val
    1355                 1360                 1365

Ser Ile  Ser Lys Thr His Ile  Ile Ile Leu Leu Asn  Asp Gly Thr
    1370                 1375                 1380

Met Tyr  Gly Cys Gly Thr Asn  Tyr His Gly Glu Leu  Leu Gln Asp
    1385                 1390                 1395

Leu Ser  Ile Asn Gln Val Asp  Glu Phe Val Gln Ile  Asn Val Ser
    1400                 1405                 1410

Asp Val  Lys His Val Ser Cys  Gly Asp Asn Phe Thr  Tyr Phe Ile
    1415                 1420                 1425

Lys Ser  Asp Asp Ser Leu Trp  Ser Ile Gly Lys Asn  Ser Glu Tyr
    1430                 1435                 1440

Gln Leu  Gly Ile Gly His Asn  Asn Pro Val Thr Glu  Leu Gln Arg
    1445                 1450                 1455

Ile Thr  Thr Ile Ser Ser Cys  Lys Glu Val His Cys  Gly Lys Asn
    1460                 1465                 1470

Tyr Thr  Leu Val Val Thr Thr  Ser Asn Glu Leu Phe  Val Gln Gly
    1475                 1480                 1485

Tyr Asn  Asp Lys Gly Ala Leu  Gly Leu Gly Ser Asp  Ser Glu Asn
    1490                 1495                 1500

Thr Ile  Ile Lys Phe Phe Thr  Lys Ala Leu Thr Asp  Ile Arg Glu
    1505                 1510                 1515

Ile Lys  Ser Tyr Gly Ser Asp  His Ile Leu Val Leu  Lys Asn Asp
    1520                 1525                 1530

Asn Ser  Val Trp Val Thr Gly  Lys Asn Arg Asp Val  Tyr Lys Ile
    1535                 1540                 1545

Glu Gln  Pro Val Glu Phe Leu  Lys Glu Phe Thr Ile  Val Pro Ile
    1550                 1555                 1560

Ser Glu  Asp Val Asn Thr Val  Lys Asp Val Leu Ala  Thr Asp Asn
    1565                 1570                 1575
```

```
Thr Leu  Tyr Ile Ile Ser Glu  Val Gly Thr Thr Asn  Ala Ala Ile
    1580                 1585                 1590

Glu Ile  Thr Glu Lys Ser Ile  Ser Ser Ile Lys Ile  Lys Ile Gln
    1595                 1600                 1605

Asp Pro  Asn Lys Asp Ile Ser  Arg Ile Glu Met Leu  Ile Asn Gly
    1610                 1615                 1620

Glu Ser  Val Lys Ser Val Ser  Asp Leu Ile Thr Glu  Lys Ile Ser
    1625                 1630                 1635

Phe Glu  Val Pro Pro Asp Lys  Ile Lys Ile Gly Glu  Asn Lys Ile
    1640                 1645                 1650

Leu Phe  Arg Ala Tyr Cys Lys  Gly Asp Asp Leu Tyr  Ala Ser Leu
    1655                 1660                 1665

Phe Ile  Phe Lys Glu Ser Thr  Gly Asn Ser Ile Ile  Lys Asp Ser
    1670                 1675                 1680

Tyr Val  Met Ile Gly Asn Arg  Met Tyr Lys Val Val  Asn Thr Thr
    1685                 1690                 1695

Ser Asn  Glu Gln Asp Ile Thr  Ile Thr Leu Asp Arg  Gly Leu Glu
    1700                 1705                 1710

Glu Asp  Leu Asn Leu Gly Asp  Pro Ile Tyr Gln Leu  Ile Asn Lys
    1715                 1720                 1725

Thr Lys  Val Gln Val Lys Ile  Asn Lys Ser Asp Leu  Phe Lys Asp
    1730                 1735                 1740

Met Lys  Leu Val Glu Ile Lys  Lys Ser Asp Ser Ser  Tyr Gln Glu
    1745                 1750                 1755

Ile Tyr  Glu Leu Glu Glu Ala  Asn Ile Lys Ser Ala  Gln Pro Lys
    1760                 1765                 1770

Ile Ile  Val Glu Lys Gly Asp  Lys Trp Thr Ala Ile  Lys Arg Pro
    1775                 1780                 1785

Ser Met  Ile Phe Arg Tyr Asp  Ala Glu Asn Asn Glu  Pro Gln
    1790                 1795                 1800


<210> SEQ ID NO 82
<211> LENGTH: 1742
<212> TYPE: PRT
<213> ORGANISM: Clostridium difficile

<400> SEQUENCE: 82

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asn Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140
```

Leu Lys Asn Asp Gly Thr Leu Tyr Ser Ala Gly Leu Asn Ser Ser Gly
145 150 155 160

Gln Leu Gly Leu Gly Asp Thr Asn Asn Arg Ala Thr Phe Thr Lys Val
165 170 175

Asn Ile Asp Ser Val Lys Asp Val Val Thr Tyr Asn Gln Ser Val Phe
180 185 190

Ile Ile Lys Met Asp Gly Thr Ala His Ala Cys Gly Leu Asn Ser Asn
195 200 205

Gly Gln Leu Gly Ile Asn Ser Thr Leu Asn Lys Ser Val Phe Asn Lys
210 215 220

Ile Glu Gly Met Asp Asn Val Lys Gln Ile Ala Cys Gly Ser Ser His
225 230 235 240

Thr Ile Leu Ile Lys Asn Asp Gly Thr Met Tyr Thr Thr Gly Tyr Asn
245 250 255

Gly Val Gly Gln Leu Gly Thr Gly Asn Asn Asn Asn Ser Ile Val Phe
260 265 270

Thr Leu Ser Ser Ile Asn Asn Val Lys Tyr Ala Ser Cys Gly Asn Asn
275 280 285

His Thr Met Ile Leu Lys Tyr Asp Asn Thr Leu Phe Ser Thr Gly Gln
290 295 300

Asn Thr Tyr Gly Gln Leu Ala Asn Ala Asn Lys Asp Val Ala Ser Arg
305 310 315 320

Asn Thr Phe Ala Lys Val Asn Val Glu Asn Ile Lys Asp Ile Lys Cys
325 330 335

Gly Ser Gln Phe Asn Phe Leu Ile Asn Gly Ser Lys Glu Ile Phe Val
340 345 350

Ser Gly Cys Asn Leu Ala Gly Gln Leu Gly Ser Phe Phe His Thr Thr
355 360 365

Phe Leu Tyr Glu Phe Ser Lys Val Gln Ser Ser Asn Leu Asp Asn Tyr
370 375 380

Ser Gly Leu Leu Val Asn Asp Asp Tyr Leu Tyr Val Thr Lys Asp Asn
385 390 395 400

Ser Glu Phe Leu Asn Val Lys Leu Ser Asp Asn Phe Gln Asp Tyr Lys
405 410 415

Lys Ile Glu Leu Thr Asp Asn Asn Met Phe Ile Val Met Asn Asp Gly
420 425 430

Thr Leu Tyr Ala Cys Gly Leu Asn Asn Tyr Gly Gln Leu Gly Leu Gly
435 440 445

Asp Thr Val Asn Arg Ser Val Met Thr Lys Val Asp Ile Asp Asn Val
450 455 460

Leu Asp Ile Lys Gly Asn Gly Asn Ser Thr Phe Val Leu Lys Asn Asn
465 470 475 480

Gly Thr Leu Tyr Ser Cys Gly Tyr Asn Ser Ser Gly Ile Leu Gly Leu
485 490 495

Lys Asp Asn Thr Asn Arg Asn Ile Phe Thr Lys Ile Glu Ile Glu Asn
500 505 510

Val Lys Ala Phe Cys Val Glu Ser Asn Tyr Ile Val Val Leu Asn His
515 520 525

Ser Lys Glu Leu Tyr Gly Trp Gly Asn Glu Ser Tyr Ile Val Tyr Gly
530 535 540

Asn Ser Arg Asn Tyr Pro Tyr Lys Asp Thr Arg Val Ser Asn Val Glu
545 550 555 560

Lys Ile Ala Thr Trp Ser Asp Thr Leu Tyr Ile Leu Asp Ser Thr Gly

```
                565                 570                 575

Ala Thr Lys Thr Ile Gly Tyr Ser Tyr Asn Gly Ser Gly Gly Tyr Pro
            580                 585                 590

Ala Pro Ser Ser Ser Ser Thr Tyr Arg Asp Gly Gly Tyr Ile Asn Lys
        595                 600                 605

Asn Thr Ser Tyr Arg Thr Leu Glu Phe Tyr Asn Thr Ser Lys Thr Lys
    610                 615                 620

Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
                645                 650                 655

Asn Ser Thr Thr Asn Glu Asn Asn Ser Leu Arg Phe Ile Asn Asn Ser
            660                 665                 670

Gly Val Tyr Tyr Thr Asn Thr Asp Gly Thr Asp Tyr Thr Cys Tyr Gln
        675                 680                 685

Trp Thr Tyr Lys Leu Ile Arg Cys Ser Ile Phe Asp Ser Pro Gln Asn
    690                 695                 700

Ile Ile Gly Asn Ser Lys Asn Ile Leu Tyr Leu Ser Lys Asn Asn Ser
705                 710                 715                 720

Thr Phe Lys Cys Thr Gly Asn Cys Ile Thr Tyr Gly Ile Asn Ser Gln
                725                 730                 735

Asn Trp Tyr Ser Tyr Phe Ser Asp Ser Ser Asn Gly Ala Ile Ala Leu
            740                 745                 750

Gly Asn Glu Phe Ile Leu Lys Asn Tyr Ser Gly Glu Cys Leu Leu Lys
        755                 760                 765

Gly Tyr Gly Lys Ala Thr Asn Gly Glu Phe Gly Asn Ser Thr Asn Ile
    770                 775                 780

Ser Ser Ile Ser Asn Tyr Asp Thr Gly Leu Lys Asp Ile Lys Asp Ile
785                 790                 795                 800

Ile Val Lys Asn Asn Thr Val Val Val Val Asp Lys Asn Asn Asn Ile
                805                 810                 815

Tyr Val Thr Gly Ala Asn Gln Phe Asn Lys Leu Gly Ile Gly Glu Tyr
            820                 825                 830

Asn Asn Gln Pro Ile Lys Lys Phe Thr Asn Ile Thr Glu Gln Ser Asn
        835                 840                 845

Ser Phe Ile Phe Met Asp Asp Ile Lys Glu Ile Thr Thr Ser Arg Asn
    850                 855                 860

Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
                885                 890                 895

Phe Thr Gln Ile Asn Leu Asp Asn Ile Lys Lys Ile Ser Thr Ser Ile
            900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
    930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asp Asn Thr Leu Tyr
                965                 970                 975

Ser Cys Gly Glu Asn Thr His Gly Gln Leu Gly Leu Gly Ser Glu Ser
            980                 985                 990
```

-continued

```
Asn His Pro Asp Val Leu Thr Phe  Thr Val Asn Asn Ile  Thr Asn Val
        995                  1000                 1005

Arg Asp  Val Tyr Cys Ser Asp  Thr Thr Thr Phe Ile  Val Lys Asp
    1010                 1015                 1020

Thr Asn  Ile Ala Tyr Cys Cys  Gly Tyr Asn Asn Asn  Ser Gln Leu
    1025                 1030                 1035

Gly Met  Gly Asn Thr Thr Asp  Gln Tyr Ser Phe Ile  Lys Cys Met
    1040                 1045                 1050

Glu Asn  Val Lys Glu Val Ile  Pro Asn Glu Ile Asn  Thr Tyr Ile
    1055                 1060                 1065

Ile Thr  Ile Tyr Asn Thr Ala  Tyr Ser Thr Gly Leu  Asn Thr Asp
    1070                 1075                 1080

Tyr Cys  Leu Gly Leu Asn Ser  Asn Ser Asn Gln Ser  Ser Phe Ser
    1085                 1090                 1095

Glu Ile  Pro Ile Ser Asn Val  Val Lys Val Ala Pro  Asn Arg Asn
    1100                 1105                 1110

Asn Ala  Val Leu Leu Leu Thr  Ser Glu Gly Asp Val  Tyr Thr Ala
    1115                 1120                 1125

Gly Lys  Cys Ser Asn Gly Ser  Gly Thr Gly Ser Glu  Thr Pro Glu
    1130                 1135                 1140

Lys Ile  Lys Lys Ile Ala Ser  Lys Ala Lys Asp Ile  Gly Met Asn
    1145                 1150                 1155

Tyr Arg  Cys Gly His Tyr Val  Ser Asp Asn Gly Asp  Leu Tyr Gly
    1160                 1165                 1170

Thr Gly  Phe Asn Asp Cys Gly  Gln Leu Gly Val Gly  Asp Val Thr
    1175                 1180                 1185

Lys Arg  Asp Thr Phe Ile Lys  Thr Asn Thr Arg Val  Lys Lys Ile
    1190                 1195                 1200

Leu Pro  Leu Glu Tyr Ala Asn  Ile Ala Ile Lys Asp  Thr Asn Asp
    1205                 1210                 1215

Ile Tyr  Ile Cys Gly Leu Asn  Asn Tyr Gly Gln Leu  Gly Val Gly
    1220                 1225                 1230

Asn Arg  Tyr Asp Ser Arg Asn  Asn Asp Asn Arg Ile  Phe Asn Tyr
    1235                 1240                 1245

Lys His  Met Asn Phe Val Met  Gly Asp Leu Thr Ser  Ile Lys Asn
    1250                 1255                 1260

Arg His  Asn Phe Ile Leu Leu  Asn Asn Lys Ile Val  Ile Pro Thr
    1265                 1270                 1275

Thr Lys  Asp Ile Asp Tyr Gly  Leu Val Leu Gly Asn  Leu Tyr Lys
    1280                 1285                 1290

Gly Asp  Leu Tyr Thr Glu Leu  Pro Tyr Glu Asp Ile  Lys Glu Val
    1295                 1300                 1305

Ser Ile  Ser Lys Thr His Ile  Ile Ile Leu Leu Asn  Asp Gly Thr
    1310                 1315                 1320

Met Tyr  Gly Cys Gly Thr Asn  Tyr His Gly Glu Leu  Leu Gln Asp
    1325                 1330                 1335

Leu Ser  Ile Asn Gln Val Asp  Glu Phe Val Gln Ile  Asn Val Ser
    1340                 1345                 1350

Asp Val  Lys His Val Ser Cys  Gly Asp Asn Phe Thr  Tyr Phe Ile
    1355                 1360                 1365

Lys Ser  Asp Asp Ser Leu Trp  Ser Ile Gly Lys Asn  Ser Glu Tyr
    1370                 1375                 1380

Gln Leu  Gly Ile Gly His Asn  Asn Pro Val Thr Glu  Leu Gln Arg
    1385                 1390                 1395
```

```
Ile Thr Thr Ile Ser Ser Cys Lys Glu Val His Cys Gly Lys Asn
    1400                1405                1410

Tyr Thr Leu Val Val Thr Thr Gly Asn Glu Leu Phe Val Gln Gly
    1415                1420                1425

Tyr Asn Asp Lys Gly Ala Leu Gly Leu Gly Ser Asp Ser Glu Asn
    1430                1435                1440

Thr Ile Ile Lys Phe Phe Thr Lys Ala Leu Thr Asp Ile Arg Glu
    1445                1450                1455

Ile Lys Ser Tyr Gly Ser Asp His Ile Leu Val Leu Lys Asn Asp
    1460                1465                1470

Asn Ser Val Trp Val Thr Gly Lys Asn Arg Asp Val Tyr Lys Ile
    1475                1480                1485

Glu Gln Pro Val Glu Phe Leu Lys Glu Phe Thr Ile Ile Pro Ile
    1490                1495                1500

Ser Glu Asp Val Asn Thr Val Lys Asp Val Leu Ala Thr Asp Asn
    1505                1510                1515

Thr Leu Tyr Ile Ile Ser Glu Val Gly Thr Thr Asn Ala Ala Ile
    1520                1525                1530

Glu Ile Thr Glu Lys Ser Ile Ser Ser Ile Lys Ile Lys Ile Gln
    1535                1540                1545

Asp Pro Asn Lys Asp Ile Ser Arg Ile Glu Met Leu Ile Asn Gly
    1550                1555                1560

Glu Ser Val Lys Ser Val Ser Asp Leu Ile Thr Glu Lys Ile Ser
    1565                1570                1575

Phe Glu Val Pro Pro Asp Lys Ile Lys Ile Gly Glu Asn Lys Ile
    1580                1585                1590

Leu Phe Arg Ala Tyr Cys Lys Gly Asp Asp Leu Tyr Ala Ser Leu
    1595                1600                1605

Phe Ile Phe Lys Glu Ser Thr Gly Asn Ser Ile Ile Lys Asp Ser
    1610                1615                1620

Tyr Val Met Ile Gly Asn Arg Met Tyr Lys Val Val Asn Thr Thr
    1625                1630                1635

Ser Asn Glu Gln Asp Ile Thr Ile Thr Leu Asp Arg Gly Leu Glu
    1640                1645                1650

Glu Asp Leu Asn Leu Gly Asp Pro Ile Tyr Gln Leu Ile Asn Lys
    1655                1660                1665

Thr Lys Val Gln Val Lys Ile Asn Lys Ser Asp Leu Phe Lys Asp
    1670                1675                1680

Met Lys Leu Val Glu Ile Lys Lys Ser Asp Ser Ser Tyr Gln Glu
    1685                1690                1695

Ile Tyr Glu Leu Glu Glu Ala Asn Ile Lys Ser Ala Gln Pro Lys
    1700                1705                1710

Ile Ile Val Glu Lys Gly Asp Lys Trp Thr Ala Ile Lys Arg Pro
    1715                1720                1725

Ser Met Ile Phe Arg Tyr Asp Ala Glu Asn Asn Glu Pro Gln
    1730                1735                1740
```

<210> SEQ ID NO 83
<211> LENGTH: 1724
<212> TYPE: PRT
<213> ORGANISM: Clostridium difficile

<400> SEQUENCE: 83

```
Met Lys Gln Asn Lys Leu Leu Gln Arg Gly Ala Tyr Phe Asn Asp Lys
1               5                   10                  15
```

```
Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Asn Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
```

-continued

```
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Asn Pro Tyr Asn Asn Ile Glu
    530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
                565                 570                 575

Leu Tyr Val Ser Gly Tyr Asn Tyr Asn Tyr Gln Leu Gly Lys Gly Asn
            580                 585                 590

Asn Ser Asn Gln Ser Lys Ala Leu Val Ser Gln Cys Arg Thr Asn Ser
        595                 600                 605

Thr Ser Ser Thr Ser Asn Gly Leu Arg Thr Leu Pro Lys Ile Thr Asn
    610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
                645                 650                 655

Pro Ser Ile Ser Asp Tyr Ser Arg Tyr Gly Thr Phe Ile Glu Ala Thr
            660                 665                 670

Asn Ser Asn His Asn Thr Tyr Phe Ile Gln Glu Thr Asp Phe Ser Gly
        675                 680                 685

Ile Glu Lys Val Ile Gly Met Ser Asn Asn Ile Leu Phe Phe Lys Lys
    690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
                725                 730                 735

Gly Ser Asn Phe Ile Ile Tyr His Ser Asn Ser Lys Leu Tyr Gly Lys
            740                 745                 750

Gly Ile Ala Asn Ser Gly Gln Phe Gly Asn Ser Thr Asn Ile Asp Gly
        755                 760                 765

Thr Ser Asn Tyr Asp Thr Gly Leu Lys Asp Ile Lys Asp Ile Ile Val
    770                 775                 780

Lys Gly Asn Thr Val Val Val Val Asp Lys Asn Asn Asn Ile Tyr Val
785                 790                 795                 800

Thr Gly Met Asn Gln Asn Asn Lys Leu Gly Ile Gly Glu Tyr Asn Asn
                805                 810                 815

Glu Pro Val Lys Lys Phe Thr Asn Ile Thr Glu Gln Ser Asn Ser Phe
            820                 825                 830

Ile Phe Met Asp Asp Ile Lys Glu Ile Thr Thr Ser Arg Asn Thr Met
        835                 840                 845

Phe Ile Val Lys Asn Asp Gly Thr Ala Tyr Ala Thr Gly Asn Asn Ser
    850                 855                 860
```

-continued

```
Ser Gly Gln Leu Gly Leu Gly Asp Thr Ile Asn Arg Asn Lys Phe Thr
865                 870                 875                 880

Gln Ile Asn Leu Asp Asn Ile Lys Lys Ile Ser Thr Ser Ile Asp Gly
                885                 890                 895

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
        915                 920                 925

Thr Phe Thr Lys Val Asn Ile Gln Asn Val Arg Asp Val Val Leu Gly
    930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
                965                 970                 975

Pro Asp Val Leu Thr Phe Thr Val Asn Asn Ile Thr Asn Val Arg Asp
            980                 985                 990

Val Tyr Cys Ser Asp Thr Thr Thr  Phe Ile Val Lys Asp  Thr Asn Ile
        995                 1000                1005

Ala Tyr  Cys Cys Gly Tyr Asn  Asn Asn Ser Gln Leu  Gly Met Gly
    1010                 1015                 1020

Asn Thr  Thr Asp Gln Tyr Ser  Phe Ile Lys Cys Met  Glu Asn Val
    1025                 1030                 1035

Lys Glu  Val Ile Pro Asn Glu  Ile Asn Thr Tyr Ile  Ile Thr Ile
    1040                 1045                 1050

Tyr Asn  Thr Ala Tyr Ser Thr  Gly Leu Asn Thr Asp  Tyr Cys Leu
    1055                 1060                 1065

Gly Leu  Asn Ser Asn Ser Asn  Gln Ser Ser Phe Ser  Glu Ile Pro
    1070                 1075                 1080

Ile Ser  Asn Val Val Lys Val  Ala Pro Asn Arg Asn  Asn Ala Val
    1085                 1090                 1095

Leu Leu  Leu Thr Ser Glu Gly  Asp Val Tyr Thr Ala  Gly Lys Cys
    1100                 1105                 1110

Ser Asn  Gly Ser Gly Thr Gly  Ser Glu Thr Pro Glu  Lys Ile Lys
    1115                 1120                 1125

Lys Ile  Ala Ser Lys Ala Lys  Asp Ile Gly Met Asn  Tyr Arg Cys
    1130                 1135                 1140

Gly His  Tyr Val Ser Asp Asn  Gly Asp Leu Tyr Gly  Thr Gly Phe
    1145                 1150                 1155

Asn Asn  Asn Gly Gln Leu Gly  Val Gly Asp Val Thr  Lys Arg Asp
    1160                 1165                 1170

Thr Phe  Ile Lys Thr Asn Thr  Arg Val Lys Lys Ile  Leu Pro Leu
    1175                 1180                 1185

Glu Tyr  Ala Asn Ile Ala Ile  Lys Asp Thr Asn Asp  Ile Tyr Ile
    1190                 1195                 1200

Cys Gly  Leu Asn Asn Tyr Gly  Gln Leu Gly Val Gly  Asn Arg Tyr
    1205                 1210                 1215

Asp Ser  Arg Asn Asn Asp Asn  Arg Ile Phe Asn Tyr  Lys His Met
    1220                 1225                 1230

Asn Phe  Val Met Gly Asp Leu  Thr Ser Ile Lys Asn  Arg His Asn
    1235                 1240                 1245

Phe Ile  Leu Leu Asn Asn Lys  Ile Val Ile Pro Thr  Thr Lys Asp
    1250                 1255                 1260

Ile Asp  Tyr Gly Leu Val Leu  Gly Asn Leu Tyr Lys  Gly Asp Leu
    1265                 1270                 1275
```

Tyr Thr Glu Leu Pro Tyr Glu Asp Ile Lys Glu Val Ser Ile Ser
    1280                1285                1290

Lys Thr His Ile Ile Ile Leu Leu Asn Asp Gly Thr Met Tyr Gly
    1295                1300                1305

Cys Gly Thr Asn Tyr His Gly Glu Leu Leu Gln Asp Leu Ser Ile
    1310                1315                1320

Asn Gln Val Asp Glu Phe Val Gln Ile Asn Val Ser Asp Val Lys
    1325                1330                1335

His Val Ser Cys Gly Asp Asn Phe Thr Tyr Phe Ile Lys Ser Asp
    1340                1345                1350

Asp Ser Leu Trp Ser Ile Gly Lys Asn Ser Glu Tyr Gln Leu Gly
    1355                1360                1365

Ile Gly His Asn Asn Pro Val Thr Glu Leu Gln Arg Ile Thr Thr
    1370                1375                1380

Ile Ser Ser Cys Lys Glu Val His Cys Gly Lys Asn Tyr Thr Leu
    1385                1390                1395

Val Val Thr Thr Gly Asn Glu Leu Phe Val Gln Gly Tyr Asn Asp
    1400                1405                1410

Lys Gly Ala Leu Gly Leu Gly Ser Asp Ser Glu Asn Thr Ile Ile
    1415                1420                1425

Lys Phe Phe Thr Lys Ala Leu Thr Asp Ile Arg Glu Ile Lys Ser
    1430                1435                1440

Tyr Gly Ser Asp His Ile Leu Val Leu Lys Asn Asp Asn Ser Val
    1445                1450                1455

Trp Val Thr Gly Lys Asn Arg Asp Val Tyr Lys Ile Glu Gln Pro
    1460                1465                1470

Val Glu Phe Leu Lys Glu Phe Thr Ile Val Pro Ile Ser Glu Asp
    1475                1480                1485

Val Asn Thr Val Lys Asp Val Leu Ala Thr Asp Asn Thr Leu Tyr
    1490                1495                1500

Ile Ile Ser Glu Val Gly Thr Thr Asn Ala Ala Ile Glu Ile Thr
    1505                1510                1515

Glu Lys Ser Ile Ser Ser Ile Lys Ile Lys Ile Gln Asp Pro Asn
    1520                1525                1530

Lys Asp Ile Ser Arg Ile Glu Met Leu Ile Asn Gly Glu Ser Val
    1535                1540                1545

Lys Ser Val Ser Asp Leu Thr Thr Glu Lys Ile Ser Phe Glu Val
    1550                1555                1560

Pro Pro Asp Lys Ile Lys Ile Gly Glu Asn Lys Ile Leu Phe Arg
    1565                1570                1575

Ala Tyr Cys Lys Gly Asp Asp Leu Tyr Ala Ser Leu Phe Ile Phe
    1580                1585                1590

Lys Glu Ser Thr Gly Asn Ser Ile Ile Lys Asp Ser Tyr Val Met
    1595                1600                1605

Ile Gly Asn Arg Met Tyr Lys Val Val Asn Thr Thr Ser Asn Glu
    1610                1615                1620

Gln Asp Ile Thr Ile Thr Leu Asp Arg Gly Leu Glu Glu Asp Leu
    1625                1630                1635

Asn Leu Gly Asp Pro Ile Tyr Gln Leu Ile Asn Lys Thr Lys Val
    1640                1645                1650

Gln Val Lys Ile Asn Lys Ser Asp Leu Phe Lys Asp Met Lys Leu
    1655                1660                1665

Val Glu Ile Lys Lys Ser Asp Ser Ser Tyr Gln Glu Ile Tyr Glu

```
    1670                1675                1680

Leu Glu  Glu Ala Asn Ile Lys  Ser Ala Gln Pro Lys  Ile Ile Val
    1685                1690                1695

Glu Lys  Gly Asp Lys Trp Thr  Ala Ile Lys Arg Pro  Ser Met Ile
    1700                1705                1710

Phe Arg  Tyr Asp Ala Glu Asn  Asn Glu Pro Gln
    1715                1720
```

<210> SEQ ID NO 84
<211> LENGTH: 1724
<212> TYPE: PRT
<213> ORGANISM: Clostridium difficile

<400> SEQUENCE: 84

```
Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
```

```
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Asn Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
        435                 440                 445

Asp Thr Val Asn Arg Ser Val Met Thr Lys Val Asp Ile Asp Asn Val
    450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Asn Pro Tyr Asn Asn Ile Glu
    530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
                565                 570                 575

Leu Tyr Val Ser Gly Tyr Asn Tyr Asn Tyr Gln Leu Gly Lys Gly Asn
            580                 585                 590

Asn Ser Asn Gln Ser Lys Ala Leu Val Ser Gln Cys Arg Thr Asn Ser
        595                 600                 605

Thr Ser Ser Thr Ser Asn Gly Leu Arg Thr Leu Pro Lys Ile Thr Asn
    610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
                645                 650                 655

Pro Ser Ile Ser Asp Tyr Ser Arg Tyr Gly Thr Phe Ile Glu Ala Thr
            660                 665                 670

Asn Ser Asn His Asn Thr Tyr Phe Ile Gln Glu Thr Asp Phe Ser Gly
        675                 680                 685

Ile Glu Lys Val Ile Gly Met Ser Asn Asn Ile Leu Phe Phe Lys Lys
    690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
                725                 730                 735

Gly Ser Asn Phe Ile Ile Tyr His Ser Asn Ser Lys Leu Tyr Gly Lys
            740                 745                 750
```

```
Gly Ile Ala Asn Ser Gly Gln Phe Gly Asn Ser Thr Asn Ile Asp Gly
        755                 760                 765

Thr Ser Asn Tyr Asp Thr Gly Leu Lys Asp Ile Lys Asp Ile Ile Val
    770                 775                 780

Lys Gly Asn Thr Val Val Val Val Asp Lys Asn Asn Asn Ile Tyr Val
785                 790                 795                 800

Thr Gly Met Asn Gln Asn Asn Lys Leu Gly Ile Gly Glu Tyr Asn Asn
                805                 810                 815

Glu Pro Val Lys Lys Phe Thr Asn Ile Thr Glu Gln Ser Asn Ser Phe
            820                 825                 830

Ile Phe Met Asp Asp Ile Lys Glu Ile Thr Thr Ser Arg Asn Thr Met
        835                 840                 845

Phe Ile Val Lys Asn Asp Gly Thr Ala Tyr Ala Thr Gly Asn Asn Ser
    850                 855                 860

Ser Gly Gln Leu Gly Leu Gly Asp Thr Ile Asn Arg Asn Lys Phe Thr
865                 870                 875                 880

Gln Ile Asn Leu Asp Asn Ile Lys Lys Ile Ser Thr Ser Ile Asp Gly
                885                 890                 895

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
        915                 920                 925

Thr Phe Thr Lys Val Asn Ile Gln Asn Val Arg Asp Val Val Leu Gly
    930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
                965                 970                 975

Pro Asp Val Leu Thr Phe Thr Val Asn Asn Ile Thr Asn Val Arg Asp
            980                 985                 990

Val Tyr Cys Ser Asp Thr Thr Thr  Phe Ile Val Lys Asp  Thr Asn Ile
        995                 1000                 1005

Ala Tyr  Cys Cys Gly Tyr Asn  Asn Asn Ser Gln Leu  Gly Met Gly
    1010                 1015                 1020

Asn Thr  Thr Asp Gln Tyr Ser  Phe Ile Lys Cys Met  Glu Asn Val
    1025                 1030                 1035

Lys Glu  Val Ile Pro Asn Glu  Ile Asn Thr Tyr Ile  Ile Thr Ile
    1040                 1045                 1050

Tyr Asn  Thr Ala Tyr Ser Thr  Gly Leu Asn Thr Asp  Tyr Cys Leu
    1055                 1060                 1065

Gly Leu  Asn Ser Asn Ser Asn  Gln Ser Ser Phe Ser  Glu Ile Pro
    1070                 1075                 1080

Ile Ser  Asn Val Val Lys Val  Ala Pro Asn Arg Asn  Asn Ala Val
    1085                 1090                 1095

Leu Leu  Leu Thr Ser Glu Gly  Asp Val Tyr Thr Ala  Gly Lys Cys
    1100                 1105                 1110

Ser Asn  Gly Ser Gly Thr Gly  Ser Glu Thr Pro Glu  Lys Ile Lys
    1115                 1120                 1125

Lys Ile  Ala Ser Lys Ala Lys  Asp Ile Gly Met Asn  Tyr Arg Cys
    1130                 1135                 1140

Gly His  Tyr Val Ser Asp Asn  Gly Asp Leu Tyr Gly  Thr Gly Phe
    1145                 1150                 1155

Asn Asn  Asn Gly Gln Leu Gly  Val Gly Asp Val Thr  Lys Arg Asp
    1160                 1165                 1170
```

-continued

```
Thr Phe  Ile Lys Thr Asn Thr  Arg Val Lys Lys Ile  Leu Pro Leu
    1175                 1180                 1185

Glu Tyr  Ala Asn Ile Ala Ile  Lys Asp Thr Asn Asp  Ile Tyr Ile
    1190                 1195                 1200

Cys Gly  Leu Asn Asn Tyr Gly  Gln Leu Gly Val Gly  Asn Arg Tyr
    1205                 1210                 1215

Asp Ser  Arg Asn Asn Asp Asn  Arg Ile Phe Asn Tyr  Lys His Met
    1220                 1225                 1230

Asn Phe  Val Met Gly Asp Leu  Thr Ser Ile Lys Asn  Arg His Asn
    1235                 1240                 1245

Phe Ile  Leu Leu Asn Asn Lys  Ile Val Ile Pro Thr  Thr Lys Asp
    1250                 1255                 1260

Ile Asp  Tyr Gly Leu Val Leu  Gly Asn Leu Tyr Lys  Gly Asp Leu
    1265                 1270                 1275

Tyr Thr  Glu Leu Pro Tyr Glu  Asp Ile Lys Glu Val  Ser Ile Ser
    1280                 1285                 1290

Lys Thr  His Ile Ile Ile Leu  Leu Asn Asp Gly Thr  Met Tyr Gly
    1295                 1300                 1305

Cys Gly  Thr Asn Tyr His Gly  Glu Leu Leu Gln Asp  Leu Ser Ile
    1310                 1315                 1320

Asn Gln  Val Asp Glu Phe Val  Gln Ile Asn Val Ser  Asp Val Lys
    1325                 1330                 1335

His Val  Ser Cys Gly Asp Asn  Phe Thr Tyr Phe Ile  Lys Ser Asp
    1340                 1345                 1350

Asp Ser  Leu Trp Ser Ile Gly  Lys Asn Ser Glu Tyr  Gln Leu Gly
    1355                 1360                 1365

Ile Gly  His Asn Asn Pro Val  Thr Glu Leu Gln Arg  Ile Thr Thr
    1370                 1375                 1380

Ile Ser  Ser Cys Lys Glu Val  His Cys Gly Lys Asn  Tyr Thr Leu
    1385                 1390                 1395

Val Val  Thr Thr Gly Asn Glu  Leu Phe Val Gln Gly  Tyr Asn Asp
    1400                 1405                 1410

Lys Gly  Ala Leu Gly Leu Gly  Ser Asp Ser Glu Asn  Thr Ile Ile
    1415                 1420                 1425

Lys Phe  Phe Thr Lys Ala Leu  Thr Asp Ile Arg Glu  Ile Lys Ser
    1430                 1435                 1440

Tyr Gly  Ser Asp His Ile Leu  Val Leu Lys Asn Asp  Asn Ser Val
    1445                 1450                 1455

Trp Val  Thr Gly Lys Asn Arg  Asp Val Tyr Lys Ile  Glu Gln Pro
    1460                 1465                 1470

Val Glu  Phe Leu Lys Glu Phe  Thr Ile Val Pro Ile  Ser Glu Asp
    1475                 1480                 1485

Val Asn  Thr Val Lys Asp Val  Leu Ala Thr Asp Asn  Thr Leu Tyr
    1490                 1495                 1500

Ile Ile  Ser Glu Val Gly Thr  Thr Asn Ala Ala Ile  Glu Ile Thr
    1505                 1510                 1515

Glu Lys  Ser Ile Ser Ser Ile  Lys Ile Lys Ile Gln  Asp Pro Asn
    1520                 1525                 1530

Lys Asp  Ile Ser Arg Ile Glu  Met Leu Ile Asn Gly  Glu Ser Val
    1535                 1540                 1545

Lys Ser  Val Ser Asp Leu Thr  Thr Glu Lys Ile Ser  Phe Glu Val
    1550                 1555                 1560

Pro Pro  Asp Lys Ile Lys Ile  Gly Glu Asn Lys Ile  Leu Phe Arg
```

```
    1565                1570                1575

Ala Tyr  Cys Lys Gly Asp Asp  Leu Tyr Ala Ser Leu  Phe Ile Phe
    1580                1585                1590

Lys Glu  Ser Thr Gly Asn Ser  Ile Ile Lys Asp Ser  Tyr Val Met
    1595                1600                1605

Ile Gly  Asn Arg Met Tyr Lys  Val Val Asn Thr Thr  Ser Asn Glu
    1610                1615                1620

Gln Asp  Ile Thr Ile Thr Leu  Asp Arg Gly Leu Glu  Glu Asp Leu
    1625                1630                1635

Asn Leu  Gly Asp Pro Ile Tyr  Gln Leu Ile Asn Lys  Thr Lys Val
    1640                1645                1650

Gln Val  Lys Ile Asn Lys Ser  Asp Leu Phe Lys Asp  Met Lys Leu
    1655                1660                1665

Val Glu  Ile Lys Lys Ser Asp  Ser Ser Tyr Gln Glu  Ile Tyr Glu
    1670                1675                1680

Leu Glu  Glu Ala Asn Ile Lys  Ser Ala Gln Pro Lys  Ile Ile Val
    1685                1690                1695

Glu Lys  Gly Asp Lys Trp Thr  Ala Ile Lys Arg Pro  Ser Met Ile
    1700                1705                1710

Phe Arg  Tyr Asp Ala Glu Asn  Asn Glu Pro Gln
    1715                1720


<210> SEQ ID NO 85
<211> LENGTH: 1772
<212> TYPE: PRT
<213> ORGANISM: Clostridium difficile

<400> SEQUENCE: 85

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
            20                  25                  30

Ile Asn Phe Phe Thr Gly Cys Cys Asn Tyr Thr Phe Gly Leu Lys Asn
        35                  40                  45

Asn Asn Ile Leu Tyr Gly Cys Gly Asp Asn Ser Asn Phe Gln Leu Gly
    50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205

Cys Tyr Ser Thr Gly Phe Asn Asn Gln Gly Gln Leu Gly Leu Gly Asp
```

-continued

```
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
            260                 265                 270

Ser Ser Leu Phe Thr Lys Ile Glu Glu Val Asn Ile Lys Thr Ile Ala
        275                 280                 285

Cys Gly His Gly Asn Thr Met Leu Ile Asp Asn Lys Gly Thr Leu Lys
    290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
            340                 345                 350

Asp Ser Tyr Cys Thr Gly Asp Asn Thr Tyr Gly Gln Leu Gly Ser Phe
        355                 360                 365

Phe Asp Asp Met His Ile Val Glu Phe Lys Lys Met Asp Ser Glu Lys
    370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480

Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Ser Tyr Val Asn Gly Leu Ser Asn Ala
545                 550                 555                 560

Leu Ile Ser Gln Tyr Thr Glu Ile Ser Leu Ser Asn Val Thr Asp Ala
                565                 570                 575

Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
625                 630                 635                 640
```

-continued

Thr Lys Ile Asn Asn Ile Ile Ile Tyr Glu Tyr Val Thr Val Phe Cys
645 650 655

Thr Asn Ile Gly Ser Phe Leu Thr Gly Tyr His Gly Thr Ser Trp Thr
660 665 670

Lys Pro Thr Asp Ser Ser Tyr Arg Val Gln Tyr Gln Gly Ile Ser Tyr
675 680 685

Ala Gly Tyr Leu Asp Ser Tyr Ile Tyr Asn Tyr Tyr Pro Thr Arg Cys
690 695 700

Thr Gln Ser Ser Ser Ser Thr Thr Phe Ala Tyr Leu Tyr Asn Gly Glu
705 710 715 720

Ser Ser Ser Asn Leu Lys Asn Val Asn Pro Asp Asn Leu Leu Ile Ser
725 730 735

Gly Gly Ser Ser Tyr Ile His Gln Tyr Gly Arg Asn Tyr Leu Asn Asn
740 745 750

Gln Ser Ser Asn Asn Ile Ala Ala Ser Asn Ile Asn Ser Gly Pro Ile
755 760 765

Thr Ser Asp Lys Ala Ile Phe Leu Tyr Lys Ala Leu Leu Tyr Leu Ser
770 775 780

Ser Asn Thr Leu Tyr Gly Phe Gly Asn Ile Ser Glu Ser Ala Lys Glu
785 790 795 800

Leu Asp Val Ser Asp Thr Gln Asp Gly Tyr Asn Ala Thr Asn Tyr Lys
805 810 815

Lys Val Met Lys Asn Ile Lys Asn Ile Phe Ile Pro Pro Tyr Asp Leu
820 825 830

Ser Arg Asp Lys Thr Arg Phe Ala Ile Leu Thr Asp Lys Ser Leu Phe
835 840 845

Ile Cys Gly Tyr Asn Ser Lys Gly Thr His Gly Ile Ser Val Asn Ser
850 855 860

Ser Leu Asn Leu Asn Asn Lys Ile Asn Tyr Asn Lys Lys Asn Ser Ser
865 870 875 880

Ser Glu Ile Ser Ser Asn Ile Gln Glu Ile Tyr Ser His Ser Lys Ser
885 890 895

Thr Tyr Leu Leu Thr Asn Asn Asn Met Leu Tyr Ser Val Gly Leu Asn
900 905 910

Asp Val Gly Gln Leu Gly Val Gly Asp Glu Ile Asn Arg Lys Val Phe
915 920 925

Thr Lys Ile Asn Ile Asp Asn Ile Lys Ser Ile Asn Val Asn Arg Phe
930 935 940

Thr Asp Asn Ser Lys His Ala Phe Ala Ile Lys Asn Asp Asn Thr Cys
945 950 955 960

Tyr Ala Val Gly Leu Asn Asn Ser Gly Gln Leu Gly Ile Gly Asp Asn
965 970 975

Val Asn Arg Asn Ile Phe Thr Lys Ile Asn Val Glu Asn Val Lys Tyr
980 985 990

Val Ala Val Tyr Gly Asn Thr Ser Leu Leu Leu Thr Asn Asp Gly Leu
995 1000 1005

Leu Tyr Gly Ala Gly Asn Asn Gly Lys Gly Gln Leu Gly Leu Gly
1010 1015 1020

Asp Thr Thr Ser Arg Asn Ile Phe Thr Arg Ile Pro Ile Asn Gly
1025 1030 1035

Val Arg Asp Val Tyr Leu Cys Asn Asp Val Ser Ile Ile Val Lys
1040 1045 1050

Asn Asp Asn Thr Cys Tyr Val Cys Gly Leu Val Asn Gly Tyr Phe
1055 1060 1065

-continued

Gly Phe Thr Glu Gly Ser Ile Ser Thr Phe Thr Lys Ile Asn Ile
1070 1075 1080

Glu Asn Val Lys Ser Val Val Thr Ala Gly Ser Glu Ala Thr Phe
1085 1090 1095

Phe Ile Thr Asn Asp Asn Met Ile Tyr Thr Thr Gly Lys Lys Glu
1100 1105 1110

Arg Val Phe Phe Ser Thr Glu Thr Asn Asp Ile Lys Gly Ile Arg
1115 1120 1125

Val Ile Asn Asn Ile Ile Asn Ala Lys Lys Ile Val Val Asn Gly
1130 1135 1140

Tyr Thr Ser Ala Ile Leu Thr Asn Asp Asn Lys Leu Phe Val Gly
1145 1150 1155

Gly Leu Ser Gly Tyr Gly Ser Ile Ala Asn Asn Asn Asn Thr Asn
1160 1165 1170

Ser Val Glu Asp Val Lys Asp Val Phe Val Thr Ala Asn Asn Thr
1175 1180 1185

Leu Tyr Ile Asp Asn Asn Asn Asn Leu Ile Ser Ser Gly Arg Asp
1190 1195 1200

Thr Tyr Gly Ile Ser Asp Glu Ser Tyr Arg Asp Met Ser Val Pro
1205 1210 1215

Tyr Tyr Lys Val Ser Ile Lys Lys Asp Val Asp Thr Val Phe Ser
1220 1225 1230

Ser Tyr Asn Thr Ile Phe Ile Lys Asp Ile Tyr Gly Lys Phe Tyr
1235 1240 1245

Ser Ser Thr Arg Asp Asn Arg Tyr Asn His Leu Gly Ile His His
1250 1255 1260

Arg Tyr Asp Asn Asp Lys Asn Glu Ala Leu Glu Gly Ser Leu His
1265 1270 1275

Ser Tyr Phe Lys Thr Asp Asn Thr Ser Asp Lys Ile Val Phe Asn
1280 1285 1290

Lys Lys Asn Glu Lys Leu Val Met Phe Asn Asp Lys Tyr Ile Lys
1295 1300 1305

Thr Asn Asn Lys Tyr Ile Asn Tyr Lys Asn Ile Phe Lys Asp Asn
1310 1315 1320

Phe Lys Tyr Thr Ser Ile Ile Leu Pro Phe Glu Val Ser Asp Ile
1325 1330 1335

Asp Ile Ser Lys Thr His Ser Leu Ala Val Ala Lys Asp Gly Lys
1340 1345 1350

Leu Tyr Gly Ile Gly Ser Asn Ser Tyr Lys Glu Ile Asn Gln Thr
1355 1360 1365

Leu Glu Asp Ile Glu Leu Leu Thr Leu Thr Glu Val Asn Ile Ser
1370 1375 1380

Asp Val Lys Lys Val Ala Cys Gly Asp Asn Tyr Ser Tyr Ile Ile
1385 1390 1395

Lys Thr Asp Asn Thr Leu Trp Ser Tyr Gly Lys Asn Thr Glu Tyr
1400 1405 1410

Gln Leu Gly Val Gly His Asn Asn Asp Val Arg Glu Leu Gln Lys
1415 1420 1425

Val Thr Gly Leu Pro Ser Val Lys Asp Ile Ser Ile Tyr Asn Ser
1430 1435 1440

Met Thr Leu Val Leu Thr Asn Glu Gly Glu Leu Tyr Ala Gln Gly
1445 1450 1455

Tyr Asn Thr Asn Gly Leu Phe Gly Leu Gly Glu Ser Glu Lys Asp

```
    1460                1465                1470

Lys Ile  Ile Arg Thr Phe Thr  Lys Val Leu Thr Asn  Val Lys Glu
    1475                1480                1485

Ile Lys  Ser His Asn Asp Asp  His Ile Leu Val Ile  Lys Asn Asp
    1490                1495                1500

Asn Ser  Leu Trp Ile Thr Gly  Lys Asn Lys Ser Met  Tyr Lys Ile
    1505                1510                1515

Ser Ile  Ser Ile Thr Asp Leu  Tyr Glu Phe Thr Lys  Ile Pro Ile
    1520                1525                1530

Pro Glu  His Leu Asn Asp Ile  Leu Asp Ile Glu Leu  Ser Asp Asp
    1535                1540                1545

Thr Ile  Tyr Met Ile Thr Lys  Val Asp Thr Ser Lys  Ala Ser Ile
    1550                1555                1560

Glu Ile  Val Glu Lys Ser Ile  Ser Gln Val Arg Val  Val Val Gln
    1565                1570                1575

Asp Pro  Asn Asn Val Ile Glu  Lys Leu Glu Met Phe  Ile Asn Asp
    1580                1585                1590

Glu Leu  Ile Ser Thr Lys Thr  Asn Leu Glu Ile Asn  Ser Ile Ile
    1595                1600                1605

Phe Glu  Ile Pro Gln Asn Lys  Ile Val Leu Gly Glu  Asn Lys Ile
    1610                1615                1620

Leu Ile  Lys Ala Ser Ser Pro  Thr Gly Asp Leu Tyr  Ser Ser Met
    1625                1630                1635

Phe Ile  Phe Lys Ser Glu Thr  Gly Leu Lys Val Lys  Lys Asp Ser
    1640                1645                1650

Ile Leu  Met Ile Asn Asn Lys  Val Tyr Ser Ile Ile  Asn Ile Thr
    1655                1660                1665

Glu Asn  Asn Thr Asp Leu Ile  Val Thr Leu Asn Glu  Gly Leu Lys
    1670                1675                1680

Asp Asp  Met Met Glu Asn Asn  Pro Ile Tyr Gln Leu  Ile Asn Lys
    1685                1690                1695

Thr Lys  Val Gln Val Lys Ile  Asn Lys Ser Asp Leu  Phe Lys Asp
    1700                1705                1710

Met Lys  Leu Val Glu Ile Lys  Lys Ser Asp Ser Ser  Tyr Gln Glu
    1715                1720                1725

Ile Tyr  Glu Leu Glu Glu Ala  Asn Ile Lys Ser Ala  Gln Pro Lys
    1730                1735                1740

Ile Ile  Val Glu Lys Gly Asp  Lys Trp Thr Ala Ile  Lys Arg Pro
    1745                1750                1755

Ser Met  Ile Phe Arg Tyr Asp  Ala Glu Asn Asn Glu  Pro Gln
    1760                1765                1770


<210> SEQ ID NO 86
<211> LENGTH: 1772
<212> TYPE: PRT
<213> ORGANISM: Clostridium difficile

<400> SEQUENCE: 86

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
            20                  25                  30

Ile Asn Phe Phe Thr Gly Cys Cys Asn Tyr Thr Phe Gly Leu Lys Asn
        35                  40                  45

Asn Asn Ile Leu Tyr Gly Cys Gly Asp Asn Ser Asn Phe Gln Leu Gly
```

-continued

```
    50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205

Cys Tyr Ser Thr Gly Phe Asn Asn Gln Gly Gln Leu Gly Leu Gly Asp
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
            260                 265                 270

Ser Ser Leu Phe Thr Lys Ile Glu Glu Val Asn Ile Lys Thr Ile Ala
        275                 280                 285

Cys Gly His Gly Asn Thr Met Leu Ile Asp Asn Lys Gly Thr Leu Lys
    290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
            340                 345                 350

Asp Ser Tyr Cys Thr Gly Asp Asn Thr Tyr Gly Gln Leu Gly Ser Phe
        355                 360                 365

Phe Asp Asp Met His Ile Val Glu Phe Lys Lys Met Asp Ser Glu Lys
    370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480
```

-continued

```
Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Ser Tyr Val Asn Gly Leu Ser Asn Ala
545                 550                 555                 560

Leu Ile Ser Gln Tyr Thr Glu Ile Ser Leu Ser Asn Val Thr Asp Ala
                565                 570                 575

Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
625                 630                 635                 640

Thr Lys Ile Asn Asn Ile Ile Ile Tyr Glu Tyr Val Thr Val Phe Cys
                645                 650                 655

Thr Asn Ile Gly Ser Phe Leu Thr Gly Tyr His Gly Thr Ser Trp Thr
            660                 665                 670

Lys Pro Thr Asp Ser Ser Tyr Arg Val Gln Tyr Gln Gly Ile Ser Tyr
        675                 680                 685

Ala Gly Tyr Leu Asp Ser Tyr Ile Tyr Asn Tyr Tyr Pro Thr Arg Cys
    690                 695                 700

Thr Gln Ser Ser Ser Ser Thr Thr Phe Ala Tyr Leu Tyr Asn Gly Glu
705                 710                 715                 720

Ser Ser Ser Asn Leu Lys Asn Val Asn Pro Asp Asn Leu Leu Ile Ser
                725                 730                 735

Gly Gly Ser Ser Tyr Ile His Gln Tyr Gly Arg Asn Tyr Leu Asn Asn
            740                 745                 750

Gln Ser Ser Asn Asn Ile Ala Ala Ser Asn Ile Asn Ser Gly Pro Ile
        755                 760                 765

Thr Ser Asp Lys Ala Ile Phe Leu Tyr Lys Ala Leu Leu Tyr Leu Ser
    770                 775                 780

Ser Asn Thr Leu Tyr Gly Phe Gly Asn Ile Ser Glu Ser Ala Lys Glu
785                 790                 795                 800

Leu Asp Val Ser Asp Thr Gln Asp Gly Tyr Asn Ala Thr Asn Tyr Lys
                805                 810                 815

Lys Val Met Lys Asn Ile Lys Asn Ile Phe Ile Pro Pro Tyr Asp Leu
            820                 825                 830

Ser Arg Asp Lys Thr Arg Phe Ala Ile Leu Thr Asp Lys Ser Leu Phe
        835                 840                 845

Ile Cys Gly Tyr Asn Ser Lys Gly Thr His Gly Ile Ser Val Asn Ser
    850                 855                 860

Ser Leu Asn Leu Asn Asn Lys Ile Asn Tyr His Lys Lys Asn Ser Ser
865                 870                 875                 880

Ser Glu Ile Ser Ser Asn Ile Gln Glu Ile Tyr Ser His Ser Lys Ser
                885                 890                 895

Thr Tyr Leu Leu Thr Asn Asn Asn Met Leu Tyr Ser Val Gly Leu Asn
            900                 905                 910
```

```
Asp Val Gly Gln Leu Gly Val Gly Asp Glu Ile Asn Arg Lys Val Phe
        915                 920                 925

Thr Lys Ile Asn Ile Asp Asn Ile Lys Ser Ile Asn Val Asn Arg Phe
    930                 935                 940

Thr Asp Asn Ser Lys His Ala Phe Ala Ile Lys Asn Asp Asn Thr Cys
945                 950                 955                 960

Tyr Ala Val Gly Leu Asn Asn Ser Gly Gln Leu Gly Ile Gly Asp Asn
                965                 970                 975

Val Asn Arg Asn Ile Phe Thr Lys Ile Asn Val Glu Asn Val Lys Tyr
            980                 985                 990

Val Ala Val Tyr Gly Asn Thr Ser  Leu Leu Leu Thr Asn  Asp Gly Leu
        995                 1000                1005

Leu Tyr  Gly Ala Gly Asn Asn  Gly Lys Gly Gln Leu  Gly Leu Gly
    1010                 1015                 1020

Asp Thr  Thr Ser Arg Asn Ile  Phe Thr Arg Ile Pro  Ile Asn Gly
    1025                 1030                 1035

Val Arg  Asp Val Tyr Leu Cys  Asn Asp Val Ser Ile  Ile Val Lys
    1040                 1045                 1050

Asn Asp  Asn Thr Cys Tyr Val  Cys Gly Leu Val Asn  Gly Tyr Phe
    1055                 1060                 1065

Gly Phe  Thr Glu Gly Ser Ile  Ser Thr Phe Thr Lys  Ile Asn Ile
    1070                 1075                 1080

Glu Asn  Val Lys Ser Val Val  Thr Ala Gly Ser Glu  Ala Thr Phe
    1085                 1090                 1095

Phe Ile  Thr Asn Asp Asn Met  Ile Tyr Thr Thr Gly  Lys Lys Glu
    1100                 1105                 1110

Arg Val  Phe Phe Ser Thr Glu  Thr Asn Asp Ile Lys  Gly Ile Arg
    1115                 1120                 1125

Val Ile  Asn Asn Ile Ile Asn  Ala Lys Lys Ile Val  Val Asn Gly
    1130                 1135                 1140

Tyr Thr  Ser Ala Ile Leu Thr  Asn Asp Asn Lys Leu  Phe Val Gly
    1145                 1150                 1155

Gly Leu  Ser Gly Tyr Gly Ser  Ile Ala Asn Asn Asn  Asn Thr Asn
    1160                 1165                 1170

Ser Val  Glu Asp Val Lys Asp  Val Phe Val Thr Ala  Asn Asn Thr
    1175                 1180                 1185

Leu Tyr  Ile Asp Asn Asn Asn  Asn Leu Ile Ser Ser  Gly Arg Asp
    1190                 1195                 1200

Thr Tyr  Gly Ile Ser Asp Glu  Ser Tyr Arg Asp Met  Ser Val Pro
    1205                 1210                 1215

Tyr Tyr  Lys Val Ser Ile Lys  Lys Asp Val Asp Thr  Val Phe Ser
    1220                 1225                 1230

Ser Tyr  Asn Thr Ile Phe Ile  Lys Asp Ile Tyr Gly  Lys Phe Tyr
    1235                 1240                 1245

Ser Ser  Thr Arg Asp Asn Arg  Tyr Asn His Leu Gly  Ile His His
    1250                 1255                 1260

Arg Tyr  Asp Asn Asp Lys Asn  Glu Ala Leu Glu Gly  Ser Leu His
    1265                 1270                 1275

Ser Tyr  Phe Lys Thr Asp Asn  Thr Ser Asp Lys Ile  Val Phe Asn
    1280                 1285                 1290

Lys Lys  Asn Glu Lys Leu Val  Met Phe Asn Asp Lys  Tyr Ile Lys
    1295                 1300                 1305

Thr Asn  Asn Lys Tyr Ile Asn  Tyr Lys Asn Ile Phe  Lys Asp Asn
```

-continued

```
    1310                1315                1320

Phe Lys  Tyr Thr Ser Ile Ile  Leu Pro Phe Glu Val  Ser Asp Ile
    1325                1330                1335

Asp Ile  Ser Lys Thr His Ser  Leu Ala Val Ala Lys  Asp Gly Lys
    1340                1345                1350

Leu Tyr  Gly Ile Gly Ser Asn  Ser Tyr Lys Glu Ile  Asn Gln Thr
    1355                1360                1365

Leu Glu  Asp Ile Glu Leu Leu  Thr Leu Thr Glu Val  Asn Ile Ser
    1370                1375                1380

Asp Val  Lys Lys Val Ala Cys  Gly Asp Asn Tyr Ser  Tyr Ile Ile
    1385                1390                1395

Lys Thr  Asp Asn Thr Leu Trp  Ser Tyr Gly Lys Asn  Thr Glu Tyr
    1400                1405                1410

Gln Leu  Gly Val Gly His Asn  Asn Asp Val Arg Glu  Leu Gln Lys
    1415                1420                1425

Val Thr  Gly Leu Pro Ser Val  Lys Asp Ile Ser Ile  Tyr Asn Ser
    1430                1435                1440

Met Thr  Leu Val Leu Thr Asn  Glu Gly Glu Leu Tyr  Ala Gln Gly
    1445                1450                1455

Tyr Asn  Thr Asn Gly Leu Phe  Gly Leu Gly Glu Ser  Glu Lys Asp
    1460                1465                1470

Lys Ile  Ile Arg Thr Phe Thr  Lys Val Leu Thr Asn  Val Lys Glu
    1475                1480                1485

Ile Lys  Ser His Asn Asp Asp  His Ile Leu Val Ile  Lys Asn Asp
    1490                1495                1500

Asn Ser  Leu Trp Ile Thr Gly  Lys Asn Lys Ser Met  Tyr Lys Ile
    1505                1510                1515

Ser Ile  Ser Ile Thr Asp Leu  Tyr Glu Phe Thr Lys  Ile Pro Ile
    1520                1525                1530

Pro Glu  His Leu Asn Asp Ile  Leu Asp Ile Glu Leu  Ser Asp Asp
    1535                1540                1545

Thr Ile  Tyr Met Ile Thr Lys  Val Asp Thr Ser Lys  Ala Ser Ile
    1550                1555                1560

Glu Ile  Val Glu Lys Ser Ile  Ser Gln Val Arg Val  Val Val Gln
    1565                1570                1575

Asp Pro  Asn Asn Val Ile Glu  Lys Leu Glu Met Phe  Ile Asn Asp
    1580                1585                1590

Glu Leu  Ile Ser Thr Lys Thr  Asn Leu Glu Ile Asn  Ser Ile Ile
    1595                1600                1605

Phe Glu  Ile Pro Gln Asn Lys  Ile Val Leu Gly Glu  Asn Lys Ile
    1610                1615                1620

Leu Ile  Lys Ala Ser Ser Pro  Thr Gly Asp Leu Tyr  Ser Ser Met
    1625                1630                1635

Phe Ile  Phe Lys Ser Glu Thr  Gly Leu Lys Val Lys  Lys Asp Ser
    1640                1645                1650

Ile Leu  Met Ile Asn Asn Lys  Val Tyr Ser Ile Ile  Asn Ile Thr
    1655                1660                1665

Glu Asn  Asn Thr Asp Leu Ile  Val Thr Leu Asn Glu  Gly Leu Lys
    1670                1675                1680

Asp Asp  Met Met Glu Asn Asn  Pro Ile Tyr Gln Leu  Ile Asn Lys
    1685                1690                1695

Thr Lys  Val Gln Val Lys Ile  Asn Lys Ser Asp Leu  Phe Lys Asp
    1700                1705                1710
```

-continued

| | | | | | | | | | | | | | | |
|---|---|---|---|---|---|---|---|---|---|---|---|---|---|---|
| Met | Lys | Leu | Val | Glu | Ile | Lys | Lys | Ser | Asp | Ser | Ser | Tyr | Gln | Glu |
| | 1715 | | | | | 1720 | | | | | 1725 | | | |
| Ile | Tyr | Glu | Leu | Glu | Glu | Ala | Asn | Ile | Lys | Ser | Ala | Gln | Pro | Lys |
| | 1730 | | | | | 1735 | | | | | 1740 | | | |
| Ile | Ile | Val | Glu | Lys | Gly | Asp | Lys | Trp | Thr | Ala | Ile | Lys | Arg | Pro |
| | 1745 | | | | | 1750 | | | | | 1755 | | | |
| Ser | Met | Ile | Phe | Arg | Tyr | Asp | Ala | Glu | Asn | Asn | Glu | Pro | Gln | |
| | 1760 | | | | | 1765 | | | | | 1770 | | | |

DIFFOCIN AND METHODS OF USE THEREOF

RELATED APPLICATIONS

This application claims benefit of priority under 35 U.S.C. §119(e) from U.S. Provisional Application Ser. No. 61/349,145, filed May 27, 2010, currently pending, the entire content of which is incorporated by reference as if fully set forth.

SEQUENCE LISTING

The instant application contains a Sequence Listing which has been submitted in ASCII format via EFS-Web and is hereby incorporated by reference in its entirety. This ASCII copy, created on May 24, 2011, is named CA2193.txt and is 356,718 bytes in size.

FIELD OF THE INVENTION

This application relates generally to the identification and isolation of a cluster of genes sufficient to produce a bacteriocin, and more specifically, an R-type high molecular weight bacteriocin that specifically kills *Clostridium difficile*, and methods to alter its bactericidal specificity, produce and use the same.

BACKGROUND OF THE INVENTION

*Clostridium difficile* is an obligate anaerobic, spore-forming, gram positive bacterium that is a notorious pathogen for humans and other mammals (Bartlett et al., 1977; Bartlett et al., 1979; Keel et al., 2007; Sunenshine & McDonald, 2006). At low densities *C. difficile* can reside innocuously in the mammalian gastrointestinal (GI) tract, but upon expansion, frequently as the result of administered antibiotics reducing the commensal bacteria, *C. difficile* bacteria produce sufficient exotoxins to cause a range of diseases from a mild diarrheal disease to a characteristic pseudo-membranous colitis, which is life-threatening, particularly to older humans and others with significant co-morbidities (Bartlett, 2002).

Because spores formed by this pathogen disseminate widely and are difficult to eradicate or inactivate in hospitals and chronic care facilities, the probability of patients being colonized by *C. difficile* increases sharply upon their entering such a facility (Bartlett, 2007). In fact, a relatively new strain of *C. difficile* that is a hypervirulent toxigenic bacterial strain of *C. difficile*, BI/NAP1/027, which causes severe disease in massive outbreak settings, has recently been well documented (Spigaglia et al., 2002; Pépin et al., 2004; McDonald et al., 2005; Muto et al., 2005; Loo et al., 2005; Belmares et al., 2009). The incidence of *C. difficile* associated disease (CDAD) in children, previously at low risk, has also increased substantially (Benson et al., 2007; Zilberberg et al., 2010).

Eliminating the pathogen prophylactically in asymptomatic carrier or colonized subjects by administering antibiotics is strongly contraindicated because of the high risk of inducing *C. difficile* associated disease.

R-type bacteriocins made by gram negative bacteria have been described and have been deployed by such bacteria to kill other competitive gram negative strains, even in some circumstances other species or genera of gram negative bacteria (Kageyama et al., 1964; Kageyama et al., 1964a; Kingsbury, D, 1966; Blackwell and Law, 1981; Blackwell et al., 1982; Campagnari et al., 1994; Strauch et al., 2001; Jabrane et al., 2002). The fusion of base plate attachment regions (BPAR) of R-type pyocins to heterologous receptor binding domains (RBD), resulting in the creation of novel R-type pyocins with novel bactericidal specificities for gram negative bacteria has been described (Williams et al., 2008; Scholl et al., 2009).

Other high-molecular-weight bacteriocins or R-type bacteriocins have been described in gram-positive bacteria (Coetzee et al., 1968; Thompson and Pattee, 1981; Zink et al., 1995). However, much less is known about R-type high molecular weight bacteriocin structures produced by gram positive bacteria. But while such have been described, none has been characterized at a genetic level or manipulated in a manner supportive or necessary for developing a useful agent. High molecular weight bacteriocins have been described for 2 *Clostridium* species, *botulinum* and *perfringens* (Ellison and Kautter, 1970; Anastasio et al., 1971; Nieves et al., 1981). None has been described that is produced by *C. difficile* or kills *C. difficile.*

SUMMARY OF THE INVENTION

This invention is based on the isolation of the entire genetic locus or gene cluster encoding the *C. difficile*-specific R-type bacteriocins (herein termed "diffocins") that are bactericidal against other strains of *C. difficile*; the expression of the diffocin gene cluster and production of diffocins in aerobic bacteria; and the discovery that the open reading frame (ORF) 1374 of the diffocin gene cluster determines the bactericidal spectrum of that diffocin against *C. difficile* strains. This invention provides a practical means of altering the specificity of diffocins by genetic engineering to produce novel diffocins and of manufacturing and administering directly or indirectly diffocins to eliminate *C. difficile* from the gastrointestinal (GI) tract of colonized animals, including humans. The administration of diffocins can treat or prevent the development of *C. difficile* infection and associated disease without harming, as do traditional antibiotics, the commensal GI bacteria so necessary for good health.

In accordance with the present invention, there are provided isolated nucleic acid molecules encoding R-type high molecular weight (hmw) bacteriocins. In one embodiment there are provided, isolated nucleic acid molecules encoding R-type high molecular weight (hmw) bacteriocins, wherein the nucleic acid molecule is from a genome of a strain of *Clostridium difficile*, and wherein the R-type hmw bacteriocin comprises a polypeptide that is at least 80% identical to a polypeptide selected from the group consisting of SEQ ID NOs: 4-16, 18, 19, and 66-80, and the R-type hmw bacteriocin has a receptor binding domain (RBD) that binds a receptor of at least one other strain of *C. difficile* and therefore has bactericidal activity against the other strain or strains of *C. difficile*. In particular embodiments, the nucleic acid molecule is from a genome of a strain of *Clostridium difficile* selected from the group consisting of Cd4, Cd16, Cd19108, Cd19123, Cd19126, Cd19145, and ATCC Accession No. 43593. In some embodiments, the strain is Cd16 and the nucleic acid molecule includes SEQ ID NO:1 or the strain is Cd4 and the nucleic acid molecule includes SEQ ID NO:61

In another embodiment of the invention, there are provided isolated R-type bacteriocins encoded by a nucleic acid molecule of the invention. In one aspect, the R-type bacteriocins are expressed in an aerobic producer bacterium.

In another embodiment of the invention, there are provided isolated R-type high molecular weight (hmw) bacteriocins having bactericidal activity, wherein the R-type hmw bacteriocin includes a base plate attachment region (BPAR) of a first strain of a first species of bacteria of genus *Clostridium*, and a receptor binding domain (RBD) from a second strain of the first species, or from a second species of the genus *Clostridium* or of a bacteriophage that infects a *Clostridium* species, or a modified form of an RBD, wherein the bacteriocin has bactericidal activity against at least one strain of *Clostridium difficile*. In particular embodiments, the BPAR is from a first strain of *Clostridium difficile* and the RBD is from a second strain of *Clostridium difficile* or from a bacteriophage that infects *Clostridium difficile*. In some embodiments, the BPAR is at least 80% identical to the corresponding segment of one or more of SEQ ID NOs: 16, 54-56 and 78. In other embodiments, the RBD is at least 80% identical to the corresponding segment of one or more of SEQ ID NOs: 17, and 49-56. In certain embodiments, the BPAR is at least 80% identical to a polypeptide containing 50 or more contiguous amino acids of SEQ ID NO:16 or 78 or containing 50 or more contiguous amino acids of SEQ ID NOs: 54-56.

In another embodiment of the invention, there are provided expression cassettes containing a nucleic acid molecule of the invention. Expression cassettes may be contained within an expression vector, such as a plasmid, or may be contained within the chromosome of a producer cell. In some embodiments, the expression cassette contains a heterologous promoter operably linked to the nucleic acid molecule encoding the R-type bacteriocin. The promoter may be inducible, repressible, or constitutively active. In one aspect, the promoter is inducible; in another aspect the promoter is repressible. In some embodiments, the promoter is induced by adding or removing a small molecule inducer, repressor, or de-repressor. In one aspect, the promoter is induced by a small molecule inducer or de-repressor. In a particular aspect, the expression of the cassette is regulated by an operably linked recA gene encoding a constitutively active RecA protein and under the control of an heterologous promoter responsive to a small molecule inducer or de-repressor.

In still another embodiment of the invention, there are provided producer cells containing the expression cassettes of the invention. The expression cassette may be contained in an episomal expression vector within the producer cell. Alternatively, the producer cells may contain within their chromosome a nucleic acid molecule or expression cassette of the invention. In certain embodiments, the producer cell is a non-pathogenic and not obligate anaerobic bacterium. In some embodiments, the non-pathogenic and not obligate anaerobic bacterium is a species from a genus of bacteria selected from the group consisting of *Bacillus, Lactobacillus*, and *Listeria*. In certain embodiments, the non-pathogenic and not obligate anaerobic bacterium is from the genus *Bacillus*. In some aspects, the bacterium is *Bacillus subtilis*. In a particular aspect, the *B. subtilis* lacks the PBSX gene cluster. In another embodiment the producer cell is an obligate anaerobic but non-pathogenic bacterium.

In yet another embodiment of the invention, there are provided methods of producing an R-type hmw bacteriocin of the invention. The method includes exposing a producer cell containing a nucleic acid sequence of the invention operably linked to an inducible or derepressible promoter sensitive to an inducing or repressing agent, to the agent in a concentration effective to induce expression of the R-type bacteriocin, and purifying the expressed R-type bacteriocin. In some embodiments, the nucleic acid molecule encoding the R-type bacteriocin is heterologous to the genome of the producer cell. In particular aspects, the nucleic acid molecule is contained within the producer cell's chromosome or is contained in an extrachromosomal expression vector within the producer cell. In certain embodiments, the producer cell is a non-pathogenic and not obligate anaerobic bacterium. In some embodiments, the non-pathogenic and not obligate anaerobic bacterium is a species from a genus of bacteria selected from the group consisting of *Bacillus, Lactobacillus*, and *Listeria*. In certain embodiments, the non-pathogenic and not obligate anaerobic bacterium is from the genus *Bacillus*. In some aspects, the bacterium is *Bacillus subtilis*. In a particular aspect, the *B. subtilis* does not lyse when induced to produce the R-type bacteriocin. In a further aspect, the *B. subtilis* lacks the PBSX gene cluster.

In a further embodiment of the invention, there are provided methods of killing a pathogenic bacterium. The method includes contacting the pathogenic bacterium with an R-type bacteriocin of the invention, whereby the R-type bacteriocin binds and kills the pathogenic bacterium. In one aspect, the pathogenic bacterium is *Clostridium difficile*. In one aspect, the *Clostridium difficile* is in an animal and a bactericidal amount of the R-type bacteriocin is administered to the animal.

In another embodiment of the invention there are provided methods of treating or preventing a disease-causing infection of *Clostridium difficile* in an animal. The method includes administering a bactericidal amount of an R-type bacteriocin of the invention directly to an animal in need thereof, administering the agent indirectly by administering producer cells, or administering spores of *C. difficile* bacteria which produce natural diffocins but have been genetically modified to not produce toxins. In particular embodiments, an infection of *Clostridium difficile* in an animal is treated by administering to an animal in need thereof an amount of a producer cell of the invention to produce a bactericidal amount of the bacteriocin, thereby treating the infection. In one aspect, the nucleic acid encoding the bacteriocin is under the control of a lac promoter and the animal is administered lactose. In some embodiments, the animal is a mammal. In one aspect, the mammal is a human.

BRIEF DESCRIPTION OF THE DRAWINGS

FIGS. 1A through 1AH provide the nucleic acid or amino acid sequences of SEQ ID NOs:1-80.

FIGS. 8A through 8E provide the results of a ClustalW analysis of partial amino acid sequences (SEQ ID NOs:81-86, respectively, in order of appearance) encoded by the ORF 1374 gene from each of 5 strains of *C. difficile* that produced active diffocins. Under each row of aligned sequences the "*" represents amino acid identities at that position encoded by all 5 genes, the ":" represents highly similar amino acids at that position encoded by all 5 genes, and the "." represents somewhat similar amino acids at that position encoded by all 5 genes; and the blank at a given position in the sequence alignment represents no amino acid similarity encoded by all 5 genes.

DETAILED DESCRIPTION OF THE INVENTION

Definitions

Figure 2:
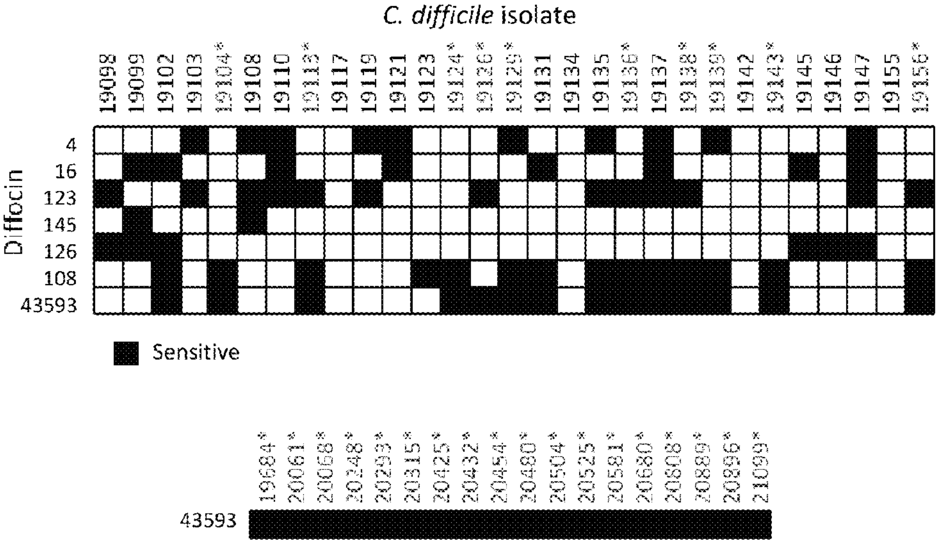
FIG. 2. Bactericidal activity of diffocins on clinical *C. difficile* isolates. The indicator strain numbers are shown along the top of the matrices; the asterisk-marked strains are NAP1/027/BI strains. The identities of the *C. difficile* sources of the diffocins tested are shown along the left borders. Strains were acquired from LC Fortier (4 and 16), ATCC (43593), or RM Alden Research Lab, Culver City, Calif.

As used herein, an "R-type high molecular weight (hmw) bacteriocin" is also known as simply an "R-type bacteriocin" and includes R-type pyocins, diffocins, monocins, enterocoliticins, meningocins, or other high molecular weight (hmw) bacteriocins related structurally or genetically to the myoviridae family of bacteriophages. An R-type bacteriocin includes modified versions of R-type pyocins, diffocins, enterocoliticins, monocins, and meningocins (Williams et al. 2008; Strauch et al., 2001; Kingsbury, 1966; Zink et al. 1995).

The term "diffocin," as used herein refers to an R-type high molecular weight bacteriocin isolated from or derived from *Clostridium difficile* and includes native particles obtained from *C. difficile* as well as particles obtained through expression of the diffocin gene cluster in a non-natural producer cell. A diffocin may also be an engineered particle comprised of polypeptides encoded by genes derived from one or more strains of *C. difficile*, and 80% or more identical to one or more polypeptides of SEQ ID NOs: 2-23, 49 and 62-80.

An R-type bacteriocin of the invention may be thermolabile, mild acid resistant, trypsin resistant, sedimentable by centrifugation at about 65,000×g, and resolvable by electron microscopy (Kageyama et al., 1962; Bradley, 1967; Daw et al., 1996; Jabrane et al., 2002; Fortier et al., 2007). In many cases, an engineered R-type bacteriocin disclosed herein has one or more, in any combination, of these properties. An additional property common to the R-type bacteriocins disclosed herein is that they do not contain nucleic acid and thus are replication deficient such that they cannot reproduce themselves after or during the killing of a target bacterium, as can many bacteriophages. They are purely proteins, not organisms.

R-type bacteriocins disclosed herein are complex molecules comprising multiple protein, or polypeptide, subunits and resemble the tail structures of bacteriophages of the myoviridae family. In naturally occurring R-type bacteriocins, the subunit structures are encoded by the bacterial genome such as that of *C. difficile* or *P. aeruginosa* and form R-type bacteriocins to serve as natural defenses against other bacteria (Kageyama, 1975). A sensitive, target bacterium can typically be killed by a single R-type bacteriocin molecule (Kageyama et al., 1964; Kageyama et al., 1964a; Morse et al., 1980; Strauch et al., 2001).

A "target bacterium" or "target bacteria" refers to a bacterium or bacteria that are bound by an R-type bacteriocin of the disclosure and/or whose growth, survival, or replication is inhibited thereby. In some embodiments, the target bacterium is from the genus *Clostridum*. In particular embodiments, the bacterium is *Clostridium difficile*. In one aspect, more than one strain of *C. difficile* is targeted. Exemplary strains of *C. difficile* include but are not limited to NAP1/BI/ribotype 027, as well as those listed in FIG. 2.

The term "growth inhibition" or variations thereof refers to the slowing or stopping of the rate of a bacterial cell's division or cessation of bacterial cell division, or to death of the bacterium or bacteria.

As used herein, a "nucleic acid" or a "nucleic acid molecule" typically refers to deoxyribonucleotide or ribonucleotides polymers (pure or mixed) in single-or double-stranded form. The term may encompass nucleic acids containing nucleotide analogs or modified backbone residues or linkages, which are synthetic, naturally occurring, and non-naturally occurring, which have similar binding, structural, or functional properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-0-methyl ribonucleotides, and peptide-nucleic acids (PNAs). The term nucleic acid may, in some contexts, be used interchangeably with gene, cDNA, mRNA, oligonucleotide, and polynucleotide.

A particular nucleic acid sequence also encompasses conservatively modified variants thereof (such as degenerate codon substitutions) and complementary sequences, as well as the sequence explicitly indicated. Specifically, degenerate codon substitutions may be achieved by generating sequences in which the third ("wobble") position of one or more selected (or all) codons is substituted with mixed-base and/or deoxyinosine residues. Thus, a nucleic acid sequence encoding a protein sequence disclosed herein also encompasses modified variants thereof as described herein.

The term "segment" as used herein in reference to an amino acid sequence refers to a contiguous sequence of amino acids that may be 10, 12, 15, 20, 25, 50, or 100 amino acid residues in length.

As used herein, the term "heterologous," when used with reference to portions of a protein or nucleic acid sequence, indicates that the sequence comprises two or more subsequences that are not usually found in the same relationship to each other in nature. In one example, the heterologous sequences are from different species of bacteria. In another example, heterologous sequences are from different strains of the same species of bacteria. In one aspect, the heterologous sequences are from different strains of *C. difficile*. In another aspect the heterologous sequences are from a bacterium and a bacteriophage or from a bacterium and a synthetic, non-natural sequence of DNA.

The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission.

Virulence factors are those molecules that contribute to the pathogenicity of an organism but not necessarily its general viability. Upon the loss of a virulence factor the organism is less pathogenic but not necessarily less viable. Virulence factors may have any one of numerous functions, for example, regulating gene expression, providing adhesion or mobility, providing a toxin, injecting a toxin, pumping out antibiotic agents, or forming protective coatings including biofilms.

Fitness factors are those molecules that contribute to the organism's general viability, growth rate or competitiveness in its environment. Upon the loss of a fitness factor, the organism is less viable or competitive and because of this compromise, indirectly less pathogenic. Fitness factors may also possess any one of numerous functions, for example, acquiring nutrients, ions or water, forming components or protectants of cell membranes or cell walls, replicating, repairing or mutagenizing nucleic acids, providing defense from or offense towards environmental or competitive insults.

The term "producer cell" as used herein refers to a cell that is capable of producing or expressing a diffocin-encoding nucleic acid molecule and which does not naturally contain such a nucleic acid molecule. The producer cell may be capable of surviving and growing in the presence of oxygen and is transformed with a vector containing nucleic acid molecule encoding the diffocin, which may be integrated into the chromosome of the producer cell or may be episomal. The producer cell may be a gram positive bacterium. In certain embodiments, the producer cell may be a bacterium from the genus *Bacillus, Lactobacillus, Clostridium*, or *Listeria*. In some embodiments, the bacterium is a species from the genus *Bacillus* selected from the group consisting of *subtilis, amyloliquefaciens*, and *megaterium*. In one aspect, the bacterium is *Bacillus subtilis*. In a particular aspect, the producer cell is a *B. subtilis* strain that lacks the PBSX gene cluster. In other embodiments, the bacterium is a species from the genus *Lactobacillus* selected from the group consisting of acidophilus, casei, and bulgaricus. In still other embodiments, the bacterium is *Listeria innocua*. In another embodiment, the non-pathogenic producer cell may be *Escherichia coli* or of the genus *Clostridium*

DETAILED DESCRIPTION OF MODES OF PRACTICING THE DISCLOSURE

R-Type Bacteriocins Isolated from *C. difficile* have Bactericidal Activity.

Figure 3:
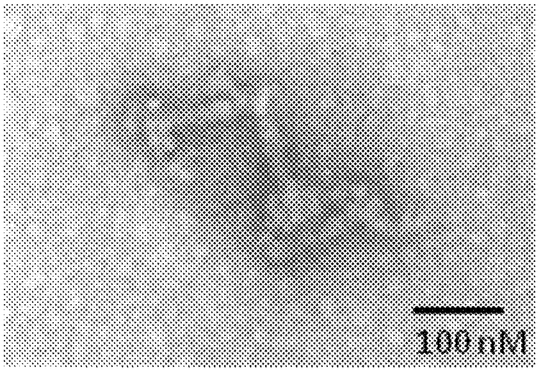
FIG. 3 shows a scanning electron micrograph of dif16. Note the flower-like tail fiber appendages.
Figure 4:
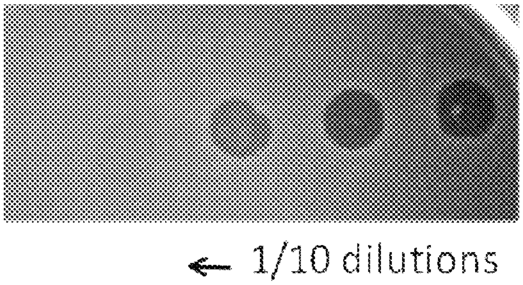
FIG. 4 shows a photograph of the results of a spot test of dif4 on the target strain Cd19135. Purified diffocin was serially diluted 10-fold, and 5 μl aliquots of the dilutions were spotted on a lawn of target *C. difficile* bacteria. After anaerobic incubation at 37° C. overnight, diffocin killing was indicated by the clearing of growth on the lawn.

To test for bactericidal activity, lysates of two *C. difficile* strains, Cd4 and Cd16 (from LC Fortier), were made by growing the cells to mid-log phase under strict anaerobic conditions throughout and then exposing the culture to 3 μg/ml of mitomycin C. After the bacterial cells lysed, particles in the lysates were concentrated and purified by high speed centrifugation (see Example 1). These preparations were shown by electron microscopy to contain concentrated headless phage-like particles (FIG. 3). After concentration and purification, the preparations were assessed for bactericidal activity by a spot plate method whereby samples were applied to an overlay lawn of target *C. difficile* bacteria, again under strict anaerobic conditions. Since most phage tail-like bacteriocins typically target strains different from the producing bacteria, target strains consisting initially of a panel of 29 *C. difficile* clinical isolates were tested. After overnight incubation, the plates were examined for the presence of killing activity as indicated by a clearing in the lawn of *C. difficile* bacteria where the purified materials were spotted. FIG. 4 shows a typical spot assay of diffocin from Cd4 (dif 4) spotted onto *C. difficile* strain, Cd19135.

Dif4 (diffocin from Cd4) and dif16 (diffocin from Cd16) demonstrated different bactericidal spectra based on spot assays (FIG. 2). Dif4 showed bactericidal activity on 10 of 29 *C. difficile* clinical isolate strains, whereas dif16 had activity against 8 of 29 strains. There was some overlap of strains susceptible to both diffocins, but the two diffocins had distinct bactericidal spectra. Diffocins from Cd108 and Cd 43593 had very similar killing spectra and killed at least 9 of the 10 NAP1/027/BI hypervirulent strains in the panel of 29 *C. difficile* clinical isolates. When tested further, dif43593 killed all 18 additional, independent NAP1/027/BI isolates. Thus, dif43593 kills all 28 tested strains of NAP1/027/BI *C. difficile*, FIG. 2.

Identification of the Diffocin Locus.

Figure 5:
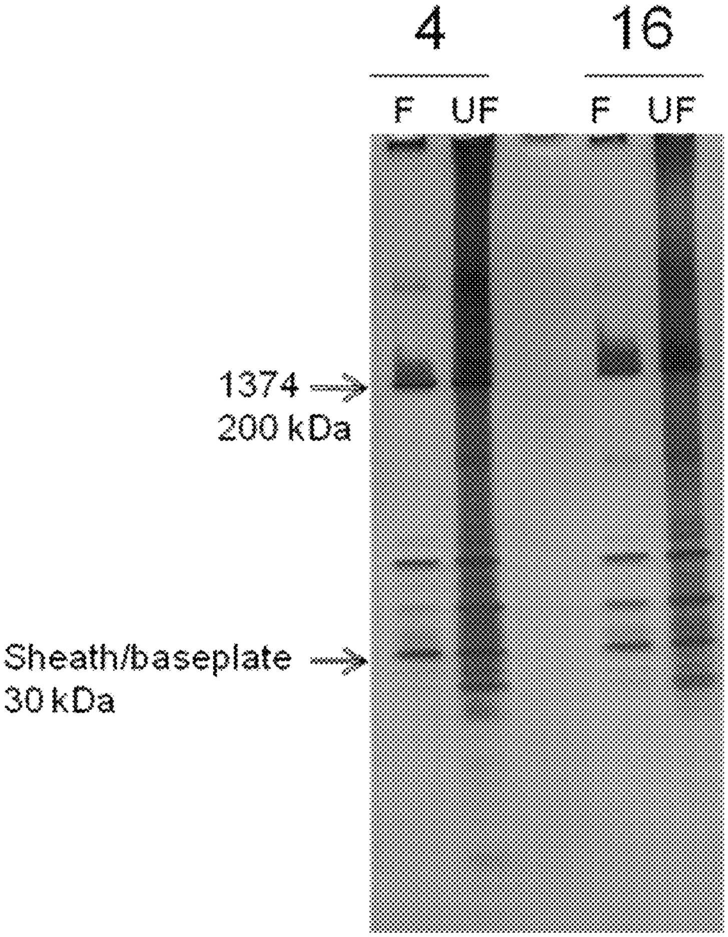
FIG. 5 shows a photograph of a silver stained SDS-PAGE of both filtered ("F") and unfiltered ("UF") preparations of dif4 ("4") and dif16 ("16"). The arrows indicate bands that were excised and identified by mass spectrometry.

Diffocin particles, isolated and purified from strain Cd4, were denatured, and the protein components were separated by sodium dodecyl sulfate polyacrylamide gel electrophoresis (SDS PAGE) and detected by silver stain (FIG. 5). Two individual bands, ~200 kD and ~40 kD, were excised and analyzed by mass spectrometry. Peptides from the 40 kD band were found to match the predicted products from two *C. difficile* open reading frames (ORF) encoded in several of the *C. difficile* strains for which the complete genomes have been sequenced, including the reference strain Cd630 (GenBank Acc. No. NC_009089.1). The first of these was ORF 1363 (SEQ ID NO:5), a 39,192 Dalton phage-like protein. The second predominant polypeptide in this band corresponded to ORF 1371 (SEQ ID NO:14), a 39,565 Dalton phage-like baseplate protein. Since these proteins were coincidentally very close in molecular weight, they migrated in the same SDS PAGE band. The 200 kD band yielded a dominant polypeptide that corresponded to a portion of the C-terminus of ORF 1374 (SEQ ID NO:17), just downstream of the two other phage-like ORFs.

Figure 6:
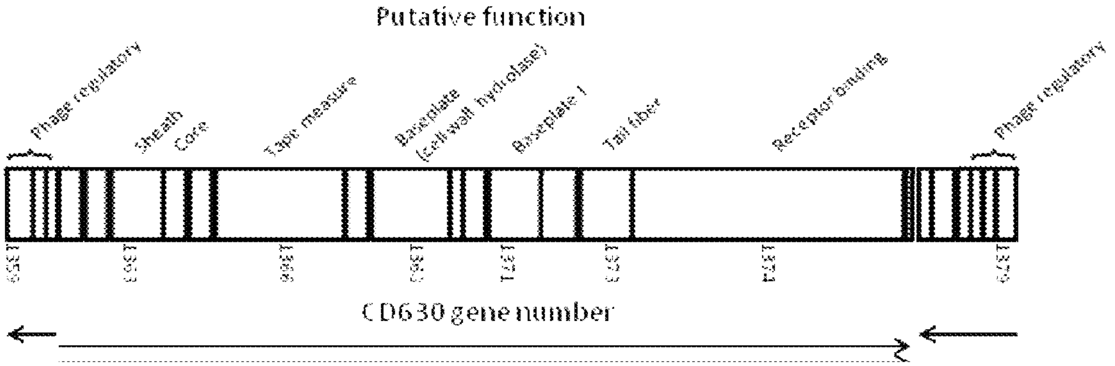
FIG. 6 shows a schematic of the diffocin gene cluster from Cd630 and Cd16. The locus consisted of the ORFs that encode structural proteins and structural assembly proteins typical of a *Myoviridae* phage tail apparatus, ORF1362 to ORF1375, indicated below the map. Flanking these genes were genes that encode putative phage-like regulatory proteins. The bottom arrows indicate the direction in which the ORFs are transcribed and the putative functions of the ORFs are indicated above the map.

Since these ORFs mapped in very close proximity within the Cd630 genome, the surrounding region was analyzed. A prophage-like element was found between bases 1574593 and 1596384, which includes ORFs 1360A-1379 (FIG. 6 and SEQ ID NO:1-23). Of particular note was that the structural genes encoded in this region corresponded only to the components of the tail structure of a typical Myoviridae phage; no genes for capsid, capsid assembly protein, or portal proteins were found. Also absent were any ORFs which encoded putative DNA replication or DNA packaging machinery. Thus, this locus was consistent with that of an R-type (Myoviridae phage tail-like) bacteriocin. Flanking the structural genes were several ORFs that encode putative phage-like regulatory proteins. Since several ORFs from this locus encoded polypeptides found in diffocin particles and the fact that the gene cluster resembled that of an R-type bacteriocin, we assigned the diffocin locus to this region.

The structural genes were all encoded on one strand and transcribed in the same direction. The organization of the genes resembled that of the genes of R-type pyocins and many Myoviridae phages. Several of the structural proteins displayed sequence similarity to known *C. difficile* bacteriophages including phages Φ119, and ΦC2 (Goh et al., 2007; Govind et al., 2006). *C. difficile* strain Cd630 was also known to encode two intact prophages, both of which were known to be inducible (Goh et al., 2007). Several of the diffocin ORFs had sequence similarity to prophage 1 and 2 of *C. difficile* strain Cd630, suggesting that these *C. difficile* Myoviridae phages and the diffocins share common ancestry.

Of particular note was ORF 1374 (SEQ ID NO:17) of the diffocin. This gene encoded a large polypeptide that is located just downstream of ORF 1373, SEQ ID NO:16, a location in the cluster that indicated that ORF 1374 was part of the R-type bacteriocin tail fiber, that is, a receptor binding domain (RBD). Since electron micrographs of what have been designated as diffocins revealed a large flower like structure in the tail fiber region, it was apparent that this structure comprised a large protein. ORF 1373 (SEQ ID NO:16) encoded the base plate attachment region, BPAR, of the diffocin tail fiber and appeared to be a truncated form of a the analogous ORF 1373 in phages of *C. difficile* which encoded the RBD as well as the BPAR, given that such phages lack an ORF 1374. Thus, the tail fibers of naturally occurring diffocins are comprised of two proteins, ORF1373 and ORF1374, which form a jointed tail fiber, whereas bacteriophages of *C. difficile* have a tail fiber comprised of a single protein, a somewhat longer ORF 1373 which provides the BPAR and the RBD functions. With this knowledge the nucleic acids encoding either ORF1373 (SEQ ID NO:16) or ORF1374 (SEQ ID NO:17) were deployed herein as substrates from which to engineer new RBD specificity functions.

Diffocins are Wide-Spread Among *C. difficile* Isolates.

A series of independent clinical isolates of *C. difficile* were tested for the ability to produce diffocin particles that might have different bactericidal spectra. Clinical isolates Cd19123, Cd19145, Cd19126, Cd19108 (from RM Alden Research Laboratory, Culver City, Calif.), and ATCC Cd43593 were induced with mitomycin C under strict anaerobic conditions, followed by purification and concentration of particles that were produced. The purified materials were then spotted separately on lawns of other *C. difficile* strains in the clinical collection to detect bactericidal activity. The results showed that each of these isolates produced particles (diffocins termed dif123, dif145, dif126, dif108, and dif43593 from clinical isolates Cd19123, Cd19145, Cd19126, Cd19108, and ATCC Cd43593, respectively) with differing bactericidal spectra (FIG. 2.). Dif108 and dif43593 had very similar and broad spectra, whereas strain Cd19145 produced particles with a narrow bactericidal spectrum. Some isolates that were tested for induction, including Cd19113 and Cd19150, lysed after exposure to mitomycin but did not produce detectable diffocin particles.

It was recognized herein that the genome sequenced laboratory strain Cd630 encoded a diffocin locus; and, in fact, this genome was used herein to identify the diffocin genes. However, while strain Cd630 lysed after induction with mitomycin C, no detectable diffocin particles were produced. Instead, small amounts of prophage 1 and prophage 2 were produced.

Identification and Cloning of a Diffocin Cluster.

Cd630 did not produce detectable diffocin particles upon induction of lysis by mitomycin C. Accordingly, the diffocin gene cluster from Cd16 was cloned, instead. A draft genome sequence of Cd16 was first obtained. A diffocin locus, analogous to that of Cd630, was identified and annotated. The entire diffocin gene cluster from producer strain Cd16 was cloned (SEQ ID NO:1) into a BAC and subsequently demonstrated to include all the genes necessary to produce an active diffocin in a non-pathogenic microorganism and one that is not an obligate anaerobe. *C. difficile* is both pathogenic and an obligate anaerobic bacterium, making it an impractical production cell for natural diffocins or diffocins modified by recombinant DNA engineering. The isolated diffocin cluster can also be engineered by recombinant DNA technology to have its expression regulated by a heterologous promoter responding to a non-toxic small molecule inducer or de-repressor added to the culture or induction medium of the producer microorganism. Such small molecules include but are not limited to tetracycline, anhydrotetracycline, lactose, arabinose, xylose and their non-metabolized analogs, such as IPTG to replace lactose.

Diffocins

Diffocins are R-type hmw bacteriocins isolated from *Clostridium difficile*, which are bactericidal against other strains of *C. difficile*. Diffocins may be isolated from *C. difficile* strains grown under anaerobic conditions in the presence of mitomycin C. In some embodiments, the diffocin is from *C. difficile* clinical isolate Cd4, Cd16, Cd19123, Cd19145, Cd19126, Cd19108, or ATCC Cd43593 (termed dif 4, dif 16, dif123, dif145, dif126, dif108, and dif43593, respectively). In one aspect, the diffocin is from Cd4; in another aspect the diffocin is from Cd16.

In another embodiment of the invention, there are provided isolated nucleic acid molecules encoding diffocins derived from the genome of the genus *Clostridium* bacteria. In one aspect, the nucleic acid molecule contains the gene cluster of SEQ ID NO:1. In another aspect, the nucleic acid molecule contains the gene cluster of SEQ ID NO:61. In other embodiments, the nucleic acid molecule encodes a diffocin that includes one or more polypeptides selected from the group consisting of SEQ ID NOs: 2-23; 49, 62-80. In still other embodiments, the nucleic acid molecule encodes a diffocin that includes one or more polypeptides selected from the group consisting of SEQ ID NOs: 4-16, 18, 19, and 66-80. In one aspect, the nucleic acid molecule encodes the polypeptides of SEQ ID NOs: 2-23. In another aspect, the nucleic acid molecule encodes the polypeptides of SEQ ID NOs: 49 and 62-80.

Also provided are variant diffocins. Variant diffocins include those diffocins having an amino acid sequence that are at least 80% identical to a polypeptide selected from the group consisting of SEQ ID NOs: 4-16, 18, 19, and 66-80. In other embodiments, the variant diffocin has an amino acid sequence that is at least 85%, 88%, 89%, 90%, 95%, 96%, 97%, 98%, or even 99% identical to a polypeptide selected from the group consisting of SEQ ID NOs: 4-16, 18, 19, and 66-80.

In some embodiments, the variant diffocin may include a heterologous base plate attachment region (BPAR), wherein the BPAR is at least 80% identical to the corresponding segment of one or more of SEQ ID NOs: 16, 54-56, and 78. In another embodiment, the BPAR is at least 85% identical to the corresponding segment of one or more of SEQ ID NOs: 16, 54-56, and 78. In another embodiment, the BPAR is at least 89% identical to the corresponding segment of one or more of SEQ ID NOs: 16, 54-56, and 78. In another embodiment, the BPAR is at least 90% identical to the corresponding segment of one or more of SEQ ID NOs: 16, 54-56, and 78. In still another embodiment, the BPAR is at least 95% identical to the corresponding segment of one or more of SEQ ID NOs: 16, 54-56, and 78. In yet another embodiment, the BPAR is at least 98% identical to the corresponding segment of one or more of SEQ ID NOs: 16, 54-56, and 78. In a further embodiment, the BPAR is at least 99% identical to the corresponding segment of one or more of SEQ ID NOs: 16, 54-56, and 78.

In further embodiments, the variant diffocin may include a heterologous receptor binding domain (RBD), wherein the RBD is at least 80% identical to the corresponding segment of one or more of SEQ ID NO:17 and 49-53, or at least 80% identical to a polypeptide containing the receptor binding domain (RBD) region of a polypeptide selected from the group consisting of SEQ ID NOs:54-56. In another embodiment, the RBD is at least 85% identical to the corresponding segment of one or more of SEQ ID NO:17 and 49-53, or at least 85% identical to a polypeptide containing the receptor binding domain (RBD) region of a polypeptide selected from the group consisting of SEQ ID NOs:54-56. In another embodiment, the RBD is at least 89% identical to the corresponding segment of one or more of SEQ ID NO:17 and 49-53, or at least 89% identical to a polypeptide containing the receptor binding domain (RBD) region of a polypeptide selected from the group consisting of SEQ ID NOs:54-56. In another embodiment, the RBD is at least 90% identical to the corresponding segment of one or more of SEQ ID NO:17 and 49-53, or at least 90% identical to a polypeptide containing the receptor binding domain (RBD) region of a polypeptide selected from the group consisting of SEQ ID NOs:54-56. In another embodiment, the RBD is at least 95% identical to the corresponding segment of one or more of SEQ ID NO:17 and 49-53, or at least 95% identical to a polypeptide containing the receptor binding domain (RBD) region of a polypeptide selected from the group consisting of SEQ ID NOs:54-56. In another embodiment, the RBD is at least 98% identical to the corresponding segment of one or more of SEQ ID NO:17 and 49-53, or at least 98% identical to a polypeptide containing the receptor binding domain (RBD) region of a polypeptide selected from the group consisting of SEQ ID NOs:54-56. In another embodiment, the RBD is at least 99% identical to the corresponding segment of one or more of SEQ ID NO:17 and 49-53, or at least 99% identical to a polypeptide containing the receptor binding domain (RBD) region of a polypeptide selected from the group consisting of SEQ ID NOs:54-56. In some embodiments, the receptor binding domain (RBD) region comprises amino acid residue 51 to the carboxy-terminal residue of SEQ ID NOs:54, 55, or 56.

In another embodiment, diffocins can be engineered to have altered bactericidal spectra by fusing phage tail RBD to the product of diffocin ORF 1373. While ORF 1374 encodes the primary spectra determinant or RBD of natural diffocins, this very large protein is complexed with the ORF 1373 protein, and ORF 1373 protein provides the BPAR, i.e., it attaches the RBD of ORF 1374 protein to the diffocin baseplate structure. ORF 1373 is analogous to, and shares amino acid sequence identity with, the tail fiber genes of myoviridae bacteriophages such as ΦCD2 (SEQ ID NO:54), ΦCD119 (SEQ ID NO:55), and ΦCD27 (SEQ ID NO:56) as well as with the tail fibers of R-type pyocins. The ORF 1373 (e.g., SEQ ID NOs:16 or 78) of diffocins shares significant sequence identity, particularly in the first 160 amino acids at the N-terminal portion or BPAR, with the tail fibers of the *C. difficile* myoviridae phage, ΦCD2 (SEQ ID NO:54). The phage tail fibers are, however, longer than diffocin ORF 1373 protein and contain a C-terminal RBD for recognizing their bacterial targets. Diffocins' ORF 1373 proteins do not contain this latter domain, the RBD function of which has been replaced by a separate polypeptide, encoded by ORF1374. Thus, ORF 1374 can be deleted altogether from the diffocin cluster and an RBD of a phage tail fiber, such as that of ΦCD2, can be fused to the diffocin BPAR, encoded by ORF 1373, thereby generating a diffocin that has a phage tail fiber-like protein and accordingly, a bactericidal spectrum related to the host range of the donor phage. Importantly, because the regions of amino acid sequence homology between the *C. difficile* phage tail fibers and the ORF 1373 protein enable successful functional fusions between the two, one can select host-range variants from mutagenized or non-mutagenized *C. difficile* phages that can then be sources of novel RBD's for creating modified diffocins with novel bactericidal spectra.

In one embodiment of an engineered diffocin, there is provided a diffocin in which the RBD has been replaced with an RBD from another strain of *C. difficile* or with an RBD from a bacteriophage that infects *C. difficile*. In one example, the nucleic acid molecule comprises a sequence encoding SEQ ID NO:16 or 78 but does not contain the corresponding native RBD (i.e., the sequence encoding SEQ ID NO:17 or 49, respectively); instead, the native RBD is replaced with a heterologous sequence encoding an RBD. In particular embodiments, the nucleic acid molecule contains a heterologous sequence encoding a receptor binding domain (RBD) of an R-type bacteriocin of a different strain of *C. difficile*. In one aspect, the nucleic acid molecule contains a sequence encoding SEQ ID NO:16 or 78 and a sequence encoding a polypeptide selected from the group consisting of SEQ ID NOs: 49-53 or the receptor binding region of a polypeptide selected from the group consisting of SEQ ID NOs: 54-56. In another aspect, the nucleic acid molecule is comprised of a sequence encoding SEQ ID NOs:2-16 and 18-23 or SEQ ID NOs: 62-80, and a heterologous sequence encoding an RBD from a polypeptide selected from the group consisting of SEQ ID NOs: 17 and 49-56.

In other embodiments of an engineered diffocin, the RBD of the diffocin may be replaced with a modified form of a native RBD. A "native RBD" refers to a RBD having an amino acid sequence that is identical to a RBD isolated or cloned from a strain of *C. difficile* or from a bacteriophage that infects *C. difficile*. Exemplary native RBDs from a number of *C. difficile* strains include SEQ ID NOs: 17 and 49-53. Exemplary native RBDs from bacteriophages that infect *C. difficile* include SEQ ID NOs: 54-56 (e.g., amino acid residue 51 to the carboxy terminal residue). In some embodiments, a modified RBD includes a change in the amino acid sequence of the RBD relative to a native RBD. Non-limiting examples of a change in amino acid sequence include substitution, insertion (or addition), or deletion of one or more amino acids. In further embodiments, a diffocin includes a substitution with, or insertion of, an RBD derived from an organism that diversifies the structure by deploying a Diversity Generating Retroelement (DGR), as described in published Patent Application US 2006-0121450, published Jun. 8, 2006 (incorporated herein by reference as if fully set forth).

In some embodiments, the modified form has a bactericidal spectrum that is different from the corresponding unmodified or native RBD. In particular embodiments, the modified form is at least 80% identical the native RBD. In other embodiments, the RBD has an amino acid sequence that is at least 85%, 88%, 89%, 90%, 95%, 96%, 97%, 98%, or even 99% identical to a polypeptide selected from the group consisting of SEQ ID NOs: 17 and 49-53 or the receptor binding region of a polypeptide selected from the group consisting of SEQ ID NOs: 54-56 and the modified RBD has a bactericidal spectrum that is different from the corresponding unmodified or native RBD.

Target Bacteria

*Clostridium difficile* strains isolated from patients vary widely by pulse gel electrophoresis and in their pathogenicity. The BI/NAP1 or ribotype 027 strains that hyperproduce toxins are particularly virulent as a result of their having lost the function of gene tcdC that negatively regulates the expression level of toxin A and toxin B (McDonald et al., 2005).

In fact, *C. difficile* strains harboring a specific mutant allele of the tcdC gene have been shown to spread epidemically within and among healthcare facilities. These epidemic and highly virulent strains are especially important target bacteria that could be eliminated prophylactically from the GI tract of carrier patients by oral application of diffocins prior to or shortly after the commencement of traditional antibiotic therapy. *C. difficile* bacteria that produce wild-type levels of toxins A and B are important target pathogens as well since they are also potentially lethal, particularly to patients older than 50 years or with co-morbidities (Bartlett J G, 2002).

Targeting surface accessible virulence or fitness factors such as S-layer proteins, prevalent on *C. difficile* strains, whether hyperproducers or not, offer an attractive means of forcing such pathogens to compromise their virulence or fitness if they emerge as resistant to the targeted R-type bacteriocin. Because of the high specificity of the RBD of diffocins, organisms other than *C. difficile* are not targets, a distinct and powerful advantage of diffocins since they will not cause collateral damage to commensal bacteria of the GI tract—bacteria necessary for normal GI function and good health.

An "infection" refers to growth of bacteria, such as in a subject or tissue or non-bacterial cell, wherein the bacteria actually or potentially could cause disease or a symptom in the subject, tissue or non-bacterial cell. Treatment of an infection may include prophylactic treatment with substances, materials, producer cells, or the spores of detoxified *C. difficile* bacteria capable of producing diffocins such as dif43593. Non-limiting examples of treated objects include donated organs, tissues, and cells; medical equipment, like a respirator or dialysis machine; or wounds, such as those during or after surgery. Other uses include the removal of target bacteria which may cause problems upon further growth. In additional embodiments, an hmw bacteriocin is used to treat food, plants or harvested parts of plants with bacterial infections or contaminations, or to treat environmental occurrences of the target bacteria, such as in a hospital or commercial setting.

As described herein, an anti-bacterial R-type bacteriocin may be used to inhibit growth, survival, or replication of a particular bacterium. The bacterium may be a pathogenic or environmentally deleterious strain, or may be treated in a prophylactic manner. A pathogenic microorganism generally causes disease, sometimes only in particular circumstances.

Preparation and Use of Diffocins

Diffocins are particles of approximately 10 million daltons and thus can be isolated and purified by differential centrifugation, differential filtration, aqueous two-phase separations, polyethylene glycol (PEG) precipitation and/or ion exchange chromatography to create biopharmaceutical grade oral anti-bacterial agents. R-type bacteriocins have been found to be stable to freezing-thawing and can be spray dried to create stable formulations.

In some embodiments of the invention, there are provided methods of producing an R-type hmw bacteriocin. The method includes exposing a producer cell to a nucleic acid sequence encoding an R-type hmw bacteriocin operably linked to an inducible promoter sensitive to an inducing agent in a concentration that brings about expression of the R-type bacteriocin, and purifying the expressed R-type bacteriocin. In one aspect, the R-type high molecular weight (hmw) bacteriocin contains one or more polypeptides selected from the group consisting of SEQ ID NOs:2-23 or SEQ ID NOs:49 and 62-80. The nucleic acid molecule is heterologous to the natural nucleic acid of the producer cell and may be contained in the producer cell's chromosome or may be contained in an episomal expression vector.

As targeted, potent antibacterial agents, diffocins will be used to remove, or decolonize, *C. difficile* from the lower GI tract of humans and other animals so as to prevent CDAD. Animals and humans treated with broad spectrum antibiotics are at high risk to develop potentially lethal CDAD if they have been colonized by *C. difficile*. Decolonization is a particularly attractive utility of diffocins because of their sparing of the healthy GI microbiota. In addition, diffocins can be administered directly or indirectly via administered producer cells or spores of detoxified *C. difficile* bacteria capable of producing diffocins to reduce the pathogen load in acute CDAD and/or to reduce the high incidence or recurrence or relapse of CDAD after successful treatment by other modalities.

Modes of Administration

R-type bacteriocins are inactivated by pH 4.0 or lower, the acidity of a normally functioning, fed stomach and upper duodenum. However, diffocins must transit the upper GI tract to reach the targeted bacterial pathogen colonizing predominately the lower GI tract. Thus, diffocins can be formulated by one or several known methods that protect a vulnerable agent from the acid and proteases of the upper GI tract and deliver such agent in an active state to the distal upper GI tract or lower GI tract. In addition, animals can be treated with anti-histamines such as cimetidine or proton pump inhibitors to prevent stomach acidification before oral administration of R-type bacteriocins. Thus, oral administration of properly formulated diffocins, producer cells capable of producing diffocins, or spores of diffocin-producing detoxified *C. difficile* bacteria to humans or animals with normal stomachs or to those in whom the acidification has been pharmaceutically prevented will enable delivery to the colonized portion of the intestine and thereby enable efficacy. Based on bowel transit time, the frequency of per oral administration directly or indirectly of diffocins to decolonize asymptomatic persons or animals may be every 6, every 12, every 18, every 24 hours, weekly, or monthly. Diffocins may also be administered to patients with CDAD, or recently "cured" of CDAD, at frequencies the same or greater. Particularly for management of active CDAD, diffocins may be formulated for and administered directly or indirectly per rectum by suppository, enema or colonic perfusion.

An engineered diffocin of the disclosure may be administered to any subject afflicted with, diagnosed as afflicted with, or suspected of being afflicted with, an infection or contamination by bacteria susceptible to the diffocin. Non-limiting examples of such a subject include animal (mammalian, reptilian, amphibian, avian, and fish) species as well as insects, plants and fungi. Representative, and non-limiting, examples of mammalian species include humans; non-human primates; agriculturally relevant species such as cattle, pigs, goats, and sheep; rodents, such as mice and rats; mammals for companionship, display, or show, such as dogs, cats, guinea pigs, rabbits, and horses; and mammals for work, such as dogs and horses. Representative, and non-limiting, examples of avian species include chickens, ducks, geese, and birds for companionship or show, such as parrots and parakeets. An animal subject treated with an engineered diffocin of the disclosure may also be a quadruped, a biped, an aquatic animal, a vertebrate, or an invertebrate, including insects.

In some embodiments, the subject to be treated is a human child or other young animal which has yet to reach maturity. Thus the disclosure includes the treatment of pediatric conditions comprising infection with bacteria or other microorganism susceptible to a diffocin of the disclosure.

The disclosure also provides for the treatment or prevention of an opportunistic infection, such as that resulting from an undesirable growth of bacteria that are present in the microbial flora of a human subject or a non-human animal. An opportunistic infection may be the result of an immunosuppressed condition in a subject or the result of antibiotic treatment that alter the commensal flora of the genitourinary (GU) or gastrointestinal (GI) tract. Thus the disclosure also provides for the treatment or prophylaxis of immunosuppressed subjects and subjects exposed to other pharmaceutical agents. A diffocin with its anti-bacterial activity may be used in combination with another anti-bacterial or anti-microbial agent, such as an antibiotic or anti-fungal agent as non-limiting examples. An "anti-microbial agent" is an agent or compound that can be used to inhibit the growth of, or to kill, single celled organisms. Anti-microbial agents include antibiotics, chemotherapeutic agents, antibodies (with or without complement), chemical inhibitors of DNA, RNA, protein, lipid, or cell wall synthesis or functions.

In some embodiments, diffocins, producer cells, or spores of detoxified *C. difficile* bacteria capable of producing diffocins are formulated with a "pharmaceutically acceptable" excipient, enteric coating or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. Non-limiting pharmaceutically suitable carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Additional formulations and pharmaceutical compositions disclosed herein comprise an isolated diffocin specific for a bacterial pathogen; a mixture of two, three, five, ten, or twenty or more different diffocins, producer cells or spores of detoxified *C. difficile* bacteria capable of producing diffocins that target the same bacterial pathogen; and a mixture of two, three, five, ten, or twenty or more that target different bacterial pathogens or different strains of the same bacterial pathogen.

Optionally, a composition comprising a diffocin or producer cells of the disclosure may also be spray dried or lyophilized using means well known in the art. Subsequent reconstitution and use may be practiced as known in the field.

A diffocin is typically used in an amount or concentration that is "safe and effective", which refers to a quantity that is sufficient to produce a desired therapeutic response without undue adverse side effects like those described above. A diffocin may also be used in an amount or concentration that is "therapeutically effective", which refers to an amount effective to yield a desired therapeutic response, such as, but not limited to, an amount effective to slow the rate of bacterial cell division, or to cause cessation of bacterial cell division, or to cause death or decrease rate of population growth of the bacteria. The safe and effective amount or therapeutically or prophylactically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

Having now generally described the inventive subject matter, the same will be more readily understood through reference to the following examples which are provided by way of illustration, and are not intended to be limiting of the disclosure, unless specified.

Examples

1. Determination of the Bactericidal Activity of Diffocins.

*C. difficile* cultures were grown under strict anaerobic conditions in a Forma Scientific environmental chamber with an atmosphere of 10% $CO_2$, 10% $H_2$, 80% $N_2$. All media, buffers, and plates were reduced in this atmosphere for at least 24 hours prior to use. Cultures were streaked on *C. difficile* selective agar plates (BD Diagnostics, BBL Cat. 222228), and incubated at 37° C. for two days. These plates as stocks were then stored anaerobically at ambient temperature.

To induce diffocins, *C. difficile* bacteria were grown in liquid cultures using *Brucella* medium (Difco) at 37° C. with no shaking. At an $OD_{600}$ of approximately 0.2, mitomycin C was added to a final concentration of 3 μg/ml. Cultures were then incubated for 3-16 hours. Bacterial lysis was detected by a visual clearing of the culture.

Cultures were removed from the anaerobic chamber, and cellular debris was removed by centrifugation at 5,000× g. The supernatants were then passed through a 0.2 μm cellulose acetate syringe filter. The filtrate was centrifuged at 90,000×g for 2 hours to pellet the diffocin particles. The pellets were resuspended in 10 mM Tris pH 7.5, 50 mM NaCl, 3% mannitol in 1/50 original culture volume.

Target strains were grown in *Brucella* broth overnight at 37° C. Culture volumes of 100 μl were added to 5 ml of tempered, reduced, *Brucella* overlay agar (0.5% agar), poured onto a *Brucella* agar plate (1.5% agar) and allowed to set. Samples of 5 μl of the diffocin preparations were spotted onto the plates and allowed to air dry (about 30 min). The plates were then incubated anaerobically at 37° C. overnight. Bactericidal activity was determined by a clearing, or lack of bacterial growth, at the position or spot where a sample was applied to the lawn.

2. Cloning of the Cd16 Diffocin Locus.

A draft genome sequence of *C. difficile* strain Cd16 was obtained by 454 instrument sequence analysis of genomic DNA. The entire dif16 locus or cluster (SEQ ID NO:1) was identified by comparison to strain Cd630 (see above).

Preparing a Backbone BAC Vector.

The starting vector was pETcoco1 (Novagen). This was modified to remove the two XhoI sites with primers AV1419 (SEQ ID NO:24) and AV1420 (SEQ ID NO:25), which have BbsI ends. To do so, a specific region was amplified from pETcoco1 DNA with these primers, and subsequently the PCR product was cut with BbsI and ligated back into the larger pETcoco1 vector fragment that was previously cut with XhoI. This ligation destroyed the two XhoI sites of pETcoco1. This latter plasmid was then further modified by a similar strategy to destroy the EcoRI sites using primers AV1416 (SEQ ID NO:26) and AV1245 (SEQ ID NO:27). The resulting vector was termed SW251.

Preparing a pUC19 Vector to Accept Fragments of the Diffocin Cluster.

The polylinker of pUC19 (New England BioLabs) was modified by digesting with EcoRI and HindIII and ligating in oligos AV1372 (SEQ ID NO:28), AV1373 (SEQ ID NO:29), AV1374 (SEQ ID NO:30), and AV1375 (SEQ ID NO:31). This changed the polylinker to NotI-NheI-KpnI-XhoI-EcoRV-BstBI-BbsI-EcoRI-NsiI-SphI-BamHI-AscI. This was termed SW232.

Cloning the Diffocin Cluster into SW232.

Three fragments of the diffocin cluster, SEQ ID NO 1, were individually amplified by PCR from Cd16 DNA. The 5' fragment (SEQ ID NO: 32) was amplified with primers 1368 (SEQ ID NO:35) and 1289 (SEQ ID NO:36), which had Not1 and Xho1 ends, respectively. The middle fragment (SEQ ID NO:33) was amplified with primers AV1288 (SEQ ID NO:37) and AV1366 (SEQ ID NO:38), which had Xho1 and EcoR1 ends, respectively. The 3' fragment, SEQ ID NO:34, was amplified with primers AV1367 (SEQ ID NO:39) and AV1300 (SEQ ID NO:40), which had EcoR1 and BamH1 ends, respectively. These three PCR fragments were separately cloned into SW232, and termed SW241, SW242, and SW243 for the 5', middle, and 3' portions, respectively.

Cloning the Diffocin Cluster into the BAC SW251.

The three fragments of the diffocin cluster (in SW241, SW242, and SW243), each having been expanded by cloning in *E. coli* and purified, were excised from the SW241, SW242, and SW243 vectors. SW241 was digested with NotI and XhoI, SW242 was digested with XhoI and EcoRI, and SW243 was digested with EcoRI and AscI. (Note that this AscI sites was part of the modified SW232 polylinker described above.)

These three fragments were assembled into SW251 that was first digested with NotI and AscI. The resulting plasmid was termed DG461 and contained the entire dif16 cluster. It was amplified in *E. coli.*

Making a Diffocin Integration Vector for Expression in *B. subtilis.*

The *B. subtilis* integration vector, pDR111, which included portions of the amyE gene flanking a cloning/promoter region and a spectinomycin-resistance gene, was used.

The pDR111 polylinker was modified by digesting the vector with HindIII and SphI and ligating in oligos DG1 (SEQ ID NO:41) and DG2 (SEQ ID NO:42). This added NotI and AscI sites to pDR111. The region containing the entire amyE front and back region with the modified polylinker was then amplified using primers DG9 (SEQ ID NO:43) and DG10 (SEQ ID NO:44), which both have BsaI ends. This fragment was ligated into the NotI and AscI sites of SW251 (resulting in destruction of the two sites) and created DG487. Note that there were new NotI and AscI sites introduced into DG487 by the modified poly linker of the pDR111-derived insert.

After expansion of DG487 in *E. coli* the NotI/AscI fragment containing the diffocin cluster from DG461 was then excised and cloned into the NotI/AscI site of DG487. This new construct was named DG488 and was the vector used to introduce the entire diffocin gene cluster into *B. subtilis* (below).

3. Expression of a Diffocin Gene Cluster in *Bacillus subtilis.*

The natural diffocin producer is *C. difficile*, an obligate anaerobe. If exposed to even traces of oxygen, *C. difficile* bacteria sporulate and die promptly. The ability to generate even trace amounts of diffocins from cultured *C. difficile* is difficult and taxing, and certainly the production of quantities of diffocins useful for prophylactic or therapeutic applications is not practical under the required strict anaerobic conditions. Accordingly, the entire diffocin gene cluster from *C. difficile* was first identified and then isolated by molecular cloning and introduced the cluster into an aerobic gram positive bacterium, *Bacillus subtilis*, for further engineering and production.

The *Bacillus subtilis* integration vector, DG488, was made as described in Example 2 and contained the entire 22,827 base diffocin locus (SEQ ID NO:1). This vector was used to recombine the diffocin locus into the *Bacillus subtilis* genome.

The recipient *Bacillus subtilis* strain was BDR123, which had a chloramphenicol resistance marker inserted within the amyE gene. When this strain was transformed with DG488, recombination occurred between the front and back amyE sequences within the vector and the genomic amyE sequences. This resulted in insertion, into the BDR123 genome, of all of the sequences between the front and back amyE regions of DG488 including the diffocin locus and the spectinomycin resistance gene. Successful recombinants were spectinomycin resistant but had become chloramphenicol-sensitive due to loss of that genomic marker as a result of the recombination event. This *B. subtilis* strain was termed BDR123-488.

Figure 7:
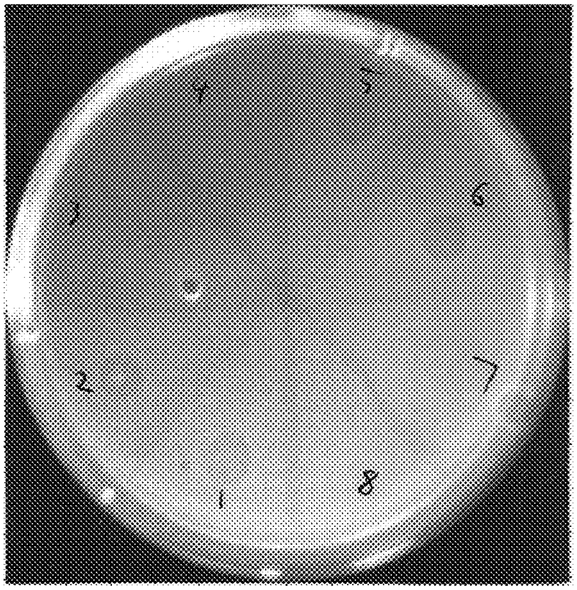
FIG. 7 is an image of spot tests of dif16 produced by *Bacillus subtilis* BDR123-488 (sector 1) and BDR123-491 (sector 2) tested on a lawn of *C. difficile* strain 19099.

Since the entire diffocin locus was inserted into the DG488 vector (Example 2), it therefore was also inserted in its entirety into BDR123-488. This inserted diffocin locus included all of the regulatory genes that were required for normal expression in *Clostridium*, and the structural diffocin particle genes were under control of these genes and/or regulatory elements. Because *Bacillus* and *Clostridium* are related bacteria, it was predicted that these diffocin regulatory elements would function in the *Bacillus* background and, as in their natural state, would be induced by DNA damage through a RecA-mediated mechanism. This in fact was the case, and diffocin particle production was induced in BDR123-488 by contact with the DNA damaging agent mitomycin C and killed strain Cd19099, FIG. 7.

Diffocin regulatory genes (ORFs 1359, 1360, 1361) were located in the 5' region of the locus in relation to the structural genes. There were also regulatory genes (ORFs 1377 (SEQ ID NO:20), 1378 (SEQ ID NO:21), and 1379 (SEQ ID NO:23)) located downstream, 3' in relation to the structural genes. To eliminate these latter regulatory genes DG491 was generated from DG488 in a single three way ligation. One PCR fragment was made from DG488 by PCR amplification with primers DG13 (SEQ ID NO:45) and DG14 (SEQ ID NO:46), and the other was made by PCR amplification with primers DG15 (SEQ ID NO:47) and DG16 (SEQ ID NO:48). Both PCR fragments were digested with AscI and SphI. DG488 was then digested with SphI, and the two digested PCR fragments were ligated into the large vector fragment from SphI-digested DG488 to produce DG491. DG491 was transformed into BDR123 (BDR123-491) to generate recombinant *B. subtilis* that contained the diffocin gene cluster lacking orfs1377 (SEQ ID NO:20), 1378 (SEQ ID NO:21), and 1379 (SEQ ID NO:23). The modified diffocin cluster lacking these ORFs expressed active diffocins upon exposure to mitomycin C (FIG. 7), as did the wild type diffocin cluster in BDR123-488.

4. Characterization of Bactericidal Spectrum-Determining Sequences from Multiple Diffocins.

A comparison of the Cd16 diffocin locus (SEQ ID NO:1) with that of Cd630 as well as other Cd strains that have been sequenced (QCD-66c26; QCD-23m63; QCD-32g58; QCD-63q42) and Cd4 (SEQ ID NO:61) showed that, with one exception, all of the open reading frames (SEQ ID NOs:1 and 61) shared 89-100% amino acid sequence identity. The exception was ORF 1374. This exceptional sequence was variable among all the sequenced diffocins and although similar in size, shared as little as 30% sequence identity. The position of ORF1374 within the diffocin cluster was consistent with that of a receptor binding domain. The sequences of the ORF1374s of the active diffocins that were isolated were determined and it was found that they too were highly variable in sequence (SEQ ID NO:17, 49-53). A comparison of these sequences is shown in FIG. 8. Furthermore, the spectra of the isolated diffocins (FIG. 2) reflected the similarities or dissimilarities of the ORF1374 amino acid sequences, FIG. 8. For example, the sequences of ORF1374 of dif16 (SEQ ID NO:17) and dif126 (SEQ ID NO:52) differed by only 1 amino acid and their bactericidal spectra were nearly identical. Whereas the sequences of ORF1374 of dif16 (SEQ ID NO:17) and dif108 (SEQ ID NO:50) differed by 188 amino acids, and their bactericidal spectra were very dissimilar with little overlap. For this reason and because ORF1374 was the only variable protein in the gene cluster, it was concluded that ORF1374 was the target recognition determinant and responsible for the unique spectrum of each particular diffocin.

5. Cloning and Expression of Dif4 in *B. subtilis.*

The diffocin 4 locus was cloned from Cd4 by methods similar to those for diffocin 16. However, some modifications were required due to the absence of an EcoR1 site within the dif4 gene cluster, SEQ ID NO:61. Plasmid SW251 (see Example 2 above) was modified to have an XhoI site in the polylinker using oligos DG211, SEQ ID NO:57 and DG212, SEQ ID NO:58, to introduce NotI and AscI sites, respectively. This created vector DG577.

The diffocin cluster from Cd4 DNA was amplified in three fragments. The first used primers DG210 (SEQ ID NO:59) and AV1288 (SEQ ID NO:37) to introduce XhoI and NcoI sites. The second used primers DG209 (SEQ ID NO:60) and DG15 (SEQ ID NO:47) to introduce NcoI and AscI sites. These two were cloned into DG577, previously cut with XhoI/AscI to create DG578. The third fragment was amplified using AV1368 (SEQ ID NO:35) and AV1289 (SEQ ID NO:36) to introduce XhoI and NotI sites and cloned into DG578, previously cut with XhoI and NotI to create DG579. This latter construct containing the dif4 cluster (SEQ ID NO:61) was the equivalent of DG491 for dif16, i.e. it lacked orf1377, orf1378 and orf1379, the unnecessary presumed regulatory sequences downstream of the structural genes for diffocin. The integration vector for introducing the dif4 cluster into *B. subtilis* was made by taking the NotI AscI fragment from DG579 and cloning it into DG487 (see Example 2 above). This constructed plasmid was DG580.

To express dif4 in *B. subtilis*, DG580, which contained the dif4 locus without orf1377-1379 (SEQ ID NO:61), was recombined into the *Bacillus subtilis* genome. The recipient *Bacillus subtilis* strain was BDR123, which had a chloramphenicol resistance marker inserted within the amyE gene. When this strain was transformed with DG580, recombination occurred between the front and back amyE sequences within the vector and the genomic amyE sequences. This resulted in insertion, into the BDR123 genome, of all of the sequences between the front and back amyE regions of DG580 including the diffocin locus and the spectinomycin resistance gene. Successful recombinants were spectinomycin resistant but had become chloramphenicol-sensitive due to loss of that genomic marker as a result of the recombination event. This *B. subtilis* strain was termed BDR123-580.

Figure 9:
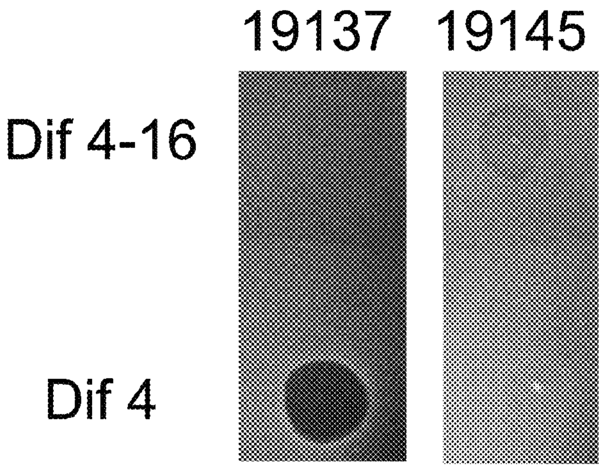
FIG. 9 is an image of spot tests of "Dif4" produced by BDR123-580 and "Dif 4-16". The latter was produced by *Bacillus subtilis* BDR123-587 in which the orf1374 of dif4 (SEQ ID NO:49) was switched to orf1374 of dif16 (SEQ ID NO:17). These two diffocins produced by *B. subtilis* were both tested on lawns of strains 19137 and 19145, as indicated. The specificity of killing by "Dif 4-16" has been switched from that of dif4 to that of dif16.

This integrated dif4 locus included all of the regulatory genes required for normal diffocin expression in *C. difficile*, and as expected and shown previously for dif16 in *B. subtilis*, dif4 particle production was induced in BDR123-580 by contact with mitomycin C, FIG. 9. Thus, the present examples provide the cloning of the genetic loci for both dif4 and dif16 and the expression of each in *B. subtilis*, an example of a non-pathogenic aerobic production bacterium.

6. Orf1374 Determines the Bactericidal Spectra of Diffocins.

Orf 1374 encodes a large predicted polypeptide (~200 kDa) that was shown by mass spectrometry to be part of the purified diffocin structure. When comparing the gene clusters of diffocins 16 and diffocin 4, most of the gene products, particularly those that are predicted to be structural components, are nearly identical at the amino acid level. The major amino acid sequence difference between the two clusters is orf1374. For this reason and other reasons discussed below, it was speculated that this gene product confers the target specificity of the diffocins. To test this, Orf 1374 of dif 4 (i.e., the sequence encoding SEQ ID NO:49) was replaced in DG580 with Orf 1374 from Cd16 (i.e., the sequence encoding SEQ ID NO:17) to create DG587. DG587 was integrated into the genome of *B. subtilis* BDR123 to make a BDR123-587 recombinant, as provided above for dif16 and dif4. The resulting BDR123-587 was exposed to mitomycin and the lysate treated so as to prepare diffocins. The resulting diffocin particles had bactericidal activity against *C. difficile* strain 19145, which was sensitive to diffocin 16, and had lost the ability to kill strain 19137, which was sensitive to dif4 (FIG. 9). This experiment was further refined. Construction of DG587 resulted in Orf1373 being a chimera of Cd4 and Cd16. A construct was made such that Orf 1373 of DG587 was restored to be 100% identical to the original Cd4 1373, SEQ ID NO:78, thus creating a construct that was a clean replacement of only Orf 1374, SEQ ID NO:17. This construct was termed DG603. This construct was integrated into the *B. subtilis* BDR123 genome and induced with mitomycin C as described above. The resulting diffocin particles had bactericidal activity against strains 19099 and 19145 and lost the ability to kill 19137. Thus, the bactericidal sprectra of diffocins was determined by the protein encoded by orf1374, and changing orf1374 changed the bactericidal spectrum of diffocin, as demonstrated herein.

7. Producer Cell Without PBSX That Does Not Lyse When RecA is Activated.

The PBSX prophage is ubiquitous in wild type *Bacillus subtilis*. The prophage when induced is defective in that it possesses a stunted head structure and contains only small, random fragments of DNA. It is under the control of RecA, thus it is induced by DNA damaging agents, e.g. mitomycin C, and other forms of severe stress to the bacterium. When induced it causes lysis of the bacterium and releases PBSX particles. In order to avoid contamination of culture medium with PBSX particles and to eliminate lysis of the *Bacillus subtilis* producer bacteria when the expression of diffocins is regulated by modifying recA or dinR/lexA activity, the PBSX gene cluster was eliminated from *Bacillus subtilis* BDR11 bacteria.

The PBSX knockout was constructed by following the procedure outlined in Liu et al. Briefly, using the primers and overlapped extension PCR techniques used in the Liu paper, the araR gene of parental strain BDR11 was deleted and replaced with the neomycin/kanamycin-resistance gene under the *Bacillus* arabinose promoter, $P_{araA}$-neo$^R$, to make strain BDG2. This deletion of the araR gene was confirmed by PCR and by the conferral of resistance to kanamycin.

Next, a DNA construct was made to delete the PBSX locus itself. To make this construct, the following five PCR products were spliced by overlapped extension PCR into one large product: 1 kb of sequence 5' of the xylB gene, amplified from BDR11; 1 kb of sequence 3' of the xylA gene, amplified from BDR11; a chloramphenicol resistance gene, cat, amplified from plasmid pJW034; araR, amplified from BDR11; and finally, 1 kb of sequence containing the xylB gene, amplified from BDR11. The overlapped extension PCR product was cloned into the XmaI and SpeI sites of pUC19. This construct was then linearized with SacII and transformed into strain BDG2 bacteria, which were plated onto LB agar plates supplemented with 5 µg chloramphenicol/ml. Colonies were picked from this plate and patched onto LB agar plates supplemented with either 5 µg chloramphenicol/ml or 20 µg kanamycin/ml. Strains that were chloramphenicol resistant and kanamycin sensitive were grown for 4 hours in LB broth with no antibiotic selection and then plated onto LB agar plates supplemented with 20 µg kanamycin/ml. The colonies that grew on these plates were tested by colony PCR for the presence of PBSX genes. The deletion of the PBSX gene cluster was confirmed in strain BDG 9 by sequencing PCR products that spanned the site of PBSX genes in wt strain BD123. Further analysis showed that unlike *Bacillus subtilis* strains BD123 or BDG2, BDG9 did not lyse or produce PBSX particles in the presence of 3 μg mitomycin C/ml.

The PBSX deletion strain, BDG9, was transformed with plasmid DG580, to create BDG27. Integration of the Cd4 diffocin cluster was confirmed by spectinomycin resistance. BDG27 was grown and induced with mitomycin C as described above. After 16 hours cells were harvested and lysed with BugBuster (Novagen) to break open the cells since, without PBSX, we expected the diffocins to accumulate intracellularly. After lysing the cells with BugBuster, debris was removed by centrifugation, and the supernatant was tested for bactericidal activity against strain 19137. The diffocin produced by BDG27 showed activity against Cd19137 but not Cd19099, thus demonstrating that diffocin 4 was produced in this non-lytic, PBSX deleted strain.

The term "comprising", which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Although the invention has been described with reference to the above examples, it will be understood that modifications and variations are encompassed within the spirit and scope of the invention. Accordingly, the invention is limited only by the following claims.

REFERENCES

Anastasio, K L, J A Soucheck, and H Sugiyama, 1971. Boticinogeny and Actions of the Bacteriocin. J. of Bacteriology 107: 143-149.

Bartlett J G, Onderdonk A B, Cisneros R L, Kasper D L. 1977. Clindamycin-associated colitis due to a toxin-producing species of *Clostridium* in hamsters. J Infect Dis. 136:701-705.

Bartlett J G, Chang T, Taylor N S, Onderdonk A B. 1979. Colitis induced by *Clostridium difficile*. Rev Infect Dis 1:370-8.

Bartlett J G. 2002. Antibiotic-associated Diarrhea. N Engl J Med 346: 334-9.

Bartlett J G, 2007. *Clostridium difficile*: Old and New Observations. J Clin Gastroenterol. 41 Suppl 1:S24-9.

Benson L, Song X, Campos J, Singh N. Changing epidemiology of *Clostridium difficile*-associated disease in children. Infect Control Hosp Epidemiol. 2007; 28:1233-5.

Blackwell, C. C. and J. A. Law. 1981. Typing of non-serogroupable *Neisseria meningitidis* by means of sensitivity to R-type pyocins of *Pseudomonas aeruginosa;*

Blackwell, C. C., F. P. Winstanley, and W. A. Telfer-Brunton. 1982. Sensitivity of thermophilic campylobacters to R-type pyocines of *Pseudomonas aeruginosa*. J. Med. Microbiol. 15:247-251.

Bradley. Bacteriocins. Bacteriol. Revs. 31:230-314, 1967.

Campagnari, A. A., R. Karalus, M. Apicella, W. Melaugh, A. J. Lesse, and B. W. Gibson. 1994. Use of pyocin to select a *Haemophilus ducreyi* variant defective in lipooligosaccharide biosynthesis. Infect. Immun. 62:2379-2386.

Coetzee, H. L., H. C. De Klerk, J. N. Coetzee, and J. A. Smit. 1968. Bacteriophage-tail-like particles associated with intra-species killing of *Proteus vulgaris*. J. Gen. Virol. 2:29-36.

Daw, M A, and F R Falkiner, 1996. Bacteriocins: nature, function and structure Review Article. Micron 27:467-479.

Ellison, J S and J A Kautter, 1970. Purification and Some Properties of Two Boticins. J. of Bacteriology, 104: 19-26.

Filiatrault, M. J., R. S. Munson, Jr., and A. A. Campagnari. 2001. Genetic analysis of a pyocin-resistant lipooligosaccharide (LOS) mutant of *Haemophilus ducreyi*: restoration of full-length LOS restores pyocin sensitivity. J. inhibition Bacteriol. 183:5756-5761.

Fortier, L C and S Moineau, 2007. Morphological and genetic diversity of temperate phages in *Clostridium difficile. Appl Environ Microbiol.* 73:7358-7366.

Goh, S, P F Ong, K P Song, T V Riley and B J Chang, 2007. The complete genome sequence of *Clostridium difficile* phage phiC2 and comparisons to phiCD119 and inducible prophages of CD630. *Microbiology,* 153: 676-685.

Govind, R, J A Fralick, and R D Rolfe, 2006. Genomic organization and molecular characterization of *Clostridium difficile* bacteriophage phiCD119. *J. Bacteriol.* 188:2568-2577.

Jabrane, A., A. Sabri, P. Compe're, P. Jacques, I. Vandenberghe, J. Van Beeumen, and P. Thenart. 2002. Characterization of serracin P, a phagetail-like bacteriocin, and its activity against *Erwinia amylovora*, the fire blight pathogen. Appl. Environ. Microbiol. 68:5704-5710.

Kageyama et al. Life Sciences 9:471-476, 1962.

Kageyama, M., K. Ikeda, and F. Egami. 1964. Studies of a pyocin. III. Biological properties of the pyocin. J. Biochem. 55:59-64.

Kageyama, M., K. Ikeda, and F. Egami. 1964a. Studies of a pyocin. I. Physical and chemical properties. J. Biochem. 55:49-53.

Kageyama, M. 1975. Bacteriocins and bacteriophages in *Pseudomonas aeruginosa*, p. 291-305. In T. Mitsuhashi and H. Hashimoto (ed.), Microbial drug resistance. University of Tokyo Press, Tokyo, Japan.

Keel, K, J S Brazier, K W Post, S Weese and J G Songer, 2007. Prevalence of PCR Ribotypes Among *Clostridium Difficile* Isolates from Pigs, Calves, and Other Species J. Clinical Microbiology, 45: 1963-1964.

Kingsbury, D, 1966. Bacteriocin production by strains of *Neisseria meningitidis*." J Bacteriol. 91:1696-9.

Krogh, S, M O'Reilly, N Nolan and K M Devine, 1996. The phage-like element PBSX and part of the skin element, which are resident at different locations on the *Bacillus subtilis* chromosome, are highly homologous. Microbiology 142: 2031-2040

Liu S, Endo K, Ara K, Ozaki K, Ogasawara N. 2008. Introduction of marker-free deletions in *Bacillus subtilis* using the AraR repressor and the ara promoter. Microbiology. 154: 2562-70.

Loo V G, Poirier L, Miller M A, Oughton M, Libman M D, Michaud S, et al. A predominantly clonal multi-institutional outbreak of *Clostridium difficile*-associated diarrhea with high morbidity and mortality. N Engl J Med. 2005; 353:2442-9.

McDonald L C, Killgore G E, Thompson A, Owens R C Jr, Kazakova S V, Sambol S P, et al. An epidemic, toxin gene-variant strain of *Clostridium difficile*. N Engl J Med. 2005; 353:2433-41.

Morse, S. A., B. V. Jones, and P. G. Lysko. 1980. Pyocin of *Neisseria gonorrhoeae*: mechanism of action. Antimicrob. Agents Chemother. 18:416-423.

Muto C A, Pokrywka M, Shutt K, Mendelsohn M B, Nouri K, Posey K, et al. A large outbreak of *Clostridium difficile*-associated disease with an unexpected proportion of deaths and colectomies at a teaching hospital following increased fluoroquinolone use. Infect Control Hosp Epidemiol. 2005; 26:273-80.

Nieves, B M, F Gil and F J Castillo, 1981. Growth inhibition activity and bacteriophage and bacteriocinlike particles associated with different species of *Clostridium*. Can. J. Microbiol. 27: 216-225.

Pépin J, Valiquette L, Alary M E, Villemure P, Pelletier A, Forget K, et al. *Clostridium difficile*-associated diarrhea in a region of Quebec from 1991 to 2003: a changing pattern of disease severity. CMAJ. 2004; 171:466-72.

Scholl, D, and D W Martin, Jr., 2008. Antibacterial efficacy of R-type pyocins towards *Pseudomonas aeruginosa* in a mouse peritonitis model. Antimicrob. Agents Chemother. 52:1647-1652.

Scholl, D, M Cooley, S R Williams, D Gebhart, D Martin, A Bates, and R Mandrell, 2009. An Engineered R-Type Pyocin Is a Highly Specific and Sensitive Bactericidal Agent for the Food-Borne Pathogen *Escherichia coli* 0157:H7. Antimicrob. Agents Chemother. 53: 3074-3080.

Strauch, E., H. Kaspar, C. Schaudinn, P. Dersch, K. Madela, C. Gewinner, S. Hertwig, J. Wecke, and B. Appel. 2001. Characterization of enterocoliticin, a phage tail-like bacteriocin, and its effect on pathogenic *Yersinia enterocolitica* strains. Appl. Environ. Microbiol. 67:5634-5642;

Sunenshine, R H & L C McDonald, 2006. *Clostridium difficile*-associated disease: New challenges from an established pathogen, Cleveland Clinic J. of Medicine, 73: 187.

Williams, S., D. Gebhart, D. W. Martin, and D. Scholl. 2008. Re-targeting R-type pyocins to generate novel bactericidal protein complexes. Appl. Environ. Microbiol. 74:3868-3876.

Wood, H E, M T Dawson, K M Devine, D J McConell, 1990. Characterization of PBSX, a Defective Prophage of *Bacillus subtilis*. J Bacteriology 172: 2667-2674.

Zilberberg, M D, Tillotson, G S and McDonald, L C., 2010 *Clostridium difficile* Infections Among Hospitalized Children, United States, 1997-2006. Emerging Infect Dis 16: 604-609.

Zink, R., M. J. Loessner, and S. Schere. 1995. Characterization of cryptic prophages (monocins) in *Listeria* and sequence analysis of a holin/endolysin gene. Microbiology 141:2577-2584.

What is claimed is:

1. An isolated nucleic acid molecule encoding an R-type high molecular weight (hmw) bacteriocin, wherein the nucleic acid molecule is from a genome of a strain of *Clostridium difficile* and comprises a polynucleotide sequence that is at least 80% identical to a polynucleotide encoding SEQ ID NOs:66-77, wherein the R-type hmw bacteriocin further comprises a base plate attachment region (BPAR), and the R-type hmw bacteriocin has a heterologous receptor binding domain (RBD) that binds a receptor of at least one other strain of *C. difficile* and has bactericidal activity against at least the one other strain of *C. difficile.*

2. The nucleic acid molecule of claim 1, wherein the nucleic acid molecule is from a genome of a strain of *Clostridium difficile* selected from the group consisting of Cd4, Cd16, Cd19108, Cd19123, Cd19126, Cd19145, and ATCC Accession No. 43593.

3. The nucleic acid molecule of claim 1, wherein the R-type hmw bacteriocin further comprises a baseplate attachment region (BPAR) at least 80% identical to a polypeptide comprised of 50 or more contiguous amino acids from the amino terminus of SEQ ID NO:16 or 78.

4. The nucleic acid molecule of claim 1, wherein the RBD comprises a polypeptide at least 80% identical to a polypeptide selected from the group consisting of SEQ ID NO:17 and 49-53, or at least 80% identical to a polypeptide comprising the receptor binding domain (RBD) region of a polypeptide selected from the group consisting of SEQ ID NOs:54-56.

5. The nucleic acid molecule of claim 1, wherein the R-type hmw bacteriocin comprises the polypeptides of SEQ ID NOs: 4-16, 18, and 19; or the polypeptides of SEQ ID NOs:66-77.

6. The isolated nucleic acid molecule of claim 4, wherein the RBD is a modified form of a native RBD selected from the group consisting of SEQ ID NOs: 17 and 49-53 or a receptor binding domain (RBD) region of a polypeptide selected from the group consisting of SEQ ID NOs:54-56, wherein the modified form is at least 80% identical to the native RBD.

7. The nucleic acid molecule of claim 2, wherein the nucleic acid molecule comprises SEQ ID NO:1 or SEQ ID NO:61.

8. An isolated R-type hmw bacteriocin encoded by a nucleic acid molecule of claim 1.

9. An expression cassette comprising a nucleic acid molecule of claim 1.

10. The expression cassette of claim 9, wherein the nucleic acid molecule is operably linked to a heterologous promoter.

11. The expression cassette of claim 10, wherein the promoter is inducible or repressible.

12. The expression cassette of claim 11, wherein the promoter is induced by a small molecule inducer or de-repressor.

13. The expression cassette of claim 10, further comprising a recA gene encoding a constitutively active RecA protein and under the control of an heterologous promoter responsive to a small molecule inducer or de-repressor.

14. A producer cell comprising the expression cassette of claim 9.

15. A producer cell comprising a nucleic acid molecule of claim 1 within its chromosome.

16. The producer cell of claim 14, wherein the cell is a non-pathogenic and not obligate anaerobic bacterium.

17. The producer cell of claim 16, wherein the non-pathogenic and not obligate anaerobic bacterium is a species from a genus of bacteria selected from the group consisting of *Bacillus, Lactobacillus*, and *Listeria.*

18. The producer cell of claim 17, wherein the species is *Bacillus subtilis.*

19. The producer cell of claim 18, wherein the *B. subtilis* lacks the PBSX gene cluster.

20. An isolated R-type high molecular weight (hmw) bacteriocin having bactericidal activity, wherein the R-type hmw bacteriocin comprises a polypeptide sequence that is at least 80% identical to SEQ ID NOs:66-77, a base plate attachment region (BPAR) of a first strain of a first species of bacteria of genus *Clostridium*, and a receptor binding domain (RBD) from a second strain of the first species, or a second species of the genus *Clostridium* or of a bacteriophage that infects a *Clostridium* species, wherein the bacteriocin has bactericidal activity against at least one strain of *Clostridium difficile.*

21. The R-type hmw bacteriocin of claim 20, wherein the BPAR is from a first strain of *Clostridium difficile* and the RBD is from a second strain of *Clostridium difficile* or from a bacteriophage that infects *Clostridium difficile.*

22. The isolated R-type hmw bacteriocin of claim 20, wherein the BPAR is at least 80% identical to a polypeptide comprised of 50 or more contiguous amino acids of SEQ ID NO:16 or 78.

23. The R-type hmw bacteriocin of claim 20, wherein the RBD is at least 80% identical to a polypeptide selected from the group consisting of SEQ ID NO:17 and 49-53, or at least 80% identical to a polypeptide comprising the receptor binding domain (RBD) region of a polypeptide selected from the group consisting of SEQ ID NOs:54-56.

24. A method of producing an R-type hmw bacteriocin, comprising exposing a producer cell comprising a nucleic acid molecule according to any one of claim 1-7, operably linked to an inducible promoter, to an inducing agent in a concentration effective to induce expression of the R-type hmw bacteriocin, and purifying the expressed R-type bacteriocin.

25. The method of claim 24, wherein the nucleic acid molecule encoding the R-type bacteriocin is heterologous to the genome of the producer cell, and wherein the nucleic acid molecule is contained within the producer cell's chromosome or is contained in an extrachromosomal expression vector within the producer cell.

26. The method of claim 24, wherein the producer cell is a non-pathogenic and not obligate anaerobic bacterium.

27. The method of claim 26, wherein the non-pathogenic and not obligate anaerobic bacterium is a species from a genus of bacteria selected from the group consisting of *Bacillus, Lactobacillus*, and *Listeria*.

28. The method of claim 27, wherein the species is *Bacillus subtilis*.

29. The method of claim 28, wherein the *B. subtilis* does not lyse when induced to produce the R-type bacteriocin.

30. The producer cell of claim 29, wherein the *B. subtilis* lacks the PBSX gene cluster.

31. A method of treating an infection of *Clostridium difficile* in an animal comprising, administering to an animal in need thereof an amount of the producer cell of claim 14 to produce a bactericidal amount of the bacteriocin, thereby treating the infection.

32. The method of claim 31, wherein the nucleic acid molecule encoding the bacteriocin is under the control of a lac promoter.

33. The nucleic acid molecule of claim 1, wherein the heterologous receptor binding domain (RBD) is encoded by a nucleic acid molecule from a second strain of *C. difficile*, or from a second species of the genus *Clostridium*, or from a bacteriophage that infects a *Clostridium* species, or of a modified form thereof, wherein the bacteriocin has bactericidal activity against at least one strain of *Clostridium difficile*.

34. A method of killing a *Clostridium difficile*, comprising contacting the pathogenic bacterium with the R-type bacteriocin of claim 8, whereby the bacteriocin binds and kills the pathogenic bacterium.

35. The method of claim 34, wherein the *Clostridium difficile* is in an animal and a bactericidal amount of the R-type bacteriocin is administered to the animal.

36. The method of claim 35, wherein the animal is a mammal.

37. The method of claim 36, wherein the mammal is a human.

38. The nucleic acid of claim 4, wherein the RBD domain comprises amino acid residue 51 to the carboxy-terminal residue of SEQ ID NOs: 54, 55, or 56.

* * * * *